(12) United States Patent
Itoh et al.

(10) Patent No.: US 7,625,887 B2
(45) Date of Patent: Dec. 1, 2009

(54) RECEPTOR AGONISTS

(75) Inventors: Fumio Itoh, Tsukuba (JP); Shuji Hinuma, Tsukuba (JP); Naoyuki Kanzaki, Osaka (JP); Yuji Kawamata, Tsukuba (JP); Taisuke Tawaraishi, Tsukuba (JP); Yuji Ishichi, Osaka (JP); Mariko Hirohashi, Shunan (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 249 days.

(21) Appl. No.: 10/543,997

(22) PCT Filed: Jan. 27, 2004

(86) PCT No.: PCT/JP2004/000706

§ 371 (c)(1),
(2), (4) Date: Oct. 31, 2005

(87) PCT Pub. No.: WO2004/067008

PCT Pub. Date: Aug. 12, 2004

(65) Prior Publication Data

US 2006/0199795 A1 Sep. 7, 2006

(30) Foreign Application Priority Data

Jan. 28, 2003 (JP) .............................. 2003-019272
Apr. 28, 2003 (JP) .............................. 2003-124311

(51) Int. Cl.
A61K 31/553 (2006.01)
A61K 45/00 (2006.01)
C07D 267/22 (2006.01)
C07D 281/02 (2006.01)

(52) U.S. Cl. .................. 514/211.09; 540/469; 540/552; 514/302

(58) Field of Classification Search .................. 540/552, 540/469; 514/211.09, 302
See application file for complete search history.

(56) References Cited

U.S. PATENT DOCUMENTS

| | | |
|---|---|---|
| 3,555,034 A | 1/1971 | Diebold et al. |
| 3,987,047 A | 10/1976 | Griss et al. |
| 4,220,778 A | 9/1980 | Ellefson et al. |
| 4,329,341 A | 5/1982 | Rochricht et al. |
| 4,647,560 A | 3/1987 | Boltze et al. |
| 4,820,834 A | 4/1989 | Evans et al. |
| 5,137,890 A | 8/1992 | Sanfilippo et al. |
| 5,324,726 A | 6/1994 | Bock et al. |
| 6,150,357 A | 11/2000 | Salata et al. |

FOREIGN PATENT DOCUMENTS

| | | |
|---|---|---|
| EP | 0167919 | 1/1986 |
| EP | 0 284 256 | 9/1988 |
| EP | 0 567 026 | 10/1993 |
| EP | 0 705 607 | 4/1996 |
| EP | 0733632 A1 | 9/1996 |
| EP | 1 273 659 | 1/2003 |
| EP | 1 347 052 | 9/2003 |
| EP | 1 378 749 | 1/2004 |
| EP | 1 407 782 | 4/2004 |
| JP | 09-291034 | 11/1997 |
| WO | WO 94/22825 | 10/1994 |
| WO | WO 95/28399 | 10/1995 |
| WO | WO 97/10224 | 3/1997 |
| WO | WO 97/30992 | 8/1997 |
| WO | WO 98/47882 | 10/1998 |
| WO | WO 99/38844 | 8/1999 |
| WO | WO 99/47132 | 9/1999 |
| WO | WO 01/55121 A1 | 8/2001 |
| WO | WO 01/77325 A1 | 10/2001 |
| WO | WO 02/40669 A1 | 5/2002 |
| WO | WO 02/084286 A1 | 10/2002 |
| WO | WO 02/099388 | 12/2002 |
| WO | WO 03/002147 | 1/2003 |
| WO | WO 04/033436 | 4/2004 |
| WO | WO 2004/043468 A1 | 5/2004 |

OTHER PUBLICATIONS

C. Papageorgiou, et al., "A Non-Peptide Ligand for the Somatostatin Receptor Having a Benzodiazepinone Structure", Biorganic & Medical Chemistry Letters, (1996), pp. 2670272, vol. 6, No. 3.

A. Terada, et al., "Studies on Benzodizepinooxazoles. III. Reactions and Rearrangements ofBenzo[6,7]-1,4-diazepino-[5,4-b]oxazole Derivatives", Chem. Pharm. Bull., (1973), pp. 742-751, vol. 21, No. 4.

H. Breslin, et al., "Synthesis and Anti-HIV Activity of 1,3,4,5-Tetrahydro-2H-1,4-benzodiazepin-2-one J(TBO) Derivatives. Truncated 4,5,6,7-Tetrahydro-5-methylimidazo[4,5,1-jk][1,4]benzodiazepin-2(1H)-ones J(TIBO) Analogues", Bioorganic & Medicinal Chemistry, (1999), pp. 2427-2436, vol. 7.

M. Kajtar, et al., "Chrioptical Properties and Conformation of 4,5-Saturated Derivatives of 5-Aryl-1,4-benzodiazepin-2-ones", Croatica Chemica Acta, J(1989), pp. 245-265, 62 (2A).

Maruyama, Takaharu et al., "Identification of Membrane-Type Receptor For Bile Acids (M-BAR)," Biochemical and Biophysical Research Communications, vol. 298, No. 5, Nov. 15, 2002, pp. 714-719.

Zhang, Zinfang et al., "Solid-Phase Synthesis of Tetrahydro-1,4-Benzodiazepin-2-one derivatives," Molecular Diversity, vol. 5, No. 3, 2000, pp. 127-130.

Supplementary European Search Report for EP 04705536.3 dated May 13, 2009.

*Primary Examiner*—Bruck Kifle
(74) *Attorney, Agent, or Firm*—Finnegan, Henderson, Farabow, Garrett & Dunner, LLP

(57) ABSTRACT

It is intended to provide a TGR5 receptor agonist containing a fused ring compound represented by the following general formula, its salt or a prodrug thereof: (1) wherein ring A represents an optionally substituted aromatic ring; and the ring B' represents a 5- to 8-membered ring having one or more substituents; which is useful in treating various diseases.

(I)

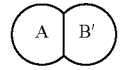

7 Claims, No Drawings

RECEPTOR AGONISTS

This application is the National Phase filing of International Patent Application No. PCT/JP2004/000706, filed Jan. 27, 2004.

TECHNICAL FIELD

The present invention relates to a TGR5 receptor agonist useful for the treatment of various diseases. Moreover, the present invention relates to a method of screening a ligand, an agonist or an antagonist for TGR5, which uses TGR5 and a TGR5 agonist having a fused ring skeleton.

BACKGROUND ART

TGR5 is a G-protein-coupled receptor protein, and an agonist or antagonist thereof is reported to be useful for the treatment of central nervous diseases, inflammatory diseases and the like (see WO01/77325, WO02/84286). However, a low molecular weight synthetic compound useful as a TGR5 agonist or antagonist has not been reported.

On the other hand, as a fused ring compound, the following compounds are reported.

1) A compound having a somatostatin receptor agonistic action, which is represented by the formula

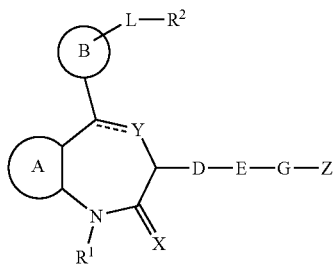

wherein ring A is an aromatic hydrocarbon optionally having substituent(s) or an aromatic heterocycle optionally having substituent(s); ring B is an aromatic hydrocarbon optionally having substituent(s) or an aromatic heterocycle optionally having substituent(s); Z is a cyclic group optionally having substituent(s) or a chain hydrocarbon group optionally having substituent(s); $R^1$ is a hydrogen atom, a hydrocarbon group optionally having substituent(s) or a heterocyclic group optionally having substituent(s); $R^2$ is an optionally substituted amino group; D is a bond or a divalent hydrocarbon group optionally having substituent(s); E is a bond, —CON($R^a$)—, —N($R^a$)CO— or the like (wherein $R^a$ is a hydrogen atom or a hydrocarbon group optionally having substituent(s)); G is a bond or a divalent hydrocarbon group optionally having substituent(s); L is a divalent group; ring B is optionally linked with $R^2$ to form a non-aromatic fused nitrogen-containing heterocycle optionally having substituent(s); X is two hydrogen atoms, an oxygen atom or a sulfur atom; and Y is a nitrogen atom, an oxygen atom, —N($R^4$)— (wherein $R^4$ is a hydrogen atom, a hydrocarbon optionally having substituent(s) or an acyl group) or S(O)n (wherein n is 0, 1 or 2), or a salt thereof (see WO98/47882).

2) A compound useful for the treatment of brain disorder, memory disorder and the like, which is represented by the formula

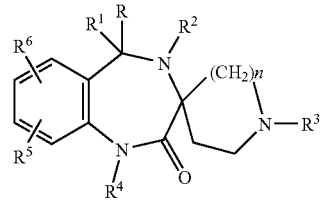

wherein R is H or the like; $R^1$ is H; $R^2$, $R^3$ and $R^4$ are each independently H, alkyl, or aralkyl wherein aromatic moiety is optionally substituted; or $R^1$ and $R^2$ in combination form a bond; $R^5$ and $R^6$ are each independently H, a halogen, a nitro, a cyano, a trifluoromethyl, a lower alkyl or a lower alkoxy; and n is an integer of 1 to 3, or a salt thereof (see U.S. Pat. No. 4,647,560).

3) A compound having an enzyme induction activity, which is represented by the formula

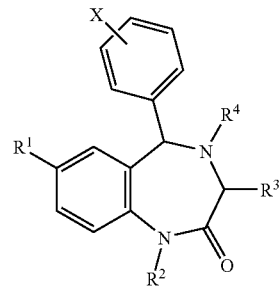

wherein $R^1$ is a hydrogen, a halogen, a trifluoromethyl or a nitro group; $R^2$ is a hydrogen atom or a $C_{1-6}$ alkyl; $R^3$ is an optionally substituted lower alkyl group or the like; $R^4$ is a hydrogen, a chlorocarbonyl or a carbamoyl; and X is a hydrogen atom, a halogen or a trifluoromethyl, or a salt thereof (see U.S. Pat. No. 4,329,341).

4) A compound useful as a cholecystokinin (CCK) antagonist, which is represented by the formula

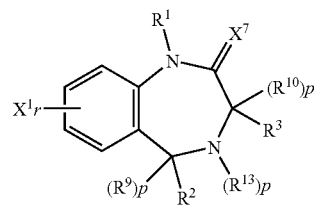

wherein $R^1$ is H, a $C_{1-5}$ straight chain or branched alkyl or the like; $R^2$ is H, a lower alkyl, a substituted or unsubstituted phenyl or the like; $R^3$ is —$(CH_2)n$-$R^7$ (wherein n is 0 to 4 and $R^7$ is a α- or β-naphthyl or the like) or the like; $R^9$ and $R^{10}$ are each independently H, OH or $CH_3$; $R^{13}$ is H, O, a lower alkyl, an acyl or a cyclo lower alkyl; p is 0 or 1; $X^1$ is H or the like; $X^7$ is O, S or the like; and r is 1 or 2, or a salt thereof (see EP-167919A).

5) A compound of the following formula:
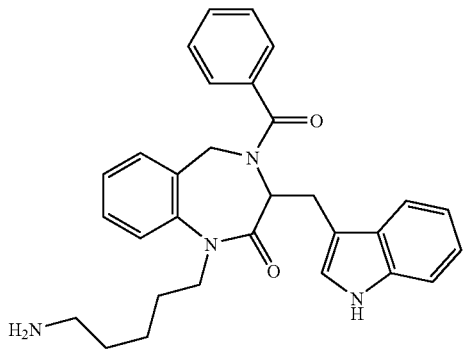
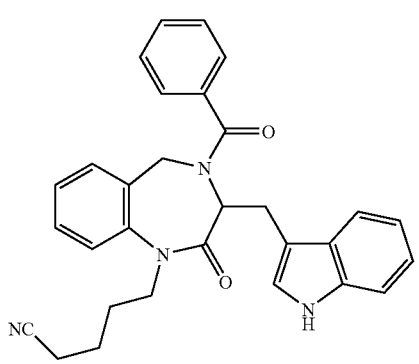
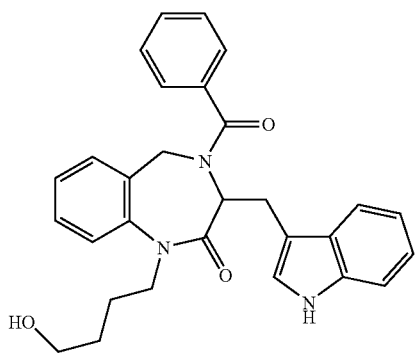
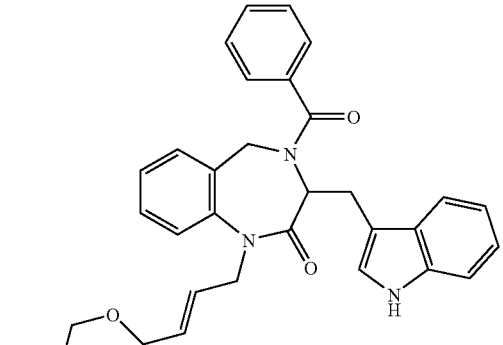
(see *Bioorg. Med. Chem. Lett.*, 6: 267-272 (1996)).
6) A compound of the following formula:
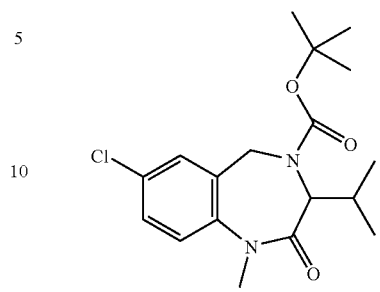
(see *Bioorg. Med. Chem.*, 7: 2427-2436 (1999)).
7) A compound of the following formula:
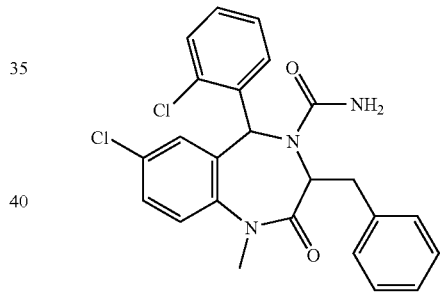
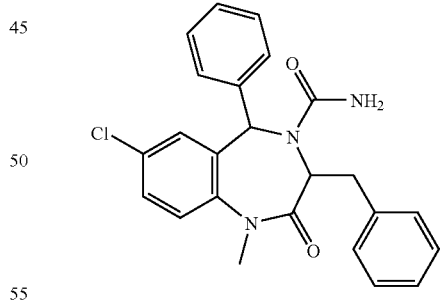
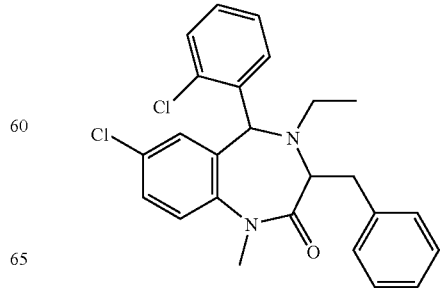

-continued

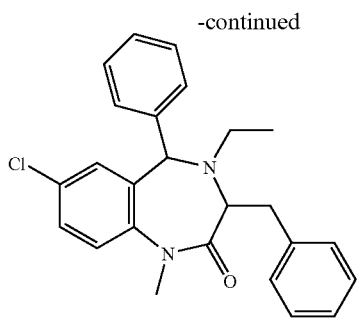

(see *Croatica Chem. Acta,* 62: 245-265 (1989)).
8) A compound of the following formula:

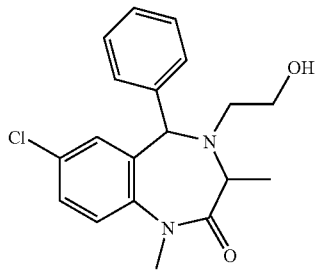

(see *Chem. Pharm. Bull.,* 21: 742-751 (1973)).
9) A compound having a tachykinin antagonistic action and useful for inflammation, allergic disease and the like, which is represented by the formula

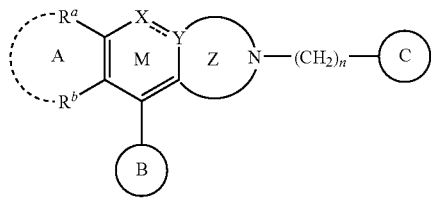

wherein ring M is a heterocycle having —N=C<, —CO—N< or —CS—N< as a partial structure: —X=Y<; $R^a$ and $R^b$ in combination form ring A, or are the same or different and each is independently a hydrogen atom or a substituent for ring M; ring A and ring B are each independently an optionally substituted homocycle or heterocycle, and at least one of them is an optionally substituted heterocycle; ring C is an optionally substituted homocycle or heterocycle; ring Z is an optionally substituted ring; and n is an integer of 1 to 6, or a salt thereof (see EP-733632A, WO99/47132).

DISCLOSURE OF THE INVENTION

The present invention aims at provision of a TGR5 receptor agonist useful for the treatment of various diseases.

Other objects of the present invention are to provide a screening method of a TGR5 agonist or antagonist, which is more efficient than conventional methods, and to provide a compound effective for the prophylaxis or treatment of various diseases, in which TGR5 is involved, using such method.

The present inventors have conducted intensive studies in an attempt to obtain a compound useful as a TGR5 receptor agonist and first found that a fused ring compound represented by the formula

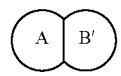  (I)

wherein ring A is an optionally substituted aromatic ring; and ring B' is a 5- to 9-membered ring having one or more substituents, or a salt thereof [hereinafter sometimes to be abbreviated as compound (I)] has a superior TGR5 receptor agonistic action, which resulted in the completion of the present invention.

Moreover, the present inventors have found that the use of the above-mentioned fused ring compound instead of a physiological (natural) ligand permits simple and efficient screening for a ligand, agonist or antagonist for TGR5, which resulted in the completion of the present invention.

Accordingly, the present invention relates to
(1) a TGR5 receptor agonist comprising compound (I) or a prodrug thereof;
(2) the agonist of the aforementioned (1), wherein the compound (I) has two or more substituents having a cyclic group;
(3) the agonist of the aforementioned (1), wherein compound (I) is a compound represented by the formula

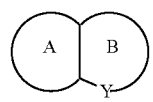  (I')

wherein ring A is an optionally substituted aromatic ring; ring B is a 6- to 8-membered ring having three or more substituents; Y is —C($R^1$)=, —CH($R^1$)—, —N($R^1$)— or —N=; and $R^1$ is a hydrogen atom or a substituent;
(4) the agonist of the aforementioned (1), wherein ring B' is a 5- to 8-membered ring having one or more substituents;
(5) the agonist of the aforementioned (1), wherein compound (I) is a compound represented by the formula

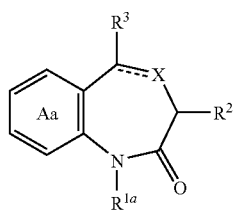  (II)

wherein ring Aa is an optionally substituted benzene ring; X is =N—, —$NR^6$— (wherein $R^6$ is a hydrogen atom or a substituent), —O— or —S(O)n- (wherein n is 0, 1 or 2); ... is void or a single bond; $R^{1a}$ and $R^3$ are each independently a hydrogen atom, an optionally substituted hydrocarbon group or an optionally substituted heterocyclic group; and $R^2$ is an optionally substituted hydrocarbon group or an optionally substituted heterocyclic group;

(6) the agonist of the aforementioned (5), wherein compound (I) is a compound represented by the formula

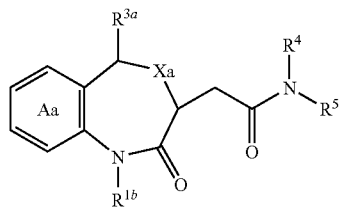

(III)

wherein ring Aa is an optionally substituted benzene ring, Xa is —O—, —S(O)n- (wherein n is 0, 1 or 2) or —NR$^6$— (wherein R$^6$ is a hydrogen atom or a substituent); R$^{1b}$ and R$^{3a}$ are each independently a hydrogen atom, an optionally substituted C$_{1-6}$ alkyl group, an optionally substituted C$_{2-6}$ alkenyl group, an optionally substituted phenyl group, an optionally substituted aralkyl group or an optionally substituted heterocyclic group; R$^4$ is a hydrogen atom or an optionally substituted C$_{1-6}$ alkyl group; and R$^5$ is a hydrogen atom, an optionally substituted hydrocarbon group, an optionally substituted heterocyclic group, an optionally substituted amino group, an optionally substituted hydroxy group or an optionally substituted sulfonyl group, or R$^4$ and R$^5$ are optionally bonded to each other to form, together with the adjacent nitrogen atom, an optionally substituted nitrogen-containing heterocycle;

(7) the agonist of the aforementioned (6), wherein R$^{3a}$ is an optionally substituted phenyl group;

(8) the agonist of the aforementioned (7), wherein R$^{3a}$ is a phenyl group having substituent(s) at the meta position;

(9) the agonist of the aforementioned (8), wherein the substituent is an acylaminomethyl group;

(10) the agonist of the aforementioned (6), wherein Xa is —O— or —NR$^6$— (wherein R$^6$ is a hydrogen atom or a substituent);

(11) the agonist of the aforementioned (6), wherein R$^{1b}$ is an optionally substituted C$_{1-6}$ alkyl group;

(12) the agonist of the aforementioned (6), wherein R$^5$ is an optionally substituted benzyl group;

(13) the agonist of the aforementioned (6), wherein ring Aa is a benzene ring optionally substituted by a halogen atom, Xa is —O— or —S—, R$^{1b}$ is an optionally substituted C$_{1-6}$ alkyl group or an optionally substituted aralkyl group, R$^{3a}$ is a phenyl group optionally substituted by substituent(s) selected from 1) a C$_{1-6}$ alkyl group optionally substituted by an optionally substituted amino group, an optionally substituted hydroxy group or an optionally substituted heterocyclic group, 2) an optionally substituted amino group, 3) an optionally substituted heterocyclic group and 4) an acyl group, R$^4$ is a hydrogen atom, and R$^5$ is an optionally substituted C$_{1-6}$ alkyl group, an optionally substituted aralkyl group, an optionally substituted phenyl group, an optionally substituted cycloalkyl group or an optionally substituted heterocyclic group;

(14) the agonist of the aforementioned (1), which is a regulator of physiological function in which TGR5 is involved, or an agent for the prophylaxis or treatment of pathology or disease in which TGR5 is involved;

(15) the agonist of the aforementioned (1), which is a cytokine production suppressor;

(16) the agonist of the aforementioned (1), which is a GLP-1 secretion promoter or an insulin secretagogue;

(17) the agonist of the aforementioned (1), which is an anorectic agent, a pancreatic regenerator, a pancreatic β cell differentiation promoter, a pancreatic β cell growth promoter or an insulin sensitizer;

(18) the agonist of the aforementioned (1), which is an agent for the prophylaxis or treatment of cardiac failure, cardiac infarction, acute kidney failure, angina pectoris, arrhythmia, bronchial asthma, chronic obstructive pulmonary disease, arteriosclerosis, rheumatoid arthritis, diabetes, obesity, insulin hyposecretion, pancreatic fatigue, gastric ulcer, ulcerative colitis, allergy, osteoarthritis, erythematosus, excessive immune reaction after transplantation or infectious disease, or an immunosuppressant;

(19) a method of activating a TGR5 receptor, which comprises administering an effective amount of compound (I) or a prodrug thereof to a mammal;

(20) use of compound (I) or a prodrug thereof for the production of a TGR5 receptor agonist;

(21) a screening method of a ligand, an agonist or an antagonist for TGR5 receptor, which comprises use of a TGR5 receptor protein or a partial peptide thereof or a salt thereof, and compound (I) or a prodrug thereof;

(22) a screening kit for a ligand, an agonist or an antagonist for TGR5 receptor, which comprises a TGR5 receptor protein or a partial peptide thereof or a salt thereof, and compound (I) or a prodrug thereof;

(23) a compound represented by the formula

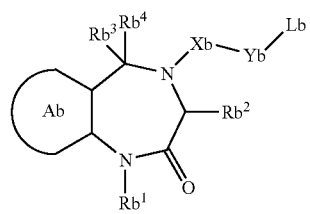

(IB)

wherein ring Ab is an optionally substituted aromatic ring; Xb is a divalent hydrocarbon group, —CO— or —SO$_2$—; Yb is a bond, a divalent hydrocarbon group, —O—, —NRb$^5$— (wherein Rb$^5$ is a hydrogen atom, an optionally substituted hydrocarbon group or an optionally substituted heterocyclic group) or —S(O)$_{nb}$— (wherein nb is 0, 1 or 2); Lb is an optionally substituted cyclic group; Rb$^1$, Rb$^3$ and Rb$^4$ are each independently a hydrogen atom, an optionally substituted hydrocarbon group or an optionally substituted heterocyclic group, or Rb$^3$ and Rb$^4$ in combination form an oxo group; and Rb$^2$ is an optionally substituted hydrocarbon group or an optionally substituted heterocyclic group, provided that Rb$^2$ is not a 3-indolylmethyl group or a 1-methyl-3-indolylmethyl group, or a salt thereof [hereinafter sometimes to be abbreviated as compound (IB)];

(24) the compound of the aforementioned (23), wherein Rb$^2$ is

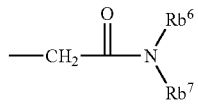

wherein Rb⁶ is a hydrogen atom or an optionally substituted $C_{1-6}$ alkyl group; and Rb⁷ is a hydrogen atom, an optionally substituted hydrocarbon group, an optionally substituted heterocyclic group, an optionally substituted amino group, an optionally substituted hydroxy group or an optionally substituted sulfonyl group, or Rb⁶ and Rb⁷ are bonded to each other to form, together with the adjacent nitrogen atom, an optionally substituted nitrogen-containing heterocycle;

(25) the compound of the aforementioned (23), wherein the aromatic ring for ring Ab is a benzene ring;
(26) the compound of the aforementioned (23), wherein Rb³ and Rb⁴ are each a hydrogen atom;
(27) the compound of the aforementioned (23), wherein Xb is a $C_{1-6}$ alkylene group or —CO—;
(28) the compound of the aforementioned (23), wherein Yb is a bond;
(29) the compound of the aforementioned (23), wherein Rb¹ is an optionally substituted $C_{1-6}$ alkyl group;
(30) the compound of the aforementioned (23), wherein the cyclic group for Lb is a heterocyclic group;
(31) the compound of the aforementioned (30), wherein the heterocyclic group is a pyridyl group;
(32) the compound of the aforementioned (31), wherein the pyridyl group is a 4-pyridyl group;
(33) the compound of the aforementioned (24), wherein Rb⁷ is an optionally substituted benzyl group;
(34) a prodrug of the compound of the aforementioned (23);
(35) a pharmaceutical agent comprising the compound of the aforementioned (23) or a prodrug thereof;
(36) the agonist of the aforementioned (1), wherein compound (I) is a compound represented by the formula

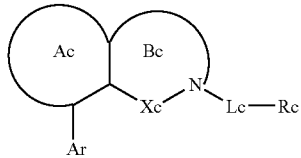

(IC)

wherein ring Ac is an optionally substituted aromatic ring; ring Bc is a nitrogen-containing 6- to 9-membered ring optionally further having substituent(s) besides -Lc-Rc; Xc is an optionally substituted methylene group; Ar is an optionally substituted aromatic group; Rc is an optionally substituted cyclic group; and Lc is an optionally substituted $C_{1-3}$ alkylene group, —CONH—, —SO₂NH— or —SO₂—;
(37) a compound represented by the formula

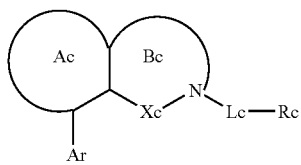

(IC)

wherein ring Ac is an optionally substituted aromatic ring; ring Bc is a nitrogen-containing 6- to 9-membered ring optionally further having substituent(s) besides -Lc-Rc; Xc is an optionally substituted methylene group; Ar is an optionally substituted aromatic group; Rc is an optionally substituted cyclic group; and Lc is an optionally substituted $C_{1-3}$ alkylene group, —CONH—, —SO₂NH— or —SO₂—, provided that Xc is not a methylene group substituted by an oxo group, or a salt thereof [hereinafter sometimes to be abbreviated as compound (IC)];
(38) the compound of the aforementioned (37), wherein ring Bc is a nitrogen-containing 6- to 9-membered ring optionally further having substituent(s) besides -Lc-Rc, and Ar is an optionally substituted $C_{6-14}$ aryl group;
(39) the compound of the aforementioned (37), wherein the aromatic ring for ring Ac is a pyridine ring;
(40) the compound of the aforementioned (37), which is represented by the formula

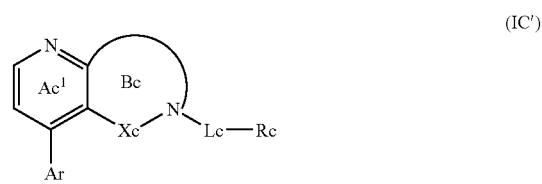

(IC')

wherein ring Ac¹ is an optionally substituted pyridine ring and other symbols are as defined in the aforementioned (37);
(41) the compound of the aforementioned (37), wherein ring Bc is

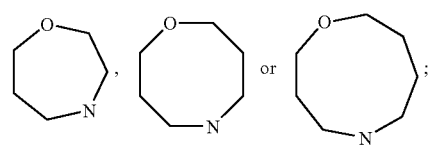

(42) the compound of the aforementioned (37), wherein Xc is a methylene group;
(43) the compound of the aforementioned (37), wherein the cyclic group for Rc is a phenyl group;
(44) the compound of the aforementioned (37), wherein Rc is a 3,5-bis(trifluoromethyl)phenyl group;
(45) the compound of the aforementioned (37), wherein Lc is a $C_{1-3}$ alkylene group optionally substituted by an oxo group or —SO₂—;
(46) the compound of the aforementioned (37), wherein Ar is an optionally substituted phenyl group;
(47) a prodrug of the compound of the aforementioned (37);
(48) a pharmaceutical agent comprising the compound of the aforementioned (37) or a prodrug thereof;
(49) a compound represented by the formula

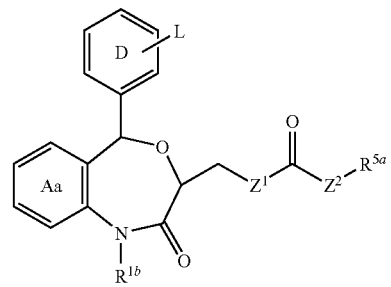

(IA)

wherein ring Aa and ring D are each independently an optionally substituted benzene ring; $R^{1b}$ is a hydrogen atom, an optionally substituted $C_{1-6}$ alkyl group, an optionally substituted $C_{2-6}$ alkenyl group, an optionally substituted phenyl group, an optionally substituted aralkyl group or an optionally substituted heterocyclic group; L is —$CH_2NHCOR^7$, —$OCH_2CONR^8R^9$ or —$CH_2$-Het (wherein $R^7$ is a hydrogen atom, a $C_{1-3}$ alkyl group or a $C_{1-3}$ alkoxy group; $R^8$ is a hydrogen atom or an optionally substituted $C_{1-6}$ alkyl group; $R^9$ is a hydrogen atom, an optionally substituted hydrocarbon group or an optionally substituted heterocyclic group; and Het is a nitrogen-containing aromatic heterocyclic group); at least one of $Z^1$ and $Z^2$ is —$NR^{4a}$— (wherein $R^{4a}$ is a hydrogen atom or an optionally substituted $C_{1-6}$ alkyl group) and the other is a bond or —$NR^{4a}$— (wherein $R^{4a}$ is as defined above); and $R^{5a}$ is a hydrogen atom, an optionally substituted hydrocarbon group or an optionally substituted heterocyclic group, or when $Z^2$ is —$NR^{4a}$— (wherein $R^{4a}$ is as defined above), $R^{5a}$ and $R^{4a}$ are optionally bonded to each other to form, together with the adjacent nitrogen atom, an optionally substituted nitrogen-containing heterocycle, or a salt thereof (provided that 3,5-trans-N-(2-fluorobenzyl)-5-(3-acetylaminomethylphenyl)-7-chloro-1-neopentyl-2-oxo-1,2,3,5-tetrahydro-4,1-benzoxazepine-3-acetamide; 3,5-trans-N-(2-fluorobenzyl)-7-chloro-5-(3-methoxycarbonylaminomethylphenyl)-1-neopentyl-2-oxo-1,2,3,5-tetrahydro-4,1-benzoxazepine-3-acetamide; and 3,5-trans-N-(2-fluorobenzyl)-5-(3-acetylaminomethylphenyl)-1-(4-biphenylmethyl)-7-chloro-2-oxo-1,2,3,5-tetrahydro-4,1-benzoxazepine-3-acetamide are excluded) [hereinafter sometimes to be abbreviated as compound (IA)];

(50) the compound of the aforementioned (49), wherein ring D is substituted by L at the meta-position;

(51) the compound of the aforementioned (49), wherein L is —$CH_2NHCOR^7$ (wherein $R^7$ is a hydrogen atom, a $C_{1-3}$ alkyl group or a $C_{1-3}$ alkoxy group);

(52) the compound of the aforementioned (51), wherein $R^7$ is a methyl group or a methoxy group;

(53) the compound of the aforementioned (49), wherein one of $Z^1$ and $Z^2$ is —NH— and the other is a bond;

(54) the compound of the aforementioned (49), wherein $R^{1b}$ is an optionally substituted $C_{1-6}$ alkyl group;

(55) the compound of the aforementioned (49), wherein $R^{5a}$ is an optionally substituted $C_{1-6}$ alkyl group, an optionally substituted $C_{7-14}$ aralkyl group, an optionally substituted $C_{3-10}$ cycloalkyl-$C_{1-6}$ alkyl group, an optionally substituted phenyl group, an optionally substituted $C_{3-10}$ cycloalkyl group or an optionally substituted heterocyclic group;

(56) the compound of the aforementioned (49), wherein $R^{5a}$ is a $C_{1-6}$ alkyl group substituted by an optionally substituted heterocyclic group, an optionally substituted $C_{7-14}$ aralkyl group or an optionally substituted $C_{3-10}$ cycloalkyl-$C_{1-6}$ alkyl group;

(57) a prodrug of the compound of the aforementioned (49);

(58) a pharmaceutical agent comprising the compound of the aforementioned (49) or a prodrug thereof; and the like.

Each substituent is defined in detail in the following.

As the aromatic ring for ring A, for example, an aromatic hydrocarbon and an aromatic heterocycle can be mentioned.

As the "aromatic hydrocarbon", for example, a $C_{6-14}$ aromatic hydrocarbon (e.g., benzene, naphthalene, anthracene, phenanthrene) can be mentioned. Among them, benzene is preferable.

As the "aromatic heterocycle", for example, a 5- or 6-membered monocyclic aromatic heterocycle having, as ring-constituting atom(s) besides a carbon atom, 1 to 4 hetero atoms selected from a nitrogen atom, an oxygen atom and a sulfur atom, a fused ring of the monocyclic aromatic heterocycle and a benzene ring, and the like can be mentioned. As specific examples of the "aromatic heterocycle", furan, thiophene, pyrrole, oxazole, isoxazole, thiazole, isothiazole, imidazole, pyrazole, 1,2,3-oxadiazole, 1,2,3-thiadiazole, 1,2,3-triazole, pyridine, pyridazine, pyrimidine, pyrazine, 1,2,4-triazine, benzofuran, isobenzofuran, benzo[b]thiophene, indole, isoindole, 1H-indazole, benzimidazole, benzoxazole, 1,2-benzisoxazole, benzothiazole, 1,2-benzisothiazole, 1H-benzotriazole, quinoline, isoquinoline, cinnoline, quinazoline, quinoxaline, phthalazine, naphthyridine and the like can be mentioned.

The aromatic ring for ring A is preferably a monocyclic aromatic ring, more preferably a benzene ring or a pyridine ring, particularly preferably a benzene ring.

The aromatic ring for ring A optionally has 1 to 4 substituents at substitutable positions. As such substituents, for example, a halogen atom (e.g., fluorine, chlorine, bromine, iodine), an optionally halogenated $C_{1-6}$ alkyl group, an amino-$C_{1-6}$ alkyl group (e.g., aminomethyl), a $C_{1-6}$ alkoxy-carbonylamino-$C_{1-6}$ alkyl group (e.g., t-butoxycarbonylaminomethyl), a $C_{2-6}$ alkenyl group (e.g., vinyl, propenyl), a $C_{2-6}$ alkynyl group (e.g., ethynyl, propargyl), a $C_{3-8}$ cycloalkyl group (e.g., cyclopropyl, cyclobutyl, cyclopentyl, cyclohexyl), a heterocyclic group (e.g., monocyclic heterocyclic group such as furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyrazinyl, pyridazinyl, pyrimidinyl, triazinyl, oxiranyl, azetidinyl, oxetanyl, thietanyl, pyrrolidinyl, tetrahydrofuranyl, thiolanyl, 1,3-dioxolanyl, 1,3-dioxanyl, 1,4-dioxanyl, 1,3-dithianyl, 1,4-dithianyl, piperidinyl, tetrahydropyranyl, morpholinyl, thiomorpholinyl, piperazinyl and the like; bi- or tricyclic fused heterocycle group such as benzofuryl, isobenzofuryl, benzo[b]thienyl, indolyl, isoindolyl, 1H-indazolyl, benzimidazolyl, benzoxazolyl, 1,2-benzisoxazolyl, benzothiazolyl, 1,2-benzisothiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acridinyl, phenoxazinyl, phenothiazinyl, phenazinyl, phenoxathiinyl, thianthrenyl, phenathridinyl, phenathrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-a]pyridazinyl, imidazo[1,2-a]pyrimidinyl, 1,2,4-triazolo[4,3-a]pyridyl, 1,2,4-triazolo[4,3-b]pyridazinyl, isochromanyl, chromanyl, indolinyl, isoindolinyl and the like or a reduced form thereof), a $C_{7-14}$ aralkyl group (e.g., benzyl, phenethyl, phenylpropyl), an optionally halogenated $C_{1-6}$ alkoxy group, a $C_{6-14}$ aryloxy group (e.g., phenoxy), a heterocyclyloxy group (e.g., pyridyloxy), a $C_{7-14}$ aralkyloxy group (e.g., benzyloxy, phenethyloxy, phenylptopyloxy), a formyloxy group, a $C_{1-6}$ alkyl-carbonyloxy group (e.g., acetyloxy), an optionally halogenated $C_{1-6}$ alkylthio group, a $C_{1-6}$ alkylsulfinyl group (e.g., methylsulfinyl), a hydroxy group, a mercapto group, a cyano group, a nitro group, a carboxyl group, a formyl group, an optionally halogenated $C_{1-6}$ alkyl-carbonyl group (e.g., acetyl, propionyl, trifluoroacetyl), a $C_{6-14}$ aryl-carbonyl group (e.g., benzoyl), a heterocyclyl-carbonyl group (e.g., nicotinoyl, isonicotinoyl, pyrrolidinocarbonyl, piperidinocarbonyl, morpholinocarbonyl, piperazinocarbonyl), a $C_{1-6}$ alkoxy-carbonyl group (e.g., methoxycarbonyl, ethoxycarbonyl, propoxycarbonyl), a $C_{6-14}$ aryloxy-carbonyl group (e.g., phenoxycarbonyl), an amino group, a mono- or di-$C_{1-6}$ alkylamino group (e.g., methylamino, ethylamino, dimethylamino, diethylamino), a formylamino group, an optionally halogenated $C_{1-6}$ alkyl-carbonylamino group (e.g., acetylamino, propionylamino, butyrylamino, trifluoroacetylamino), a $C_{1-6}$ alkoxy-carbonylamino group (e.g., methoxycarbonylamino, ethoxycarbonylamino, propoxycarbonylamino, t-butoxycarbonylamino), an ureido group, a mono-, di- or tri-$C_{1-6}$ alkyl-ureido group (e.g., 1-methylureido, 3-methylureido, 3,3-dimethylureido, 1,3-dimethylureido, 1,3,3-trimethylureido), an optionally halogenated $C_{1-6}$ alkyl-sulfonylamino group (e.g., methylsulfonylamino, trifluoromethanesulfonylamino), a carbamoyl group, a mono- or di-$C_{1-6}$ alkyl-carbamoyl group (e.g., N-methylcarbamoyl, N-ethylcarbamoyl, N,N-dimethylcarbamoyl, N,N-diethylcarbamoyl), a sulfo group, an optionally halogenated $C_{1-6}$ alkylsulfonyl group (e.g., methylsulfonyl, ethylsulfonyl, propylsulfonyl, sec-propylsulfonyl, butylsulfonyl, t-butylsulfonyl, trifluoromethanesulfonyl), a $C_{6-14}$ arylsulfonyl group (e.g., phenylsulfonyl, naphthylsulfonyl), a heterocyclyl-sulfonyl group (e.g., pyridylsulfonyl, thienylsulfonyl, pyrrolidinosulfonyl, piperidinosulfonyl, morpholinosulfonyl, piperazinosulfonyl), a sulfamoyl group, a mono- or di-$C_{1-6}$ alkyl-sulfamoyl group (e.g., N-methylsulfamoyl, N-ethylsulfamoyl, N,N-dimethylsulfamoyl, N,N-diethylsulfamoyl), a $C_{6-14}$ aryl-carbonyl-$C_{1-6}$ alkoxy group (e.g., benzoylmethyloxy), a hydroxy-$C_{1-6}$ alkoxy group (e.g., hydroxyethyloxy), a $C_{1-6}$ alkoxy-carbonyl-$C_{1-6}$ alkoxy group (e.g., methoxycarbonylmethyloxy), a $C_{3-14}$ cycloalkyl-$C_{1-6}$ alkoxy group (e.g., cyclohexylmethyloxy), a heterocyclyl-$C_{1-6}$ alkoxy group (e.g., imidazol-1-ylpropyloxy), a $C_{7-14}$ aralkyloxy-carbonyl-$C_{1-6}$ alkoxy group (e.g., benzyloxycarbonylmethyloxy), a hydroxyphenyl-$C_{1-6}$ alkoxy group (e.g., [3-(4-hydroxyphenyl)propyl]oxy), a $C_{7-14}$ aralkyloxy-carbonyl group (e.g., benzyloxycarbonyl), a mono- or di-$C_{1-6}$ alkylamino-$C_{1-6}$ alkoxy (e.g., methylaminoethoxy, ethylaminoethoxy, dimethylaminoethoxy), a mono- or di-$C_{1-6}$ alkylaminocarbonyloxy (e.g., methylaminocarbonyloxy, ethylaminocarbonyloxy, dimethylaminocarbonyloxy), an optionally substituted $C_{6-14}$ aryl group and the like can be mentioned.

As the aforementioned "optionally halogenated $C_{1-6}$ alkyl group", for example, a $C_{1-6}$ alkyl group (e.g., methyl, ethyl, propyl, isopropyl, butyl, isobutyl, sec-butyl, tert-butyl, pentyl, isopentyl, neopentyl, hexyl) optionally having 1 to 5, preferably 1 to 3, halogen atoms (e.g., fluorine, chlorine, bromine, iodine) can be mentioned. As specific examples, methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl, 6,6,6-trifluorohexyl and the like can be mentioned.

As the aforementioned "optionally halogenated $C_{1-6}$ alkoxy group", for example, a $C_{1-6}$ alkoxy group (e.g., methoxy, ethoxy, propoxy, butoxy, pentyloxy, hexyloxy) optionally having 1 to 5, preferably 1 to 3, halogen atoms (e.g., fluorine, chlorine, bromine, iodine), and the like can be mentioned. As specific examples, methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy, isopentyloxy, hexyloxy and the like can be mentioned.

As the aforementioned "optionally halogenated $C_{1-6}$ alkylthio group", for example, a $C_{1-6}$ alkylthio group (e.g., methylthio, ethylthio, propylthio, isopropylthio, butylthio, sec-butylthio, tert-butylthio, pentylthio, hexylthio) optionally having 1 to 5, preferably 1 to 3, halogen atoms (e.g., fluorine, chlorine, bromine, iodine), and the like can be mentioned. As specific examples, methylthio, difluoromethylthio, trifluoromethylthio, ethylthio, propylthio, isopropylthio, butylthio, 4,4,4-trifluorobutylthio, pentylthio, hexylthio and the like can be mentioned.

As the "$C_{6-14}$ aryl group" of the aforementioned "optionally substituted $C_{6-14}$ aryl group", for example, phenyl, naphthyl, anthryl, phenanthryl, acenaphthylenyl and the like can be mentioned. The "$C_{6-14}$ aryl group" optionally has 1 to 4 substituents at substitutable positions. As such substituents, for example, a halogen atom (e.g., fluorine, chlorine, bromine, iodine), a nitro group, a cyano group, a $C_{1-6}$ alkyl group, an amino group optionally mono- or di-substituted by a $C_{1-6}$ alkyl group (e.g., methylamino, dimethylamino, ethylamino), a hydroxy group, a $C_{1-6}$ alkoxy group (e.g., methoxy, ethoxy, propoxy, isopropoxy) and the like can be mentioned.

Ring A is preferably an optionally substituted benzene ring, more preferably a benzene ring optionally substituted by a halogen atom (preferably a chlorine atom).

As ring A, a pyridine ring optionally substituted by substituent(s) selected from an optionally halogenated $C_{1-6}$ alkyl group, an optionally substituted aromatic group and the like is also preferable. Here, as the "optionally substituted aromatic group", the aforementioned "optionally substituted $C_{6-14}$ aryl group" and "heterocyclic group (only the aromatic ones)" can be mentioned. The "optionally substituted aromatic group" is preferably an "optionally substituted $C_{6-14}$ aryl group", more preferably a phenyl group optionally substituted by 1 to 3 halogen atoms and the like.

As the "5- to 9-membered ring" for ring B', for example, a benzene ring, a $C_{5-9}$ non-aromatic cyclic hydrocarbon, a 5- to 9-membered aromatic heterocycle, a 5- to 9-membered non-aromatic heterocycle and the like can be mentioned.

Here, as the $C_{5-9}$ non-aromatic cyclic hydrocarbon, for example, a $C_{5-9}$ cycloalkane, a $C_{5-9}$ cycloalkene, a $C_{5-9}$ cycloalkadiene and the like can be mentioned.

As specific examples of the $C_{5-9}$ cycloalkane, cyclopentane, cyclohexane, cycloheptane, cyclooctane, cyclononane and the like can be mentioned.

As specific examples of the $C_{5-9}$ cycloalkene, cyclopentene, cyclohexene, cycloheptene, cyclooctene, cyclononene and the like can be mentioned.

As specific examples of the $C_{5-9}$ cycloalkadiene, cyclopenta-1,3-diene, cyclohexa-1,3-diene, cyclohexa-1,4-diene, cyclohepta-1,3-diene, cyclohepta-1,4-diene, cycloocta-1,3-diene, cycloocta-1,4-diene, cycloocta-1,5-diene and the like can be mentioned.

As the 5- to 9-membered aromatic heterocycle, for example, a 5- to 9-membered aromatic heterocycle having, as ring-constituting atom(s) besides a carbon atom, 1 to 4 hetero atoms selected from a nitrogen atom, an oxygen atom and a sulfur atom can be mentioned. As specific examples of the 5- to 9-membered aromatic heterocycle, furan, thiophene, pyrrole, oxazole, isoxazole, thiazole, isothiazole, imidazole, pyrazole, oxadiazole, thiadiazole, triazole, tetrazole, pyridine, pyrazine, pyrimidine, pyridazine, azepine, diazepine, oxazepine, thiazepine, azocine, diazocine, oxazocine, thiazocine, azonine, diazonine, oxazonine, thiazonine and the like can be mentioned.

As the 5- to 9-membered non-aromatic heterocycle, for example, a 5- to 9-membered non-aromatic heterocycle having, as ring-constituting atom(s) besides a carbon atom, 1 to 4 hetero atoms selected from a nitrogen atom, an oxygen atom and a sulfur atom can be mentioned. As specific examples of the 5- to 9-membered non-aromatic heterocycle, tetrahydrofuran, tetrahydrothiophene, pyrrolidine, imidazolidine, pyrazolidine, piperidine, dihydropyridine, dihydropyrazine, tetrahydropyrazine, 2,3-dehydromorpholine, 2,3-dehydrothiomorpholine, tetrahydropyrimidine, tetrahydropyridazine, dihydroazepine, tetrahydroazepine, dihydrodiazepine, tetrahydrodiazepine, dihydro[1,4]oxazepine, 2,3,4,7-tetrahydro[1,4]oxazepine, 4,5,6,7-tetrahydro[1,4]oxazepine, dihydro[1,4]thiazepine, 2,3,4,7-tetrahydro[1,4]thiazepine, 4,5,6,7-tetrahydro[1,4]thiazepine, tetrahydroazocine, hexahydroazocine, tetrahydrodiazocine, hexahydrodiazocine, tetrahydrooxazocine, tetrahydrothiazocine, tetrahydroazonine, hexahydroazonine, tetrahydrodiazonine, hexahydrodiazonine, tetrahydrooxazonine, hexahydrooxazonine, tetrahydrothiazonine, hexahydrothiazonine and the like can be mentioned.

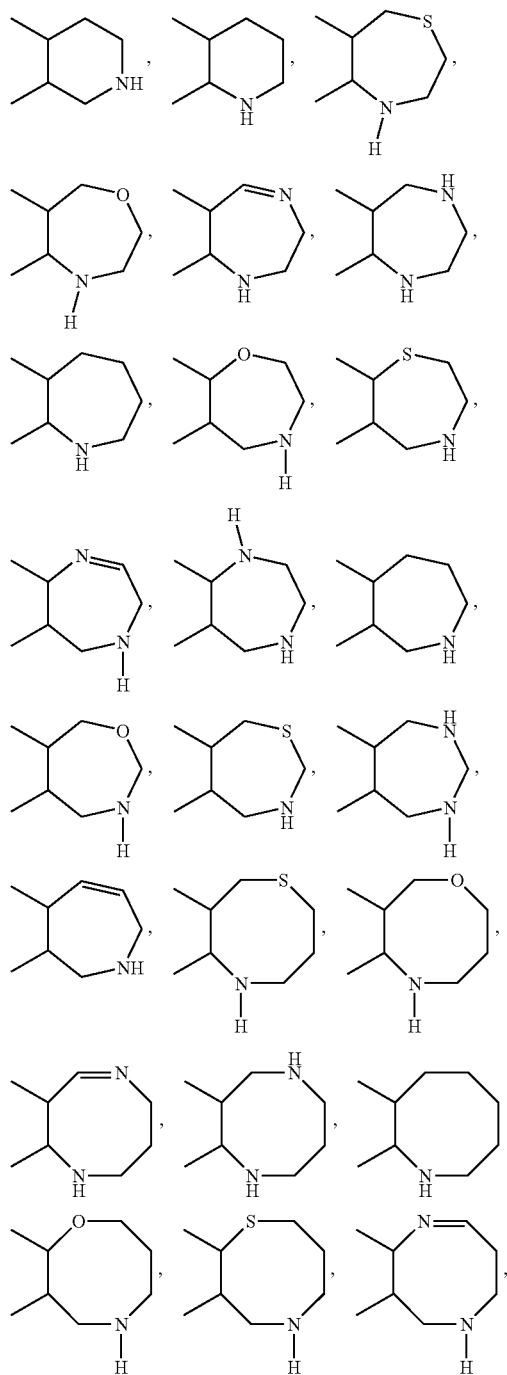

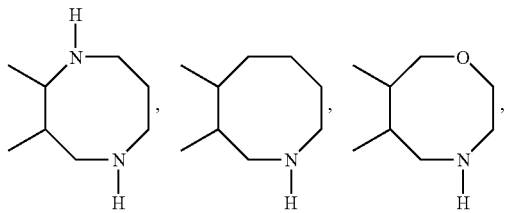

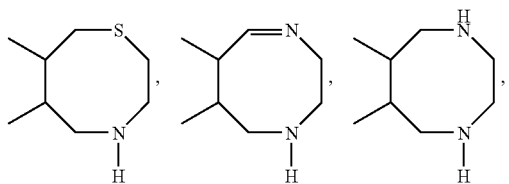

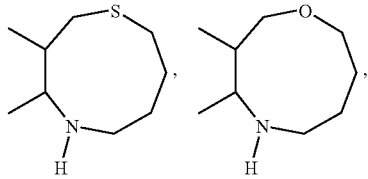

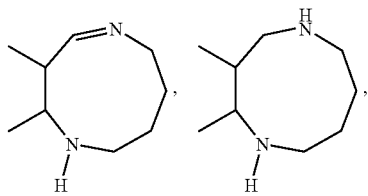

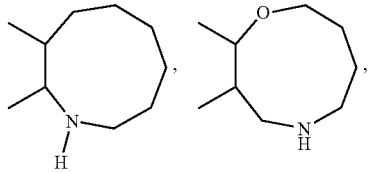

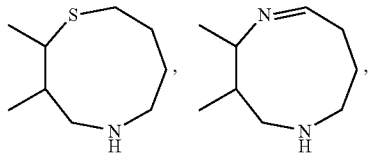

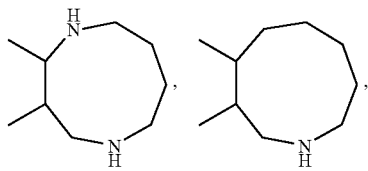

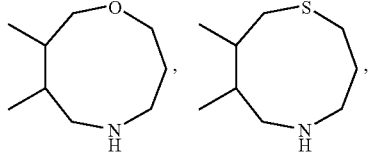

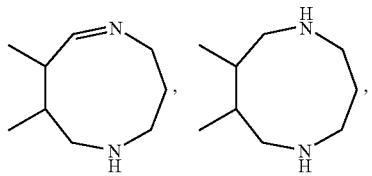

-continued

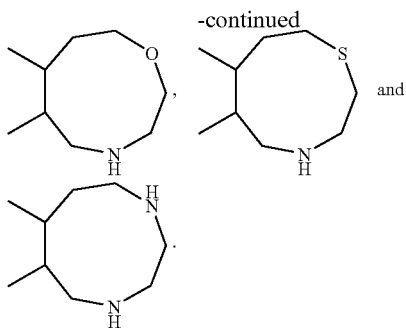

The "5- to 9-membered ring" for ring B' optionally has one or more (preferably 1 to 5) substituents at substitutable positions. As such substituents, for example, a nitro group, an oxo group, a thioxo group, a halogen atom (e.g., fluorine, chlorine, bromine, iodine), a hydroxy group, a mercapto group, a cyano group, an optionally halogenated $C_{1-6}$ alkoxy group, a $C_{6-14}$ aryloxy group (e.g., phenoxy), a $C_{7-14}$ aralkyloxy group (e.g., benzyloxy, phenethyloxy, phenylpropyloxy), a formyloxy group, a $C_{1-6}$ alkyl-carbonyloxy group (e.g., acetyloxy), an optionally halogenated $C_{1-6}$ alkylthio group, an optionally substituted heterocyclic group, an optionally substituted hydrocarbon group, a carboxyl group, a formyl group, a $C_{1-6}$ alkyl-carbonyl group (e.g., acetyl, propionyl), an optionally substituted $C_{6-14}$ aryl-carbonyl group (e.g., benzoyl), an optionally substituted heterocyclyl-carbonyl group (e.g., nicotinoyl, isonicotinoyl, pyrrolidinocarbonyl, piperidinocarbonyl, morpholinocarbonyl, piperazinocarbonyl), an optionally substituted $C_{3-8}$ cycloalkyl-carbonyl group (e.g., cyclopropylcarbonyl, cyclobutylcarbonyl, cyclopentylcarbonyl, cyclohexylcarbonyl), a $C_{7-14}$ aralkyl-carbonyl group (e.g., benzylcarbonyl), a $C_{1-6}$ alkoxy-carbonyl group (e.g., methoxycarbonyl, ethoxycarbonyl, propoxycarbonyl), a $C_{6-14}$ aryloxy-carbonyl group (e.g., phenoxycarbonyl), a $C_{7-14}$ aralkyloxy-carbonyl group (e.g., benzyloxycarbonyl), an amino group, a mono- or di-$C_{1-6}$ alkylamino group (e.g., methylamino, ethylamino, dimethylamino, diethylamino), a formylamino group, a $C_{1-6}$ alkyl-carbonylamino group (e.g., acetylamino, propionylamino, butyrylamino), a carbamoyl group, a mono- or di-$C_{1-6}$ alkyl-carbamoyl group (e.g., N-methylcarbamoyl, N-ethylcarbamoyl, N,N-dimethylcarbamoyl, N,N-diethylcarbamoyl), an optionally substituted $C_{6-14}$ arylcarbamoyl group (e.g., phenylcarbamoyl, naphthylcarbamoyl), an optionally substituted heterocyclyl-carbamoyl group (e.g., pyridylcarbamoyl, thienylcarbamoyl, pyrrolidinocarbamoyl, piperidinocarbamoyl, morpholinocarbamoyl, piperazinocarbamoyl), an optionally substituted $C_{3-8}$ cycloalkyl-carbamoyl group (e.g., cyclopropylcarbamoyl, cyclobutylcarbamoyl, cyclopentylcarbamoyl, cyclohexylcarbamoyl), a $C_{7-14}$ aralkyl-carbamoyl group (e.g., benzylcarbamoyl), a sulfo group, a $C_{1-6}$ alkylsulfonyl group (e.g., methylsulfonyl, ethylsulfonyl, propylsulfonyl, sec-propylsulfonyl, butylsulfonyl, t-butylsulfonyl), an optionally substituted $C_{6-14}$ arylsulfonyl group (e.g., phenylsulfonyl, naphthylsulfonyl), an optionally substituted heterocyclyl-sulfonyl group (e.g., pyridylsulfonyl, thienylsulfonyl, pyrrolidinosulfonyl, piperidinosulfonyl, morpholinosulfonyl, piperazinosulfonyl), an optionally substituted $C_{3-8}$ cycloalkylsulfonyl group (e.g., cyclopropylsulfonyl, cyclobutylsulfonyl, cyclopentylsulfonyl, cyclohexylsulfonyl)), a $C_{7-14}$ aralkylsulfonyl group (e.g., benzylsulfonyl), a sulfamoyl group, a mono- or di-$C_{1-6}$ alkyl-sulfamoyl group (e.g., N-methylsulfamoyl, N-ethylsulfamoyl, N,N-dimethylsulfamoyl, N,N-diethylsulfamoyl), an optionally substituted $C_{6-14}$ arylsulfamoyl group (e.g., phenylsulfamoyl, naphthylsulfamoyl), an optionally substituted heterocyclyl-sulfamoyl group (e.g., pyridylsulfamoyl, thienylsulfamoyl, pyrrolidinosulfamoyl, piperidinosulfamoyl, morpholinosulfamoyl, piperazinosulfamoyl), an optionally substituted $C_{3-8}$ cycloalkylsulfamoyl group (e.g., cyclopropylsulfamoyl, cyclobutylsulfamoyl, cyclopentylsulfamoyl, cyclohexylsulfamoyl), a $C_{7-14}$ aralkylsulfamoyl group (e.g., benzylsulfamoyl) and the like can be mentioned.

As the above-mentioned "optionally halogenated $C_{1-6}$ alkoxy group" and "optionally halogenated $C_{1-6}$ alkylthio group", those exemplified as the substituents for ring A can be used.

As the "heterocyclic group" of the above-mentioned "optionally substituted heterocyclic group", for example, a 5- or 6-membered monocyclic heterocyclic group having, as ring-constituting atom(s) besides a carbon atom, 1 to 4 hetero atoms selected from a nitrogen atom, an oxygen atom and a sulfur atom (e.g., furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl, oxiranyl, azetidinyl, oxetanyl, thietanyl, pyrrolidinyl, tetrahydrofuranyl, thiolanyl, piperidinyl, tetrahydropyranyl, morpholinyl, thiomorpholinyl, piperazinyl, dioxolanyl), a bi- or tricyclic fused heterocycle group (e.g., benzofuryl, isobenzofuryl, benzo[b]thienyl, indolyl, isoindolyl, 1H-indazolyl, benzimidazolyl, benzoxazolyl, 1,2-benzisoxazolyl, benzothiazolyl, 1,2-benzisothiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acridinyl, phenoxazinyl, phenothiazinyl, phenazinyl, phenoxathiinyl, thianthrenyl, phenathridinyl, phenathrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-a]pyridazinyl, imidazo[1,2-a]pyrimidinyl, 1,2,4-triazolo[4,3-a]pyridyl, 1,2,4-triazolo[4,3-b]pyridazinyl, isochromanyl, chromanyl, indolinyl, isoindolinyl, benzodioxolyl) and the like can be mentioned.

The "heterocyclic group" optionally has 1 to 5 substituents at substitutable positions, and as such substituents, those exemplified as the substituents for ring A can be used.

As the hydrocarbon group of the above-mentioned "optionally substituted hydrocarbon group", for example, an aliphatic hydrocarbon group, an alicyclic hydrocarbon group, an aryl group, an aralkyl group and a group obtained by combining these groups can be mentioned.

Here, the "aliphatic hydrocarbon group" is preferably a $C_{1-10}$ aliphatic hydrocarbon group (e.g., a $C_{1-10}$ alkyl group, a $C_{2-10}$ alkenyl group, a $C_{2-10}$ alkynyl group) and the like.

As the "$C_{1-10}$ alkyl group", for example, methyl, ethyl, propyl, isopropyl, butyl, isobutyl, sec-butyl, t-butyl, pentyl, isopentyl, neopentyl, 1-methylpropyl, hexyl, isohexyl, 1,1-dimethylbutyl, 2,2-dimethylbutyl, 3,3-dimethylbutyl, 3,3-dimethylpropyl, 2-ethylbutyl, heptyl and the like can be mentioned.

As the "$C_{2-10}$ alkenyl group", for example, vinyl, allyl, isopropenyl, 2-methylallyl, 1-propenyl, 2-methyl-1-propenyl, 2-methyl-2-propenyl, 1-butenyl, 2-butenyl, 3-butenyl, 2-ethyl-1-butenyl, 2-methyl-1-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl, 5-hexenyl and the like can be mentioned.

As the "$C_{2-10}$ alkynyl group", for example, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and the like can be mentioned.

The "alicyclic hydrocarbon group" is preferably a $C_{3-10}$ alicyclic hydrocarbon group (e.g., a $C_{3-10}$ cycloalkyl group, a $C_{3-10}$ cycloalkenyl group, a $C_{5-10}$ cycloalkadienyl group) and the like.

As the "$C_{3-10}$ cycloalkyl group", for example, cyclopropyl, cyclobutyl, cyclopentyl, cyclohexyl, cycloheptyl, cyclooctyl, cyclononyl and the like can be mentioned.

As the "$C_{3-10}$ cycloalkenyl group", for example, 1-cyclobuten-1-yl, 1-cyclopenten-1-yl, 2-cyclopenten-1-yl, 3-cyclopenten-1-yl, 2-cyclohexen-1-yl, 3-cyclohexen-1-yl and the like can be mentioned.

As the "$C_{5-10}$ cycloalkadienyl group", for example, 2,4-cyclopentadien-1-yl, 2,5-cyclohexadien-1-yl and the like can be mentioned.

As the "aryl group", for example, a $C_{6-14}$ aryl group (e.g., phenyl, naphthyl, anthryl, phenanthryl, acenaphthylenyl, indenyl) and the like can be mentioned. The aryl group may be partially saturated and as the partially saturated aryl group, for example, indanyl, dihydronaphthyl, tetrahydronaphthyl and the like can be mentioned.

As the "aralkyl group", for example, a $C_{7-14}$ aralkyl group (e.g., benzyl, 1-phenethyl, 2-phenethyl, 2-phenylpropyl, 3-phenylpropyl, 4-phenylbutyl, 2-naphthylmethyl, benzhydryl), a trityl group and the like can be mentioned.

As the hydrocarbon group, moreover, a $C_{1-6}$ alkyl-$C_{6-14}$ aryl group (e.g., methylphenyl, ethylphenyl), a $C_{1-6}$ alkyl-$C_{3-10}$ cycloalkyl group (e.g., methylcyclohexyl, ethylcyclohexyl), a $C_{1-6}$ alkyl-$C_{7-14}$ aralkyl group (e.g., methylbenzyl, ethylbenzyl), a $C_{1-6}$ alkylidene group (e.g., methylidene, ethylidene, propylidene), a $C_{3-10}$ cycloalkyl-$C_{1-6}$ alkyl group (e.g., cyclopropylmethyl, cyclohexylmethyl, cyclohexylethyl, cycloheptylmethyl) and the like can be also mentioned.

The above-mentioned "hydrocarbon group" optionally has 1 to 5, preferably 1 to 3, substituents at substitutable positions. As such substituents, for example, a halogen atom (e.g., fluorine, chlorine, bromine, iodine), a nitro group, a cyano group, an oxo group, an optionally substituted heterocyclic group, an optionally halogenated $C_{1-6}$ alkylthio group, an optionally substituted amino group, an optionally substituted hydroxy group, an acyl group, an optionally substituted carbamoyl group and the like can be mentioned.

Here, as the "optionally substituted heterocyclic group", those exemplified as the substituents for ring B' can be used. The "optionally substituted heterocyclic group" is preferably a nitrogen-containing aromatic heterocyclic group (e.g., pyrrolyl, oxazolyl, isoxazolyl, thiazolyl, isothiazolyl, imidazolyl, pyrazolyl, oxadiazolyl, furazanyl, thiadiazolyl, triazolyl, tetrazolyl, pyridyl, pyridazinyl, pyrimidinyl, pyrazinyl).

As the "optionally halogenated $C_{1-6}$ alkylthio group", those exemplified as the substituents for ring A can be mentioned.

As the substituents for the "optionally substituted amino group", for example, a $C_{1-6}$ alkyl group (e.g., methyl, ethyl, propyl, isopropyl), a $C_{6-14}$ aryl group (e.g., phenyl) and a $C_{7-14}$ aralkyl group (e.g., benzyl), each optionally substituted by 1 to 5 halogen atoms (e.g., fluorine, chlorine, bromine, iodine); an acyl group and the like can be mentioned. The number of the substituents is 1 or 2.

As the acyl group, a formyl group, an optionally halogenated $C_{1-6}$ alkyl-carbonyl group (e;g., acetyl, propionyl, butyryl, t-butylcarbonyl, trifluoroacetyl), a $C_{6-14}$ aryl-carbonyl group (e.g., benzoyl), a heterocyclyl-carbonyl group (e.g., nicotinoyl, isonicotinoyl, pyrrolidinocarbonyl, piperidinocarbonyl, morpholinocarbonyl, piperazinocarbonyl), a $C_{7-14}$ aralkyl-carbonyl group (e.g., benzylcarbonyl), a $C_{1-6}$ alkoxy-carbonyl group (e.g., methoxycarbonyl, ethoxycarbonyl, propoxycarbonyl, sec-propoxycarbonyl, butoxycarbonyl, t-butoxycarbonyl), a $C_{7-14}$ aralkyloxy-carbonyl group (e.g., benzyloxycarbonyl), a $C_{6-14}$ aryloxy-carbonyl group (e.g., phenoxycarbonyl), a $C_{1-6}$ alkylthio-carbonyl group (e.g., methylthiocarbonyl, ethylthiocarbonyl), an optionally halogenated $C_{1-6}$ alkylsulfonyl group (e.g., methylsulfonyl, ethylsulfonyl, propylsulfonyl, sec-propylsulfonyl, butylsulfonyl, t-butylsulfonyl, trifluoromethanesulfonyl), a $C_{6-10}$ arylsulfonyl group (e.g., phenylsulfonyl, toluenesulfonyl), a heterocyclyl-sulfonyl group (e.g., pyridylsulfonyl, thienylsulfonyl, pyrrolidinosulfonyl, piperidinosulfonyl, morpholinosulfonyl, piperazinosulfonyl), a sulfamoyl group, a mono- or di-$C_{1-6}$ alkyl-sulfamoyl group (e.g., N-methylsulfamoyl, N-ethylsulfamoyl, N,N-dimethylsulfamoyl, N,N-diethylsulfamoyl), a carbamoyl group, a mono- or di-$C_{1-6}$ alkyl-carbamoyl group (e.g., N-methylcarbamoyl, N-ethylcarbamoyl, N,N-dimethylcarbamoyl, N,N-diethylcarbamoyl), a mono- or di-(heterocyclyl(preferably imidazolyl)-$C_{1-6}$ alkyl)-carbamoyl group (e.g., imidazolylpropylcarbamoyl), a mono- or di-$C_{7-14}$ aralkyl-carbamoyl group (e.g., benzylcarbamoyl, phenethylcarbamoyl), a mono- or di-$C_{6-14}$ aryl-carbamoyl group (e.g., phenylcarbamoyl, naphthylcarbamoyl), a mono- or di-heterocyclyl-carbamoyl group (e.g., pyridylcarbamoyl, thiazolylcarbamoyl), a carbazoyl group and the like can be mentioned. These acyl groups optionally have, at substitutable positions, 1 to 3 substituents selected from a halogen atom (e.g., fluorine, chlorine, bromine, iodine), a nitro group, a cyano group, an optionally halogenated $C_{1-6}$ alkyl group, an amino group optionally mono- or di-substituted by a $C_{1-6}$ alkyl group (e.g., methylamino, dimethylamino, ethylamino), a hydroxy group, a $C_{1-6}$ alkoxy group (e.g., methoxy, ethoxy, propoxy, isopropoxy) and the like.

As the substituent for the above-mentioned "optionally substituted hydroxy group", for example, (i) an optionally substituted $C_{1-6}$ alkyl group, (ii) an optionally substituted $C_{6-10}$ aryl group, (iii) an optionally substituted $C_{7-14}$ aralkyl group, (iv) an acyl group and the like can be mentioned.

Here, as the "$C_{1-6}$ alkyl group" of the "optionally substituted $C_{1-6}$ alkyl group", for example, methyl, ethyl, propyl, isopropyl, butyl, pentyl and the like can be mentioned.

The "$C_{1-6}$ alkyl group" optionally has 1 to 3 substituents at substitutable positions. As such substituents, for example, a halogen atom (e.g., fluorine, chlorine, bromine, iodine), a hydroxy group, a $C_{1-6}$ alkoxy group (e.g., methoxy, ethoxy, propoxy, isopropoxy), a formyl group, a $C_{1-6}$ alkyl-carbonyl group (e.g., acetyl, propionyl, butyryl), a carboxyl group, a $C_{1-6}$ alkoxy-carbonyl group (e.g., methoxycarbonyl, ethoxycarbonyl, propoxycarbonyl, sec-propoxycarbonyl, butoxycarbonyl, t-butoxycarbonyl), an amino group, a mono- or di-$C_{1-6}$ alkylamino group (e.g., methylamino, ethylamino, dimethylamino, diethylamino), a 5- or 6-membered nitrogen-containing heterocyclic group (e.g., pyrrolidinyl, piperidinyl, morpholinyl, thiomorpholinyl, piperazinyl), a carbamoyl group, a mono- or di-$C_{1-6}$ alkyl-carbamoyl group (e.g., N-methylcarbamoyl, N-ethylcarbamoyl, N,N-dimethylcarbamoyl, N,N-diethylcarbamoyl), a mono- or di-(heterocyclyl(preferably imidazolyl)-$C_{1-6}$ alkyl)-carbamoyl group (e.g., imidazolylpropylcarbamoyl), a mono- or di-$C_{7-14}$ aralkyl-carbamoyl group (e.g., benzylcarbamoyl, phenethylcarbamoyl), a $C_{6-14}$ aryloxy group (e.g., phenoxy), a mono- or di-$C_{1-6}$ alkyl-carbamoyloxy group (e.g., N-methylcarbamoyloxy, N-ethylcarbamoyloxy, N,N-dimethylcarbamoyloxy, N,N-ethylcarbamoyloxy), a formylamino group, a $C_{1-6}$ alkyl-carbonylamino group (e.g., acetylamino, propionylamino, butyrylamino), a formyloxy group, a $C_{1-6}$ alkyl-carbonyloxy group (e.g., acetoxy), an optionally halogenated $C_{1-6}$ alkylsulfonyl group (e.g., methylsulfonyl, ethylsulfonyl, propylsulfonyl, isopropylsulfonyl, butylsulfonyl, t-butylsulfonyl, trifluoromethanesulfonyl) and the like can be mentioned.

As the "$C_{6-10}$ aryl group" of the "optionally substituted $C_{6-10}$ aryl group", for example, phenyl, naphthyl and the like can be mentioned.

As the "$C_{7-14}$ aralkyl group" of the "optionally substituted $C_{7-14}$ aralkyl group", for example, benzyl, phenethyl and the like can be mentioned.

The above-mentioned "$C_{6-10}$ aryl group" and "$C_{7-14}$ aralkyl group" each optionally have 1 to 5 substituents at substitutable positions. As such substituents, for example, the substituents exemplified for the aforementioned "optionally substituted $C_{1-6}$ alkyl group", a $C_{1-6}$ alkyl group optionally substituted by 1 to 5 halogen atoms (e.g., methyl, ethyl, propyl, isopropyl, trifluoromethyl) and the like can be mentioned.

As the "acyl group", those exemplified as the substituents for the aforementioned "optionally substituted amino group" can be used.

As the "acyl group" exemplified as the substituents for the above-mentioned "hydrocarbon group", a formyl group, an optionally halogenated $C_{1-6}$ alkyl-carbonyl group (e.g., acetyl, propionyl, butyryl, t-butylcarbonyl, trifluoroacetyl), a $C_{6-14}$ aryl-carbonyl group (e.g., benzoyl), a heterocyclyl-carbonyl group (e.g., nicotinoyl, isonicotinoyl, pyrrolidinocarbonyl, piperidinocarbonyl, morpholinocarbonyl, piperazinocarbonyl), a $C_{1-6}$ alkoxy-carbonyl group (e.g., methoxycarbonyl, ethoxycarbonyl, propoxycarbonyl, sec-propoxycarbonyl, butoxycarbonyl, t-butoxycarbonyl), a $C_{7-14}$ aralkyloxy-carbonyl group (e.g., benzyloxycarbonyl), a $C_{6-14}$ aryloxy-carbonyl group (e.g., phenoxycarbonyl), a $C_{1-6}$ alkylthio-carbonyl group (e.g., methylthiocarbonyl, ethylthiocarbonyl), an optionally halogenated $C_{1-6}$ alkylsulfonyl group (e.g., methylsulfonyl, ethylsulfonyl, propylsulfonyl, sec-propylsulfonyl, butylsulfonyl, t-butylsulfonyl, trifluoromethanesulfonyl), a $C_{6-10}$ arylsulfonyl group (e.g., phenylsulfonyl, toluenesulfonyl), a heterocyclyl-sulfonyl group (e.g., pyridylsulfonyl, thienylsulfonyl, pyrrolidinosulfonyl, piperidinosulfonyl, morpholinosulfonyl, piperazinosulfonyl) and the like can be mentioned.

As the "optionally substituted carbamoyl group" exemplified as the substituents for the above-mentioned "hydrocarbon group", —CON($R^4$)($R^5$) [wherein $R^4$ is a hydrogen atom or an optionally substituted $C_{1-6}$ alkyl group, and $R^5$ is a hydrogen atom, an optionally substituted hydrocarbon group, an optionally substituted heterocyclic group, an optionally substituted amino group, an optionally substituted hydroxy group or an optionally substituted sulfonyl group, or $R^4$ and $R^5$ are optionally bonded to each other to form, together with the adjacent nitrogen atom, an optionally substituted nitrogen-containing heterocycle] and the like can be mentioned.

Here, as the "optionally substituted $C_{1-6}$ alkyl group" for $R^4$, the "optionally substituted $C_{1-6}$ alkyl group" exemplified as the substituents for the aforementioned "optionally substituted hydroxy group" can be used. Particularly, a $C_{1-6}$ alkyl group is preferable.

As the "hydrocarbon group" of the "optionally substituted hydrocarbon group" for $R^5$, those similar to the "hydrocarbon group" of the "optionally substituted hydrocarbon group", which is a substituent for ring B', can be used.

The "hydrocarbon group" optionally has 1 to 3 substituents at substitutable positions. As such substituents, those exemplified as the substituents for the aforementioned "optionally substituted $C_{1-6}$ alkyl group" can be used.

As the "optionally substituted heterocyclic group", "optionally substituted amino group" and "optionally substituted hydroxy group" for $R^5$, those exemplified as the substituents for the "optionally substituted hydrocarbon group", which is a substituent for ring B', can be used respectively.

As the "optionally substituted sulfonyl group" for $R^5$, for example, an optionally substituted $C_{6-10}$ arylsulfonyl (e.g., phenylsulfonyl, toluenesulfonyl), an optionally halogenated $C_{1-6}$ alkylsulfonyl group (e.g., methylsulfonyl, ethylsulfonyl, propylsulfonyl, sec-propylsulfonyl, butylsulfonyl, t-butylsulfonyl, trifluoromethanesulfonyl) and the like can be mentioned.

Here, as the substituents for the "optionally substituted $C_{6-10}$ arylsulfonyl", for example, a halogen atom, a nitro group, a cyano group, an optionally halogenated $C_{1-6}$ alkyl group, an optionally halogenated $C_{1-6}$ alkoxy group, an optionally substituted $C_{6-14}$ aryl group, a heterocyclic group and the like can be mentioned. As these substituents, those exemplified as the substituents for ring A can be used respectively. The number of the substituents is, for example, 1 to 3.

As the "nitrogen-containing heterocycle" of the "optionally substituted nitrogen-containing heterocycle" formed by $R^4$ and $R^5$ bonded to each other, together with the adjacent nitrogen atom, for example, a 3- to 8-membered nitrogen-containing heterocycle containing, as ring-constituting atom(s) besides carbon atoms, at least one nitrogen atom, and optionally further containing 1 to 3 hetero atoms selected from a nitrogen atom, a sulfur atom and an oxygen atom can be mentioned. As specific examples of such nitrogen-containing heterocycle, a monocyclic heterocycle such as aziridine, azetidine, morpholine, thiomorpholine, piperidine, piperazine, pyrrolidine, azepane, azocane, hexahydropyrimidine, 1,4-diazepane and the like; and a bicyclic heterocycle such as indoline, tetrahydroquinoline, tetrahydroisoquinoline, benzoxazine, benzoazepane, benzoxazepane and the like can be mentioned.

The "nitrogen-containing heterocycle" optionally has 1 to 4 substituents at substitutable positions, and as such substituents, those exemplified as the substituents for the aforementioned ring A can be used.

$R^4$ is preferably a hydrogen atom.

$R^5$ is preferably an optionally substituted $C_{1-6}$ alkyl group, an optionally substituted aralkyl group (preferably a $C_{7-14}$ aralkyl group), an optionally substituted $C_{3-10}$ cycloalkyl-$C_{1-6}$ alkyl group, an optionally substituted phenyl group, an optionally substituted cycloalkyl group. (preferably a $C_{3-10}$ cycloalkyl group) or an optionally substituted heterocyclic group.

Here, as preferable specific examples of the "optionally substituted $C_{1-6}$ alkyl group", a $C_{1-6}$ alkyl group (preferably methyl, ethyl, propyl) optionally having 1 to 3 substituents selected from a halogen atom, a carboxyl group, an optionally substituted heterocyclic group (preferably furyl, thienyl, pyridyl, tetrahydrofuranyl), a $C_{1-6}$ alkoxy-carbonyl group (preferably t-butoxycarbonyl) and the like, and the like can be mentioned.

As preferable specific examples of the "optionally substituted aralkyl group", a $C_{7-14}$ aralkyl group (preferably benzyl, phenethyl, 2-phenylpropyl) optionally having 1 to 3 substituents selected from a halogen atom, an optionally halogenated $C_{1-6}$ alkyl group (preferably trifluoromethyl), a $C_{1-6}$ alkylsulfonyl group (preferably methylsulfonyl), a $C_{1-6}$ alkylthio group (preferably methylthio), a $C_{1-6}$ alkoxy group (preferably methoxy) and the like, and the like can be mentioned.

As preferable specific examples of the "optionally substituted $C_{3-10}$ cycloalkyl-$C_{1-6}$ alkyl group", a $C_{3-10}$ cycloalkyl-$C_{1-6}$ alkyl group (preferably cyclopropylmethyl, cyclohexylmethyl, cycloheptylmethyl) optionally having 1 to 3 substituents selected from a carboxyl group, a $C_{1-6}$ alkoxycarbonyl group (preferably methoxycarbonyl) and the like, and the like can be mentioned.

As preferable specific examples of the "optionally substituted phenyl group", a phenyl group and the like can be mentioned.

As preferable specific examples of the "optionally substituted cycloalkyl group", a $C_{3-10}$ cycloalkyl group (preferably cyclohexyl) and the like can be mentioned.

$R^5$ is more preferably an optionally substituted aralkyl group (preferably a $C_{7-14}$ aralkyl, more preferably benzyl). $R^5$ is particularly preferably a $C_{7-14}$ aralkyl (preferably benzyl) optionally substituted by a halogen atom (preferably a fluorine atom).

As the substituent for the "optionally substituted $C_{6-14}$ aryl-carbonyl group", "optionally substituted heterocyclyl-carbonyl group", "optionally substituted $C_{3-8}$ cycloalkyl-carbonyl group", "optionally substituted $C_{6-14}$ aryl-carbamoyl group", "optionally substituted heterocyclyl-carbamoyl group", "optionally substituted $C_{3-8}$ cycloalkyl-carbamoyl group", "optionally substituted $C_{6-14}$ arylsulfonyl group", "optionally substituted heterocyclyl-sulfonyl group", "optionally substituted $C_{3-8}$ cycloalkylsulfonyl group", "optionally substituted $C_{6-14}$ arylsulfamoyl group", "optionally substituted heterocyclyl-sulfamoyl group" and "optionally substituted $C_{3-8}$ cycloalkylsulfamoyl group", those exemplified as the substituent for the "optionally substituted $C_{6-14}$ aryl group", which is a substituent for ring A, can be mentioned. The number of the substituents is, for example, 1 to 4.

The substituent for ring B' is preferably an oxo group, an optionally substituted heterocyclic group or an optionally substituted hydrocarbon group, more preferably an oxo group or an optionally substituted hydrocarbon group.

The compound (I) preferably has two or more (preferably 2 to 4) "substituents having a cyclic group". The substituents may be present on either one of ring A and ring B', or both ring A and ring B'. The two or more "substituents having a cyclic group" that compound (I) has may be the same as or different from each other.

The "substituent having a cyclic group" means a substituent having a cyclic group such as a $C_{3-8}$ cycloalkyl group, a $C_{6-14}$ aryl group, a heterocyclic group and the like as a constituent element, and as specific examples thereof, the "$C_{3-8}$ cycloalkyl group", "heterocyclic group", "$C_{7-14}$ aralkyl group", "$C_{6-14}$ aryloxy group", "heterocyclyloxy group", "$C_{7-14}$ aralkyloxy group", "$C_{6-14}$ aryloxy-carbonyl group", "$C_{6-14}$ aryl-carbonyl-$C_{1-6}$ alkoxy group", "$C_{3-14}$ cycloalkyl-$C_{1-6}$ alkoxy group", "heterocyclyl-$C_{1-6}$ alkoxy group", "$C_{7-14}$ aralkyloxy-carbonyl-$C_{1-6}$ alkoxy group", "hydroxyphenyl-$C_{1-6}$ alkoxy group", "$C_{7-14}$ aralkyloxy-carbonyl group" and "optionally substituted $C_{6-14}$ aryl group", exemplified as the substituents for the aforementioned ring A; and the "optionally substituted heterocyclic group", "optionally substituted hydrocarbon group (containing a cyclic group (e.g., a $C_{3-8}$ cycloalkyl group, a $C_{6-14}$ aryl group, a heterocyclic group and the like) as a constituent element)", "optionally substituted $C_{6-14}$ aryl-carbonyl group", "optionally substituted heterocyclyl-carbonyl group", "optionally substituted $C_{3-8}$ cycloalkyl-carbonyl group", "$C_{7-14}$ aralkyl-carbonyl group", "optionally substituted $C_{6-14}$ aryl-carbamoyl group", "optionally substituted heterocyclyl-carbamoyl group", "optionally substituted $C_{3-8}$ cycloalkyl-carbamoyl group", "$C_{7-14}$ aralkyl-carbamoyl group", "optionally substituted $C_{6-14}$ arylsulfonyl group", "optionally substituted heterocyclyl-sulfonyl group", "optionally substituted $C_{3-8}$ cycloalkylsulfonyl group", "$C_{7-14}$ aralkylsulfonyl group", "optionally substituted $C_{6-14}$ arylsulfamoyl group", "optionally substituted heterocyclyl-sulfamoyl group", "optionally substituted $C_{3-8}$ cycloalkylsulfamoyl group" and "$C_{7-14}$ aralkylsulfamoyl group", exemplified as the substituents for ring B', and the like can be mentioned.

The compound (I) is a compound preferably represented by the formula

(I')

wherein the symbols in the formula are as defined above, or a salt thereof [hereinafter sometimes to be abbreviated as compound (I')].

As the "6- to 8-membered ring having three or more substituents" for ring B, a 6- to 8-membered ring having three or more substituents from the "5- to 9-membered ring having one or more substituents" for the aforementioned ring B', can be mentioned.

Y is —C($R^1$)=, —CH($R^1$)—, —N($R^1$)— or —N=, preferably —N($R^1$)—.

$R^1$ is a hydrogen atom or a substituent, preferably a substituent. As the substituent, those exemplified as the substituents for ring B' can be mentioned. Among them, an optionally substituted hydrocarbon group, an optionally substituted heterocyclic group and the like are preferable.

$R^1$ is preferably an optionally substituted hydrocarbon group, more preferably an optionally substituted $C_{1-6}$ alkyl group. Specifically, a $C_{1-6}$ alkyl group is preferable and neopentyl is particularly preferable.

When $R^1$ is a substituent, the substituent is counted as a substituent for ring B'. The number of the substituents for ring B' is preferably 4.

The compound (I) is more preferably a compound represented by the formula

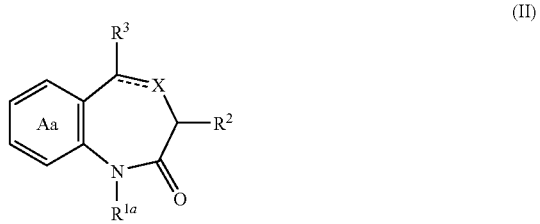

(II)

wherein the symbols in the formula are as defined above, or a salt thereof [hereinafter sometimes to be abbreviated as compound (II)].

Here, the benzene ring for ring Aa optionally has 1 to 4 substituents at substitutable positions, and as such substituents, those exemplified as the substituents for the aforementioned ring A can be used. The substituent for ring Aa is preferably a halogen atom (preferably a chlorine atom).

In the formula (II), when X is =N—, then ... is a single bond, and when X is —$NR^6$—, —O— or —S(O)n-, then ... is void.

As the substituents for $R^6$, those exemplified as the substituents for ring B' can be used.

$R^6$ is preferably 1) an optionally substituted $C_{6-14}$ arylcarbonyl group, an optionally substituted heterocyclyl-carbonyl group, an optionally substituted $C_{3-8}$ cycloalkyl-carbonyl group, a $C_{7-14}$ aralkyl-carbonyl group, a $C_{6-14}$ aryloxy-carbonyl group, a $C_{7-14}$ aralkyloxy-carbonyl group, an optionally substituted $C_{6-14}$ aryl-carbamoyl group, an optionally substituted heterocyclyl-carbamoyl group, an optionally substituted $C_{3-8}$ cycloalkyl-carbamoyl group, an $C_{7-14}$ aralkyl-carbamoyl group, an optionally substituted $C_{6-14}$ arylsulfonyl group, an optionally substituted heterocyclyl-sulfonyl group, an optionally substituted $C_{3-8}$ cycloalkylsulfonyl group, a $C_{7-14}$ aralkylsulfonyl group, an optionally substituted $C_{6-14}$ arylsulfamoyl group, an optionally substituted heterocyclyl-sulfamoyl group, an optionally substituted $C_{3-8}$ cycloalkyl-sulfamoyl group, a $C_{7-14}$ aralkylsulfamoyl group; 2) a $C_{7-14}$ aralkyl group or a $C_{1-10}$ alkyl group substituted by an optionally substituted heterocyclic group, and the like. Among them, an optionally substituted $C_{6-14}$ aryl-carbonyl group, an optionally substituted heterocyclyl-carbonyl group and the like are preferable.

As preferable specific examples of $R^6$, a $C_{6-14}$ aryl-carbonyl group (preferably benzoyl) and a heterocyclyl-carbonyl group (preferably pyridyl-carbonyl, furyl-carbonyl, thienyl-carbonyl, pyrrolyl-carbonyl, oxazolyl-carbonyl, isoxazolyl-carbonyl, thiazolyl-carbonyl, isothiazolyl-carbonyl, pyrazinyl-carbonyl, piperidinyl-carbonyl, quinolyl-carbonyl or isoquinolyl-carbonyl), each optionally having 1 to 4 substituents selected from a halogen atom, an optionally halogenated $C_{1-6}$ alkyl group, an optionally halogenated $C_{1-6}$ alkoxy group, an optionally halogenated $C_{1-6}$ alkylthio group, a hydroxy group, a mercapto group, a cyano group, a nitro group, a carboxyl group, a carbamoyl group, a formyl group, an optionally halogenated $C_{1-6}$ alkyl-carbonyl group, a $C_{1-6}$ alkoxy-carbonyl group, an amino group, a mono- or di-$C_{1-6}$ alkylamino group, a formylamino group, an optionally halogenated $C_{1-6}$ alkyl-carbonylamino group and the like can be mentioned.

X is preferably —O—, —S(O)n- or —$NR^6$—, more preferably —O— or —$NR^6$—.

As the "optionally substituted hydrocarbon group" and "optionally substituted heterocyclic group" for $R^{1a}$, $R^3$ or $R^2$, those exemplified as the substituents for ring B' can be used. Here, as the "optionally substituted hydrocarbon group", an optionally substituted $C_{1-6}$ alkyl group, an optionally substituted $C_{2-6}$ alkenyl group, an optionally substituted phenyl group, an optionally substituted aralkyl group (preferably a $C_{7-14}$ aralkyl group) and the like are preferable.

$R^{1a}$ is preferably an optionally substituted hydrocarbon group, more preferably an optionally substituted $C_{1-6}$ alkyl group. Particularly, a $C_{1-6}$ alkyl group optionally substituted by substituent(s) selected from 1) a heterocyclic group (preferably furyl, thienyl, quinolyl) optionally substituted by substituent(s) selected from a phenyl group optionally substituted by a $C_{1-6}$ alkoxy group and a heterocyclic group (preferably furyl, thienyl), 2) a hydroxy group, 3) a $C_{1-6}$ alkyl-carbonyloxy group (e.g., acetyloxy) and 4) a $C_{1-6}$ alkylsulfonyloxy group (e.g., methylsulfonyloxy) is preferable. $R^{1a}$ is particularly preferably a $C_{1-6}$ alkyl group, specifically neopentyl.

In the formula (II), when X is —O—, =N— or —S(O)n-, then $R^3$ is preferably an optionally substituted $C_{6-14}$ aryl group or an optionally substituted heterocyclic group. $R^3$ is more preferably an optionally substituted phenyl group or an optionally substituted piperidinyl group. Among them, a phenyl group having substituent(s) at the meta position is preferable. As used herein, as the substituent on the phenyl group, 1) a $C_{1-6}$ alkyl group optionally substituted by substituent(s) selected from a halogen atom, an optionally substituted amino group, an optionally substituted hydroxy group and an optionally substituted heterocyclic group, 2) an optionally substituted amino group, 3) an optionally substituted heterocyclic group, 4) an optionally substituted hydroxy group, 5) an acyl group and the like are preferable.

Here, as the "halogen atom", "optionally substituted amino group", "optionally substituted hydroxy group" and "optionally substituted heterocyclic group", those exemplified as the substituent for the "optionally substituted hydrocarbon group", which is a substituent for ring B', can be used respectively. As the $C_{1-6}$ alkyl group, for example, methyl, ethyl, propyl, isopropyl, butyl, isobutyl, sec-butyl, tert-butyl, pentyl, isopentyl, neopentyl, hexyl and the like can be mentioned.

As the "acyl group" which is a substituent on the phenyl group, those exemplified as the substituent for the "optionally substituted amino group", which is a substituent for the "optionally substituted hydrocarbon group", which is a substituent for ring B' can be used.

As preferable specific examples of the substituent on the aforementioned phenyl group, 1) a $C_{1-6}$ alkyl group optionally substituted by substituent(s) selected from a halogen atom (preferably fluorine, chlorine), an acylamino group (preferably a formylamino, a $C_{1-6}$ alkyl-carbonylamino group, a $C_{6-14}$ aryl-carbonylamino group, a $C_{1-6}$ alkoxy-carbonylamino group, a $C_{7-14}$ aralkyloxy-carbonylamino group, a $C_{1-6}$ alkylsulfonylamino group, a carbamoylamino group or a mono- or di-$C_{1-6}$ alkyl-carbamoylamino group, each optionally having 1 to 3 substituents selected from a halogen atom, a nitro group, a cyano group, a $C_{1-6}$ alkyl group, an amino group optionally mono- or di-substituted by a $C_{1-6}$ alkyl group, a hydroxy group, a $C_{1-6}$ alkoxy group and the like), an optionally substituted hydroxy group (preferably a hydroxy group, a carboxyl-$C_{1-6}$ alkoxy group, a $C_{1-6}$ alkoxy-carbonyl-$C_{1-6}$ alkoxy group) and an optionally substituted heterocyclic group (preferably a nitrogen-containing aromatic heterocyclic group (e.g., pyrrolyl, oxazolyl, isoxazolyl, thiazolyl, isothiazolyl, imidazolyl, pyrazolyl, oxadiazolyl, furazanyl, thiadiazolyl, triazolyl, tetrazolyl, pyridyl, pyridazinyl, pyrimidinyl, pyrazinyl)), 2) an amino group, 3) an optionally substituted heterocyclic group (preferably dioxolanyl), 4) a $C_{1-6}$ alkoxy group optionally substituted by the substituent(s) selected from a carbamoyl group, a mono- or di-$C_{1-6}$ alkyl-carbamoyl group, a mono- or di-(heterocyclyl (preferably imidazolyl)-$C_{1-6}$ alkyl)-carbamoyl group (e.g., imidazolylpropylcarbamoyl) and a mono- or di-$C_{7-14}$ aralkyl-carbamoyl group, and 5) an acyl group (preferably formyl) can be mentioned.

The above-mentioned substituent on the phenyl group is more preferably, (1) a $C_{1-6}$ alkyl group optionally substituted by an "optionally substituted amino group" or an "optionally substituted heterocyclic group", or (2) an optionally substituted $C_{1-6}$ alkoxy group, and a acylaminomethyl group is particularly preferable.

Here, as preferable specific examples of the "optionally substituted amino group", an acylamino and the like can be mentioned.

As the aforementioned acylamino, a formylamino, a $C_{1-6}$ alkyl-carbonylamino group (e.g., acetylamino, propionylamino, butyrylamino, t-butylcarbonylamino), a $C_{6-14}$ arylcarbonylamino group (e.g., benzoylamino), a $C_{1-6}$ alkoxycarbonylamino group (e.g., methoxycarbonylamino, ethoxycarbonylamino, propoxycarbonylamino, sec-propoxycarbonylamino, butoxycarbonylamino, t-butoxycarbonylamino), a $C_{7-14}$ aralkyloxy-carbonylamino group (e.g., benzyloxycarbonylamino), a $C_{1-6}$ alkylsulfonylamino group (e.g., methylsulfonylamino, ethylsulfonylamino, propylsulfonylamino, sec-propylsulfonylamino, butylsulfonylamino, t-butylsulfonylamino), a carbamoylamino group, a mono- or di-$C_{1-6}$ alkyl-carbamoylamino group (e.g., N-methylcarbamoylamino, N-ethylcarbamoylamino, N,N-dimethylcarbamoylamino, N,N-diethylcarbamoylamino) and the like, each optionally having 1 to 3 substituents selected from a halogen atom (e.g., fluorine, chlorine, bromine, iodine), a nitro group, a cyano group, a $C_{1-6}$ alkyl group, an amino group optionally mono- or di-substituted by a $C_{1-6}$ alkyl group (e.g., methylamino, dimethylamino, ethylamino), a hydroxy group, a $C_{1-6}$ alkoxy group (e.g., methoxy, ethoxy, propoxy, isopropoxy) and the like are preferable. Among them, a formylamino, a $C_{1-3}$ alkyl-carbonylamino group, a $C_{1-3}$ alkoxy-carbonylamino group and the like are preferable. As preferable examples of the "optionally substituted heterocyclic group", a nitrogen-containing aromatic heterocyclic group, specifically an aromatic heterocyclic group having, as ring-constituting atom(s) besides carbon atoms, at least one nitrogen atom (e.g., pyrrolyl, oxazolyl, isoxazolyl, thiazolyl, isothiazolyl, imidazolyl, pyrazolyl, oxadiazolyl, furazanyl, thiadiazolyl, triazolyl, tetrazolyl, pyridyl, pyridazinyl, pyrimidinyl, pyrazinyl) and the like can be mentioned from the heterocyclic groups exemplified as the substituents for ring B'.

As preferable specific examples of the "optionally substituted $C_{1-6}$ alkoxy group", a $C_{1-6}$ alkoxy group optionally substituted by substituent(s) selected from a carbamoyl group, a mono- or di-$C_{1-6}$ alkyl-carbamoyl group (e.g., N-methylcarbamoyl, N-ethylcarbamoyl, N,N-dimethylcarbamoyl, N,N-diethylcarbamoyl), a mono- or di-(heterocyclyl (preferably imidazolyl)-$C_{1-6}$ alkyl)-carbamoyl group (e.g., imidazolylpropylcarbamoyl) and a mono- or di-$C_{7-14}$ aralkyl-carbamoyl group (e.g., benzylcarbamoyl, phenethylcarbamoyl), and the like can be mentioned.

$R^3$ is particularly preferably a phenyl group having an acylaminomethyl group at the meta position.

In the formula (II), when X is —$NR^6$—, then $R^3$ is preferably a hydrogen atom.

$R^2$ is preferably an "optionally substituted hydrocarbon group", more preferably a $C_{1-6}$ alkyl group substituted by —$CON(R^4)(R^5)$ [wherein $R^4$ and $R^5$ are as defined above].

The compound (II) is preferably a compound represented by the formula

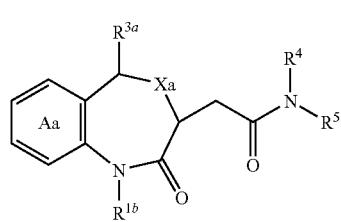

(III)

wherein the symbols in the formula are as defined above, or a salt thereof [hereinafter sometimes to be abbreviated as compound (III)].

Xa is preferably —O—, —S— or —$NR^6$—, more preferably —O— or —$NR^6$—. Among them, —O— is particularly preferable.

As the "optionally substituted $C_{1-6}$ alkyl group", "optionally substituted $C_{2-6}$ alkenyl group", "optionally substituted phenyl group" and "optionally substituted aralkyl group" for $R^{1b}$ or $R^{3a}$, the "optionally substituted $C_{1-6}$ alkyl group", "optionally substituted $C_{2-6}$ alkenyl group", "optionally substituted phenyl group" and "optionally substituted aralkyl group (preferably a $C_{7-14}$ aralkyl group)" exemplified as the "optionally substituted hydrocarbon group" with regard to the aforementioned $R^{1a}$ can be used respectively.

As the "optionally substituted heterocyclic group" for $R^{1b}$ or $R^{3a}$, those exemplified as the substituents for ring B' can be used.

$R^{1b}$ is preferably an optionally substituted $C_{1-6}$ alkyl group or an optionally substituted aralkyl group (preferably a $C_{7-14}$ aralkyl group), more preferably an optionally substituted $C_{1-6}$ alkyl group. Among them, a $C_{1-6}$ alkyl group optionally substituted by substituent(s) selected from 1) a heterocyclic group (preferably furyl, thienyl, quinolyl) optionally substituted by substituent(s) selected from a phenyl group optionally substituted by a $C_{1-6}$ alkoxy group and a heterocyclic group (preferably furyl, thienyl), 2) a hydroxy group, 3) a $C_{1-6}$ alkyl-carbonyloxy group (e.g., acetyloxy) and 4) a $C_{1-6}$ alkylsulfonyloxy group (e.g., methylsulfonyloxy) is preferable.

$R^{1b}$ is particularly preferably a $C_{1-6}$ alkyl group, specifically preferably neopentyl.

In the formula (III), when Xa is —O— or —S(O)n—, then $R^{3a}$ is preferably an optionally substituted phenyl group or an optionally substituted piperidinyl group. Among them, a phenyl group having substituent(s) at the meta position is preferable. As used herein, as the substituent on the phenyl group, 1) a $C_{1-6}$ alkyl group optionally substituted by substituent(s) selected from a halogen atom, an optionally substituted amino group, an optionally substituted hydroxy group and an optionally substituted heterocyclic group, 2) an optionally substituted amino group, 3) an optionally substituted heterocyclic group, 4) an optionally substituted hydroxy group, 5) an acyl group and the like are preferable, as in the case of the aforementioned $R^3$.

Of the above-mentioned substituents, a $C_{1-6}$ alkyl group optionally substituted by an optionally substituted amino group is preferable, and an acylaminomethyl group is particularly preferable.

Here, as the acylamino of the acylaminomethyl group, those used for the aforementioned $R^3$ can be mentioned. $R^{3a}$ is particularly preferably a phenyl group having an acylaminomethyl group at the meta position.

In the formula (III), when Xa is —$NR^6$—, then $R^{3a}$ is preferably a hydrogen atom.

Of compounds (III), a compound wherein
ring Aa is a benzene ring optionally substituted by a halogen atom,
Xa is —O— or —S—,
$R^{1b}$ is an optionally substituted $C_{1-6}$ alkyl group or an optionally substituted aralkyl group,
$R^{3a}$ is a phenyl group optionally substituted by substituent(s) selected from 1) a $C_{1-6}$ alkyl group optionally substituted by an optionally substituted amino group, an optionally substituted hydroxy group or an optionally substituted heterocyclic group, 2) an optionally substituted amino group, 3) an optionally substituted heterocyclic group and 4) an acyl group, $R^4$ is a hydrogen atom, and $R^5$ is an optionally substituted $C_{1-6}$ alkyl group, an optionally substituted aralkyl group, an optionally substituted phenyl group, an optionally substituted cycloalkyl group or an optionally substituted heterocyclic group; and a compound wherein ring Aa is a benzene ring optionally substituted by a halogen atom, Xa is —$NR^6$—, $R^6$ is 1) an optionally substituted $C_{6-14}$ aryl-carbonyl group; 2) an optionally substituted heterocyclyl-carbonyl group; 3) a $C_{7-14}$ aralkyl group; or 4) a $C_{1-10}$ alkyl group substituted by an optionally substituted heterocyclic group, $R^{1b}$ is an optionally substituted $C_{1-6}$ alkyl group or an optionally substituted aralkyl group, $R^{3a}$ is a hydrogen atom, $R^4$ is a hydrogen atom, and $R^5$ is an optionally substituted $C_{1-6}$ alkyl group, an optionally substituted aralkyl group, an optionally substituted phenyl group, an optionally substituted cycloalkyl group or an optionally substituted heterocyclic group, are preferable.

As preferable specific examples of compound (III), a compound wherein ring Aa is a benzene ring optionally substituted by a halogen atom, Xa is —O— or —S—, $R^{1b}$ is a $C_{1-6}$ alkyl group optionally substituted by substituent(s) selected from 1) a heterocyclic group (preferably furyl, thienyl, quinolyl) optionally substituted by substituent(s) selected from a phenyl group optionally substituted by a $C_{1-6}$ alkoxy group and a heterocyclic group (preferably furyl, thienyl), 2) a hydroxy group, 3) a $C_{1-6}$ alkyl-carbonyloxy group (e.g., acetyloxy) and 4) a $C_{1-6}$ alkylsulfonyloxy group (e.g., methylsulfonyloxy), $R^{3a}$ is a phenyl group optionally substituted by substituent(s) selected from 1) a $C_{1-6}$ alkyl group optionally substituted by substituent(s) selected from a halogen atom (preferably fluorine, chlorine), an acylamino group (preferably a formylamino, a $C_{1-6}$ alkyl-carbonylamino group, a $C_{6-14}$ aryl-carbonylamino group, a $C_{1-6}$ alkoxy-carbonylamino group, a $C_{7-14}$ aralkyloxy-carbonylamino group, a $C_{1-6}$ alkylsulfonylamino group, a carbamoylamino group or a mono- or di-$C_{1-6}$ alkyl-carbamoylamino group, each of which optionally has 1 to 3 substituents selected from a halogen atom, a nitro group, a cyano group, a $C_{1-6}$ alkyl group, an amino group optionally mono- or di-substituted by a $C_{1-6}$ alkyl group, a hydroxy group, a $C_{1-6}$ alkoxy group and the like), an optionally substituted hydroxy group (preferably a hydroxy group, a carboxyl-$C_{1-6}$ alkoxy group, a $C_{1-6}$ alkoxy-carbonyl-$C_{1-6}$ alkoxy group) and an optionally substituted heterocyclic group (preferably a nitrogen-containing aromatic heterocyclic group (e.g., pyrrolyl, oxazolyl, isoxazolyl, thiazolyl, isothiazolyl, imidazolyl, pyrazolyl, oxadiazolyl, furazanyl, thiadiazolyl, triazolyl, tetrazolyl, pyridyl, pyridazinyl, pyrimidinyl, pyrazinyl)), 2) an amino group, 3) an optionally substituted heterocyclic group (preferably dioxolanyl), 4) a $C_{1-6}$ alkoxy group optionally substituted by substituent(s) selected from a carbamoyl group, a mono- or di-$C_{1-6}$ alkyl-carbamoyl group, a mono- or di-(heterocyclyl (preferably imidazolyl)-$C_{1-6}$ alkyl)-carbamoyl group (e.g., imidazolylpropylcarbamoyl) and a mono- or di-$C_{7-14}$ aralkyl-carbamoyl group and 5) an acyl group (preferably formyl), $R^4$ is a hydrogen atom, and $R^5$ is (1) a $C_{1-6}$ alkyl group optionally having 1 to 3 substituents selected from a halogen atom, a carboxyl group, an optionally substituted heterocyclic group (preferably furyl, thienyl, pyridyl, tetrahydrofuranyl), a $C_{1-6}$ alkoxy-carbonyl group and the like, (2) a $C_{7-14}$ aralkyl group optionally having 1 to 3 substituents selected from a halogen atom, an optionally halogenated $C_{1-6}$ alkyl group, a $C_{1-6}$ alkylsulfonyl group, a $C_{1-6}$ alkylthio group, a $C_{1-6}$ alkoxy group and the like, (3) a $C_{3-10}$ cycloalkyl-$C_{1-6}$ alkyl group optionally having 1 to 3 substituents selected from a carboxyl group, a $C_{1-6}$ alkoxy-carbonyl group and the like, (4) a phenyl group or (5) a $C_{3-10}$ cycloalkyl group;

a compound wherein ring Aa is a benzene ring optionally substituted by a halogen atom, Xa is —$NR^6$—, $R^6$ is a $C_{6-14}$ aryl-carbonyl group (preferably benzoyl) or a heterocyclyl-carbonyl group (preferably pyridyl-carbonyl, furyl-carbonyl, thienyl-carbonyl, pyrrolyl-carbonyl, oxazolyl-carbonyl, isoxazolyl-carbonyl, thiazolyl-carbonyl, isothiazolyl-carbonyl, pyrazinyl-carbonyl, piperidinyl-carbonyl, quinolyl-carbonyl or isoquinolyl-carbonyl), each of which optionally has 1 to 4 substituents selected from a halogen atom, an optionally halogenated $C_{1-6}$ alkyl group, an optionally halogenated $C_{1-6}$ alkoxy group, an optionally halogenated $C_{1-6}$ alkylthio group, a hydroxy group, a mercapto group, a cyano group, a nitro group, a carboxyl group, a carbamoyl group, a formyl group, an optionally halogenated $C_{1-6}$ alkyl-carbonyl group, a $C_{1-6}$ alkoxy-carbonyl group, an amino group, a mono- or di-$C_{1-6}$ alkylamino group, a formylamino group, an optionally halogenated $C_{1-6}$ alkyl-carbonylamino group and the like;

$R^{1b}$ is a $C_{1-6}$ alkyl group optionally substituted by substituent(s) selected from 1) a heterocyclic group (preferably furyl, thienyl, quinolyl) optionally substituted by substituent(s) selected from a phenyl group optionally substituted by a $C_{1-6}$ alkoxy group and a heterocyclic group (preferably furyl, thienyl), 2) a hydroxy group, 3) a $C_{1-6}$ alkyl-carbonyloxy group (e.g., acetyloxy) and 4) a $C_{1-6}$ alkylsulfonyloxy group (e.g., methylsulfonyloxy), $R^{3a}$ is a hydrogen atom, $R^4$ is a hydrogen atom, and $R^5$ is (1) a $C_{1-6}$ alkyl group optionally having 1 to 3 substituents selected from a halogen atom, a carboxyl group, an optionally substituted heterocyclic group (preferably furyl, thienyl, pyridyl, tetrahydrofuranyl), a $C_{1-6}$ alkoxy-carbonyl group and the like, (2) a $C_{7-14}$ aralkyl group optionally having 1 to 3 substituents selected from a halogen atom, an optionally halogenated $C_{1-6}$ alkyl group, a $C_{1-6}$ alkylsulfonyl group, a $C_{1-6}$ alkylthio group, a $C_{1-6}$ alkoxy group and the like, (3) a $C_{3-10}$ cycloalkyl-$C_{1-6}$ alkyl group optionally having 1 to 3 substituents selected from a carboxyl group, a $C_{1-6}$ alkoxy-carbonyl group and the like, (4) a phenyl group or (5) a $C_{3-10}$ cycloalkyl group;

and the like can be also mentioned.

As compound (I), a compound represented by the formula

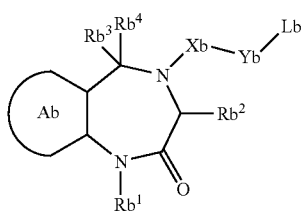

(IB)

wherein the symbols in the formula are as defined above, or a salt thereof and the like can be also mentioned.

As the "optionally substituted aromatic ring" for ring Ab, those exemplified for the aforementioned ring A can be mentioned. The aromatic ring for ring Ab is preferably a benzene ring. The ring Ab is preferably a benzene ring.

As the "divalent hydrocarbon group" for Xb or Yb, for example,
(1) a $C_{1-6}$ alkylene group (e.g., —CH$_2$—, —(CH$_2$)$_2$—, —(CH$_2$)$_3$—, —(CH$_2$)$_4$—, —(CH$_2$)$_5$—, —(CH$_2$)$_6$—, —CH(CH$_3$)—, —C(CH$_3$)$_2$—, —CH(CH$_3$)CH$_2$—, —C(CH$_3$)$_2$CH$_2$—, —CH(CH$_2$CH$_3$)CH$_2$—, —(CH(CH$_3$))$_2$—, —(CH$_2$)$_2$C(CH$_3$)$_2$—, —CH$_2$C(CH$_3$)$_2$CH$_2$—, —CH(CH$_2$CH$_3$)(CH$_2$)$_2$—, —(CH$_2$)$_3$C(CH$_3$)$_2$—, —(CH$_2$)$_3$CH(CH$_3$)CH$_2$—);
(2) a $C_{2-6}$ alkenylene group (e.g., —CH=CH—, —CH$_2$—CH=CH—, —C(CH$_3$)$_2$—CH=CH—, —CH$_2$—CH=CH—CH$_2$—, —CH$_2$—CH$_2$—CH=CH—, —CH=CH—CH=CH—, —CH=CH—CH$_2$—CH$_2$—CH$_2$—);
(3) a $C_{2-6}$ alkynylene group (e.g., —C≡C—, —CH$_2$—C≡C—, —CH$_2$—C≡C—CH$_2$—CH$_2$—);
(4) a $C_{3-6}$ cycloalkylene group (e.g., cyclopropylene, cyclobutylene, cyclopentylene, cyclohexylene);
(5) a $C_{3-6}$ cycloalkenylene group (e.g., cyclopropenylene, cyclobutenylene, cyclopentenylene, cyclohexenylene);
(6) a phenylene group;
and the like can be mentioned.

The "divalent hydrocarbon group" is preferably a $C_{1-6}$ alkylene group.

Xb is preferably a $C_{1-6}$ alkylene group (preferably —CH$_2$—) or —CO—, more preferably —CO—.

Yb is preferably a bond, a $C_{1-6}$ alkylene group (preferably —CH$_2$—) or —NH—, more preferably a bond.

In the "optionally substituted cyclic group" for Lb, as the cyclic group, for example, a heterocyclic group, an alicyclic hydrocarbon group, an aryl group and the like can be mentioned. As the heterocyclic group, the heterocyclic group exemplified for the "optionally substituted heterocyclic group", which is a substituent for the aforementioned ring B' can be mentioned. As the alicyclic hydrocarbon group and aryl group, those exemplified as the hydrocarbon group of the "optionally substituted hydrocarbon group", which is a substituent for the aforementioned ring B' can be mentioned.

The cyclic group optionally has 1 to 4 substituents at substitutable positions. As such substituents, those similar to the substituents for the aforementioned ring A can be mentioned. The substituent is preferably a halogen atom (e.g., fluorine, chlorine, bromine, iodine), an optionally halogenated $C_{1-6}$ alkyl group, an optionally halogenated $C_{1-6}$ alkoxy group, an optionally halogenated $C_{1-6}$ alkylthio group, a hydroxy group, a mercapto group, a cyano group, a nitro group, a carboxyl group, a carbamoyl group, a formyl group, an optionally halogenated $C_{1-6}$ alkyl-carbonyl group (e.g., acetyl, propionyl, trifluoroacetyl), a $C_{1-6}$ alkoxy-carbonyl group (e.g., methoxycarbonyl, ethoxycarbonyl, propoxycarbonyl), an amino group, a mono- or di-$C_{1-6}$ alkylamino group (e.g., methylamino, ethylamino, dimethylamino, diethylamino), a formylamino group, an optionally halogenated $C_{1-6}$ alkyl-carbonylamino group (e.g., acetylamino, propionylamino, butyrylamino, trifluoroacetylamino) and the like.

The cyclic group is preferably a phenyl group or a heterocyclic group (preferably pyridyl, furyl, thienyl, pyrrolyl, oxazolyl, isoxazolyl, thiazolyl, isothiazolyl, pyrazinyl, piperidinyl, quinolyl or isoquinolyl; more preferably pyridyl or quinolyl; particularly preferably pyridyl), more preferably a pyridyl group (preferably a 4-pyridyl group).

As the "optionally substituted hydrocarbon group" and "optionally substituted heterocyclic group" for Rb$^1$, Rb$^2$, Rb$^3$, Rb$^4$ or Rb$^5$, those exemplified as the substituents for the aforementioned ring B' can be used.

Rb$^1$ is preferably an optionally substituted $C_{1-6}$ alkyl group, more preferably a $C_{1-6}$ alkyl group optionally substituted by a $C_{1-6}$ alkyl-carbonyloxy group (e.g., acetyloxy). Particularly, a $C_{1-6}$ alkyl group is preferably, and neopentyl is particularly preferable.

Rb$^3$, Rb$^4$ and Rb$^5$ are preferably hydrogen atoms.

Rb$^2$ is preferably an "optionally substituted hydrocarbon group", more preferably a $C_{1-6}$ alkyl group substituted by —CON(Rb$^6$) (Rb$^7$) wherein Rb$^6$ and Rb$^7$ are as defined above. Particularly,

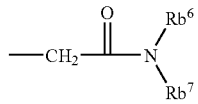

wherein Rb$^6$ and Rb$^7$ are as defined above, is preferable.

As used herein, as the "optionally substituted $C_{1-6}$ alkyl group" for Rb$^6$, those exemplified for the aforementioned R$^4$ can be mentioned.

As the "optionally substituted hydrocarbon group", "optionally substituted heterocyclic group", "optionally substituted amino group", "optionally substituted hydroxy group" and "optionally substituted sulfonyl group" for Rb$^7$, those exemplified for the aforementioned R$^5$ can be mentioned.

As the "optionally substituted nitrogen-containing heterocycle" formed by Rb$^6$ and Rb$^7$ bonded to each other, together with the adjacent nitrogen atom, those similar to the "optionally substituted nitrogen-containing heterocycle" formed by aforementioned R$^4$ and R$^5$ can be mentioned.

Rb$^6$ is preferably a hydrogen atom.

Rb$^7$ is preferably an optionally substituted $C_{7-14}$ aralkyl group (preferably benzyl), more preferably a $C_{7-14}$ aralkyl (preferably benzyl) optionally substituted by substituent(s) selected from a halogen atom and an optionally halogenated $C_{1-6}$ alkyl group. Particularly, a $C_{7-14}$ aralkyl (preferably benzyl) optionally substituted by a halogen atom (preferably a fluorine atom) is preferable.

Of compounds (IB), a compound wherein
ring Ab is a benzene ring;
Xb is a $C_{1-6}$ alkylene group or —CO—;
Yb is a bond;
Lb is a pyridyl group (preferably a 4-pyridyl group) optionally having 1 to 4 substituents selected from a halogen atom, an optionally halogenated $C_{1-6}$ alkyl group, an optionally halogenated $C_{1-6}$ alkoxy group, an optionally halogenated C$_{1-6}$ alkylthio group, a hydroxy group, a mercapto group, a cyano group, a nitro group, a carboxyl group, a carbamoyl group, a formyl group, an optionally halogenated C$_{1-6}$ alkyl-carbonyl group, a C$_{1-6}$ alkoxy-carbonyl group, an amino group, a mono- or di-C$_{1-6}$ alkylamino group, a formylamino group, an optionally halogenated C$_{1-6}$ alkyl-carbonylamino group and the like;

Rb$^1$ is a C$_{1-6}$ alkyl group;

Rb$^3$ and Rb$^4$ are each a hydrogen atom; and

Rb$^2$ is

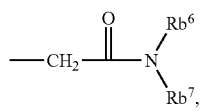

Rb$^6$ is a hydrogen atom, and Rb$^7$ is a C$_{7-14}$ aralkyl (preferably benzyl) optionally substituted by a halogen atom (preferably a fluorine atom), is preferable.

As compound (I), a compound represented by the formula

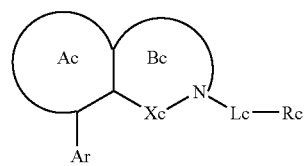

(IC)

wherein the symbols in the formula are as defined above, or a salt thereof and the like can be also mentioned.

As the "optionally substituted aromatic ring" for ring Ac, those exemplified for the aforementioned ring A can be mentioned. The aromatic ring is preferably a pyridine ring. In addition, ring Ac is preferably a pyridine ring optionally substituted by an optionally halogenated C$_{1-6}$ alkyl group, more preferably a pyridine ring.

Of compounds (IC), a compound represented by the formula

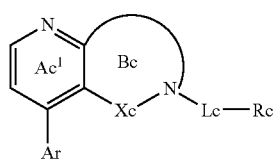

(IC′)

wherein ring Ac$^1$ is an optionally substituted pyridine ring and other symbols are as defined above, is preferable.

As the "optionally substituted pyridine ring" for ring Ac$^1$, the "optionally substituted aromatic ring" for ring Ac, wherein the aromatic ring is a pyridine ring, can be mentioned. Ring Ac$^1$ is preferably a pyridine ring optionally substituted by an optionally halogenated C$_{1-6}$ alkyl group, more preferably a pyridine ring.

As the "nitrogen-containing 6- to 9-membered ring" for ring Bc, the following nitrogen-containing 6- to 9-membered rings (preferably 6- to 8-membered rings) can be mentioned.

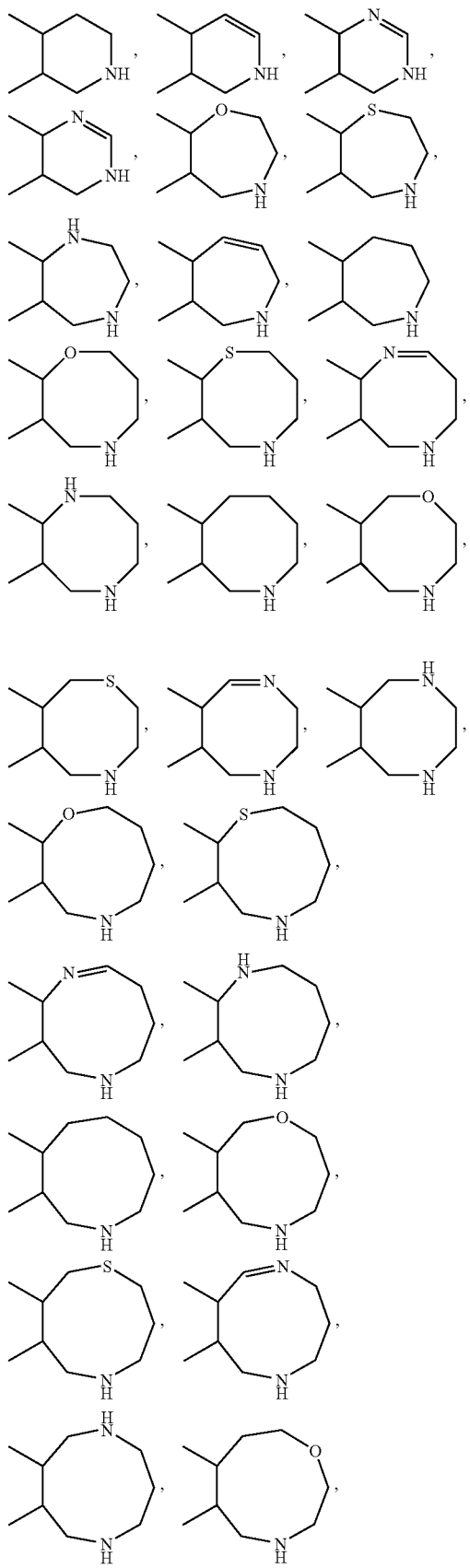

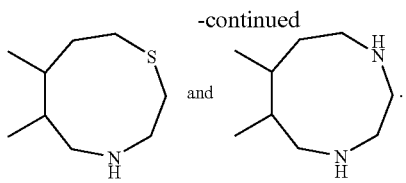

The "nitrogen-containing 6- to 9-membered ring" optionally has 1 to 4 substituents at substitutable positions, and as such substituents, for example, a halogen atom (e.g., fluorine, chlorine, bromine, iodine), a nitro group, a cyano group, an optionally halogenated $C_{1-6}$ alkyl group, an amino group optionally mono- or di-substituted by a $C_{1-6}$ alkyl group (e.g., methylamino, dimethylamino, ethylamino), a hydroxy group, an optionally halogenated $C_{1-6}$ alkoxy group (e.g., methoxy, ethoxy, propoxy, isopropoxy), an oxo group, a thioxo group, a carboxyl group, a formyl group, a $C_{1-6}$ alkyl-carbonyl group (e.g., acetyl, propionyl), a $C_{6-14}$ aryl-carbonyl group (e.g., benzoyl), a $C_{1-6}$ alkoxy-carbonyl group (e.g., methoxycarbonyl, ethoxycarbonyl, propoxycarbonyl) and the like can be mentioned.

Ring Bc is preferably

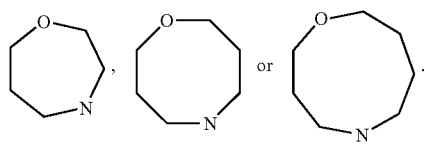

The methylene group for Xc optionally has 1 or 2 substituents. As such substituents, for example, a nitro group, a cyano group, an optionally halogenated $C_{1-6}$ alkyl group (e.g., methyl, ethyl, trifluoromethyl), a $C_{3-8}$ cycloalkyl group (e.g., cyclopropyl, cyclobutyl, cyclopentyl, cyclohexyl), an optionally halogenated $C_{1-6}$ alkylidene group (e.g., methylidene, ethylidene, propylidene), a $C_{6-14}$ aryl group (e.g., phenyl), a heterocyclic group (e.g., thienyl, furyl, pyridyl), a carboxyl group, a $C_{1-6}$ alkoxy-carbonyl group (e.g., methoxycarbonyl, ethoxycarbonyl, propoxycarbonyl), a $C_{6-14}$ aryloxy-carbonyl group (e.g., phenoxycarbonyl), a carbamoyl group, a mono- or di-$C_{1-6}$ alkyl-carbamoyl group (e.g., N-methylcarbamoyl, N-ethylcarbamoyl, N,N-dimethylcarbamoyl, N,N-diethylcarbamoyl), an oxo group, a thioxo group and the like can be mentioned. Xc is preferably a methylene group.

As the "optionally substituted aromatic group" for Ar, the "optionally substituted $C_{6-14}$ aryl group" and "heterocyclic group (only the aromatic ones)" exemplified as the substituents for the aromatic ring for the aforementioned ring A can be mentioned. Ar is preferably an optionally substituted $C_{6-14}$ aryl group, more preferably an optionally substituted phenyl (preferably a phenyl group optionally substituted by 1 to 3 halogen atoms), particularly preferably phenyl.

As the "optionally substituted cyclic group" for Rc, those exemplified for the aforementioned Lb and the like can be mentioned. The cyclic group is preferably phenyl, naphthyl (preferably 1-naphthyl group), indanyl, pyridyl, benzothienyl, benzofuryl, quinolyl, isoquinolyl, benzodioxolyl and the like. The substituent for the cyclic group is preferably a halogen atom (e.g., fluorine, chlorine, bromine, iodine), a nitro group, a cyano group, an optionally halogenated $C_{1-6}$ alkyl group, an amino-$C_{1-6}$ alkyl group (e.g., aminomethyl), a $C_{1-6}$ alkoxy-carbonylamino-$C_{1-6}$ alkyl group (e.g., t-butoxycarbonylaminomethyl), an amino group optionally mono- or di- substituted by a $C_{1-6}$ alkyl group (e.g., methylamino, dimethylamino, ethylamino), a hydroxy group, an optionally halogenated $C_{1-6}$ alkoxy group (e.g., methoxy, ethoxy, propoxy, isopropoxy) and the like.

Rc is preferably a phenyl group optionally having 1 to 4 substituents selected from a halogen atom (e.g., fluorine, chlorine, bromine, iodine), a nitro group, a cyano group, an optionally halogenated $C_{1-6}$ alkyl group, an amino-$C_{1-6}$ alkyl group (e.g., aminomethyl), a $C_{1-6}$ alkoxy-carbonylamino-$C_{1-6}$ alkyl group (e.g., t-butoxycarbonylaminomethyl), an amino group optionally mono- or di-substituted by a $C_{1-6}$ alkyl group (e.g., methylamino, dimethylamino, ethylamino), a hydroxy group, an optionally halogenated $C_{1-6}$ alkoxy group (e.g., methoxy, ethoxy, propoxy, isopropoxy) and the like. Rc is more preferably a 3,5-bis(trifluoromethyl)phenyl group.

As the "$C_{1-3}$ alkylene group" of the "optionally substituted $C_{1-3}$ alkylene group" for Lc, for example, —$CH_2$—, —$(CH_2)_2$—, —$(CH_2)_3$—, —$CH(CH_3)$—, —$C(CH_3)_2$—, —$CH(CH_3)CH_2$— and the like can be mentioned. Among them, a methylene group is preferable. The "$C_{1-3}$ alkylene group" optionally has 1 to 3 substituents at substitutable positions. As such substituents, for example, a halogen atom (e.g., fluorine, chlorine, bromine, iodine), a nitro group, a cyano group, an amino group optionally mono- or di-substituted by a $C_{1-6}$ alkyl group (e.g., methylamino, dimethylamino, ethylamino), a hydroxy group, an optionally halogenated $C_{1-6}$ alkoxy group (e.g., methoxy, ethoxy, propoxy, isopropoxy), an oxo group, a thioxo group, a $C_{6-14}$ aryl group (e.g., phenyl), a heterocyclic group (e.g., thienyl, furyl, pyridyl) and the like can be mentioned. Lc is preferably a $C_{1-3}$ alkylene group optionally substituted by an oxo group, or —$SO_2$—; more preferably —$CH_2$— (a methylene group), —$CH(CH_3)$—, —CO—, —$COCH_2$— or —$SO_2$—.

Of compounds (IC), the following compounds are preferable.

[Compound (IC-01)]

A compound wherein ring Ac is a pyridine ring optionally substituted by an optionally halogenated $C_{1-6}$ alkyl group;

ring Bc is

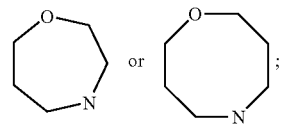

Xc is a methylene group;

Ar is a phenyl;

Rc is a phenyl, naphthyl, benzothienyl or benzofuryl group (preferably a phenyl group), each optionally having 1 to 4 substituents selected from a halogen atom (e.g., fluorine, chlorine, bromine, iodine), a nitro group, a cyano group, an optionally halogenated $C_{1-6}$ alkyl group, an amino group optionally mono- or di-substituted by a $C_{1-6}$ alkyl group (e.g., methylamino, dimethylamino, ethylamino), a hydroxy group, an optionally halogenated $C_{1-6}$ alkoxy group (e.g., methoxy, ethoxy, propoxy, isopropoxy) and the like; and Lc is a methylene group, —CO— or —$SO_2$—.

[Compound (IC-02)]

A compound represented by the formula (IC') wherein ring $Ac^1$ is a pyridine ring optionally substituted by an optionally halogenated $C_{1-6}$ alkyl group;

ring Bc is

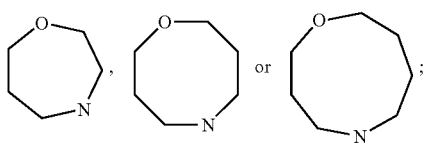

Xc is a methylene group;

Ar is a phenyl group optionally substituted by 1 to 3 halogen atoms;

Rc is a phenyl, a naphthyl, a indanyl, a pyridyl, a benzothienyl, a benzofuryl, a quinolyl, a isoquinolyl or a benzodioxolyl, each optionally having 1 to 4 substituents selected from a halogen atom, a nitro group, a cyano group, an optionally halogenated $C_{1-6}$ alkyl group, an amino-$C_{1-6}$ alkyl group, a $C_{1-6}$ alkoxy-carbonylamino-$C_{1-6}$ alkyl group, an amino group optionally mono- or di-substituted by a $C_{1-6}$ alkyl group, a hydroxy group, an optionally halogenated $C_{1-6}$ alkoxy group and the like; (Rc is particularly preferably a 3,5-bis(trifluoromethyl)phenyl group); and Lc is —$CH_2$—, —$CH(CH_3)$—, —CO— or —$SO_2$—.

As compound (I), a compound represented by the formula

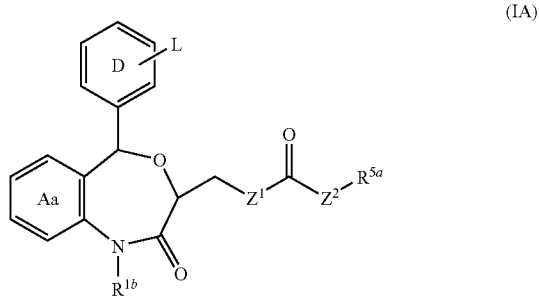

(IA)

wherein the symbols in the formula are as defined above, or a salt thereof (provided 3,5-trans-N-(2-fluorobenzyl)-5-(3-acetylaminomethylphenyl)-7-chloro-1-neopentyl-2-oxo-1,2,3,5-tetrahydro-4,1-benzoxazepine-3-acetamide;

3,5-trans-N-(2-fluorobenzyl)-7-chloro-5-(3-methoxycarbonylaminomethylphenyl)-1-neopentyl-2-oxo-1,2,3,5-tetrahydro-4,1-benzoxazepine-3-acetamide; and 3,5-trans-N-(2-fluorobenzyl)-5-(3-acetylaminomethylphenyl)-1-(4-biphenylmethyl)-7-chloro-2-oxo-1,2,3,5-tetrahydro-4,1-benzoxazepine-3-acetamide are excluded) and the like can be also mentioned.

The benzene ring for ring D optionally has 1 to 3 substituents besides L. As such substituents, for example, a halogen atom (e.g., fluorine, chlorine, bromine, iodine), a nitro group, a cyano group, an optionally halogenated $C_{1-6}$ alkyl group, an optionally halogenated $C_{1-6}$ alkoxy group, a hydroxy group, a carboxyl group, a formyl group, an optionally halogenated $C_{1-6}$ alkyl-carbonyl group (e.g., acetyl, propionyl, trifluoroacetyl), a $C_{1-6}$ alkoxy-carbonyl group (e.g., methoxycarbonyl, ethoxycarbonyl, propoxycarbonyl), an amino group, a mono- or di-$C_{1-6}$ alkylamino group (e.g., methylamino, ethylamino, dimethylamino, diethylamino) and the like can be mentioned. Among them, a $C_{1-6}$ alkoxy group and the like are preferable.

$R^{1b}$ is preferably an optionally substituted $C_{1-6}$ alkyl group, more preferably, a $C_{1-6}$ alkyl group optionally substituted by substituent(s) selected from 1) a heterocyclic group (preferably furyl, thienyl, quinolyl) optionally substituted by substituent(s) selected from a phenyl group optionally substituted by a $C_{1-6}$ alkoxy group and a heterocyclic group (preferably furyl, thienyl), 2) a hydroxy group, 3) a $C_{1-6}$ alkyl-carbonyloxy group (e.g., acetyloxy) and 4) a $C_{1-6}$ alkyl-sulfonyloxy group (e.g., methylsulfonyloxy).

L is —$CH_2NHCOR^7$, —$OCH_2CONR^8R^9$ or —$CH_2$-Het (wherein $R^7$ is a hydrogen atom, a $C_{1-3}$ alkyl group or a $C_{1-3}$ alkoxy group; $R^8$ is a hydrogen atom or an optionally substituted $C_{1-6}$ alkyl group; $R^9$ is a hydrogen atom, an optionally substituted hydrocarbon group or an optionally substituted heterocyclic group; and Het is a nitrogen-containing aromatic heterocyclic group). Particularly, —$CH_2NHCOR^7$ (wherein $R^7$ is as defined above) is preferable.

Here, as the $C_{1-3}$ alkyl group for $R^7$, for example, methyl, ethyl, propyl, isopropyl and the like can be mentioned.

As the $C_{1-3}$ alkoxy group for $R^7$, for example, methoxy, ethoxy, propoxy, isopropoxy and the like can be mentioned.

$R^7$ is preferably a methyl group or a methoxy group.

As the "optionally substituted $C_{1-6}$ alkyl group" for $R^8$, those exemplified for the aforementioned $R^4$ can be used. As the "optionally substituted hydrocarbon group" and "optionally substituted heterocyclic group" for $R^9$, those exemplified for the aforementioned $R^5$ can be used respectively. $R^8$ is preferably a hydrogen atom or a $C_{1-6}$ alkyl group. $R^9$ is preferably a hydrogen atom, a $C_{1-6}$ alkyl group optionally substituted by a heterocyclic group (preferably imidazolyl) or a $C_{7-14}$ aralkyl group (preferably phenethyl).

As the nitrogen-containing aromatic heterocyclic group for Het, an aromatic heterocyclic group having at least one nitrogen atom as a ring-constituting atom (e.g., pyrrolyl, oxazolyl, isoxazolyl, thiazolyl, isothiazolyl, imidazolyl, pyrazolyl, oxadiazolyl, furazanyl, thiadiazolyl, triazolyl, tetrazolyl, pyridyl, pyridazinyl, pyrimidinyl, pyrazinyl) can be used from the heterocyclic group exemplified as the substituents for ring B'. Particularly, imidazolyl and triazolyl are preferable.

Ring D is preferably substituted by L at the meta position.

As the "optionally substituted $C_{1-6}$ alkyl group" for $R^{4a}$, those exemplified for the aforementioned $R^4$ can be used. Particularly, a $C_{1-6}$ alkyl group is preferable. $R^{4a}$ is preferably a hydrogen atom or a methyl group, more preferably a hydrogen atom.

As the "optionally substituted hydrocarbon group" and "optionally substituted heterocyclic group" for $R^{5a}$, those exemplified for the aforementioned $R^5$ can be used respectively.

$R^{5a}$ is preferably an "optionally substituted $C_{1-6}$ alkyl group", an "optionally substituted $C_{7-14}$ aralkyl groups", an "optionally substituted $C_{3-10}$ cycloalkyl-$C_{1-6}$ alkyl group", an "optionally substituted phenyl group", an "optionally substituted $C_{3-10}$ cycloalkyl group" or an "optionally substituted heterocyclic group".

Here, as preferable specific examples of the "optionally substituted $C_{1-6}$ alkyl group", a $C_{1-6}$ alkyl group (preferably methyl, ethyl, propyl) optionally having 1 to 3 substituents selected from a halogen atom, a carboxyl group, an optionally substituted heterocyclic group (preferably furyl, thienyl, pyridyl, tetrahydrofuranyl), a $C_{1-6}$ alkoxy-carbonyl group (preferably t-butoxycarbonyl) and the like, and the like can be mentioned.

As preferable specific examples of the "optionally substituted $C_{7-14}$ aralkyl group", a $C_{7-14}$ aralkyl group (preferably benzyl, phenethyl, 2-phenylpropyl) optionally having 1 to 3 substituents selected from a halogen atom, an optionally halogenated $C_{1-6}$ alkyl group (preferably trifluoromethyl), a $C_{1-6}$ alkylsulfonyl group (preferably methylsulfonyl), a $C_{1-6}$ alkylthio group (preferably methylthio), a $C_{1-6}$ alkoxy group (preferably methoxy) and the like, and the like can be mentioned.

As preferable specific examples of the "optionally substituted $C_{3-10}$ cycloalkyl-$C_{1-6}$ alkyl group", a $C_{3-10}$ cycloalkyl-$C_{1-6}$ alkyl group (preferably cyclopropylmethyl, cyclohexylmethyl, cycloheptylmethyl) optionally having 1 to 3 substituents selected from a carboxyl group, a $C_{1-6}$ alkoxycarbonyl group (preferably methoxycarbonyl) and the like, and the like can be mentioned.

As preferable specific examples of the "optionally substituted phenyl group", a phenyl group and the like can be mentioned.

As preferable specific examples of the "optionally substituted $C_{3-10}$ cycloalkyl group", a $C_{3-10}$ cycloalkyl group (preferably cyclohexyl) and the like can be mentioned.

$R^{5a}$ is more preferably a $C_{1-6}$ alkyl group substituted by an optionally substituted heterocyclic group (preferably furyl, thienyl, pyridyl, tetrahydrofuranyl), an optionally substituted $C_{7-14}$ aralkyl group or an optionally substituted $C_{3-10}$ cycloalkyl-$C_{1-6}$ alkyl group.

When $Z^2$ is —$NR^{4a}$— (wherein $R^{4a}$ is as defined above), as the "optionally substituted nitrogen-containing heterocycle" formed by $R^{5a}$ and $R^{4a}$ bonded to each other, together with the adjacent nitrogen atom, those similar to the "optionally substituted nitrogen-containing heterocycle" formed by the aforementioned $R^4$ and $R^5$ can be mentioned. Particularly, tetrahydroisoquinoline and the like are preferable.

In compound (IA), preferably, one of $Z^1$ and $Z^2$ is —NH— and the other is a bond.

Of compounds (IA), a compound wherein ring Aa is a benzene ring optionally substituted by a halogen atom (preferably a chlorine atom);

ring D is a benzene ring optionally having a $C_{1-6}$ alkoxy group besides L;

$R^{1b}$ is a $C_{1-6}$ alkyl group optionally substituted by substituent(s) selected from 1) a heterocyclic group (preferably furyl, thienyl, quinolyl) optionally substituted by substituent(s) selected from a phenyl group optionally substituted by a $C_{1-6}$ alkoxy group and a heterocyclic group (preferably furyl, thienyl), 2) a hydroxy group, 3) a $C_{1-6}$ alkyl-carbonyloxy group and 4) a $C_{1-6}$ alkylsulfonyloxy group;

L is —$CH_2NHCOR^7$ (wherein $R^7$ is a hydrogen atom, a $C_{1-3}$ alkyl group or a $C_{1-3}$ alkoxy group) which substitutes the meta position of ring D;

$R^{5a}$ is (1) a $C_{1-6}$ alkyl group substituted by an optionally substituted heterocyclic group (preferably furyl, thienyl, pyridyl, tetrahydrofuranyl); (2) a $C_{7-14}$ aralkyl group optionally having 1 to 3 substituents selected from a halogen atom, an optionally halogenated $C_{1-6}$ alkyl group, a $C_{1-6}$ alkylsulfonyl group, a $C_{1-6}$ alkylthio group, a $C_{1-6}$ alkoxy group and the like; or (3) a $C_{3-10}$ cycloalkyl-$C_{1-6}$ alkyl group optionally having 1 to 3 substituents selected from a carboxyl group, a $C_{1-6}$ alkoxy-carbonyl group and the like; and one of $Z^1$ and $Z^2$ is —NH— and the other is a bond (preferably $Z^1$ is a bond, $Z^2$ is —NH—), is preferable.

As preferable specific examples of compound (I), the following compounds can be mentioned.

2-[3,5-trans-5-(3-aminophenyl)-7-chloro-1-neopentyl-2-oxo-1,2,3,5-tetrahydro-4,1-benzoxazepin-3-yl]-N-(2-fluorobenzyl)acetamide, 2-[3,5-trans-7-chloro-5-[3-([1,3]dioxolan-2-yl)phenyl]-1-neopentyl-2-oxo-1,2,3,5-tetrahydro-4,1-benzoxazepin-3-yl]-N-(2-fluorobenzyl)acetamide, 2-[3,5-trans-5-[3-(acetylaminomethyl)phenyl]-7-chloro-1-neopentyl-2-oxo-1,2,3,5-tetrahydro-4,1-benzoxazepin-3-yl]-N-(2-fluorobenzyl)acetamide, 2-{3,5-trans-7-chloro-5-[3-(methanesulfonylaminomethyl)phenyl]-1-neopentyl-2-oxo-1,2,3,5-tetrahydro-4,1-benzoxazepin-3-yl}-N-(2-fluorobenzyl)acetamide, N-[3-[3,5-trans-7-chloro-3-[2-[(2-fluorobenzyl)amino]-2-oxoethyl]-1-neopentyl-2-oxo-1,2,3,5-tetrahydro-4,1-benzoxazepin-5-yl]benzyl]-2,2,2-trifluoroacetamide, methyl [3-[3,5-trans-7-chloro-3-[2-[(2-fluorobenzyl)amino]-2-oxoethyl]-1-neopentyl-2-oxo-1,2,3,5-tetrahydro-4,1-benzoxazepin-5-yl]benzyl]carbamate, 2-[3,5-trans-7-chloro-5-[3-[[[(methylamino)carbonyl]amino]methyl]phenyl]-1-neopentyl-2-oxo-1,2,3,5-tetrahydro-4,1-benzoxazepin-3-yl]-N-(2-fluorobenzyl)acetamide, 2-[3,5-trans-7-chloro-5-(3-formylphenyl)-1-neopentyl-2-oxo-1,2,3,5-tetrahydro-4,1-benzoxazepin-3-yl]-N-(2-fluorobenzyl)acetamide, 2-[3,5-trans-7-chloro-5-(3-hydroxymethylphenyl)-1-neopentyl-2-oxo-1,2,3,5-tetrahydro-4,1-benzoxazepin-3-yl]-N-(2-fluorobenzyl)acetamide, N-[3-[3,5-trans-7-chloro-3-[2-[(2-fluorobenzyl)amino]-2-oxoethyl]-1-neopentyl-2-oxo-1,2,3,5-tetrahydro-4,1-benzoxazepin-5-yl]benzyl]propanamide, N-[3-[3,5-trans-7-chloro-3-[2-[(2-fluorobenzyl)amino]-2-oxoethyl]-1-neopentyl-2-oxo-1,2,3,5-tetrahydro-4,1-benzoxazepin-5-yl]benzyl]butanamide, ethyl [3-[3,5-trans-7-chloro-3-[2-[(2-fluorobenzyl)amino]-2-oxoethyl]-1-neopentyl-2-oxo-1,2,3,5-tetrahydro-4,1-benzoxazepin-5-yl]benzyl]carbamate, ethyl 3,5-trans-5-[3-(acetylaminomethyl)phenyl]-7-chloro-1-neopentyl-2-oxo-1,2,3,5-tetrahydro-4,1-benzoxazepine-3-acetate, 2-[3,5-trans-5-[3-(acetylaminomethyl)phenyl]-7-chloro-1-neopentyl-2-oxo-1,2,3,5-tetrahydro-4,1-benzoxazepin-3-yl]-N-benzylacetamide, 2-[3,5-trans-5-[3-(acetylaminomethyl)phenyl]-7-chloro-1-neopentyl-2-oxo-1,2,3,5-tetrahydro-4,1-benzoxazepin-3-yl]-N-(2-pyridylmethyl)acetamide, 2-[3,5-trans-5-[3-(acetylaminomethyl)phenyl]-7-chloro-1-neopentyl-2-oxo-1,2,3,5-tetrahydro-4,1-benzoxazepin-3-yl]-N-(cyclohexylmethyl)acetamide, 2-[3,5-trans-5-[3-(acetylaminomethyl)phenyl]-7-chloro-1-neopentyl-2-oxo-1,2,3,5-tetrahydro-4,1-benzoxazepin-3-yl]-N-(2-bromobenzyl)acetamide, 2-[3,5-trans-5-[3-(acetylaminomethyl)phenyl]-7-chloro-1-neopentyl-2-oxo-1,2,3,5-tetrahydro-4,1-benzoxazepin-3-yl]-N-(2,6-difluorobenzyl)acetamide, methyl [3-[3,5-trans-7-chloro-1-neopentyl-2-oxo-3-[2-oxo-2-[[2-(trifluoromethyl)benzyl]amino]ethyl]-1,2,3,5-tetrahydro-4,1-benzoxazepin-5-yl]benzyl]carbamate, methyl [3-[3,5-trans-7-chloro-3-[2-[(cyclohexylmethyl)amino]-2-oxoethyl]-1-neopentyl-2-oxo-1,2,3,5-tetrahydro-4,1-benzoxazepin-5-yl]benzyl]carbamate, N-{[3,5-trans-5-[3-(acetylaminomethyl)phenyl]-7-chloro-1-neopentyl-2-oxo-1,2,3,5-tetrahydro-4,1-benzoxazepin-3-yl]methyl}-2-(2-fluorophenyl)acetamide, N-[3-[3,5-trans-7-chloro-3-[[[[(2-fluorobenzyl)amino]carbonyl]amino]methyl]-1-neopentyl-2-oxo-1,2,3,5-tetrahydro-4,1-benzoxazepin-5-yl]benzyl]acetamide, 3-[3,5-trans-5-[3-(acetylaminomethyl)phenyl]-7-chloro-3-[2-[(2-fluorobenzyl)amino]-2-oxoethyl]-2-oxo-2,3-dihydro-4,1-benzoxazepin-1(5H)-yl]-2,2-dimethylpropyl acetate, 3-[3,5-trans-7-chloro-3-[2-[(2-fluorobenzyl)amino]-2-oxoethyl]-5-[3-(methoxycarbonylaminomethyl)phenyl]-2-oxo-2,3-dihydro-4,1-benzoxazepin-1(5H)-yl]-2,2-dimethylpropyl acetate, 2-[3,5-trans-5-[3-(acetylaminomethyl)phenyl]-7-chloro-1-(3-hydroxy-2,2-dimethylpropyl)-2-oxo-1,2,3,5-tetrahydro-4,1-benzoxazepin-3-yl]-N-(2-fluorobenzyl)acetamide, methyl [3-[3,5-trans-7-chloro-3-[2-[(2-fluorobenzyl)amino]-2-oxoethyl]-1-(3-hydroxy-2,2-dimethylpropyl)-2-oxo-1,2,3,5-tetrahydro-4,1-benzoxazepin-5-yl]benzyl]carbamate, 3-[3,5-trans-7-chloro-5-[3-(methoxycarbonylaminomethyl)phenyl]-2-oxo-3-[2-oxo-2-[[2-(trifluoromethyl)benzyl]amino]ethyl]-2,3-dihydro-4,1-benzoxazepin-1(5H)-yl]-2,2-dimethylpropyl acetate, methyl [3-[3,5-trans-7-chloro-1-(3-hydroxy-2,2-dimethylpropyl)-2-oxo-3-[2-oxo-2-[[2-(trifluoromethyl)benzyl]amino]ethyl]-1,2,3,5-tetrahydro-4,1-benzoxazepin-5-yl]benzyl]carbamate, 2-[3,5-trans-5-[3-(acetylaminomethyl)phenyl]-7-chloro-1-neopentyl-2-oxo-1,2,3,5-tetrahydro-4,1-benzoxazepin-3-yl]-N-(2-furylmethyl)acetamide, N-(2-fluorobenzyl)-2-(4-isonicotinoyl-1-neopentyl-2-oxo-2,3,4,5-tetrahydro-1H-1,4-benzodiazepin-3-yl)acetamide, N-(2-fluorobenzyl)-2-[4-(2-methylisonicotinoyl)-1-neopentyl-2-oxo-2,3,4,5-tetrahydro-1H-1,4-benzodiazepin-3-yl]acetamide, 2-[4-(2-chloroisonicotinoyl)-1-neopentyl-2-oxo-2,3,4,5-tetrahydro-1H-1,4-benzodiazepin-3-yl]-N-(2-fluorobenzyl)acetamide, N-(2-fluorobenzyl)-2-[1-neopentyl-2-oxo-4-(pyridin-4-ylmethyl)-2,3,4,5-tetrahydro-1H-1,4-benzodiazepin-3-yl]acetamide, 4-(3,4-dichlorobenzyl)-6-phenyl-2,3,4,5-tetrahydropyrido[3,2-f][1,4]oxazepine hydrochloride, 4-[3,5-bis(trifluoromethyl)benzyl]-6-phenyl-2,3,4,5-tetrahydropyrido[3,2-f][1,4]oxazepine, 4-(3,5-dinitrobenzyl)-6-phenyl-2,3,4,5-tetrahydropyrido[3,2-f][1,4]oxazepine, 4-[3,5-bis(trifluoromethyl)benzoyl]-6-phenyl-2,3,4,5-tetrahydropyrido[3,2-f][1,4]oxazepine, 5-[3,5-bis(trifluoromethyl)benzoyl]-7-phenyl-3,4,5,6-tetrahydro-2H-pyrido[2,3-b][1,5]oxazocine, 4-{[3,5-bis(trifluoromethyl)phenyl]sulfonyl}-6-phenyl-2,3,4,5-tetrahydropyrido[3,2-f][1,4]oxazepine, 5-{[3,5-bis(trifluoromethyl)phenyl]sulfonyl}-7-phenyl-3,4,5,6-tetrahydro-2H-pyrido[2,3-b][1,5]oxazocine, 4-(3,5-dichlorobenzoyl)-6-phenyl-2,3,4,5-tetrahydropyrido[3,2-f][1,4]oxazepine, 4-{1-[3,5-bis(trifluoromethyl)phenyl]ethyl}-6-phenyl-2,3,4,5-tetrahydropyrido[3,2-f][1,4]oxazepine hydrochloride, 4-{2-[3,5-bis(trifluoromethyl)phenyl]ethyl}-6-phenyl-2,3,4,5-tetrahydropyrido[3,2-f][1,4]oxazepine hydrochloride, 5-{[3,5-bis(trifluoromethyl)phenyl]sulfonyl}-7-(4-fluorophenyl)-3,4,5,6-tetrahydro-2H-pyrido[2,3-b][1,5]oxazocine, 6-[3,5-bis(trifluoromethyl)benzoyl]-8-(4-fluorophenyl)-2,3,4,5,6,7-hexahydropyrido[2,3-b][1,5]oxazonine.

Of compound (I), compound (IB), compound (IC) and compound (IA) are novel compounds.

As the salts of the compound represented by the formula (I) [including compounds represented by the formulas (I'), (II), (III), (IB), (IC) and (IA)], a pharmacologically acceptable salt is preferable, and salts with inorganic bases, salts with organic bases, salts with inorganic acids, salts with organic acids, salts with basic or acidic amino acids and the like can be mentioned.

Preferable examples of the salt with inorganic base include alkali metal salts such as sodium salt, potassium salt, lithium salt and the like; alkaline earth metal salts such as calcium salt, magnesium salt and the like; aluminum salt, ammonium salts, and the like.

Preferable examples of the salt with organic base include salts with trimethylamine, triethylamine, pyridine, picoline, ethanolamine, diethanolamine, triethanolamine, dicyclohexylamine, N,N-dibenzylethylenediamine and the like.

Preferable examples of the salt with inorganic acid include salts with hydrochloric acid, hydrobromic acid, nitric acid, sulfuric acid, phosphoric acid and the like.

Preferable examples of the salt with organic acid include salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid and the like.

Preferable examples of the salt with basic amino acid include salts with arginine, lysine, ornithine and the like.

Preferable examples of the salt with acidic amino acid include salts with aspartic acid, glutamic acid and the like.

The compound (I) can be produced according to a method known per se, such as methods described in WO98/47882 (JP-A-11-209356), EP733632 and the like, or methods analogous thereto.

The production methods of compound (IB), compound (IC) and compound (IA) are described in detail below.

In the following production methods, when alkylation reaction, amidation reaction, esterification reaction, reductive reaction, reductive amination reaction and the like are performed, these reactions are carried out according to a method known per se. As such method, for example, methods described in *ORGANIC FUNCTIONAL GROUP PREPARATIONS,* 2nd ed., ACADEMIC PRESS, INC., 1989; *Comprehensive Organic Transformations*, VCH Publishers Inc., 1989 and the like can be mentioned.

In the following production methods, moreover, when a starting compound can form a salt, the compound may be used as a salt. As such salt, those exemplified as the salt of compound (I) can be used.

The compound (IB) can be produced by, for example, Method A to Method E shown below, or methods analogous thereto.

The compound (IB) can be produced by, for example, reacting compound (IBa) with compound (IBb).

[Method A]

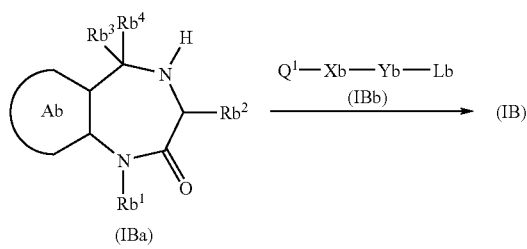

wherein $Q^1$ is a leaving group, and other symbols are as defined above.

As the leaving group for $Q^1$, for example, a halogen atom (e.g., chlorine, bromine, iodine), optionally halogenated $C_{1-6}$ alkylsulfonyloxy (e.g., methylsulfonyloxy, ethylsulfonyloxy, trifluoromethylsulfonyloxy), a $C_{6-10}$ arylsulfonyloxy optionally substituted by $C_{1-6}$ alkyl (e.g., benzenesulfonyloxy, toluenesulfonyloxy), hydroxy, $C_{1-6}$ alkoxy and the like can be mentioned.

[Method A-1]

When Xb is a divalent hydrocarbon group, Method A is performed according to an alkylation reaction known per se. In this case, the leaving group for $Q^1$ is preferably a halogen atom (e.g., chlorine, bromine, iodine), $C_{1-6}$ alkylsulfonyloxy (e.g., methylsulfonyloxy), $C_{6-10}$ arylsulfonyloxy optionally substituted by $C_{1-6}$ alkyl (e.g., benzenesulfonyloxy, toluenesulfonyloxy), and the like.

This reaction is generally carried out in a solvent that does not adversely affect the reaction. As such solvent, for example, ether solvents (e.g., diethyl ether, tetrahydrofuran, dioxane), halogenated hydrocarbon solvents (e.g., dichloromethane, dichloroethane, chloroform, carbon tetrachloride), amide solvents (e.g., dimethylformamide), sulfoxide solvents (e.g., dimethylsulfoxide), nitrile solvents (e.g., acetonitrile) and the like can be mentioned. These solvents may be used in a mixture of two or more kinds thereof at an appropriate ratio.

Where necessary, this reaction may be carried out in the presence of a base (e.g., amines such as triethylamine, triethylenediamine, tetramethylethylenediamine and the like; alkali metal salts such as sodium hydrogencarbonate, potassium hydrogencarbonate, sodium carbonate, potassium carbonate, sodium hydride, potassium hydride and the like). The amount of the base to be used is generally 1 to 10 molar equivalents, preferably 1 to 5 molar equivalents, per 1 mol of compound (IBa).

The amount of compound (IBb) to be used is generally 1 to 10 molar equivalents, preferably 1 to 3 molar equivalents, per 1 mol of compound (IBa).

The reaction temperature is generally 0° C. to 150° C., preferably 20° C. to 100° C.

The reaction time is generally 1 to 48 hrs, preferably 1 to 20 hrs.

[Method A-1a]

The compound (IB) can be also produced by subjecting the compound (IBb') and compound (IBa) to a reductive amination reaction using compound (IBb') represented by formula: $Rb^8$—CO-Xb'-Yb-Lb (wherein $Rb^8$ is a hydrogen atom or a hydrocarbon group, Xb' is a bond or a divalent hydrocarbon group, and other symbols are as defined above) instead of the aforementioned compound (IBb).

Here, as the hydrocarbon group for $Rb^8$, those similar to the "hydrocarbon group" of the "optionally substituted hydrocarbon group", which is a substituent for the aforementioned ring B', can be used. The "hydrocarbon group" is preferably $C_{1-6}$ alkyl or the like. In addition, $Rb^8$ is preferably a hydrogen atom or $C_{1-6}$ alkyl.

As the divalent hydrocarbon group for Xb', those exemplified for the aforementioned Xb can be used. Xb' is preferably a bond or $C_{1-5}$ alkylene.

This reaction is generally carried out in a solvent that does not adversely affect the reaction.

As the solvent that does not adversely affect the reaction, for example, ether solvents (e.g., diethyl ether, tetrahydrofuran, dioxane), hydrocarbon solvents (e.g., benzene, toluene, hexane, heptane), alcohol solvents (e.g., methanol, ethanol, propanol), ester solvents (e.g., methyl acetate, ethyl acetate) and the like can be mentioned. These solvents may be used in a mixture of two or more kinds thereof at an appropriate ratio. The reductive amination reaction is carried out by, for example, a catalytic reduction using palladium, platinum and the like as a catalyst; a reduction using a reducing agent (e.g., sodium borohydride, sodium cyanoborohydride, sodium triacetoxyborohydride and the like. The amount of the reducing agent to be used is generally 0.5 to 10 equivalents, preferably 0.5 to 2 molar equivalents, per 1 mol of compound (IBa).

This reaction may be carried out in the presence of an acid (e.g., acetic acid) where necessary. The amount of the acid to be used is generally 1 to 10 equivalents, preferably 1 to 2 molar equivalents, per 1 mol of compound (IBa).

The amount of compound (IBb') to be used is generally 1 to 10 molar equivalents, preferably 1 to 2 molar equivalents, per 1 mol of compound (IBa).

The reaction temperature is generally 0° C. to 100° C., preferably 10° C. to 70° C.

The reaction time is generally 1 to 48 hrs, preferably 1 to 20 hrs.

The above-mentioned compound (IBb') can be produced according to a method known per se.

[Method A-2]

When Xb is —CO—, Method A is performed according to an amidation reaction known per se. The amidation reaction is carried out using, for example, "a method of directly condensing compound (IBa) and compound (IBb)", "a method of reacting a reactive derivative of compound (IBb) with compound (IBa)" and the like.

Here, the "method of directly condensing compound (IBa) and compound (IBb)" is generally carried out in the presence of a condensing agent in a solvent that does not adversely affect the reaction.

As the condensing agent, a condensing agent employed for general peptide synthesis are used, and specific examples thereof include carbodiimide condensing reagents such as dicyclohexylcarbodiimide, diisopropylcarbodiimide, 1-ethyl-3-(3-dimethylaminopropyl)carbodiimide and hydrochloride thereof and the like; phosphoric acid condensing reagents such as diethyl cyanophosphate, diphenylphosphoryl azide and the like; carbonyldiimidazole, 2-chloro-1,3-dimethylimidazolium tetrafluoroborate and the like can be mentioned. The amount of the condensing agent to be used is generally 1 to 10 molar equivalents, preferably 1 to 2 molar equivalents, per 1 mol of compound (IBa).

As the solvent that does not adversely affect the reaction, for example, ether solvents (e.g., diethyl ether, tetrahydrofuran, dioxane), halogenated hydrocarbon solvents (e.g., dichloromethane, dichloroethane, chloroform, carbon tetrachloride), hydrocarbon solvents (e.g., benzene, toluene, hexane, heptane), amide solvents (e.g., dimethylformamide), nitrile solvents (e.g., acetonitrile) and the like can be mentioned. These solvents may be used in a mixture of two or more kinds thereof at an appropriate ratio.

Where necessary, this reaction may be carried out in the presence of a base (e.g., amines such as 4-dimethylaminopyridine, triethylamine, triethylenediamine, tetramethylethylenediamine and the like). The amount of the base to be used is generally 1 to 10 molar equivalents, preferably 1 to 5 molar equivalents, per 1 mol of compound (IBa).

The amount of compound (IBb) to be used is generally 1 to 10 molar equivalents, preferably 1 to 2 molar equivalents, per 1 mol of compound (IBa).

The reaction temperature is generally 0° C. to 150° C., preferably 10° C. to 50° C.

The reaction time is generally 1 to 48 hrs, preferably 1 to 20 hrs.

The aforementioned "method of reacting a reactive derivative of compound (IBb) with compound (IBa)" is generally carried out in a solvent that does not adversely affect the reaction.

Here, as the reactive derivative of compound (IBb), for example, acid halide, acid anhydride, activated ester, acid imidazolide, acid azide, haloformate, isocyanate and the like can be mentioned.

As the solvent that does not adversely affect the reaction, for example, ether solvents (e.g., diethyl ether, tetrahydrofuran, dioxane), halogenated hydrocarbon solvents (e.g., dichloromethane, dichloroethane, chloroform, carbon tetrachloride), hydrocarbon solvents (e.g., benzene, toluene, hexane, heptane), amide solvents (e.g., dimethylformamide, dimethylacetamide), nitrile solvents (e.g., acetonitrile), amine solvents (e.g., pyridine), ester solvents (e.g., methyl acetate, ethyl acetate) and the like can be mentioned. These solvents may be used in a mixture of two or more kinds thereof at an appropriate ratio.

Where necessary, this reaction may be carried out in the presence of water and/or a base (e.g., amines such as 4-dimethylaminopyridine, triethylamine, triethylenediamine, tetramethylethylenediamine and the like; alkali metal salts such as sodium hydrogencarbonate, potassium hydrogencarbonate, sodium carbonate, potassium carbonate, sodium hydride, potassium hydride and the like). The amount of the base to be used is generally 1 to 10 molar equivalents, preferably 1 to 5 molar equivalents, per 1 mol of compound (IBa).

The amount of the reactive derivative of compound (IBb) to be used is generally 1 to 10 molar equivalents, preferably 1 to 3 molar equivalents, per 1 mol of compound (IBa).

The reaction temperature is generally −50° C. to 100° C., preferably 0° C. to 50° C.

The reaction time is generally 1 to 48 hrs, preferably 1 to 20 hrs.

[Method A-3]

When Xb is —$SO_2$—, Method A is performed according to a sulfonylation reaction known per se. In this case, the leaving group for $Q^1$ is preferably a halogen atom (e.g., chlorine, bromine, iodine).

This reaction is generally carried out in a solvent that does not adversely affect the reaction. As such solvent, for example, ether solvents (e.g., diethyl ether, tetrahydrofuran, dioxane), halogenated hydrocarbon solvents (e.g., dichloromethane, dichloroethane, chloroform, carbon tetrachloride), hydrocarbon solvents (e.g., benzene, toluene, hexane, heptane), ester solvents (e.g., methyl acetate, ethyl acetate), ketone solvents (e.g., acetone), amide solvents (e.g., dimethylformamide, dimethylacetamide), sulfoxide solvents (e.g., dimethylsulfoxide), amine solvents (e.g., pyridine) and the like can be mentioned. These solvents may be used in a mixture of two or more kinds thereof at an appropriate ratio.

Where necessary, this reaction may be carried out in the presence of water and/or a base (e.g., amines such as 4-dimethylaminopyridine, triethylamine, triethylenediamine, tetramethylethylenediamine and the like; alkali metal salts such as sodium hydrogencarbonate, potassium hydrogencarbonate, sodium carbonate, potassium carbonate, sodium hydride, potassium hydride and the like). The amount of the base to be used is generally 1 to 10 molar equivalents, preferably 1 to 5 molar equivalents, per 1 mol of compound (IBa).

The amount of compound (IBb) to be used is generally 1 to 10 molar equivalents, preferably 1 to 3 molar equivalents, per 1 mol of compound (IBa).

The reaction temperature is generally −50° C. to 100° C., preferably 0° C. to 50° C.

The reaction time is generally 1 to 48 hrs, preferably 1 to 20 hrs.

Compound (IBb) used as the starting compounds in this method can be produced according to a method known per se.

The compound (IB) can be also produced by, for example, subjecting compound (IBc) to a cyclization reaction.

[Method B]

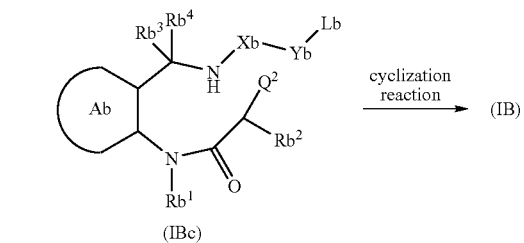

wherein $Q^2$ is a leaving group, and other symbols are as defined above.

As the leaving group for $Q^2$, for example, a halogen atom (e.g., chlorine, bromine, iodine), optionally halogenated $C_{1-6}$ alkylsulfonyloxy (e.g., methylsulfonyloxy, ethylsulfonyloxy, trifluoromethylsulfonyloxy), $C_{6-10}$ arylsulfonyloxy optionally substituted by $C_{1-6}$ alkyl (e.g., benzenesulfonyloxy, toluenesulfonyloxy) and the like can be mentioned. Among them, a halogen atom (e.g., chlorine, bromine, iodine) is preferable.

This reaction is generally carried out in a solvent that does not adversely affect the reaction. As such solvent, for example, ether solvents (e.g., diethyl ether, tetrahydrofuran, dioxane), hydrocarbon solvents (e.g., benzene, toluene, hexane, heptane), halogenated hydrocarbon solvents (e.g., dichloromethane, dichloroethane, chloroform, carbon tetrachloride), alcohol solvents (e.g., methanol, ethanol, propanol), ketone solvents (e.g., acetone), amide solvents (e.g., dimethylformamide), sulfoxide solvents (e.g., dimethylsulfoxide), nitrile solvents (e.g., acetonitrile) and the like can be mentioned. These solvents may be used in a mixture of two or more kinds thereof at an appropriate ratio.

Where necessary, this reaction may be carried out in the presence of water and/or a base (e.g., alkali metal salts such as sodium hydrogencarbonate, potassium hydrogencarbonate, sodium carbonate, potassium carbonate, sodium hydride, potassium hydride and the like; alkali metal alkoxides such as sodium methoxide, sodium ethoxide and the like). The amount of the base to be used is generally 1 to 10 molar equivalents, preferably 1 to 5 molar equivalents, per 1 mol of compound (IBc).

The reaction temperature is generally −20° C. to 200° C., preferably, 0° C. to 120° C.

The reaction time is generally 1 to 48 hrs, preferably 1 to 20 hrs.

The compound (IB) can be also produced by, for example, subjecting compound (IBd) to a cyclization reaction.

[Method C]

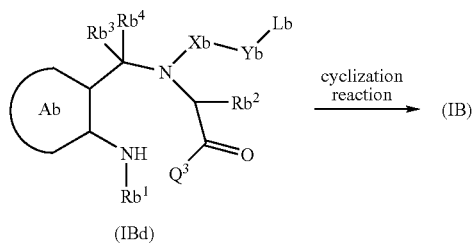

(IBd)

wherein $Q^3$ is a leaving group, and other symbols are as defined above.

As the leaving group for $Q^3$, those exemplified for the aforementioned $Q^1$ can be mentioned. Particularly, hydroxy and $C_{1-6}$ alkoxy are preferable.

For example, when $Q^3$ is hydroxy, this reaction is generally carried out in the presence of a condensing agent in a solvent that does not adversely affect the reaction.

Here, as the condensing agent, those exemplified in the aforementioned [Method A-2] can be used. The amount of the condensing agent to be used is generally 1 to 10 molar equivalents, preferably 1 to 2 molar equivalents, per 1 mol of compound (IBd).

As the solvent that does not adversely affect the reaction, for example, ether solvents (e.g., diethyl ether, tetrahydrofuran, dioxane), halogenated hydrocarbon solvents (e.g., dichloromethane, dichloroethane, chloroform, carbon tetrachloride), hydrocarbon solvents (e.g., benzene, toluene, hexane, heptane), amide solvents (e.g., dimethylformamide), nitrile solvents (e.g., acetonitrile) and the like can be mentioned. These solvents may be used in a mixture of two or more kinds thereof at an appropriate ratio.

Where necessary, this reaction may be carried out in the presence of a base (e.g., amines such as 4-dimethylaminopyridine, triethylamine, triethylenediamine, tetramethylethylenediamine and the like). The amount of the base to be used is generally 1 to 10 molar equivalents, preferably 1 to 2 molar equivalents, per 1 mol of compound (IBd).

The reaction temperature is generally 0° C. to 100° C., preferably 10° C. to 50° C.

The reaction time is generally 1 to 48 hrs, preferably 1 to 20 hrs.

When $Q^3$ is $C_{1-6}$ alkoxy, this reaction is generally carried out in a solvent that does not adversely affect the reaction. As such solvent, for example, ether solvents (e.g., diethyl ether, tetrahydrofuran, dioxane), hydrocarbon solvents (e.g., benzene, toluene, hexane, heptane), halogenated hydrocarbon solvents (e.g., dichloromethane, dichloroethane, chloroform, carbon tetrachloride), alcohol solvents (e.g., methanol, ethanol), amide solvents (e.g., dimethylformamide), nitrile solvents (e.g., acetonitrile) and the like can be mentioned. These solvents may be used in a mixture of two or more kinds thereof at an appropriate ratio.

Where necessary, this reaction may be carried out in the presence of a base (e.g., alkali metal salts such as sodium hydrogencarbonate, potassium hydrogencarbonate, sodium carbonate, potassium carbonate, sodium hydride, potassium hydride and the like; alkali metal alkoxides such as sodium methoxide, sodium ethoxide and the like).

When an aprotic solvent such as toluene and the like is used as a solvent that does not adversely affect the reaction, the reaction can be also carried out in the presence of a Lewis acid (e.g., trimethylaluminum).

The amount of the aforementioned base and Lewis acid to be used is generally 0.01 to 5 molar equivalents, preferably 0.1 to 1 molar equivalent, per 1 mol of compound (IBd).

The reaction temperature is generally −20° C. to 200° C., preferably 0° C. to 120° C.

The reaction time is generally 1 to 48 hrs, preferably 1 to 20 hrs.

The compounds (IB) obtained by the above-mentioned method can be isolated and purified by a known separation and purification means, such as concentration, concentration under reduced pressure, solvent extraction, crystallization, recrystallization, phase transfer, chromatography and the like.

Of compounds (IB), compound (IB-1) wherein $Rb^2$ is a methyl group substituted by an electron-withdrawing group selected from a $C_{1-6}$ alkoxy-carbonyl group, a $C_{6-14}$ aryloxy-carbonyl group, a $C_{1-6}$ alkyl-carbonyl group, a $C_{6-14}$ aryl-carbonyl group, a $C_{1-6}$ alkylsulfonyl group, a $C_{6-10}$ arylsulfonyl group, a cyano group and a nitro group, can be produced by, for example, subjecting compound (IBe) to a cyclization reaction.

[Method D]

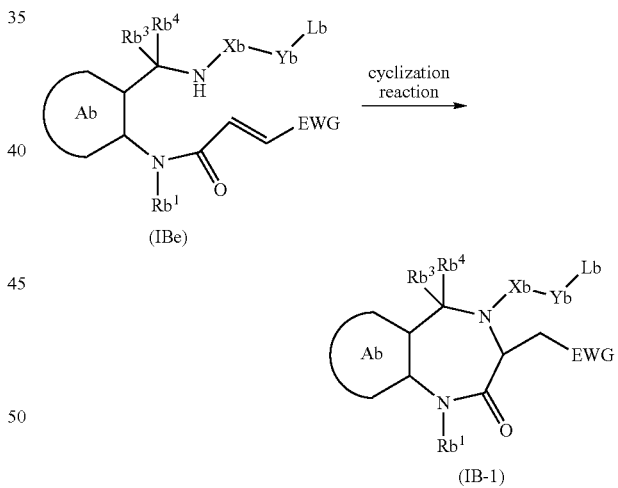

wherein EWG is an electron-withdrawing group selected from a $C_{1-6}$ alkoxy-carbonyl group, a $C_{6-14}$ aryloxy-carbonyl group, a $C_{1-6}$ alkyl-carbonyl group, a $C_{6-14}$ aryl-carbonyl group, a $C_{1-6}$ alkylsulfonyl group, a $C_{6-10}$ arylsulfonyl group, a cyano group and a nitro group, and other symbols are as defined above.

As the $C_{1-6}$ alkoxy-carbonyl group, $C_{6-14}$ aryloxy-carbonyl group, $C_{1-6}$ alkyl-carbonyl group, $C_{6-14}$ aryl-carbonyl group, $C_{1-6}$ alkylsulfonyl group and $C_{6-10}$ arylsulfonyl group for EWG, those exemplified as the "substituent" for the "optionally substituted hydrocarbon group", which is a substituent for the aforementioned ring B' can be respectively used.

Among them, $C_{1-6}$ alkoxy-carbonyl and the like are preferable.

This reaction is carried out in the same manner as in the aforementioned [Method B].

The compound (IB-1) thus obtained can be isolated and purified by a known separation and purification means, such as concentration, concentration under reduced pressure, solvent extraction, crystallization, recrystallization, phase transfer, chromatography and the like.

Of compounds (IB), compound (IB-3) wherein $Rb^2$ is $—CH_2—CO—N(Rb^6)(Rb^7)$ [wherein the symbols are as defined above] can be produced by, for example, subjecting, from compounds (IB-1), compound (IB-1') wherein EWG is a $C_{1-6}$ alkoxy-carbonyl group to hydrolysis reaction to give compound (IB-2) and reacting compound (IB-2) with compound (IBf).

[Method E]

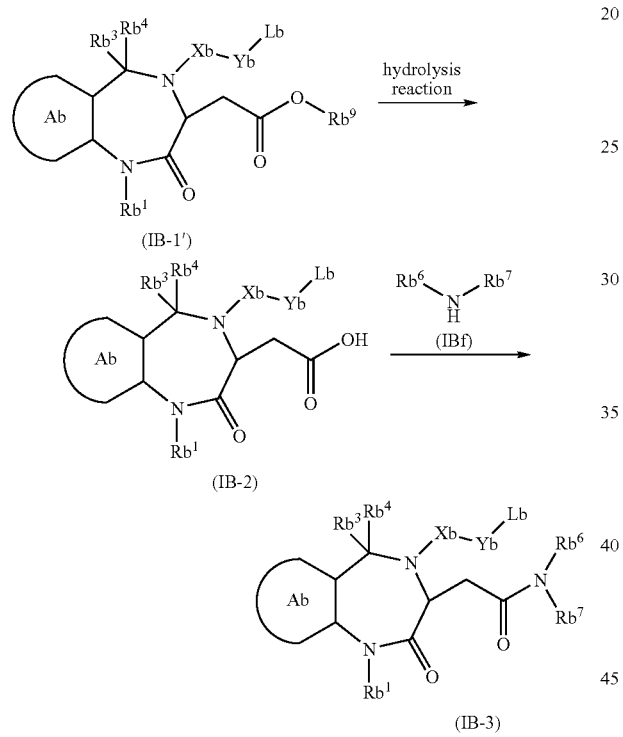

wherein $Rb^9$ is a $C_{1-6}$ alkyl group, and other symbols are as defined above.

As the $C_{1-6}$ alkyl group for $Rb^9$, for example, methyl, ethyl, tert-butyl and the like can be mentioned.

The hydrolysis reaction of compound (IB-1') is generally carried out in the presence of acid or base, in a solvent that does not adversely affect the reaction.

Here, as the acid or base, for example, mineral acids (e.g., nitric acid, hydrochloric acid, hydrobromic acid, sulfuric acid), alkali metal hydroxides (e.g., sodium hydroxide, potassium hydroxide, lithium hydroxide) and the like can be mentioned. The strength of these acid and base is preferably 1 to 10N, more preferably 1 to 6N.

As the solvent that does not adversely affect the reaction, for example, water, a mixed solvent of water and an ether solvent (e.g., diethyl ether, tetrahydrofuran, dioxane) or an alcohol solvent (e.g., methanol, ethanol, propanol) at an appropriate ratio and the like can be used.

The reaction temperature is generally 0° C. to 150° C., preferably 20° C. to 100° C.

The reaction time is generally 1 to 48 hrs, preferably 1 to 10 hrs.

The reaction of compound (IB-2) with compound (IBf) can be carried out in the same manner as in the reaction in the aforementioned [Method C] wherein $Q^3$ is hydroxy.

The compound (IB-3) thus obtained can be isolated and purified by a known separation and purification means, such as concentration, concentration under reduced pressure, solvent extraction, crystallization, recrystallization, phase transfer, chromatography and the like.

The compound (IBf) used as the starting compound in this method is commercially available as a reagent, or can be produced according to a method known per se.

The compound (IBa) used as the starting compound in the aforementioned [Method A] can be produced by the method shown below.

[Method F]

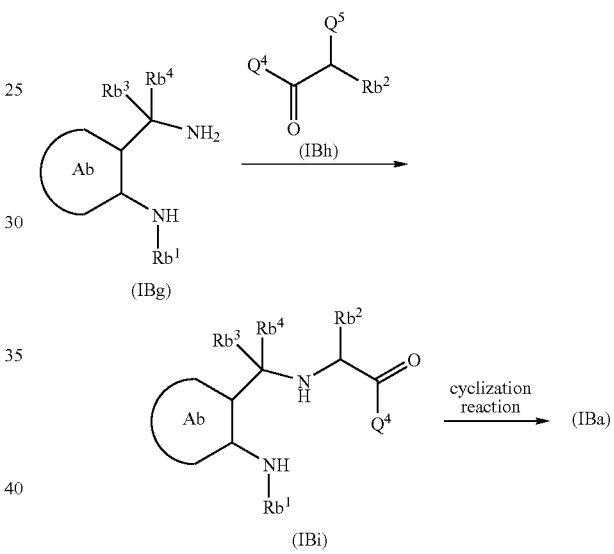

wherein $Q^4$ and $Q^5$ are each a leaving group, and other symbols are as defined above.

As the leaving group for $Q^4$ or $Q^5$, those exemplified for the aforementioned $Q^1$ can be mentioned. $Q^4$ is preferably hydroxy, $C_{1-6}$ alkoxy and $Q^5$ is preferably a halogen atom (e.g., chlorine, bromine, iodine).

In this method, compound (IBi) is produced by reacting compound (IBg) with compound (IBh). This reaction is carried out in the same manner as in the aforementioned [Method A-1].

By subjecting compound (IBi) to a cyclization reaction, compound (IBa) can be produced. This reaction is carried out in the same manner as in the aforementioned [Method C].

The compound (IBa) thus obtained can be isolated and purified by a known separation and purification means, such as concentration, concentration under reduced pressure, solvent extraction, crystallization, recrystallization, phase transfer, chromatography and the like.

The compound (IBg) and compound (IBh) used as the starting compounds in this method can be produced according to a method known per se.

Of compounds (IBa) used as the starting compound in the aforementioned [Method A], compound (IBa-1) wherein $Rb^2$ is a methyl group substituted by EWG (as defined above), can be also produced by, for example, the method shown below.

[Method G]

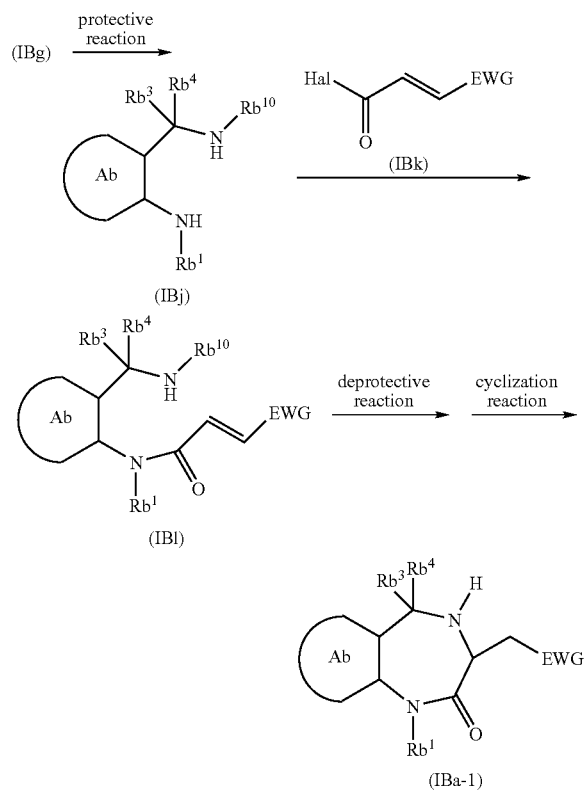

wherein Hal is a halogen atom, $Rb^{10}$ is an amino-protecting group, and other symbols are as defined above.

As the halogen atom for Hal, chlorine, bromine, iodine and the like can be mentioned. Among them, chlorine is preferable.

As the an amino-protecting group for $Rb^{10}$, for example, formyl, $C_{1-6}$ alkyl-carbonyl (e.g., acetyl, propionyl and the like), $C_{1-6}$ alkoxy-carbonyl (e.g., methoxycarbonyl, ethoxycarbonyl, tert-butoxycarbonyl and the like), benzoyl, $C_{7-13}$ aralkyl-carbonyl (e.g., benzylcarbonyl and the like), $C_{7-13}$ aralkyloxy-carbonyl (e.g., benzyloxycarbonyl, 9-fluorenylmethoxycarbonyl and the like), trityl, phthaloyl, N,N-dimethylaminomethylene, silyl (e.g., trimethylsilyl, triethylsilyl, dimethylphenylsilyl, tert-butyldimethylsilyl, tert-butyldiethylsilyl and the like), $C_{7-13}$ aralkyl (e.g., benzyl), $C_{2-6}$ alkenyl (e.g., 1-allyl and the like) and the like can be mentioned. These groups are optionally substituted by 1 to 3 halogen atoms (e.g., fluorine, chlorine, bromine, iodine and the like), $C_{1-6}$ alkoxy (e.g., methoxy, ethoxy, propoxy and the like), nitro and the like. $Rb^{10}$ is preferably $C_{1-6}$ alkoxy-carbonyl or $C_{7-13}$ aralkyloxy-carbonyl, more preferably tert-butoxycarbonyl or benzyloxycarbonyl.

In this method, compound (IBg) is subjected to a protective reaction (protection of amino group) to give compound (IBj), which is reacted with compound (IBk) to give compound (IBl), which is subjected to a deprotective reaction (deprotection of amino group) and further to a cyclization reaction to give compound (IBa-1)

The protective reaction and deprotective reaction are carried out according to a method known per se, such as the method described in *Protective Groups in Organic Synthesis*, John Wiley and Sons (1980), or a method analogous thereto.

For example, when $Rb^{10}$ is tert-butoxycarbonyl, the protective reaction is carried out by reacting compound (IBg) with di-tert-butyl dicarbonate in a solvent that does not adversely affect the reaction.

Here, as the solvent that does not adversely affect the reaction, for example, ether solvents (e.g., diethyl ether, tetrahydrofuran, dioxane), halogenated hydrocarbon solvents (e.g., dichloromethane, dichloroethane, chloroform, carbon tetrachloride), hydrocarbon solvents (e.g., benzene, toluene, hexane, heptane), amide solvents (e.g., dimethylformamide), nitrile solvents (e.g., acetonitrile), amine solvents (e.g., pyridine), ester solvents (e.g., methyl acetate, ethyl acetate) and the like can be mentioned. These solvents may be used in a mixture of two or more kinds thereof at an appropriate ratio.

This reaction may be carried out in the presence of, where necessary, water and/or a base (e.g., amines such as 4-dimethylaminopyridine, triethylamine, triethylenediamine, tetramethylethylenediamine and the like; alkali metal salts such as sodium hydrogencarbonate, potassium hydrogencarbonate, sodium carbonate, potassium carbonate, sodium hydride, potassium hydride and the like). The amount of the base to be used is generally 0 to 5 equivalents, preferably 1 to 1.5 molar equivalents, per 1 mol of compound (IBg).

The amount of di-tert-butyl dicarbonate to be used is generally 1 to 2 molar equivalents, preferably 1 to 1.2 molar equivalents, per 1 mol of compound (IBg).

The reaction temperature is generally −50° C. to 100° C., preferably 0° C. to 50° C.

The reaction time is generally 1 to 48 hrs, preferably 1 to 20 hrs.

The reaction between compound (IBj) and compound (IBk) is carried out in the same manner as in the "method for reacting a reactive derivative of compound (IBb) with compound (IBa)" in the aforementioned [Method A-2].

When $Rb^{10}$ is tert-butoxycarbonyl, the deprotective reaction is carried out by, for example, reacting compound (IBl) with acid (e.g., hydrochloric acid, hydrobromic acid, trifluoroacetic acid, solution of hydrogen chloride in ethyl acetate etc.).

The reaction temperature is generally −20° C. to 50° C., preferably 0° C. to 30° C.

The reaction time is generally 1 to 20 hrs, preferably 1 to 5 hrs.

The cyclization reaction of the deprotected compound (IBl) is generally carried out in a solvent that does not adversely affect the reaction. As such solvent, for example, ether solvents (e.g., diethyl ether, tetrahydrofuran, dioxane), halogenated hydrocarbon solvents (e.g., dichloromethane, dichloroethane, chloroform, carbon tetrachloride), alcohol solvents (e.g., methanol, ethanol, propanol), hydrocarbon solvents (e.g., benzene, toluene, hexane, heptane), nitrile solvents (e.g., acetonitrile), ester solvents (e.g., methyl acetate, ethyl acetate) and the like can be mentioned. These solvents may be used in a mixture of two or more kinds thereof at an appropriate ratio.

Where necessary, this reaction may be carried out in the presence of a base (e.g., alkali metal salts such as sodium hydrogencarbonate, potassium hydrogencarbonate, sodium carbonate, potassium carbonate, sodium hydride, potassium hydride and the like; alkali metal alkoxides such as sodium methoxide, sodium ethoxide and the like). The amount of the base to be used is generally 0.1 to 10 equivalents, preferably 0.1 to 2 molar equivalents, per 1 mol of the deprotected compound (IBl).

The reaction temperature is generally −20° C. to 100° C., preferably 0° C. to 50° C.

The reaction time is generally 1 to 48 hrs, preferably 1 to 20 hrs.

Compound (IBa-1) thus obtained can be isolated and purified by a known separation and purification means, such as concentration, concentration under reduced pressure, solvent extraction, crystallization, recrystallization, phase transfer, chromatography and the like.

The compound (IBk) used as the starting compound in this method can be produced according to a method known per se.

Of compounds (IBj) used in the aforementioned [Method G], compound (IBj-1) wherein $Rb^1$ is a hydrogen atom and $Rb^{10}$ is $C_{1-6}$ alkoxy-carbonyl, can be also produced by the method shown below.

[Method H]

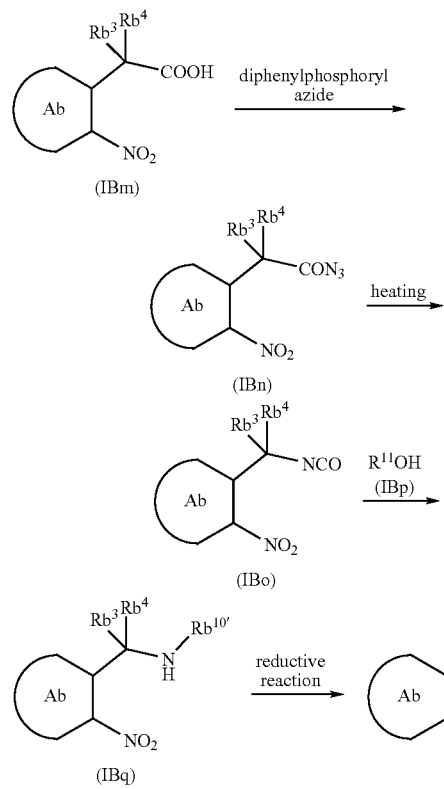

wherein $Rb^{10'}$ is $C_{1-6}$ alkoxy-carbonyl, $Rb^{11}$ is $C_{1-6}$ alkyl, and other symbols are as defined above.

As the $C_{1-6}$ alkoxy-carbonyl for $Rb^{10'}$, those exemplified for the aforementioned $Rb^{10}$ can be mentioned. Particularly, tert-butoxycarbonyl is preferable. As the $C_{1-6}$ alkyl for $Rb^{11}$, for example, methyl, ethyl, tert-butyl and the like can be mentioned. Among them, tert-butyl is preferable.

In this method, compound (IBm) is reacted with diphenylphosphoryl azide to give compound (IBn), which is then subjected to a Curtius rearrangement reaction to give compound (IBo), which is then reacted with compound (IBp) to give compound (IBq), which is then subjected to a reductive reaction to give compound (IBj-1).

This method is performed according to a method known per se.

First, compound (IBm) is reacted with diphenylphosphoryl azide generally in a solvent that does not adversely affect the reaction in the presence of a base.

As the solvent that does not adversely affect the reaction, for example, hydrocarbon solvents (e.g., benzene, toluene, hexane, heptane), ether solvents (e.g., diethyl ether, tetrahydrofuran, dioxane), halogenated hydrocarbon solvents (e.g., dichloromethane, dichloroethane, chloroform, carbon tetrachloride), amide solvents (e.g., dimethylformamide) and the like can be mentioned. These solvents may be used in a mixture of two or more kinds thereof at an appropriate ratio.

As the base, for example, amines such as triethylamine, triethylenediamine, pyridine and the like can be mentioned.

The amount of each of diphenylphosphoryl azide and the base to be used is generally 1 to 10 molar equivalents, preferably 1 to 3 molar equivalents, per 1 mol of compound (IBm).

The reaction temperature is generally −20° C. to 50° C., preferably 0° C. to 30° C.

The reaction time is generally 0.5 to 5 hrs, preferably 1 to 2 hrs.

The Curtius rearrangement reaction is carried out by, for example, heating compound (IBn) in a solvent such as hydrocarbon solvents (e.g., benzene, toluene) and the like.

The temperature during heating is generally 50° C. to 150° C., preferably 80° C. to 120° C.

The time of heating is generally 1 to 10 hrs, preferably 1 to 5 hrs.

The compound (IBo) can be reacted with compound (IBp) generally in a solvent that does not adversely affect the reaction. As such solvent, for example, hydrocarbon solvents (e.g., benzene, toluene) and the like can be mentioned.

Where necessary, this reaction may be carried out in the presence of a base (e.g., pyridine). The amount of the base to be used is generally 0.1 to 5 equivalents per 1 mol of compound (IBo).

The amount of compound (IBp) to be used is generally 1 to 10 molar equivalents, preferably 1 to 3 molar equivalents, per 1 mol of compound (IBo).

The reaction temperature is generally 20° C. to 150° C., preferably 50° C. to 120° C.

The reaction time is generally 1 to 48 hrs, preferably 1 to 20 hrs.

The reductive reaction of compound (IBq) can be carried out according to a method known per se.

The reductive reaction is specifically carried out by a catalytic reduction using palladium, platinum and the like as a catalyst; a reduction using iron or zinc and the like in acetic acid; a reduction using sodium hydrosulfite; and the like.

The reductive reaction is generally carried out in a solvent that does not adversely affect the reaction. As such solvent, for example, ether solvents (e.g., diethyl ether, tetrahydrofuran, dioxane), halogenated hydrocarbon solvents (e.g., dichloromethane, dichloroethane, chloroform, carbon tetrachloride), alcohol solvents (e.g., methanol, ethanol, propanol), hydrocarbon solvents (e.g., benzene, toluene, hexane, heptane), nitrile solvents (e.g., acetonitrile), ester solvents (e.g., methyl acetate, ethyl acetate), water and the like can be mentioned. These solvents may be used in a mixture of two or more kinds thereof at an appropriate ratio.

The reaction temperature is generally 0° C. to 100° C., preferably 20° C. to 50° C.

The reaction time is generally 1 to 48 hrs, preferably 1 to 20 hrs.

The compound (IBj-1) thus obtained can be isolated and purified by a known separation and purification means, such as concentration, concentration under reduced pressure, solvent extraction, crystallization, recrystallization, phase transfer, chromatography and the like.

The compound (IBm) and compound (IBp) used as the starting compounds in this method can be produced according to a method known per se.

Of compounds (IBa) used as the starting compound in the aforementioned [Method A], compound (IBa-2) wherein $Rb^3$ and $Rb^4$ are hydrogen atoms, can be also produced by, for example, the method shown below.

[Method I]

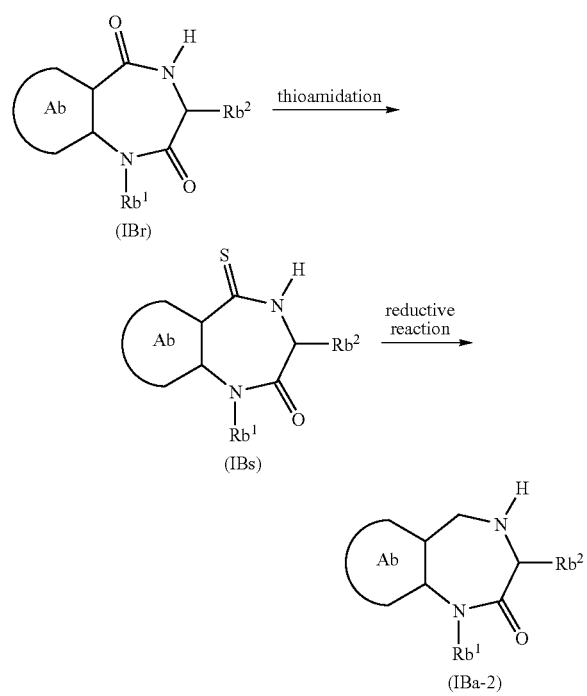

wherein the symbols in the formula are as defined above.

In this method, compound (IBr) is subjected to a thioamidation reaction to give compound (IBs), which is subjected to a reductive reaction to give compound (IBa-2).

The thioamidation reaction is carried out by reacting compound (IBr) with a sulfurating reagent in a solvent that does not adversely affect the reaction.

As the sulfurating reagent, for example, Lawesson reagent, phosphorus pentasulfide and the like can be mentioned. The amount of the sulfurating reagent to be used is generally 1 to 10 molar equivalents, preferably 1 to 3 molar equivalents, per 1 mol of compound (IBr).

As the solvent that does not adversely affect the reaction, for example, ether solvents (e.g., diethyl ether, tetrahydrofuran, dioxane), hydrocarbon solvents (e.g., benzene, toluene, hexane, heptane), alcohol solvents (e.g., methanol, ethanol, propanol), halogenated hydrocarbon solvents (e.g., dichloromethane, chloroform), amide solvents (e.g., hexamethylphosphoric triamide), amine solvents (e.g., pyridine), sulfoxide solvents (e.g., dimethylsulfoxide) and the like can be mentioned. These solvents may be used in a mixture of two or more kinds thereof at an appropriate ratio.

The reaction temperature is generally 0° C. to 150° C., preferably 50° C. to 100° C.

The reaction time is generally 1 to 48 hrs, preferably 1 to 10 hrs.

The reductive reaction of compound (IBs) can be carried out according to a method known per se. The reductive reaction is carried out by, for example, reacting compound (IBs) with Raney-nickel in a solvent that does not adversely affect the reaction. As such solvent, for example, alcohol solvents (e.g., methanol, ethanol, propanol), ether solvents (e.g., diethyl ether, tetrahydrofuran, dioxane) and the like can be mentioned. These solvents may be used in a mixture of two or more kinds thereof at an appropriate ratio. The reaction temperature is generally 0° C. to 150° C., preferably 10° C. to 100° C.

The reaction time is generally 1 to 48 hrs, preferably 1 to 20 hrs.

The compound (IBa-2) thus obtained can be isolated and purified by a known separation and purification means, such as concentration, concentration under reduced pressure, solvent extraction, crystallization, recrystallization, phase transfer, chromatography and the like.

The compound (IBr) used as the starting compound in this method can be produced according to a method known per se.

Compound (IBc) used as the starting compound in the aforementioned [Method B] can be produced by, for example, the method shown below.

[Method J]

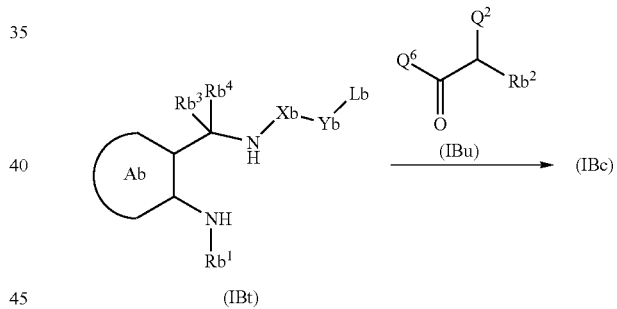

wherein $Q^6$ is a leaving group, and other symbols are as defined above.

As the leaving group for $Q^6$, those exemplified for the aforementioned $Q^1$ can be mentioned. Among them, a halogen atom (e.g., chlorine, bromine, iodine) is preferable.

This reaction is carried out in the same manner as in the "method of reacting a reactive derivative of compound (IBb) with compound (IBa)" in the aforementioned [Method A-2].

The compound (IBc) thus obtained can be isolated and purified by a known separation and purification means, such as concentration, concentration under reduced pressure, solvent extraction, crystallization, recrystallization, phase transfer, chromatography and the like.

The compound (IBt) used as the starting compound in this method can be produced by reacting compound (IBg) with compound (IBb). This reaction is carried out in the same manner as in the aforementioned [Method A].

The compound (IBt) thus obtained can be isolated and purified by a known separation and purification means, such as concentration, concentration under reduced pressure, solvent extraction, crystallization, recrystallization, phase transfer, chromatography and the like.

In addition, compound (IBu) used as the starting compound can be produced according to a method known per se.

The compound (IBd) used as the starting compound in the aforementioned [Method C] can be produced by, for example, the method shown below.

[Method K]

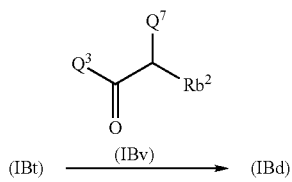

wherein $Q^7$ is a leaving group, and other symbols are as defined above.

As the leaving group for $Q^7$, those exemplified for the aforementioned $Q^1$ can be mentioned. Among them, a halogen atom (e.g., chlorine, bromine, iodine) is preferable.

This reaction is carried out in the same manner as in the aforementioned [Method A-1].

Of compounds (IBd) obtained in the aforementioned [Method K], compound (IBd) wherein $Q^3$ is $C_{1-6}$ alkoxy is further subjected to a hydrolysis reaction to give compound (IBd) wherein $Q^3$ is hydroxy. Here, the hydrolysis reaction is carried out by a method known per se. The compound (IBd) thus obtained can be isolated and purified by a known separation and purification means, such as concentration, concentration under reduced pressure, solvent extraction, crystallization, recrystallization, phase transfer, chromatography and the like.

The compound (IBv) used as the starting compound in this method can be produced according to a method known per se.

The compound (IBe) used as the starting compound in the aforementioned [Method D] can be produced by reacting compound (IBt) with compound (IBk).

This reaction is carried out in the same manner as in the "method of reacting a reactive derivative of compound (IBb) with compound (IBa)" in the aforementioned [Method A-2].

The compound (IBe) thus obtained can be isolated and purified by a known separation and purification means, such as concentration, concentration under reduced pressure, solvent extraction, crystallization, recrystallization, phase transfer, chromatography and the like.

The compound (IC) can be produced by, for example, Method AA to Method AC shown below, or methods analogous thereto.

The compound (IC) can be produced by, for example, reacting compound (ICa) with compound (ICb).

[Method AA]

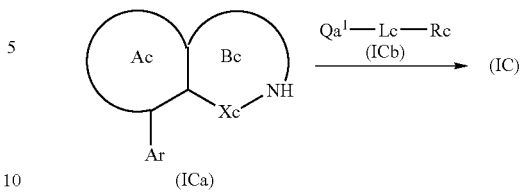

wherein $Qa^1$ is a leaving group, and other symbols are as defined above.

As the leaving group for $Qa^1$, those exemplified for the aforementioned $Q^1$ can be used. Among them, a halogen atom (e.g., chlorine, bromine, iodine), $C_{1-6}$ alkylsulfonyloxy (e.g., methylsulfonyloxy), hydroxy and the like are preferable.

Where necessary, this reaction can be carried out in a solvent that does not adversely affect the reaction. As such solvent, for example, hydrocarbon solvents (e.g., benzene, toluene, hexane, heptane), alcohol solvents (e.g., methanol, ethanol, propanol), ether solvents (e.g., diethyl ether, tetrahydrofuran, dioxane), halogenated hydrocarbon solvents (e.g., dichloromethane, dichloroethane, chloroform, carbon tetrachloride), nitrile solvents (e.g., acetonitrile), amide solvents (e.g., dimethylformamide), ketone solvents (e.g., acetone), sulfoxide solvents (e.g., dimethylsulfoxide), carboxylic acid solvents (e.g., acetic acid), ester solvents (e.g., methyl acetate, ethyl acetate), water and the like can be mentioned. These solvents may be used in a mixture of two or more kinds thereof at an appropriate ratio. Among them, alcohol solvents (e.g., ethanol), ether solvents (e.g., tetrahydrofuran), hydrocarbon solvents (e.g., toluene), amide solvents (e.g., dimethylformamide) and the like are preferable.

In addition, compound (ICa) and/or compound (ICb) may be used as a solvent.

Where necessary, this reaction can be carried out in the presence of a base, and the base may be used as a solvent. As such base, for example,
1) strong bases such as alkali metal or alkaline earth metal hydrides (e.g., lithium hydride, sodium hydride, potassium hydride, calcium hydride), alkali metal or alkaline earth metal amides (e.g., lithium amide, sodium amide, lithium diisopropylamide, lithium dicyclohexylamide, lithium hexamethyldisilazide, sodium hexamethyldisilazide, potassium hexamethyldisilazide), alkali metal or alkaline earth metal lower($C_{1-6}$) alkoxides (e.g., sodium methoxide, sodium ethoxide, potassium tert-butoxide) and the like;
2) inorganic bases such as alkali metal or alkaline earth metal hydroxides (e.g., sodium hydroxide, potassium hydroxide, lithium hydroxide, barium hydroxide), alkali metal or alkaline earth metal carbonates (e.g., sodium carbonate, potassium carbonate, cesium carbonate), alkali metal or alkaline earth metal hydrogencarbonates (e.g., sodium hydrogencarbonate, potassium hydrogencarbonate) and the like; and
3) organic bases such as amines such as triethylamine, diisopropylethylamine, N-methylmorpholine and the like; amidines such as DBU (1,8-diazabicyclo[5.4.0]undec-7-ene), DBN (1,5-diazabicyclo[4.3.0]non-5-ene) and the like; basic heterocyclic compounds such as pyridine, dimethylaminopyridine, imidazole, 2,6-lutidine and the like, and the like, and the like can be mentioned.

Among them, alkali metal carbonates (e.g., potassium carbonate), alkali metal hydrogencarbonates (e.g., sodium hydrogencarbonate), amines (e.g., triethylamine, diisopropylethylamine) and the like are preferable. The amount of the base to be used is generally 0.1 to 10 equivalents, preferably 0.1 to 2 molar equivalents, per 1 mol of compound (ICa).

The amount of compound (ICb) to be used is generally 1 to 10 molar equivalents, preferably 1 to 3 molar equivalents, per 1 mol of compound (ICa).

The reaction temperature is generally −100° C. to 200° C., preferably 0° C. to 150° C.

The reaction time is, for example, 1 minute to several days.

In the compounds (ICb), when $Qa^1$ is hydroxy, Lc is $C_{1-3}$ alkylene substituted by an oxo group, and a part or the entirety of Lc and $Qa^1$ form COOH (e.g., when $Qa^1$-Lc is HOOC, $HOOCCH_2$ and the like), this reaction can be also carried out in the presence of a suitable coupling reagent. As the coupling reagent, those generally used for peptide synthesis (e.g., those described in *Basics and Experiments of Peptide Synthesis* (1985; Maruzen)) can be used. Particularly, dicyclohexylcarbodiimide (DCC), diphenylphosphoryl azide (DPPA), carbonyldiimidazole (CDI) and the like are preferable. The amount of the coupling reagent to be used is generally 0.1 to 10 equivalents, preferably 0.1 to 2 molar equivalents, per 1 mol of compound (ICa).

The compound (IC) thus obtained can be isolated and purified by a known separation and purification means, such as concentration, concentration under reduced pressure, solvent extraction, crystallization, recrystallization, phase transfer, chromatography and the like.

The compound (ICb) used as the starting compound in this method can be produced by a method known per se, for example, methods described in *Comprehensive Organic Transformation*, VCH Publishers Inc., 1989; *Journal of the Organic Chemistry* (J. Org. Chem.) 52, 5560 (1987); *Organic Synthesis* (Org. Syn.) Coll. Vol. 4, 921 (1963); *Journal of the American Chemical Society* (J. Am. Chem. Soc.) 42, 599 (1920) and the like, or methods analogous thereto.

[Method AB]

Of compounds (IC), compound (IC-1) wherein Lc is an optionally substituted $C_{1-3}$ alkylene group can be also produced by subjecting compound (ICa) and a compound represented by the formula: OHC-$Lc^1$-Rc (wherein $Lc^1$ is an optionally substituted $C_{1-2}$ alkylene group and Rc is as defined above) [hereinafter sometimes to be abbreviated as compound (ICc)] to a reductive alkylation reaction.

Here, as the optionally substituted $C_{1-2}$ alkylene group for $Lc^1$, an optionally substituted $C_{1-3}$ alkylene group represented by the aforementioned $Lc^1$, wherein the alkylene moiety has 1 or 2 carbon atoms can be mentioned.

Where necessary, this reaction can be carried out in a solvent that does not adversely affect the reaction. As such solvent, those exemplified in the aforementioned [Method AA] can be used. Particularly, alcohol solvents (e.g., ethanol), ether solvents (e.g., tetrahydrofuran), hydrocarbon solvents (e.g., toluene), carboxylic acid solvents (e.g., acetic acid) and the like are preferable.

In addition, compound (ICa) and/or compound (ICc) may be used as a solvent.

This reaction is carried out by a reduction using a reducing agent; a catalytic reduction using palladium, platinum and the like as a catalyst, and the like.

Here, as the reducing agent, for example, aluminum reagents such as lithium aluminum hydride ($LiAlH_4$), diisobutyl aluminum hydride (DIBALH), bis(2-methoxyethoxy)aluminum hydride (Red-Al), alane ($AlH_3$) and the like; boron reagents such as sodium tetrahydroborate ($NaBH_4$), sodium cyanoborohydride ($NaBH_3CN$), sodium triacetoxyborohydride ($NaBH(OAc)_3$), 9-borabicyclo[3.3.1] nonane (9-BBN), borane ($BH_3$) and the like, and the like can be mentioned. Among them, boron reagents such as sodium tetrahydroborate, sodium cyanoborohydride, sodium triacetoxyborohydride and the like are preferable. The amount of the reducing agent to be used is generally 0.1 to 10 equivalents, preferably 0.1 to 2 molar equivalents, per 1 mol of compound (ICa).

This reaction is preferably carried out by a reduction using a boron reagent such as sodium tetrahydroborate, sodium cyanoborohydride, sodium triacetoxyborohydride and the like as a reducing agent; or a catalytic reduction using palladium, platinum and the like as a catalyst.

The amount of compound (ICc) to be used is generally 0.1 to 10 equivalents, preferably 0.1 to 2 molar equivalents, per 1 mol of compound (ICa).

The reaction temperature is generally −100° C. to 200° C., preferably −20° C. to 100° C.

The reaction time is, for example, 1 minute to several days.

The compound (IC-1) thus obtained can be isolated and purified by a known separation and purification means, such as concentration, concentration under reduced pressure, solvent extraction, crystallization, recrystallization, phase transfer, chromatography and the like.

The compound (ICc) used as the starting compound in this method can be produced by a method known per se.

[Method AC]

Of compounds (IC), compound (IC-2) wherein Xc is a methylene group can be also produced by the method shown below.

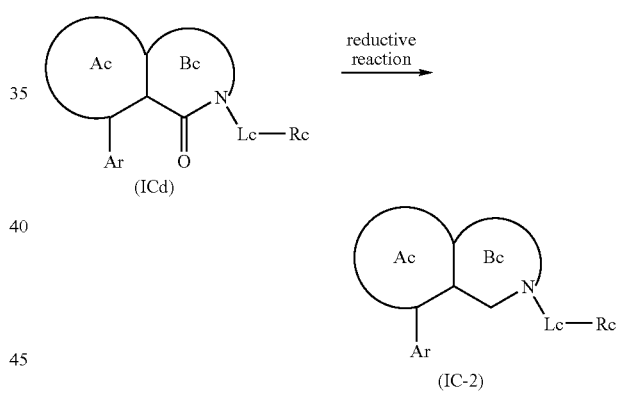

wherein the symbols in the formula are as defined above.

In this method, compound (IC-2) is produced by subjecting compound (ICd) to a reductive reaction.

This reaction can be carried out using a reducing agent, where necessary, in a solvent that does not adversely affect the reaction. As such solvent, those exemplified in the aforementioned [Method AA] can be used. Particularly, ether solvents (e.g., tetrahydrofuran), hydrocarbon solvents (e.g., toluene) and the like are preferable.

As the reducing agent, those exemplified in the aforementioned [Method AB] can be used. Particularly, lithium aluminum hydride, diisobutylaluminum hydride, borane and the like are preferable.

The reaction temperature is generally −100° C. to 200° C., preferably −200° C. to 100° C.

The reaction time is, for example, 1 minute to several days.

The compound (IC-2) thus obtained can be isolated and purified by a known separation and purification means, such as concentration, concentration under reduced pressure, solvent extraction, crystallization, recrystallization, phase transfer, chromatography and the like.

The compound (ICd) used as the starting compound in this method can be produced by, for example, the methods described in EP-A733632 and the like, the aforementioned [Method AA], or methods analogous thereto.

Of compounds (ICa) used as the starting compound in the aforementioned [Method AA] and [Method AB], compound (ICa-1) wherein Xc is a methylene group, can be produced according to, for example, the method shown below.

[Method AD]

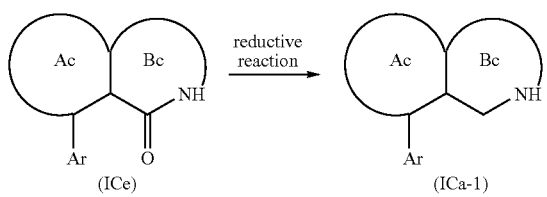

wherein the symbols in the formula are as defined above.

In this method, compound (ICa-1) is produced by subjecting compound (ICe) to a reductive reaction.

This reaction is carried out in the same manner as in the reductive reaction in the aforementioned [Method AC].

The compound (ICa-1) thus obtained can be isolated and purified by a known separation and purification means, such as concentration, concentration under reduced pressure, solvent extraction, crystallization, recrystallization, phase transfer, chromatography and the like.

The compound (ICe) used as the starting compound in the above-mentioned method can be produced by a method known per se, for example, methods described in EP-A733632, JP-A-9-263585 and the like, or methods analogous thereto.

Of compounds (ICa), compound (ICa-2) wherein ring Bc is

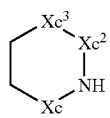

wherein Xc2 is a methylene group, an ethylene group, a trimethylene group or a tetramethylene group, $Xc^3$ is as defined for the aforementioned Xa and Xc is as defined above, can be produced according to, for example, the method shown below.

[Method AE]

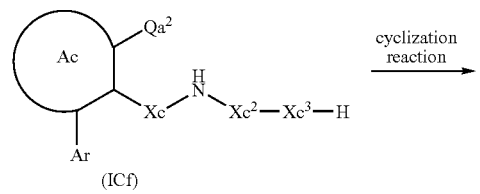

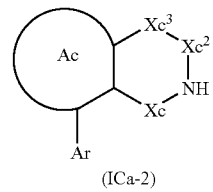

wherein $Qa^2$ is a leaving group, and other symbols are as defined above.

$Xc^3$ is preferably O or S, more preferably O.

As the leaving group for $Qa^2$, those exemplified for the aforementioned $Q^2$ can be used. Particularly, a halogen atom (e.g., chlorine, bromine, iodine) and the like are preferable.

In this method, compound (ICa-2) is produced by subjecting compound (ICf) to a cyclization reaction.

Where necessary, this reaction is carried out in a solvent that does not adversely affect the reaction. As such solvent, those exemplified in the aforementioned [Method AA] can be used. Particularly, ether solvents (e.g., tetrahydrofuran), hydrocarbon solvents (e.g., toluene), amide solvents (e.g., dimethylformamide) and the like are preferable.

Where necessary, this reaction may be carried out in the presence of a base. As such base, for example, those exemplified in the aforementioned [Method AA] can be used. Particularly, alkali metal hydrides (e.g., sodium hydride), alkali metal lower($C_{1-6}$) alkoxides (e.g., potassium tert-butoxide), amines (e.g., DBU) and the like are preferable. The amount of the base to be used is generally 0.1 to 10 equivalents, preferably 0.1 to 2 molar equivalents, per 1 mol of compound (ICf).

The reaction temperature is generally −100° C. to 200° C., preferably 0° C. to 150° C.

The reaction time is, for example, 1 minute to several days.

The compound (ICa-2) thus obtained can be isolated and purified by a known separation and purification means, such as concentration, concentration under reduced pressure, solvent extraction, crystallization, recrystallization, phase transfer, chromatography and the like.

The compound (ICf) used as the starting compound in this method can be produced according to, for example, the method shown below.

[Method AF]

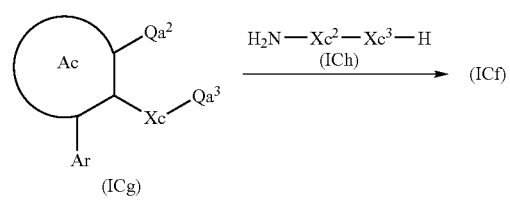

wherein $Qa^3$ is a leaving group, and other symbols are as defined above.

As the leaving group for $Qa^3$, those exemplified for the aforementioned $Q^2$ can be used. Particularly, a halogen atom (e.g., chlorine, bromine, iodine), $C_{1-6}$ alkylsulfonyloxy (e.g., methylsulfonyloxy), $C_{6-10}$ arylsulfonyloxy optionally substituted by $C_{1-6}$ alkyl (e.g., toluenesulfonyloxy) and the like are preferable.

In this method, compound (ICf) is produced by reacting compound (ICg) with compound (ICh).

This reaction is carried out in the same manner as in the aforementioned [Method AA]. As the solvent to be used, alcohol solvents (e.g., ethanol), ether solvents (e.g., tetrahydrofuran), hydrocarbon solvents (e.g., toluene) and the like are preferable.

As the base, alkali metal carbonates (e.g., potassium carbonate), amines (e.g., triethylamine) and the like are preferable.

The compound (ICf) thus obtained can be isolated and purified by a known separation and purification means, such as concentration, concentration under reduced pressure, solvent extraction, crystallization, recrystallization, phase transfer, chromatography and the like.

Of compounds (ICg) used as the starting compound in this method, compound (ICg-1) wherein Xc is a methylene group, $Qa^3$ is $C_{6-10}$ arylsulfonyloxy optionally substituted by $C_{1-6}$ alkyl, $C_{1-6}$ alkylsulfonyloxy or a halogen atom, can be produced according to, for example, the method shown below.

[Method AG]

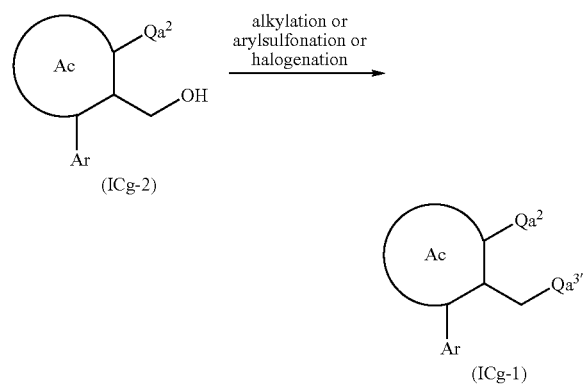

wherein $Qa^3$ is $C_{1-6}$ alkylsulfonyloxy, $C_{6-10}$ arylsulfonyloxy optionally substituted by $C_{1-6}$ alkyl or halogen atom, and other symbols are as defined above.

As the $C_{1-6}$ alkylsulfonyloxy, $C_{6-10}$ arylsulfonyloxy optionally substituted by $C_{1-6}$ alkyl and the-halogen atom for $Qa^3$, those exemplified for the aforementioned $Qa^3$ can be used.

In this method, compound (ICg-1) is produced by subjecting compound (ICg-2) to an alkylation or an arylsulfonylation reaction, or a halogenation reaction.

Here, the alkylation or arylsulfonylation reaction is carried out by, for example, methods described in *Journal of the Organic Chemistry* (J. Org. Chem.) 39, 1036 (1974); *Synthesis*, 665 (1974) and the like, or methods analogous thereto.

In addition, the halogenation reaction is carried out by, for example, methods described in *Journal of the American Chemical Society* (J. Am. Chem. Soc.) 78, 653 (1956); ibid. 75, 2053 (1953); *Angewandte Chemie International Edition in English* (Angew. Chem. Int. Ed.) 14, 801 (1975) and the like, or methods analogous thereto.

The compound (ICg-1) thus obtained can be isolated and purified by a known separation and purification means, such as concentration, concentration under reduced pressure, solvent extraction, crystallization, recrystallization, phase transfer, chromatography and the like.

The compound (ICg-2) used as the starting compound in this method can be produced according to, for example, the method shown below.

[Method AH]

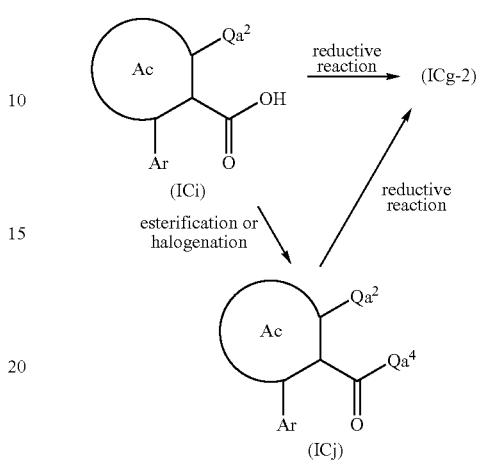

wherein $Qa^4$ is $C_{1-6}$ alkoxy or a halogen atom, and other symbols are as defined above.

As the $C_{1-6}$ alkoxy for $Qa^4$, for example, methoxy, ethoxy, propoxy and the like can be mentioned. As the halogen atom for $Qa^4$, for example, chlorine, bromine, iodine and the like can be mentioned.

In this method, compound (ICg-2) is produced by subjecting compound (ICi) to a reductive reaction.

In this method, moreover, compound (ICj) is produced by subjecting compound (ICi) to an esterification or halogenation reaction, and compound (ICg-2) is produced by subjecting compound (ICj) to a reductive reaction.

The reductive reaction of compound (ICi) and the reductive reaction of compound (ICj) can be carried out in the same manner as in the aforementioned [Method AD].

The esterification reaction of compound (ICi) is carried out by, for example, methods described in *Organic Synthesis* (Org. Syn.) Coll. Vol. 1, 241 (1941); *Synthesis*, 961 (1979); *Organic Synthesis* (Org. Syn.) Coll. Vol. 2, 165 (1943) and the like, or methods analogous thereto.

The halogenation reaction of compound (ICi) is carried out by, for example, methods described in *Organic Synthesis* (Org. Syn.) Coll. Vol. 1, 12-(1941); *Journal of the American Chemical Society* (J. Am. Chem. Soc.) 42, 599 (1920) and the like, or methods analogous thereto.

The compound (ICg-2) thus obtained can be isolated and purified by a known separation and purification means, such as concentration, concentration under reduced pressure, solvent extraction, crystallization, recrystallization, phase transfer, chromatography and the like.

The compound (ICi) used as the starting compound in this method can be produced by a method known per se, for example, methods described in *Australian Journal of chemistry* (Aust. J. Chem.) 36, 1455 (1983); JP-A-6-41116 and the like, or methods analogous thereto.

The compound (IA) can be produced by, for example, [Method AAA], [Method AAC] to [Method AAI] shown below, or methods analogous thereto.

Of compounds (IA), compound (IAa) wherein $Z^1$ is a bond and $Z^2$ is $—NR^{4a}—$ (wherein $R^{4a}$ is as defined above) can be produced by, for example, the following method. [Method AAA]

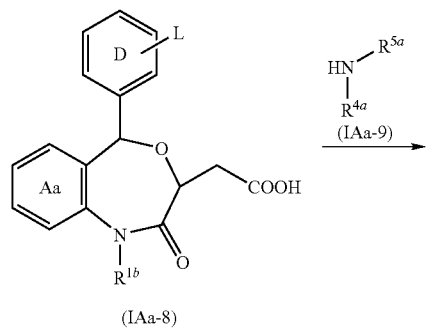

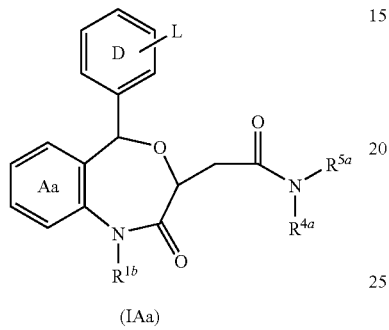

wherein the symbols in the formula are as defined above.

The compound (IAa) can be produced by reacting compound (IAa-8) with compound (IAa-9). This reaction can be carried out using a condensing agent in a solvent that does not adversely affect the reaction and, where necessary, in the presence of a base.

As the solvent that does not adversely affect the reaction, for example, ether solvents (e.g., diethyl ether, tetrahydrofuran, dioxane etc.), hydrocarbon solvents (e.g., benzene, toluene, hexane, heptane etc.), halogen solvents (e.g., dichloromethane, dichloroethane, chloroform, carbon tetrachloride etc.), acetonitrile, dimethylformamide and the like can be mentioned.

As the base, for example, triethylamine, 4-dimethylaminopyridine, triethylenediamine, tetramethylethylenediamine and the like can be mentioned.

As the condensing agent, for example, condensing agents used for peptide synthesis and the like can be mentioned. Specifically, for example, dicyclohexylcarbodiimide, diethyl cyanophosphate, 1-ethyl-3-(3-dimethylaminopropyl)carbodiimide and the like are used.

The amount of compound (IAa-9) to be used is generally about 0.5 to 2 molar equivalents, preferably about 1 to 1.2 molar equivalents, per 1 mol of compound (IAa-8).

The amount of the condensing agent to be used is generally about 0.5 to 5 molar equivalents, preferably about 1 to 2 molar equivalents, per 1 mol of compound (IAa-8).

The amount of the base to be used is generally about 1 to 10 molar equivalents, preferably about 1 to 5 molar equivalents, per 1 mol of compound (IAa-8).

The reaction temperature is generally about 0° C. to 100° C., preferably about 20° C. to 50° C.

The reaction time is generally about 0.5 to 24 hrs, preferably about 1 to 5 hrs.

The compound (IAa) thus obtained can be isolated and purified by a known separation and purification means, such as concentration, concentration under reduced pressure, solvent extraction, crystallization, recrystallization, phase transfer, chromatography and the like.

The compound (IAa-9) used as the starting compound in the aforementioned [Method AAA] is commercially available as a reagent or can be produced by a method known per se.

The compound (IAa-8) used as the starting compound in the aforementioned [Method AAA] can be produced by a method known per se, for example, the following method or a method analogous thereto.

[Method AAB]

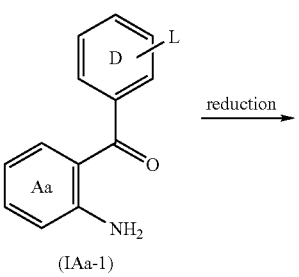

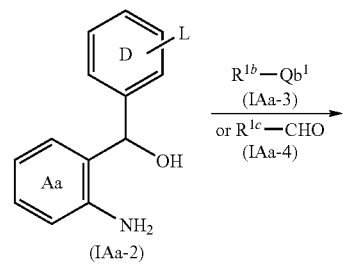

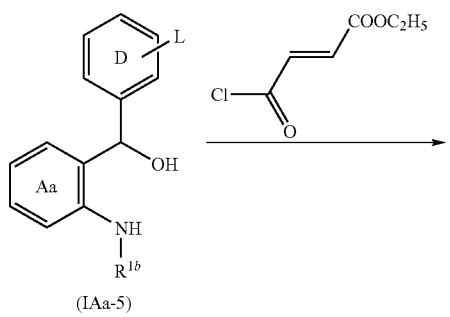

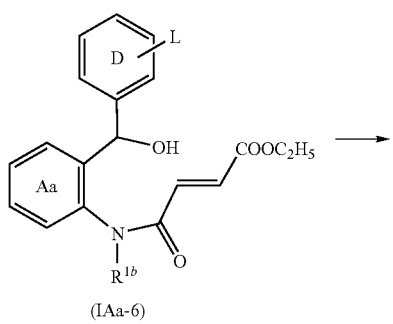

(IAa-7)

(IAa-8)

wherein $Qb^1$ is a leaving group, $R^{1c}$ is a group obtained by removing a methylene group from the aforementioned "optionally substituted $C_{1-6}$ alkyl group, optionally substituted $C_{2-6}$ alkenyl group or optionally substituted aralkyl group" for $R^{1b}$, and other symbols are as defined above.

As the leaving group for $Qb^1$, those exemplified for the aforementioned $Q^1$ can be used. Particularly, a halogen atom (e.g., chlorine, bromine, iodine), $C_{1-6}$ alkylsulfonyloxy (e.g., methylsulfonyloxy), $C_{6-10}$ arylsulfonyloxy optionally substituted by $C_{1-6}$ alkyl (e.g., toluenesulfonyloxy) and the like are preferable.

As $R^{1c}$, an "optionally substituted $C_{1-5}$ alkyl group, optionally substituted $C_{2-5}$ alkenyl group or optionally substituted aralkyl group" wherein "$R^{1c}$—$CH_2$—" is as defined for the "optionally substituted $C_{1-6}$ alkyl group, optionally substituted $C_{2-6}$ alkenyl group or optionally substituted aralkyl group" for the aforementioned $R^{1b}$, can be used.

The compound (IAa-2) can be produced by subjecting compound (IAa-1) to a reductive reaction.

This reductive reaction is carried out using a reducing agent such as metal hydride complexes (e.g., lithium aluminum hydride, sodium aluminum hydride, sodium triethoxyaluminum hydride, sodium borohydride etc.) and the like in a solvent such as protic solvents (e.g., methanol, ethanol, propanol, butanol etc.), aprotic solvents (e.g., ethyl ether, tetrahydrofuran, dioxane etc.) and the like.

The amount of the reducing agent to be used is generally about 0.3 to 5 molar equivalents, preferably about 0.5 to 2 molar equivalents, per 1 mol of compound (IAa-1).

The reaction temperature is generally about −20° C. to 100° C., preferably about 0° C. to 50° C.

The reaction time is, for example, about 0.5 to 24 hrs.

The compound (IAa-5) can be produced by reacting compound (IAa-2) with compound (IAa-3). This reaction can be carried out in a solvent such as ether solvents (e.g., diethyl ether, tetrahydrofuran, dioxane etc.), hydrocarbon solvents (e.g., benzene, toluene, hexane, heptane etc.), alcohol solvents (e.g., methanol, ethanol, propanol etc.), acetone, dimethylformamide and the like and, where necessary, in the presence of a base (e.g., sodium hydrogencarbonate, potassium hydrogencarbonate, sodium carbonate, potassium carbonate, sodium hydride, potassium hydride etc.).

The amount of compound (IAa-3) to be used is generally about 1 to 10 molar equivalents, preferably about 1 to 2 molar equivalents, per 1 mol of compound (IAa-2).

The amount of the base to be used is generally about 1 to 10 molar equivalents, preferably about 1 to 5 molar equivalents, per 1 mol of compound (IAa-2).

The reaction temperature is generally about 0° C. to 100° C., preferably about 20° C. to 50° C.

The reaction time is generally about 1 to 24 hrs, preferably about 3 to 10 hrs.

The compound (IAa-5) can be also produced by subjecting compound (IAa-2) and compound (IAa-4) to a catalytic reduction, or a reductive amination reaction using a reducing agent.

These reactions are carried out in a solvent that does not adversely affect the reactions. As such solvent, for example, ether solvents (e.g., diethyl ether, tetrahydrofuran, dioxane etc.), hydrocarbon solvents (e.g., benzene, toluene, hexane, heptane etc.), alcohol solvents (e.g., methanol, ethanol, propanol, butanol etc.) and the like can be mentioned.

This reaction may be carried out in the presence of an acid as necessary, such as acetic acid, trifluoroacetic acid.

As the above-mentioned reducing agent, for example, sodium borohydride, sodium cyanoborohydride, sodium triacetoxyborohydride and the like can be used.

The amount of compound (IAa-4) to be used is generally about 1 to 10 molar equivalents, preferably about 1 to 2 molar equivalents, per 1 mol of compound (IAa-2).

The amount of the reducing agent to be used is generally about 0.3 to 5 molar equivalents, preferably about 0.5 to 1 molar equivalent.

The reaction temperature is generally about 0° C. to 100° C., preferably about 10° C. to 70° C.

The reaction time is generally about 1 to 24 hrs, preferably about 3 to 10 hrs.

The compound (IAa-6) can be produced by reacting compound (IAa-5) with fumaryl chloride mono ethyl ester.

This reaction is carried out by an acylation reaction known per se. The acylation reaction can be carried out in a solvent such as ether solvents (e.g., diethyl ether, tetrahydrofuran, dioxane etc.), halogen solvents (e.g., dichloromethane, dichloroethane, chloroform, carbon tetrachloride etc.), hydrocarbon solvents (e.g., benzene, toluene, hexane, heptane etc.), dimethylformamide, dimethylsulfoxide, ester solvents (ethyl acetate, methyl acetate etc.) and the like and, where necessary, in the presence of water and a base (e.g., 4-dimethylaminopyridine, triethylamine, triethylenediamine, tetramethylethylenediamine, sodium hydrogencarbonate, potassium hydrogencarbonate, sodium carbonate, potassium carbonate, sodium hydride, potassium hydride etc.).

The amount of fumaryl chloride mono ethyl ester to be used is generally about 1 to 10 molar equivalents, preferably about 1 to 3 molar equivalents, per 1 mol of compound (IAa-5).

The amount of the base to be used is generally about 1 to 10 molar equivalents, preferably about 1 to 5 molar equivalents, per 1 mol of compound (IAa-5).

The reaction temperature is generally about −50° C. to 100° C., preferably about 0° C. to 50° C.

The reaction time is generally about 1 to 48 hrs, preferably about 5 to 10 hrs.

The compound (IAa-7) can be produced by subjecting the compound (IAa-6) to a cyclization reaction.

The cyclization reaction can be carried out, for example, in a solvent such as ether solvents (e.g., diethyl ether, tetrahydrofuran, dioxane etc.), hydrocarbon solvents (e.g., benzene, toluene, hexane, heptane etc.), alcohol solvents (e.g., methanol, ethanol, propanol, butanol etc.), acetone, dimethylformamide and the like and, where necessary, in the presence of a base (e.g., sodium hydrogencarbonate, potassium hydrogencarbonate, sodium carbonate, potassium carbonate, sodium hydride, potassium hydride etc.).

The amount of the base to be used is about 1 to 5 molar equivalents, preferably about 1 to 2 molar equivalents, per 1 mol of compound (IAa-6).

The reaction temperature is generally about −20° C. to 200° C., preferably about 20° C. to 100° C.

The reaction time is generally 1 to 20 hrs, preferably about 2 to 5 hrs.

The compound (IAa-8) can be produced by subjecting compound (IAa-7) to a hydrolysis reaction.

This reaction is carried out, for example, in an aqueous solution of acid or base.

As the acid, for example, mineral acids (e.g., nitric acid, hydrochloric acid, hydrobromic acid, hydroiodic acid, sulfuric acid etc.) can be mentioned and as the base, for example, hydroxides of alkali metal or alkaline earth metal (e.g., sodium hydroxide, potassium hydroxide, barium hydroxide, lithium hydroxide etc.) and the like can be mentioned.

The strength of acid and base is preferably about 1N to 10 N, more preferably about 4N to 10N.

The reaction temperature is generally about 0° C. to 150° C., preferably about 20° C. to 50° C.

The reaction time is generally about 1 to 24 hrs, preferably about 2 to 10 hrs.

The compound (IAa-8) thus obtained can be isolated and purified by a known separation and purification means, such as concentration, concentration under reduced pressure, solvent extraction, crystallization, recrystallization, phase transfer, chromatography and the like.

The compounds (IAa-1), (IAa-3) and (IAa-4) used as the starting compounds in the aforementioned [Method AAB] can be produced by a method known per se.

Of compounds (IA), compound (IAb) wherein $Z^1$ is —NH— and $Z^2$ is a bond, can be produced by, for example, a method shown below.

[Method AAC]

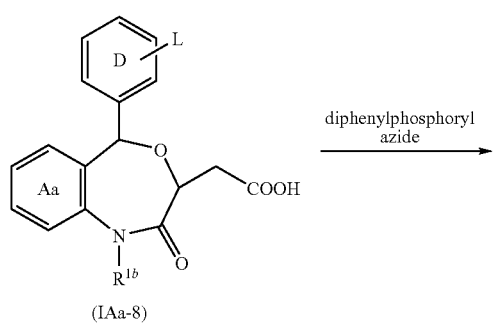

(IAa-8)

-continued

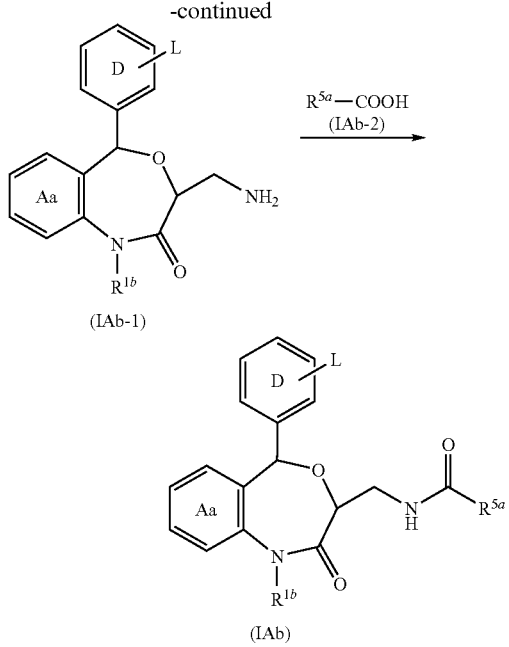

wherein the symbols in the formula are as defined above.

The compound (IAa-8) is reacted with diphenylphosphoryl azide in a solvent that does not adversely affect the reaction in the presence of a base, the resulting compound is subjected to a thermal rearrangement, and the obtained product is reacted with an acid in a solvent that does not adversely affect the reaction, whereby compound (IAb-1) can be produced.

As the "solvent that does not adversely affect the reaction" to be used for the reaction between compound (IAa-8) and diphenylphosphoryl azide, for example, ether solvents (e.g., diethyl ether, tetrahydrofuran, dioxane etc.), halogen solvents (e.g., dichloromethane, dichloroethane, chloroform etc.), dimethylformamide, acetonitrile, toluene and the like can be mentioned.

As the base to be used in the reaction, for example, triethylamine, 4-dimethylaminopyridine, triethylenediamine, tetramethylethylenediamine and the like can be mentioned.

The amount of diphenylphosphoryl azide to be used is generally about 1 to 10 molar equivalents, preferably about 1.5 to 3 molar equivalents, per 1 mol of compound (IAa-8).

The amount of the base to be used is generally about 1 to 10 molar equivalents, preferably about 1 to 5 molar equivalents, per 1 mol of compound (IAa-8).

The reaction temperature is generally about −20° C. to 50° C., preferably about 0° C. to 20° C.

The reaction time is generally about 0.5 to 5 hrs, preferably about 1 to 2 hrs.

The thermal rearrangement is carried out by heating. The temperature of heating is generally about 60° C. to 150° C., preferably about 80° C. to about 100° C., and heating time is generally about 0.5 to 5 hrs, preferably about 1 to about 2 hrs.

As the "solvent that does not adversely affect the reaction" to be used for reacting the product obtained by the above-mentioned thermal rearrangement with an acid, for example, water, dioxane, dimethylformamide and the like can be mentioned. As the acid, for example, mineral acids such as sulfuric acid, hydrochloric acid, nitric acid, hydrobromic acid and the like can be mentioned.

The amount of the acid to be used is generally about 1 to 10 molar equivalents, preferably about 1 to 5 molar equivalents, per 1 mol of compound (IAa-8).

The reaction temperature is generally about 20° C. to 200° C., preferably about 50° C. to 100° C.

The reaction time is generally about 0.5 to 5 hrs, preferably about 1 to 2 hrs.

The compound (IAb) can be produced by subjecting compound (IAb-1) and compound (IAb-2) to a condensation reaction.

This reaction is carried out in the same manner as in, for example, the aforementioned [Method AAA].

The compound (IAb) thus obtained can be isolated and purified by a known separation and purification means, such as concentration, concentration under reduced pressure, solvent extraction, crystallization, recrystallization, phase transfer, chromatography and the like.

The compound (IAb-2) used as the starting compound in the aforementioned [Method AAC] is commercially available as a reagent or can be produced by a method known per se.

Of compounds (IA), compound (IAc) wherein $Z^1$ and $Z^2$ are —NH— can be produced by, for example, a method shown below.

[Method AAD]

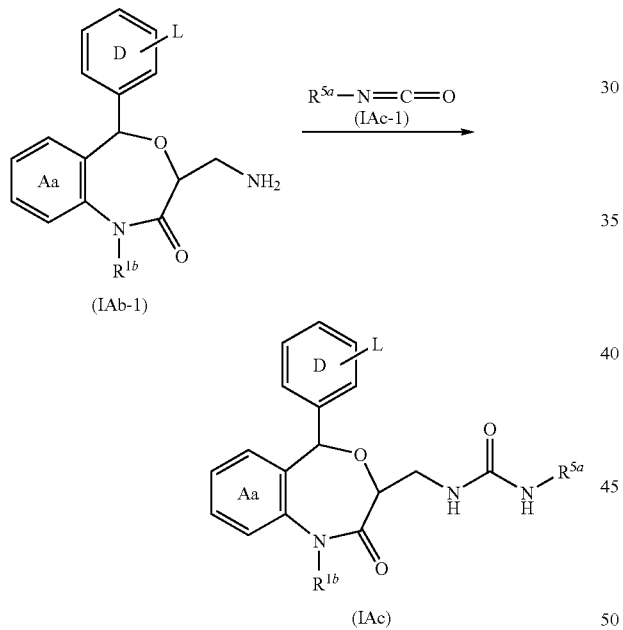

(IAb-1)

(IAc)

wherein the symbols in the formula are as defined above.

The compound (IAc) can be produced by reacting compound (IAb-1) with compound (IAc-1). This reaction is carried out in a solvent that does not adversely affect the reaction.

As the solvent that does not adversely affect the reaction, for example, ether solvents (e.g., diethyl ether, tetrahydrofuran, dioxane etc.), halogen solvents (e.g., dichloromethane, dichloroethane, chloroform etc.), acetonitrile, toluene, pyridine, dimethylformamide and the like can be mentioned.

This reaction is carried out in the presence of, where necessary, a base (e.g., triethylamine, 4-dimethylaminopyridine, triethylenediamine, tetramethylethylenediamine etc.).

The amount of compound (IAc-1) to be used is generally about 0.5 to 3 molar equivalents, preferably about 1 to 1.5 molar equivalents, per 1 mol of compound (IAb-1).

The amount of the base to be used is generally about 1 to 10 molar equivalents, preferably about 1 to 5 molar equivalents, per 1 mol of compound (IAb-1).

The reaction temperature is generally about 0° C. to 150° C., preferably about 30° C. to 100° C.

The reaction time is generally about 0.5 to 24 hrs, preferably about 1 to 3 hrs.

The compound (IAc) thus obtained can be isolated and purified by a known separation and purification means, such as concentration, concentration under reduced pressure, solvent extraction, crystallization, recrystallization, phase transfer, chromatography and the like.

The compound (IAc-1) used as the starting compound in the aforementioned [Method AAD] is commercially available as a reagent or can be produced by a method known per se.

Of compounds (IA), compound (IAd) wherein L is —CH$_2$NHCOR$^7$ (wherein R$^7$ is as defined above), can be produced by, for example, a method shown below.

[Method AAE]

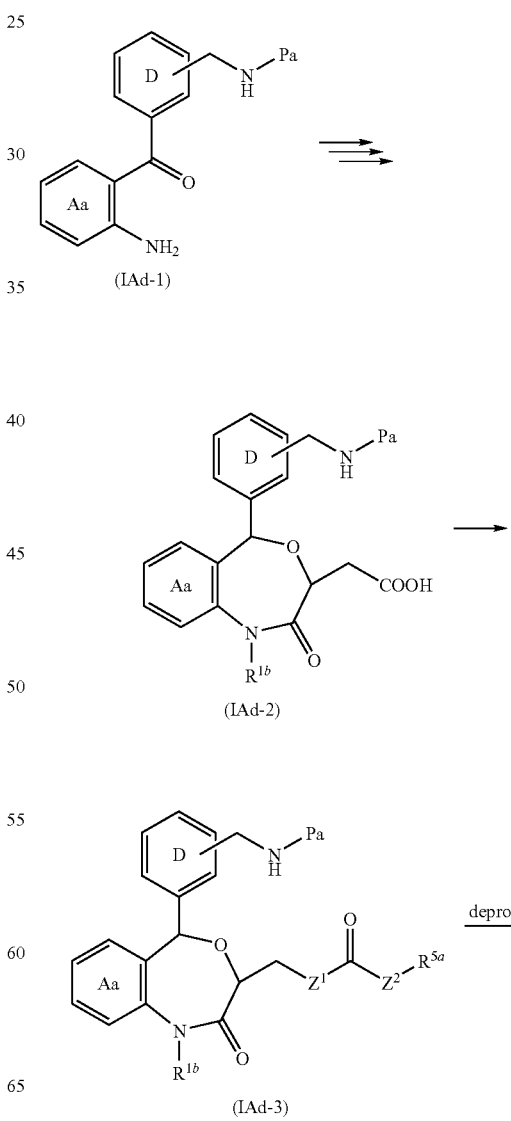

(IAd-1)

(IAd-2)

(IAd-3)

-continued

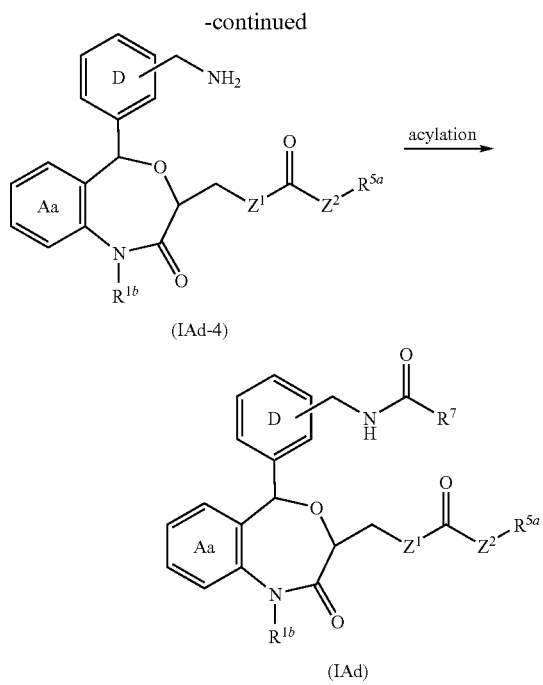

wherein Pa is an amino-protecting group, and other symbols are as defined above.

As the amino-protecting group for Pa, those exemplified for the aforementioned $Rb^{10}$ can be used.

The compound (IAd-2) can be produced from compound (IAd-1) in the same manner as in the aforementioned

[Method AAB]

Then, compound (IAd-3) can be produced from compound (IAd-2) in the same manner as in the aforementioned [Method AAA], [Method AAC] or [Method AAD].

The compound (IAd-4) can be produced by subjecting compound (IAd-3) to a deprotective reaction of the amino group.

This reaction is carried out according to a method known per se in a solvent that does not adversely affect the reaction.

As such solvent, for example, ether solvents (e.g., diethyl ether, tetrahydrofuran, dioxane etc.), hydrocarbon solvents (e.g., benzene, toluene, hexane, heptane etc.), alcohol solvents (e.g., methanol, ethanol, propanol, butanol etc.), halogen solvents (e.g., dichloromethane, dichloroethane, chloroform etc.), acetone, acetonitrile, ethyl acetate, dimethylformamide and the like can be mentioned.

This reaction is carried out by, for example, a catalytic reduction using, for example, palladium, platinum and the like as a catalyst when Pa is a benzyloxycarbonyl group; or by, for example, dissolving or suspending in an acid (e.g., hydrochloric acid, hydrobromic acid, trifluoroacetic acid etc.) when Pa is a tert-butoxycarbonyl group.

The reaction temperature is generally about 0° C. to 100° C., preferably about 10° C. to 50° C.

The reaction time is generally about 0.1 to 24 hrs, preferably about 1 to 10 hrs.

The compound (IAd) can be produced by subjecting compound (IAd-4) to an acylation reaction.

This reaction is carried out using an acylation reaction known per se. The acylation reaction is carried out by, for example, reacting compound (IAd-4) with a compound represented by the formula: $R^7COOH$ (IAd-5) [wherein $R^7$ is as defined above] or a reactive derivative thereof (e.g., acid halide, acid anhydride, activated ester, acid imidazolide and the like).

The reaction using compound (IAd-5) is carried out in the same manner as in, for example, the aforementioned [Method AAA].

The reaction using a reactive derivative of compound (IAd-5) can be carried out in a solvent such as ether solvents (e.g., diethyl ether, tetrahydrofuran, dioxane etc.), halogen solvents (e.g., dichloromethane, dichloroethane, chloroform, carbon tetrachloride etc.), hydrocarbon solvents (e.g., benzene, toluene, hexane, heptane etc.), dimethylformamide, dimethylsulfoxide, ester solvents (ethyl acetate, methyl acetate etc.) and the like and in the presence of, where necessary, water and a base (e.g., 4-dimethylaminopyridine, triethylamine, triethylenediamine, tetramethylethylenediamine, sodium hydrogencarbonate, potassium hydrogencarbonate, sodium carbonate, potassium carbonate, sodium hydride, potassium hydride etc.).

The amount of the reactive derivative of compound (IAd-5) to be used is about 1 to 10 molar equivalents, preferably about 1 to 3 molar equivalents, per 1 mol of compound (IAd-4).

The amount of the base to be used is generally about 1 to 10 molar equivalents, preferably about 1 to 5 molar equivalents, per 1 mol of compound (IAd-4).

The reaction temperature is generally about −50° C. to 100° C., preferably about 0° C. to 50° C.

The reaction time is generally about 1 to 48 hrs, preferably about 5 to 10 hrs.

The compound (IAd) thus obtained can be isolated and purified by a known separation and purification means, such as concentration, concentration under reduced pressure, solvent extraction, crystallization, recrystallization, phase transfer, chromatography and the like.

The compound (IAd-1) used as the starting compound in the aforementioned [Method AAE] can be produced by a method known per se.

Of compounds (IA), compound (IAe) wherein L is —$OCH_2CONR^8R^9$ (wherein $R^8$ and $R^9$ are as defined above), can be produced by, for example, a method shown below.

[Method AAF]

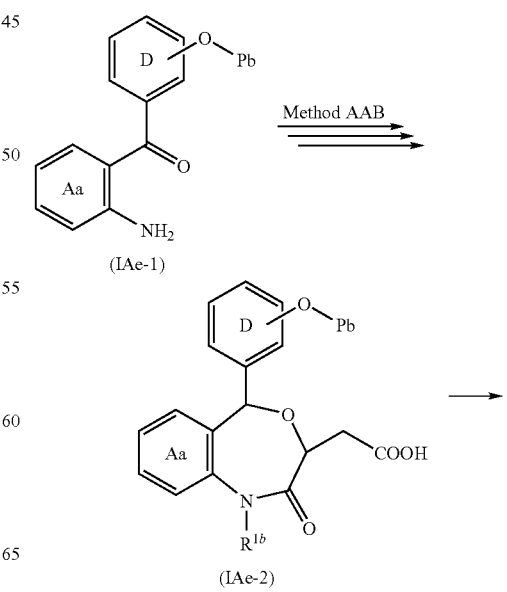

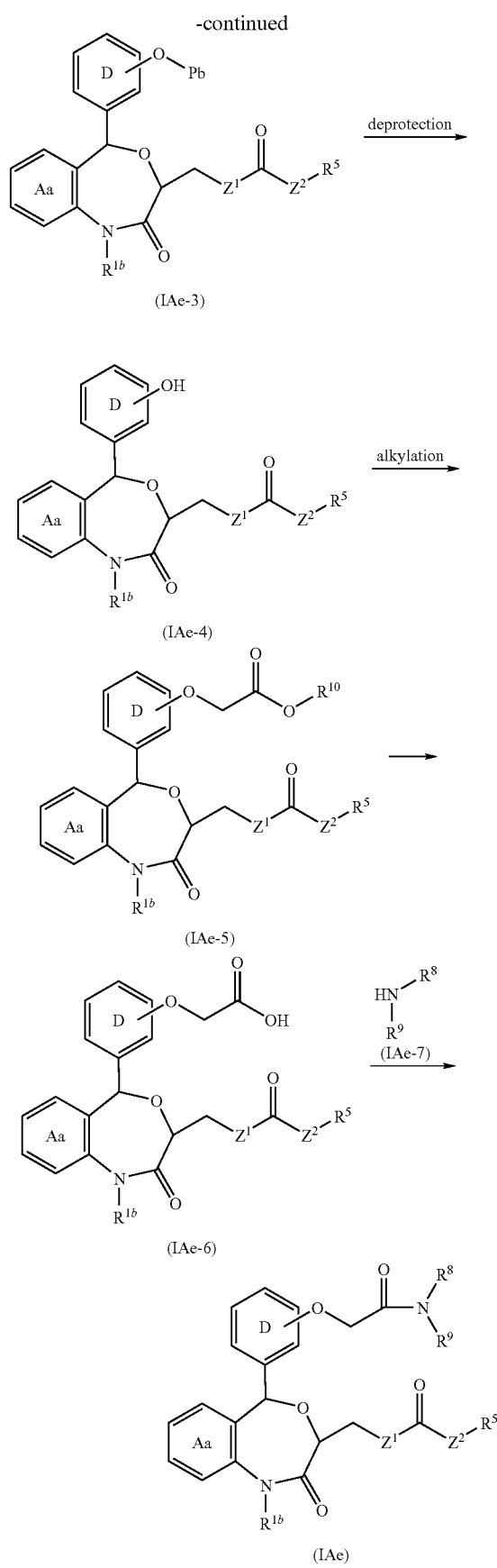

wherein Pb is a protecting group for a phenolic hydroxy group, $R^{10}$ is a $C_{1-4}$ alkyl group, and other symbols are as defined above.

As the protecting group for a phenolic hydroxyl group for Pb, for example, methyl, $C_{1-6}$ alkoxymethyl (e.g., methoxymethyl, ethoxymethyl and the like), trityl, $C_{7-11}$ aralkyl (e.g., benzyl and the like), formyl, $C_{1-6}$ alkyl-carbonyl (e.g., acetyl, propionyl and the like), benzoyl, $C_{7-11}$ aralkyl-carbonyl (e.g., benzylcarbonyl and the like), 2-tetrahydropyranyl, 2-tetrahydrofuranyl, silyl (e.g., trimethylsilyl, triethylsilyl, dimethylphenylsilyl, tert-butyldimethylsilyl, tert-butyldiethylsilyl and the like), allyl and the like can be mentioned. These groups are optionally substituted by 1 to 3 halogen atoms (e.g., fluorine, chlorine, bromine, iodine), a $C_{1-6}$ alkoxy group (e.g., methoxy, ethoxy, propoxy) or a nitro group and the like.

As the $C_{1-4}$ alkyl group for $R^{10}$, for example, methyl, ethyl, propyl, tert-butyl and the like can be mentioned.

The compound (IAe-2) can be produced from compound (IAe-1) in the same manner as in the aforementioned [Method AAB].

Then, compound (IAe-3) can be produced from compound (IAe-2) in the same manner as in the aforementioned [Method AAA], [Method AAC] or [Method AAD].

The compound (IAe-4) can be produced by subjecting compound (IAe-3) to a deprotection of a phenolic hydroxyl group.

This reaction is carried out according to a method known per se in a solvent that does not adversely affect the reaction.

As such solvent, for example, ether solvents (e.g., diethyl ether, tetrahydrofuran, dioxane etc.), hydrocarbon solvents (e.g., benzene, toluene, hexane, heptane etc.), alcohol solvents (e.g., methanol, ethanol, propanol, butanol etc.), halogen solvents (e.g., dichloromethane, dichloroethane, chloroform etc.), acetone, acetonitrile, ethyl acetate, dimethylformamide and the like can be mentioned.

This reaction is carried out by, for example, a catalytic reduction using, for example, palladium, platinum and the like as a catalyst, when Pb is a benzyl group.

The reaction temperature is generally about 0° C. to 100° C., preferably about 20° C. to 70° C.

The reaction time is generally about 1 to 24 hrs, preferably about 1 to 5 hrs.

The compound (IAe-5) can be produced by subjecting compound (IAe-4) to an alkylation reaction.

This reaction is carried out according to a method known per se and using an alkylating reagent corresponding to compound (IAe-5).

As the alkylating reagent, for example, chloroacetate or bromoacetate and the like can be mentioned.

This reaction is carried out in a solvent such as aprotic solvents (e.g., ethyl ether, tetrahydrofuran, dioxane, acetonitrile, toluene, dimethylformamide etc.) and the like in the presence of, where necessary, an inorganic base (e.g., sodium hydrogencarbonate, potassium hydrogencarbonate, sodium carbonate, potassium carbonate etc.), an organic base (e.g., triethylamine, 4-dimethylaminopyridine, triethylenediamine, tetramethylethylenediamine etc.), sodium hydride, cesium fluoride and the like.

The amount of the alkylating reagent to be used is generally about 0.5 to 5 molar equivalents, preferably about 1 to 2 molar equivalents, per 1 mol of compound (IAe-4).

The amount of the inorganic base, the organic base and the like to be used is generally about 1 to 10 molar equivalents, preferably about 1 to 5 molar equivalents, per 1 mol of compound (IAe-4).

The reaction temperature is generally about 0° C. to 200° C., preferably about 20° C. to 100° C.

The reaction time is generally about 10 min to 5 hrs, preferably about 30 min to 2 hrs.

The compound (IAe-6) can be produced by subjecting compound (IAe-5) to a hydrolysis reaction.

This reaction is carried out in the same manner as in the hydrolysis reaction of compound (IAa-7) in the aforementioned [Method AAB].

The compound (IAe) can be produced by reacting compound (IAe-6) with compound (IAe-7).

This reaction is carried out in the same manner as in the aforementioned [Method AAA].

The compound (IAe) thus obtained can be isolated and purified by a known separation and purification means, such as concentration, concentration under reduced pressure, solvent extraction, crystallization, recrystallization, phase transfer, chromatography and the like.

The compound (IAe-1) and compound (IAe-7) used as the starting compounds in the aforementioned [Method AAF] can be produced by a method known per se.

Of compounds (IA), compound (IAf) wherein L is —CH$_2$— Het$^1$ (wherein Het$^1$ is a nitrogen-containing aromatic heterocyclic group bonded via a nitrogen atom) can be produced by, for example, a method shown below.

As the nitrogen-containing aromatic heterocyclic group for Het$^1$, those from the nitrogen-containing aromatic heterocyclic groups exemplified for the aforementioned Het, that are bonded via a nitrogen atom, can be mentioned.

[Method AAG]

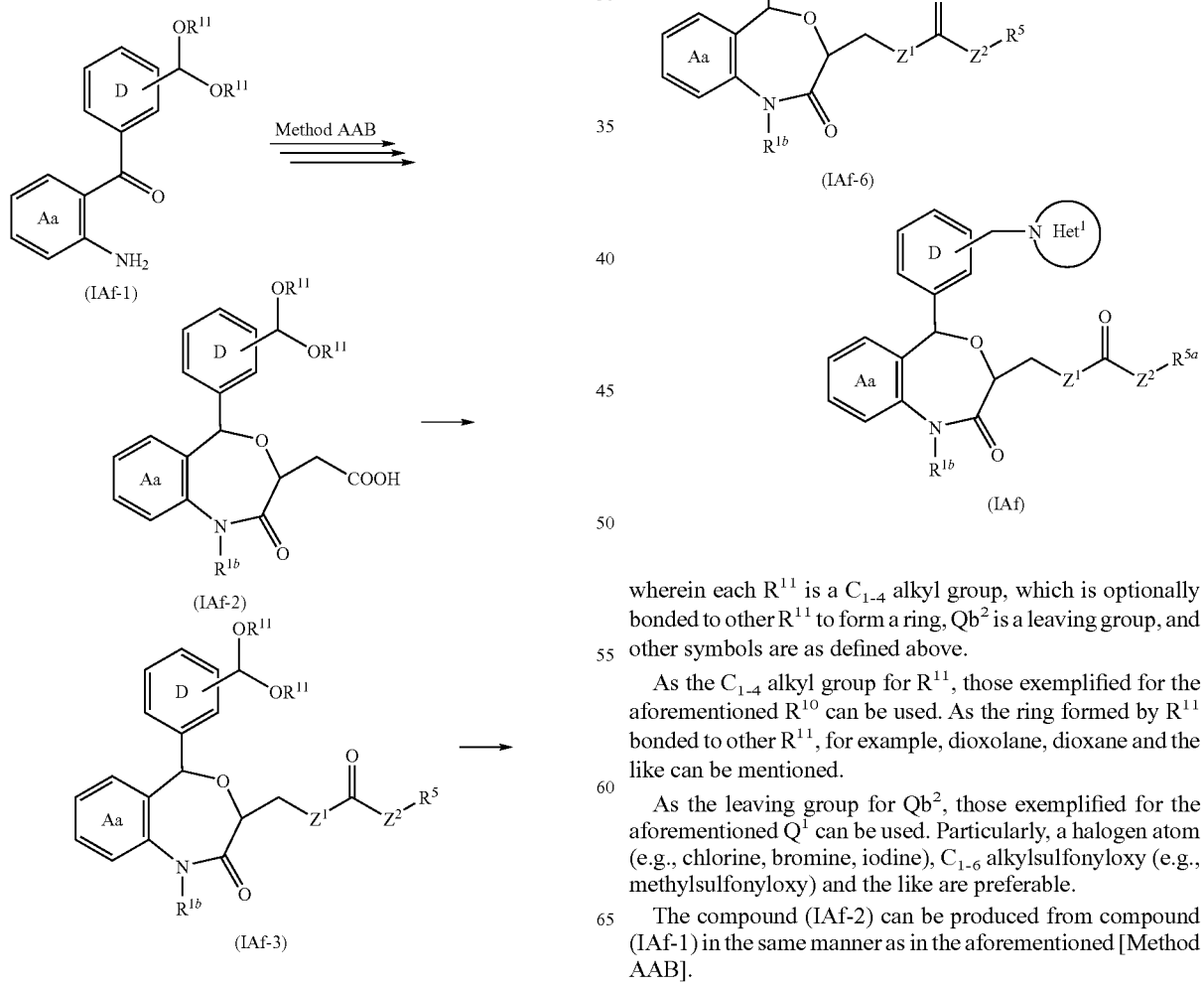

wherein each $R^{11}$ is a $C_{1-4}$ alkyl group, which is optionally bonded to other $R^{11}$ to form a ring, $Qb^2$ is a leaving group, and other symbols are as defined above.

As the $C_{1-4}$ alkyl group for $R^{11}$, those exemplified for the aforementioned $R^{10}$ can be used. As the ring formed by $R^{11}$ bonded to other $R^{11}$, for example, dioxolane, dioxane and the like can be mentioned.

As the leaving group for $Qb^2$, those exemplified for the aforementioned $Q^1$ can be used. Particularly, a halogen atom (e.g., chlorine, bromine, iodine), $C_{1-6}$ alkylsulfonyloxy (e.g., methylsulfonyloxy) and the like are preferable.

The compound (IAf-2) can be produced from compound (IAf-1) in the same manner as in the aforementioned [Method AAB].

Then compound (IAf-3) can be produced from compound (IAf-2) in the same manner as in the aforementioned [Method AAA], [Method AAC] or [Method AAD].

The compound (IAf-4) can be produced by subjecting compound (IAf-3) to an aldehyde conversion reaction.

This reaction is carried out according to a method known per se in, for example, a mixed solvent of a solvent selected from ether solvents (e.g., diethyl ether, tetrahydrofuran, dioxane etc.), hydrocarbon solvents (e.g., benzene, toluene, hexane, heptane etc.), alcohol solvents (e.g., methanol, ethanol, propanol, butanol etc.), halogen solvents (e.g., dichloromethane, dichloroethane, chloroform etc.), acetone and ethyl acetate and water in the presence of an acid (e.g., hydrochloric acid, hydrobromic acid, trifluoroacetic acid, toluenesulfonic acid, methanesulfonic acid etc.).

The amount of the acid to be used is generally about 1 to 10 molar equivalents, preferably about 1 to 5 molar equivalents, per 1 mol of compound (IAf-3).

The reaction temperature is generally about 0° C. to 100° C., preferably about 30° C. to 70° C.

The reaction time is generally about 0.1 to 24 hrs, preferably about 1 to 10 hrs.

The compound (IAf-5) can be produced by subjecting compound (IAf-4) to a reductive reaction. This reaction is carried out in the same manner as in the reductive reaction of compound (IAa-1) in the aforementioned [Method AAB].

The compound (IAf-6) can be produced by subjecting compound (IAf-5) to a conversion reaction of the hydroxyl group to a leaving group.

This reaction is carried out according to a method known per se.

For example, when $Qb^2$ in compound (IAf-6) is a methanesulfonyloxy group, this reaction is carried out by reacting compound (IAf-5) with methanesulfonyl chloride in a solvent that does not adversely affect the reaction in the presence of a base.

This reaction is carried out in the same manner as in the acylation reaction of (IAd-4) in the aforementioned [Method AAE].

When $Qb^2$ in compound (IAf-6) is a chlorine atom, this reaction is carried out by heating compound (IAf-5) with a chlorinating reagent (e.g., thionyl chloride, sulfuryl chloride, phosphorus oxychloride, phosphorus pentachloride and the like) without solvent or in the presence of a solvent such as toluene and the like.

The temperature of the heating is generally about 70° C. to 130° C., preferably about 80° C. to about 100° C., and the heating time is generally about 0.5 to 24 hrs, preferably about 1 to about 5 hrs.

The compound (IAf) can be produced by reacting compound (IAf-6) with compound (IAf-9).

This reaction is carried out according to a method known per se and in the same manner as in, for example, the alkylation reaction of compound (IAe-4) in the aforementioned [Method AAF].

The compound (IAf) thus obtained can-be isolated-and purified by a known separation and purification means, such as concentration, concentration-under reduced pressure, solvent extraction, crystallization, recrystallization, phase transfer, chromatography and the like.

The compound (IAf-1) and compound (IAf-9) used as the starting compounds in the aforementioned [Method AAG] can be produced by a method known per se.

Of compounds (IAf), compound (IAfa) wherein $Het^1$ is a 1,2,4-triazol-4-yl group and compound (IAfb) wherein $Het^1$ is a pyrrol-1-yl group can be also produced by the following method.

[Method AAH]

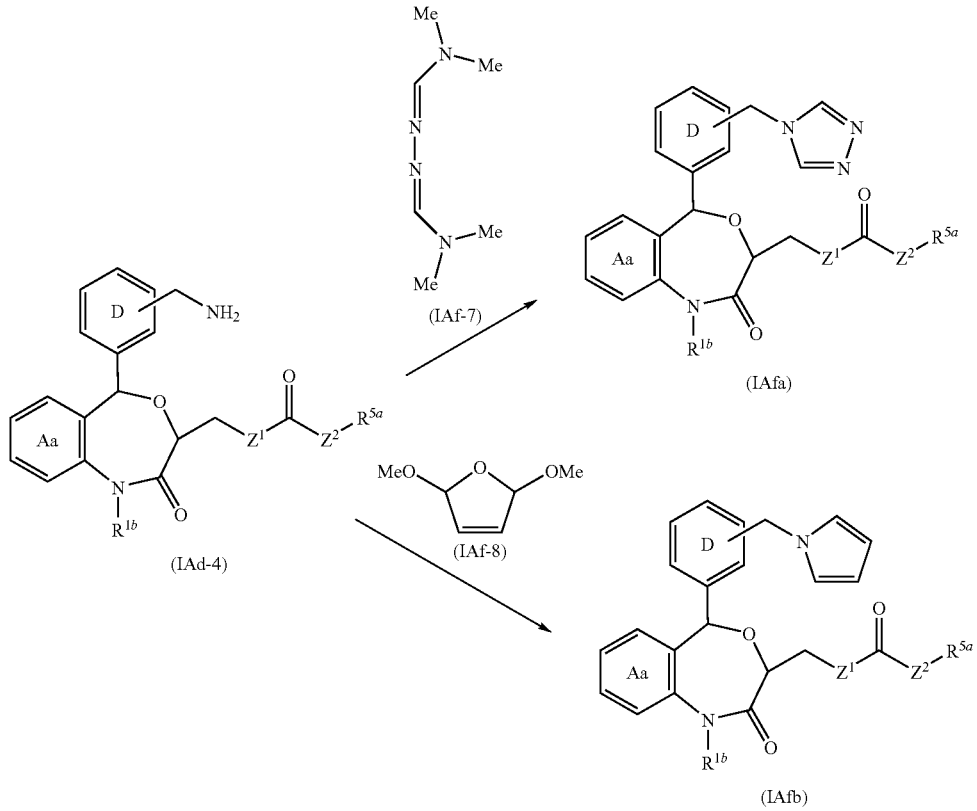

wherein the symbols in the formula are as defined above.

The compound (IAfa) can be produced by reacting compound (IAd-4) with compound (IAf-7).

This reaction is carried out in a solvent such as aprotic solvents (e.g., ethyl ether, tetrahydrofuran, dioxane, acetonitrile, dimethylformamide, pyridine etc.) and the like in the presence of, where necessary, a base such as inorganic bases (e.g., sodium-hydrogencarbonate, potassium hydrogencarbonate, sodium carbonate, potassium carbonate etc.), organic bases (e.g., triethylamine, 4-dimethylaminopyridine, pyridine, tetramethylethylenediamine etc.) and the like.

The amount of compound (IAf-7) to be used is generally about 0.5 to 5 molar equivalents, preferably about 1 to 3 molar equivalents, per 1 mol of compound (IAd-4).

The amount of the base to be used is generally about 1 to 10 molar equivalents, preferably about 1 to 5 molar equivalents, per 1 mol of compound (IAd-4).

The reaction temperature is generally about 0° C. to 200° C., preferably about 20° C. to 100° C.

The reaction time is generally about 10 min to 24 hrs, preferably about 1 to 10 hrs.

The compound (IAfa) thus obtained can be isolated and purified by a known separation and purification means, such as concentration, concentration under reduced pressure, solvent extraction, crystallization, recrystallization, phase transfer, chromatography and the like.

The compound (IAfb) can be produced by reacting compound (IAd-4) with compound (IAf-8). This reaction is carried out in a solvent such as acetic acid and the like in the presence of, where necessary, sodium acetate and the like.

The amount of compound (IAf-8) to be used is generally about 0.5 to 5 molar equivalents, preferably about 1 to 3 molar equivalents, per 1 mol of compound (IAd-4).

The amount of the sodium acetate to be used is generally about 1 to 10 molar equivalents, preferably about 1 to 5 molar equivalents, per 1 mol of compound (IAd-4).

The reaction temperature is generally about 0° C. to 200° C., preferably about 20° C. to 100° C.

The reaction time is generally about 10 min to 24 hrs, preferably about 1 to 10 hrs.

Compound (IAfb) thus obtained can be isolated and purified by a known separation and purification means, such as concentration, concentration under reduced pressure, solvent extraction, crystallization, recrystallization, phase transfer, chromatography and the like.

The compound (IAf-7) and compound (IAf-8) used as the starting compounds in the aforementioned [Method AAH] can be produced by a method known per se.

Of compounds (IA), compound (IAg) wherein L is —$CH_2$— $Het^2$ (wherein $Het^2$ is a nitrogen-containing aromatic heterocyclic group bonded via a carbon atom) can be produced by, for example, a method shown below.

As the nitrogen-containing aromatic heterocyclic group for $Het^2$, those from the nitrogen-containing aromatic heterocyclic groups exemplified-for the aforementioned Het, that are bonded via a carbon atom, can be mentioned.

[Method AAI]

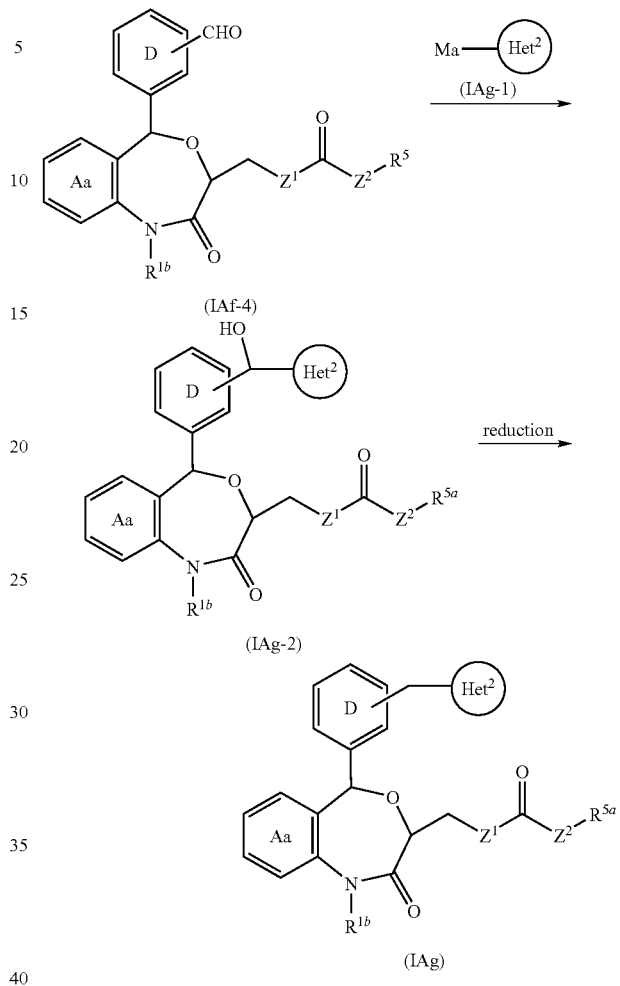

wherein Ma is Li; a metal moiety (e.g., MgBr, MgCl etc.) of a Grignard reagent, and other symbols are as defined above.

The compound (IAg-2) can be produced by reacting compound (IAf-4) with compound (IAg-1).

This reaction is carried out according to an addition reaction of an organic lithium or a Grignard reagent to a carbonyl group, known per se.

This reaction is carried out in a solvent that does not adversely affect the reaction. As such solvent, for example, aprotic solvents (e.g., ethyl ether, tetrahydrofuran, dioxane, toluene, hexane etc.) and the like can be mentioned. This reaction may be carried out in the presence of, where necessary, cerium chloride and the like.

The amount of compound (IAg-1) to be used is generally about 0.5 to 5 molar equivalents, preferably about 1 to 1.5 molar equivalents, per 1 mol of compound (IAf-4).

The reaction temperature is generally about −78° C. to 20° C., preferably about —78° C. to 0° C.

The reaction time is generally about 10 min to 24 hrs, preferably about 30 min to 5 hrs.

The compound (IAg) can be produced by subjecting compound (IAg-2) to a reductive reaction.

This reaction is carried out by, for example, a catalytic reduction in a solvent such as ether solvents (e.g., diethyl ether, tetrahydrofuran, dioxane etc.), hydrocarbon solvents (e.g., benzene, toluene, hexane, heptane etc.), alcohol solvents (e.g., methanol, ethanol, propanol, butanol etc.), halogen solvents (e.g., dichloromethane, dichloroethane, chloroform etc.), acetone, acetonitrile, ethyl acetate, dimethylformamide and the like using, for example, palladium, platinum and the like as a catalyst.

The reaction temperature is generally about 0° C. to 100° C., preferably about 20° C. to 70° C.

The reaction time is generally about 1 to 24 hrs, preferably about 1 to 5 hrs.

The compound (IAg) thus obtained can be isolated and purified by a known separation and purification means, such as concentration, concentration under reduced pressure, solvent extraction, crystallization, recrystallization, phase transfer, chromatography and the like.

The compound (IAg-1) used as the starting compound in the aforementioned [Method AAI] can be produced by a method known per se.

When the compound of the present invention contains an optical isomer, a stereoisomer, a positional isomer or a rotational isomer, these are also encompassed in the compound of the present invention, and can be obtained as a single product according to a synthetic method and separation method known per se. For example, when the compound of the present invention has an optical isomer, an optical isomer resolved from this compound is also encompassed in the compound of the present invention.

The optical isomer can be produced by a method known per se. To be specific, an optically active synthetic intermediate is used, or the final racemate product is subjected to optical resolution according to a conventional method to give an optical isomer.

The method of optical resolution may be a method known per se, such as a fractional recrystallization method, a chiral column method, a diastereomer method and the like.

1) Fractional Recrystallization Method

A salt of a racemate with an optically active compound (e.g., (+)-mandelic acid, (−)-mandelic acid, (+)-tartaric acid, (−)-tartaric acid, (+)-1-phenethylamine, (−)-1-phenethylamine, cinchonine, (−)-cinchonidine, brucine and the like) is formed, which is separated by a fractional recrystallization method, and a free optical isomer is obtained by a neutralization step where desired.

2) Chiral Column Method

A racemate or a salt thereof is applied to a column for separation of an optical isomer (chiral column) to allow separation. In the case of a liquid chromatography, for example, a mixture of an optical isomer is applied to a chiral column such as ENANTIO-OVM (manufactured by Tosoh Corporation) or CHIRAL series (manufactured by Daicel Chemical Industries, Ltd.) and the like, and developed with water, various buffers (e.g., phosphate buffer) and organic solvents (e.g., ethanol, methanol, isopropanol, acetonitrile, trifluoroacetic acid, diethylamine and the like) solely or in admixture to separate the optical isomer. In the case of a gas chromatography, for example, a chiral column such as CP-Chirasil-DeX CB (manufactured by GL Sciences Inc.) and the like is used to allow separation.

3) Diastereomer Method

A racemic mixture is prepared into a diastereomeric mixture by chemical reaction with an optically active reagent, which is prepared into a single substance by a typical separation means (e.g., fractional recrystallization, chromatography method and the like) and the like, and subjected to a chemical treatment such as hydrolysis reaction and the like to separate an optically active reagent moiety, whereby an optical isomer is obtained. For example, when the compound of the present invention contains hydroxy or primary or secondary amino in a molecule, the compound and an optically active organic acid (e.g., MTPA [α-methoxy-α-(trifluoromethyl)phenylacetic acid], (−)-menthoxyacetic acid and the like) and the like are subjected to condensation reaction to give an ester form diastereomer or amide form diastereomer, respectively. When the compound of the present invention has a carboxylic acid group, this compound and an optically active amine or an optically alcohol reagent are subjected to condensation reaction to give an amide form diastereomer or ester form diastereomer, respectively. The separated diastereomer is converted to an optical isomer of the original compound by acidic hydrolysis or basic hydrolysis reaction.

A prodrug of compound (I) is a compound that converts to compound (I) due to the reaction by enzyme, gastric acid and the like under the physiological conditions in the body; that is, a compound that converts to compound (I) by enzymatic oxidation, reduction, hydrolysis and the like, and a compound that converts to compound (I) by hydrolysis and the like by gastric acid and the like. Examples of a prodrug of compound (I) include a compound wherein an amino group of compound (I) is acylated, alkylated or phosphorylated (e.g., a compound where an amino group of compound (I) is eicosanoylated, alanylated, pentylaminocarbonylated, (5-methyl-2-oxo-1,3-dioxolen-4-yl) methoxycarbonylated, tetrahydrofuranylated, tetrahydropyranylated, pyrrolidylmethylated, pivaloyloxymethylated, tert-butylated and the like); a compound wherein a hydroxy group of compound (I) is acylated, alkylated, phosphorylated or borated (e.g., a compound where a hydroxy group of compound (I) is acetylated, palmitoylated, propanoylated, pivaloylated, succinylated, fumarylated, alanylated, dimethylaminomethylcarbonylated, tetrahydropyranylated and the like); a compound wherein a carboxyl group of compound (I) is esterified or amidated (e.g., a compound where a carboxyl group of compound (I) is ethyl esterified, phenyl esterified, carboxymethyl esterified, dimethylaminomethyl esterified, pivaloyloxymethyl esterified, ethoxycarbonyloxyethyl esterified, phthalizyl esterified, (5-methyl-2-oxo-1,3-dioxolen-4-yl)methyl esterified, cyclohexyloxycarbonylethyl esterified, methylamidated and the like) and the like. These compounds can be produced from compound (I) by a method known per se.

A prodrug of compound (I) may be a compound that converts to compound (I) under physiological conditions as described in IYAKUHIN NO KAIHATSU, vol. 7, BUNSHI SEKKEI, 163-198, Hirokawa Shoten (1990).

In addition, the compound (I) may be labeled with an isotope (e.g., $^3$H, $^{14}$C, $^{35}$S, $^{125}$I and the like) or the like.

The compound (I) may be an anhydride or a hydrate.

The compound (I) and a prodrug thereof (hereinafter sometimes to be abbreviated as the compound of the present invention) is low in toxicity (e.g., acute toxicity, chronic-toxicity, genetic toxicity, reproductive toxicity, cardiac toxicity, drug interaction, carcinogenicity) and can be used safely as a TGR5 receptor agonist as they are or by admixing with a pharmacologically acceptable carrier and the like to give a pharmaceutical composition.

Here, various organic or inorganic carriers conventionally used as materials for pharmaceutical reparations are used as a pharmacologically acceptable carrier, which are added as excipient, lubricant, binder, disintegrant for solid preparations; and solvent, dissolution aids, suspending agent, isotonicity agent, buffer, soothing agent and the like for liquid preparations. Where necessary, additive for pharmaceutical preparations such as preservative, antioxidant, coloring agent, sweetening agent and the like can be used.

Preferable examples of the excipient include lactose, sucrose, D-mannitol, D-sorbitol, starch, pregelatinized starch, dextrin, crystalline cellulose, low-substituted hydroxypropyl cellulose, sodium carboxymethylcellulose, gum acacia, pullulan, light silicic anhydride, synthetic aluminum silicate, magnesium aluminate metasilicate and the like.

Preferable examples of the lubricant include magnesium stearate, calcium stearate, talc, colloidal silica and the like.

Preferable examples of the binder include pregelatinized starch, saccharose, gelatin, gum acacia, methylcellulose, carboxymethylcellulose, sodium carboxymethylcellulose, crystalline cellulose, sucrose, D-mannitol, trehalose, dextrin, pullulan, hydroxypropyl cellulose, hydroxypropyl methylcellulose, polyvinylpyrrolidone and the like.

Preferable examples of the disintegrant include lactose, sucrose, starch, carboxymethylcellulose, calcium carboxymethylcellulose, sodium croscarmellose, sodium carboxymethyl starch, light silicic anhydride, low-substituted hydroxypropyl cellulose and the like.

Preferable examples of the solvent include water for injection, physiological brine, Ringer's solution, alcohol, propylene glycol, polyethylene glycol, sesame oil, corn oil, olive oil, cottonseed oil and the like.

Preferable examples of the dissolution aids include polyethylene glycol, propylene glycol, D-mannitol, trehalose, benzyl benzoate, ethanol, trisaminomethane, cholesterol, triethanolamine, sodium carbonate, sodium citrate, sodium salicylate, sodium acetate and the like.

Preferable examples of the suspending agent include surfactants such as stearyltriethanolamine, sodium lauryl sulfate, lauryl aminopropionate, lecithin, benzalkonium chloride, benzethonium chloride, glycerol monostearate and the like; hydrophilic polymers such as polyvinyl alcohol, polyvinylpyrrolidone, sodium carboxymethylcellulose, methylcellulose, hydroxymethylcellulose, hydroxyethylcellulose, hydroxypropylcellulose and the like; polysorbates, polyoxyethylene hydrogenated castor oil; and the like.

Preferable examples of the isotonicity agent include sodium chloride, glycerol, D-mannitol, D-sorbitol, glucose and the like.

Preferable examples of the buffer include phosphate buffer, acetate buffer, carbonate buffer, citrate buffer and the like.

Preferable examples of the soothing agent include benzyl alcohol and the like.

Preferable examples of the preservative include p-oxybenzoates, chlorobutanol, benzyl alcohol, phenethyl alcohol, dehydroacetic acid, sorbic acid and the like.

Preferable examples of the antioxidant include sulfite, ascorbate and the like.

Preferable examples of the coloring agent include water-soluble edible tar pigments (e.g., foodcolors such as Food Color Red Nos. 2 and 3, Food Color Yellow Nos. 4 and 5, Food Color Blue Nos. 1 and 2 and the like), water insoluble lake pigments (e.g., aluminum salt of the aforementioned water-soluble edible tar pigment and the like), natural pigments (e.g., beta carotene, chlorophil, red iron oxide etc.) and the like.

Preferable examples of the sweetening agent include saccharin sodium, dipotassium glycyrrhizinate, aspartame, stevia and the like.

The above-mentioned pharmaceutical composition can be produced according to a method conventionally used in the field of pharmaceutical preparation, such as the method described in Japan Pharmacopoeia (e.g., 13th Ed.). The content of the compound of the present invention in the pharmaceutical composition is, for example, about 0.1-100 wt % of the whole composition.

The dosage form of the pharmaceutical composition is, for example, an oral agent such as tablets (inclusive of sublingual tablets and orally disintegrable tablets), capsules (inclusive of soft capsules and micro capsules), powders, granules, troches, syrups and the like; or a parenteral agent such as injections (e.g., subcutaneous injections, intravenous injections, intramuscular injections, intraperitoneal injections, drip infusions etc.), external agents (e.g., transdermal preparations, ointments etc.), suppositories (e.g., rectal suppositories, vaginal suppositories etc.), pellets, nasal preparations, pulmonary preparations (inhalations), ophthalmic preparations and the like. These agents may be controlled-release preparations such as rapid-release preparations and sustained-release preparations (e.g., sustained-release microcapsules).

The TGR5 receptor agonist of the present invention is useful as a regulator of physiological functions in which TGR5 is involved, an agent for the prophylaxis or treatment of pathology or disease in which TGR5 is involved and the like.

As the physiological function of a "regulator of physiological functions in which TGR5 is involved", cytokine production, immune reaction, GLP (glucagon-like peptide)-1 secretion, insulin secretion, appetite, pancreatic regeneration, pancreatic β cell differentiation, pancreatic β cell growth, insulin resistance and the like can be mentioned. As the regulator (promoter or suppressant) of the physiological function, for example, cytokine production suppressant, immunosuppressant, GLP-1 secretion promoter, insulin secretagogue, hypoglycemic agent, anorectic agent, pancreatic regenerator, pancreatic β cell differentiation promoter, pancreatic β cell growth promoter, insulin sensitizer and the like can be mentioned. As the aforementioned cytokine, for example, tumor necrosis factor (TNF) α, interleukin (IL) 6 and the like can be mentioned. In addition, as the "pathology or disease in which TGR5 is involved", for example, cardiac failure, cardiac infarction, acute kidney failure, angina pectoris, arrhythmia, bronchial asthma, chronic obstructive pulmonary disease, arteriosclerosis, rheumatoid arthritis, diabetes (including type I diabetes, type II diabetes, gestational diabetes), obesity, insulin hyposecretion, pancreatic fatigue, gastric ulcer, ulcerative colitis, allergy, osteoarthritis, erythematosus, excessive immune reaction after transplantation, infectious disease and the like can be mentioned.

For diagnostic criteria of diabetes, Japan Diabetes Society reported new diagnostic criteria in 1999.

According to this report, diabetes is a condition showing any of a fasting blood glucose level (glucose concentration of intravenous plasma) of not less than 126 mg/dl, a 75 g oral glucose tolerance test (75 g OGTT) 2 h level (glucose concentration of intravenous plasma) of not less than 200 mg/dl, and a non-fasting blood glucose level (glucose concentration of intravenous plasma) of not less than 200 mg/dl. A condition not falling under the above-mentioned diabetes and different from "a condition showing a fasting blood glucose level (glucose concentration of intravenous plasma) of less than 110 mg/dl or a 75 g oral glucose tolerance test (75 g OGTT) 2 h level (glucose concentration of intravenous plasma) of less than 140 mg/dl" (normal type) is called a "borderline type."

In addition, ADA (American Diabetes Association) reported new diagnostic criteria of diabetes in 1997 and WHO in 1998.

According to these reports, diabetes is a condition showing a fasting blood glucose level (glucose concentration of intravenous plasma) of not less than 126 mg/dl and a 75 g oral glucose tolerance test 2 h level (glucose concentration of intravenous plasma) of not less than 200 mg/dl.

According to the above-mentioned reports, impaired glucose tolerance is a condition showing a fasting blood glucose level (glucose concentration of intravenous plasma) of less than 126 mg/dl and a 75 g oral glucose tolerance test 2 h level (glucose concentration of intravenous plasma) of not less than 140 mg/dl and less than 200 mg/dl. According to the report of ADA, a condition showing a fasting blood glucose level (glucose concentration of intravenous plasma) of not less than 110 mg/dl and less than 126 mg/dl is called IFG (Impaired Fasting Glucose). According to the report of WHO, among the IFG (Impaired Fasting Glucose), a condition showing a 75 g oral glucose tolerance test 2 h level (glucose concentration of intravenous plasma) of less than 140 mg/dl is called IFG (Impaired Fasting Glycemia).

The TGR receptor agonist of the present invention can be also used as an agent for the prophylaxis or treatment of diabetes, borderline type, impaired glucose tolerance, IFG (Impaired Fasting Glucose) and IFG (Impaired Fasting Glycemia), as determined according to the above-mentioned new diagnostic criteria. Moreover, the TGR receptor agonist of the present invention can prevent progress of borderline type, impaired glucose tolerance, IFG (Impaired Fasting Glucose) or IFG (Impaired Fasting Glycemia) into diabetes.

Furthermore, as the "pathology or disease in which TGR5 is involved", for example, Alzheimer's disease, dementia, eating disorder, hypertension, cardiac hypertrophy, nonsmall cell lung cancer, ovarian cancer, prostate cancer, stomach cancer, bladder cancer, breast cancer, cervical cancer, colon cancer, rectal cancer, pneumonia, bronchitis, lung fibrosis, Crohn's disease, atopic dermatitis, immune deficiency, leukemia, liver cirrhosis, hepatitis, liver failure, cholestasis, calculus, gastrointestinal ulcer, enteritis, obesity and the like can be mentioned.

The TGR5 receptor agonist of the present invention can be administered safely to mammals (e.g., human, mouse, rat, rabbit, guinea pig, hamster, dog, cat, bovine, horse, pig, monkey etc.).

While the dose of the TGR5 receptor agonist of the present invention varies depending on the administration subject, administration route, target disease and the like, for example, when the agonist is orally administered as an immunosuppressant to an adult (about 60 kg), it is about 0.1 to 100 mg, preferably about 1.0 to 50 mg, more preferably about 1.0 to 20 mg, based on the compound of the present invention, which is the active ingredient, per day. The dose may be given at once or in several portions. When the TGR5 receptor agonist of the present invention is parenterally (e.g., intravenous injection) administered as an immunosuppressant to an adult (about 60 kg), the dose is about 0.01 to 30 mg, preferably about 0.1 to 20 mg, more preferably about 0.1 to 10 mg, based on the compound of the present invention, which is the active ingredient, per day. The dose may be given at once or in several portions.

The TGR5 receptor agonist of the present invention can be used in combination with pharmaceutical agents such as therapeutic agents for diabetes, therapeutic agents for diabetic complications, therapeutic agents for hyperlipidemia, antihypertensive agents, antiobestic agents, diuretics, chemotherapeutic agents, immunotherapeutic agents, antiinflammatory drugs, antithrombotic agents, therapeutic agents for osteoporosis, vitamins, antidementia agents, therapeutic agents for incontinentia or pollakiuria, therapeutic agents for dysuria and the like (hereinafter sometimes to be abbreviated as drug X).

As the aforementioned therapeutic agents for diabetes, insulin preparations (e.g., animal insulin preparations extracted from the pancreas of bovine and pig; human insulin preparations genetically synthesized using *Escherichia coli*, yeast; zinc insulin; protamine zinc insulin; fragment or derivative of insulin (e.g., INS-1 etc.), oral insulin preparation and the like), insulin sensitizers (e.g., Pioglitazone or a salt thereof (preferably hydrochloride), Rosiglitazone or a salt thereof (preferably maleate), Reglixane (JTT-501), Netoglitazone (MCC-555), GI-262570, FK-614, CS-011, compounds described in WO99/58510 (e.g., (E)-4-[4-(5-methyl-2-phenyl-4-oxazolylmethoxy)benzyloxyimino]-4-phenylbutyric acid), compounds described in WO01/38325, Tesaglitazar (AZ-242), BM-13-1258, LM-4156, MBX-102, LY-519818, MX-6054, LY-510929, Balaglitazone (NN-2344), T-131 or a salt thereof, THR-0921), α-glucosidase inhibitors (e.g., voglibose, acarbose, miglitol, emiglitate etc.), biguanides (e.g., phenformin, metformin, buformin or a salt thereof (e.g., hydrochlide, fumarate, succinate) etc.), insulin secretagogues [sulfonylurea (e.g., tolbutamide, glibenclamide, gliclazide, chlorpropamide, tolazamide, acetohexamide, glyclopyramide, glimepiride etc.), repaglinide, senaglinide, mitiglinide or calcium salt hydrate thereof, nateglinide, etc.], GLP-1 receptor agonists [e.g., GLP-1, GLP-1MR agent, NN-2211, AC-2993 (exendin-4), BIM-51077, Aib(8,35)hGLP-1(7,37)$NH_2$, CJC-1131 etc.], dipeptidyl peptidase IV inhibitor (e.g., NVP-DPP-278, PT-100, P32/98, P93/01, NVP-DPP7728, LAF237, TS-021 etc.), β3 agonist (e.g., CL-316243, SR-58611-A, UL-TG-307, AJ-9677, AZ40140 etc.), amylin agonists (e.g., pramlintide etc.), phosphotyrosine phosphatase inhibitors (e.g., sodium vanadate etc.), gluconeogenesis inhibitors (e.g., glycogen phosphorylase inhibitor, glucose-6-phosphatase inhibitor, glucagon antagonist etc.), SGLT (sodium-glucose cotransporter) inhibitors (e.g., T-1095 etc.), 11β-hydroxysteroid dehydrogenase inhibitors (e.g., BVT-3498 etc.), adiponectin or agonist thereof, IKK inhibitors (e.g., AS-2868 etc.), leptin resistance improving drugs, somatostatin receptor agonists (compounds described in WO01/25228, WO03/42204, WO98/44921, WO98/45285, WO99/22735 etc.), glucokinase activators (e.g., Ro-28-1675) and the like can be mentioned.

Examples of the therapeutic agent for diabetic complications include aldose reductase inhibitors (e.g., Tolrestat, Epalrestat, Zenarestat, Zopolrestat, Fidarestat (SNK-860), AS-3201, Minalrestat (ARI-509), CT-112 etc.), neurotrophic factors and increasing drugs thereof (e.g., NGF, NT-3, BDNF, neurotrophin production-secretion promoters described in WO01/14372 (e.g., 4-(4-chlorophenyl)-2-(2-methyl-l-imidazolyl)-5-[3-(2-methylphenoxy)propyl]oxazole etc.) and the like), protein kinase C (PKC) inhibitors (e.g., LY-333531 etc.), AGE inhibitors (e.g., ALT-945, pimagedine, pyratoxanthine, N-phenacylthiazolium bromide (ALT-76.6), EXO-226, ALT-711, Pyridorin, Pyridoxamine etc.), active oxygen scavengers (e.g., thioctic acid etc.), cerebral vasodilators (e.g., tiapride etc.), somatostatin receptor agonists (BIM23190), apoptosis signal regulating kinase-1 (ASK-1) inhibitors and the like.

Examples of the therapeutic agent of hyperlipidemia include HMG-CoA reductase inhibitors (e.g., pravastatin, simvastatin, lovastatin, atorvastatin, fluvastatin, pitavastatin, rosuvastatin and salts thereof (e.g., sodium salt etc.) etc.), squalene synthase inhibitors (e.g., compounds described in WO97/10224, such as N-[[(3R,5S)-1-(3-acetoxy-2,2-dimethylpropyl)-7-chloro-5-(2,3-dimethoxyphenyl)-2-oxo-1,2,3,5-tetrahydro-4,1-benzoxazepin-3-yl]acetyl]piperidine-4-acetic acid etc.), fibrate compounds (e.g., bezafibrate, clofibrate, simfibrate, clinofibrate etc.), antioxidant (e.g., lipoic acid, probucol) and the like.

Examples of the antihypertensive agent include angiotensin converting enzyme inhibitors (e.g., captopril, enalapril, delapril etc.), angiotensin II receptor antagonists (e.g., losartan, candesartan cilexetil, eprosartan, valsartan, telmisartan, irbesartan, olmesartan medoxomil, tasosartan, 1-[[2'-(2,5-dihydro-5-oxo-4H-1,2,4-oxadiazol-3-yl)biphenyl-4-yl]methyl]-2-ethoxy-1H-benzimidazole-7-carboxylic acid etc.), calcium antagonist (e.g., manidipine, nifedipine, amlodipine, efonidipine, nicardipine etc.), Clonidine and the like.

Examples of the antiobestic agent include antiobestic agents acting on the central nervous system (e.g., Dexfenfluramine, fenfluramine, phentermine, Sibutramine, amfepramone, dexamphetamine, Mazindol, phenylpropanolamine, clobenzorex; MCH receptor antagonists (e.g., SB-568849; SNAP-7941; compounds described in WO01/82925 and WO01/87834 etc.); neuropeptide Y antagonists (e.g., CP-422935 etc.); cannabinoid receptor antagonists (e.g., SR-141716, SR-147778 etc.); ghrelin antagonist; 11β-hydroxysteroid dehydrogenase inhibitors (e.g., BVT-3498 etc.) and the like), pancreatic lipase inhibitors (e.g., orlistat, ATL-962 etc.), β3 agonists (e.g., CL-316243,.SR-58611-A, UL-TG-307, AJ-9677, AZ40140 etc.), peptidic anorexiants (e.g., leptin, CNTF (Ciliary Neurotropic Factor) etc.), cholecystokinin agonists (e.g., lintitript, FPL-15849 etc.), feeding deterrent (e.g., P-57 etc.) and the like.

Examples of the diuretic include xanthine derivatives (e.g., sodium salicylate and theobromine, calcium salicylate and theobromine etc.), thiazide preparations (e.g., ethiazide, cyclopenthiazide, trichloromethiazide, hydrochlorothiazide, hydroflumethiazide, benzylhydrochlorothiazide, penflutizide, polythiazide, methyclothiazide etc.), antialdosterone preparations (e.g., spironolactone, triamterene etc.), carbonate dehydratase inhibitors (e.g., acetazolamide etc.), chlorobenzenesulfonamide preparations (e.g., chlortalidone, mefruside, indapamide etc.), azosemide, isosorbide, etacrynic acid, piretanide, bumetanide, furosemide and the like.

Examples of the chemotherapeutic agent include alkylation agents (e.g., cyclophosphamide, ifosfamide etc.), metabolic antagonists (e.g., methotrexate, 5-fluorouracil and derivatives thereof etc.), anti-cancer antibiotics (e.g., mitomycin, adriamycin etc.), plant-derived anti-cancer agents (e.g., vincristin, vindesine, taxol etc.), cisplatin, carboplatin, etoposide and the like. Among them, furtulon and neofurtulon, which are 5-fluorouracil derivatives, and the like are preferable.

Examples of the immunotherapeutic agent include microorganism or bacterial components (e.g., muramyl dipeptide derivative, picibanil etc.), polysaccharides having immunity potentiating activity (e.g., lentinan, sizofiran, krestin etc.), cytokines obtained by genetic engineering techniques (e.g., interferon, interleukin (IL) etc.), colony stimulating factors (e.g., granulocyte colony stimulating factor, erythropoietin etc.) and the like, with preference given to interleukins such as IL-1, IL-2 and IL-12.

As the antiinflammatory drug, for example, non-steroidal antiinflammatory agents such as aspirin, acetaminophen, indomethacin and the like can be mentioned.

Examples of the antithrombotic agent include heparin (e.g., heparin sodium, heparin calcium, dalteparin sodium etc.), warfarin (e.g., warfarin potassium etc.), anti-thrombin drugs (e.g., aragatroban etc.), thrombolytic agents (e.g., urokinase, tisokinase, alteplase, nateplase, monteplase, pamiteplase etc.), platelet aggregation inhibitors (e.g., ticlopidine hydrochloride, cilostazol, ethyl icosapentate, beraprost sodium, sarpogrelate hydrochloride etc.) and the like.

Examples of the therapeutic agent of osteoporosis include alfacalcidol, calcitriol, elcatonin, calcitonin salmon, estriol, ipriflavone, pamidronate disodium, alendronate sodium hydrate, incadronate disodium and the like.

As the vitamin, for example, vitamin B1, vitamin B12 and the like can be mentioned.

Examples of the antidementia agent include tacrine, donepezil, rivastigmine, galanthamine and the like.

Examples of the therapeutic agent for incontinentia or pollakiuria include flavoxate hydrochloride, oxybutynin hydrochloride, propiverine hydrochloride and the like.

Examples of the therapeutic agent for dysuria include acetylcholine esterase inhibitors (e.g., distigmine) and the like.

The above-mentioned drug X may be a combination of two or more kinds thereof at an appropriate ratio.

By combining the compound of the present invention and a drug X, a superior effect such as, (1) the dose of TGR5 receptor agonist of the present invention and/or drug X can be reduced as compared to single administration of TGR5 receptor agonist of the present invention or drug X, (2) a synergistic effect can be afforded by a combined use of the compound of the present invention and drug X, and the like, can be achieved.

For the use of the TGR5 receptor agonist of the 30 present invention and drug X in combination, the administration time of TGR5 receptor agonist of the present invention and drug X is not restricted, and TGR5 receptor agonist of the present invention and drug X can be administered to an administration subject simultaneously, or may be administered at staggered times. The dosage of the drug X may be determined according to the dose clinically used, and can be appropriately selected depending on an administration subject, administration route, disease, combination and the like.

The administration mode of TGR5 receptor agonist of the present invention and drug X is not particularly restricted, as long as TGR5 receptor agonist of the present invention and drug X are combined in administration. Examples of such administration mode include the following methods: (1) TGR5 receptor agonist of the present invention and drug X are simultaneously formulated to give a single preparation which is administered. (2) TGR5 receptor agonist of the present invention and drug X are separately formulated to give two kinds of preparations which are administered simultaneously by the same administration route. (3) TGR5 receptor agonist of the present invention and drug X are separately formulated to give two kinds of preparations which are administered by the same administration route at staggered times. (4) TGR5 receptor agonist of the present invention and drug X are separately formulated to give two kinds of preparations which are administered simultaneously by the different administration routes. (5) TGR5 receptor agonist of the present invention and drug X are separately formulated to give two kinds of preparations which are administered by the different administration routes at staggered times (for example, TGR5 receptor agonist of the present invention and drug X are administered in this order, or in the reverse order), and the like.

The present invention further provides a pharmaceutical agent comprising compound (IB), compound (IC), compound (IA) or a prodrug thereof. The pharmaceutical agent is low in toxicity (e.g., acute toxicity, chronic toxicity, genetic toxicity, reproductive toxicity, cardiac toxicity, drug interaction, carcinogenicity) and can be produced and used safely in the same manner as in the aforementioned TGR5 receptor agonist.

The pharmaceutical agent can be safely administered to mammals (e.g., human, mouse, rat, rabbit, guinea pig, hamster, dog, cat, bovine, horse, pig, monkey etc.) as, for example, the aforementioned "regulator of physiological functions in which TGR5 is involved, agent for the prophylaxis or treatment of pathology or disease in which TGR5 is involved" and the like. The dose of the pharmaceutical agent is the same as that of the aforementioned TGR5 receptor agonist.

The present invention further relates to a screening method of a ligand, an agonist or an antagonist for a TGR5 receptor, which comprises use of a TGR5 receptor protein or a partial peptide thereof or a salt thereof and the compound of the present invention.

The TGR5 receptor protein (hereinafter to be simply abbreviated as "TGR5") to be used for the screening method of the present invention is a G-protein-coupled receptor (GPCR) protein containing an amino acid sequence identical or substantially identical to the amino acid sequence shown by SEQ ID NO:2, SEQ ID NO:4, SEQ ID NO:6, SEQ ID NO:8, SEQ ID NO:10 or SEQ ID NO:12, preferably, a G-protein-coupled receptor (GPCR) protein containing an amino acid sequence identical or substantially identical to the amino acid sequence shown by SEQ ID NO:2.

TGR5 may be derived from any type of cells of humans and other mammals (e.g., guinea pig, rat, mouse, rabbit, hamster, dog, pig, sheep, bovine, monkey etc.), for example, splenocytes, neurons, glia cells, pancreatic β cells, bone marrow cells, mesangium cells, Langerhans cells, intestinal L cells, epidermal cells, epithelial cells, endothelial cells, fibroblasts, fibre cells, muscle cells, adipocytes, immune cells (e.g., macrophages, T cells, B cells, natural killer cells, mast cells, neutrophils, basophils, eosinophils, monocytes), megakaryocytes, synovial cells, chondrocytes, osteocytes, osteoblasts, osteoclasts, mammary cells,.hepatocytes and interstitial cells, precursor cells, stem cells and cancer cells of said cells, and cells in the blood cell system. The receptor protein may also derived from any tissue in which said cells are present, for example, the brain, each region of the brain (e.g., olfactory bulbs, amyglada, basal ganglia, hippocampus, thalamus, hypothalamus, subthalamic nucleus, cerebral cortex, medulla oblongata, cerebelleum, occipital lobes, frontal lobe, lateral lobe, putamen, caudate nucleus, corpus callosum, substantia nigra), spinal cord, pituitary gland, stomach, pancreas, kidneys, liver, gonads, thyroid gland, gallbladder, bone marrow, adrenal glands, skin, muscle, lung, digestive tract (e.g., large intestine, small intestine), vascular vessels, heart, thymus, spleen, submandibular gland, peripheral blood, peripheral blood cells, prostate, orchis, testes, ovaries, placenta, uterus, bones, joints, skeletal muscles and the like. The receptor protein may also be synthetic.

The amino acid sequences substantially identical to the amino acid sequence shown by SEQ ID NO:2, SEQ ID NO:4, SEQ ID NO:6, SEQ ID NO:8, SEQ ID NO:10 or SEQ ID NO:12 are amino acid sequences having about 50% or more homology, preferably about 60% or more homology, more preferably about 70% or more homology, further more preferably about 80% or more homology, particularly preferably about 90% or more homology, most preferably about 95% or more homology, to the amino acid sequences shown by SEQ ID NO:2, SEQ ID NO:4, SEQ ID NO:6, SEQ ID NO:8, SEQ ID NO:10 and SEQ ID NO:12.

As proteins containing amino acid sequences substantially identical to the amino acid sequence shown by SEQ ID NO:2, SEQ ID NO:4, SEQ ID NO:6, SEQ ID NO:8, SEQ ID NO:10 and SEQ ID NO:12, for example, proteins containing amino acid sequences substantially identical to the amino acid sequence shown by SEQ ID NO:2, SEQ ID NO:4, SEQ ID NO:6, SEQ ID NO:8, SEQ ID NO:10 or SEQ ID NO:12 and having substantially the same activity as that of a receptor protein consisting of the amino acid sequence shown by SEQ ID NO:2 are preferable.

The substantially same activity includes ligand-binding activity, signal transduction activity and the like. The "substantially the same" means that the quality of the activity is the same. Therefore, although it is preferable that the activities such as ligand-binding activities, signal transduction activities and the like are equivalent (e.g., about 0.01- to 100-fold, preferably about 0.5- to 20-fold, more preferably about 0.5- to 2-fold), quantitative factors such as the level of activity, the molecular weight of the protein and the like may differ.

The activities such as the ligand-binding activity, signal transduction activity and the like can be determined according to known methods and, for example, these activities can be determined according to the screening methods of ligands, agonists or antagonists as described below.

Proteins containing the following amino acid sequences are also used as TGR5: 1) amino acid sequences shown by SEQ ID NO:2, SEQ ID NO:4, SEQ ID NO:6, SEQ ID NO:8, SEQ ID NO:10 or SEQ ID NO:12 in which one, two or more amino acids (preferably 1-30 amino acids, more preferably 1-10 amino acids, most preferably several (1-5) amino acids) are deleted, 2) amino acid sequences shown by SEQ ID NO:2, SEQ ID NO:4, SEQ ID NO:6, SEQ ID NO:8, SEQ ID NO:10 or SEQ ID NO:12 in which one, two, or more amino acids (preferably 1-30 amino acids, more preferably 1-10 amino acids, and most preferably several (1-5) amino acids) are added, 3) amino acid sequences shown by SEQ ID NO:2, SEQ ID NO:4, SEQ ID NO:6, SEQ ID NO:8, SEQ ID NO:10 or SEQ ID NO:12 in which one, two, or more amino acids (preferably 1-30 amino acids, more preferably 1-10 amino acids, and most preferably several (1-5) amino acids) are substituted by other amino acids; or 4) a protein containing a combination of such amino acid sequences and the like.

The protein in the present specification is presented according to the conventional presentation manner of peptides: the left end presents the N-terminal (amino terminal) and the right end presents the C-terminal (carboxyl terminal). In TGR5s including the receptor protein containing the amino acid sequence shown by SEQ ID NO:2, SEQ ID NO:4, SEQ ID NO:6, SEQ ID NO:8, SEQ ID NO:10 or SEQ ID NO:12, the C-terminal may be any of a carboxyl group (—COOH), carboxylate (—COO$^-$), amide (—CONH2) and ester (—COOR).

For R in the esters, for example, $C_{1-6}$ alkyl groups such as methyl, ethyl, n-propyl, isopropyl and n-butyl, for example, $C_{3-8}$ cycloalkyl groups such as cyclopentyl and cyclohexyl, for example, $C_{6-12}$ aryl groups such as phenyl and c-naphthyl, for example, $C_{7-14}$ aralkyl groups including phenyl-$C_{1-2}$ alkyl groups such as benzyl and phenethyl and α-naphthyl-$C_{1-2}$ alkyl groups such as α-naphthylmethyl are used, and pivaloyloxymethyl groups, which are commonly used for oral esters, and the like are also used.

When the TGR5 has a carboxyl group (or carboxylate) at a site other than the C-terminal, TGR5 having an amidated or esterified carboxyl group are also included in TGR5. For the ester form in this case, for example, the C-terminal esters described above and the like are used.

Further, the TGR5 also includes proteins described above in which the amino group of the N-terminal methionine residue is protected by a protecting group (e.g., $C_{1-6}$ acyl groups such as formyl group, $C_{2-6}$ alkanoyl groups such as acetyl and the like, and the like), those in which the N-terminal is cleaved in vivo and the glutamyl group produced is converted to pyroglutamate, those in which substituents on amino acid side chains in the molecule (e.g., —OH, —SH, amino group, imidazole group, indole group, guanidino group and the like) are protected by appropriate protecting groups (e.g., $C_{1-6}$ acyl groups such as formyl group, $C_{2-6}$ alkanoyl groups such as acetyl and the like, and the like), or complex proteins to which sugar chains are bound, that is glycoproteins.

As a specific example of TGR5, for example, receptor protein consisting of an amino acid sequence shown by SEQ ID NO:2, SEQ ID NO:4, SEQ ID NO:6, SEQ ID NO:8, SEQ ID NO:10 or SEQ ID NO:12 and the like are used.

For the partial peptides of TGR5 (hereinafter sometimes to be simply abbreviated as "partial peptides"), any partial peptide may be used as long as it has a partial amino acid sequence of TGR5 described above. For example, of the molecules of TGR5, a region exposed to the outside of the cell membrane, which has substantially the same receptor activity as that of a complete molecule, and the like are used.

Concretely, the partial peptides of TGR5 having amino acid sequence shown by SEQ ID NO:2, SEQ ID NO:4, SEQ ID NO:6, SEQ ID NO:8, SEQ ID NO:10 or SEQ ID NO:12 are peptides containing the regions that are shown to be the extracellular domains (hydrophilic regions) by the hydrophobicity plot analysis. Part of peptides partially containing hydrophobic region may also be used. Peptides containing individual domains can be used, but peptides of a part containing multiple domains may also be used.

The number of amino acids in the partial peptides of the present invention is preferably peptide having at least 20 or more, preferably 50 or more, and more preferably 100 or more of the constitutive amino acid sequence of TGR5 described above and the like.

The substantially identical amino acid sequences are amino acid sequences that have about 50% or more, preferably about 60% or more, more preferably about 70% or more, further more preferably about 80% or more, particularly preferably about 90% or more, most preferably about 95% or more, homology to these amino acid sequences.

Here, the "substantially identical receptor activity" means the same definition as described above. The "substantially identical receptor activity" can be determined as described above.

In the partial peptides of the present invention, one, two, or more amino acids (preferably about 1-10 amino acids, more preferably several (1-5) amino acids) may be deleted, one, two, or more amino acids preferably about 1-20 amino acids, preferably about 1-10 amino acids, and more preferably several (1-5) amino acids) may be added, or one, two, or more amino acids (preferably about 1-10 amino acids, more preferably several amino acids, and most preferably about 1-5 amino acids) may be substituted by other amino acids.

In the partial peptides of the present invention, the C-terminal may generally be any of carboxyl group (—COOH) and carboxylate (—COO⁻), or the C-terminal may be amide (—CONH$_2$) or ester (—COOR) as in the above-mentioned protein of the present invention. When the partial peptide of the present invention has a carboxyl group (or carboxylate) besides C-terminal, the partial peptide of the present invention also encompasses one wherein a carboxyl group is amidated or esterified. As the ester in this case, for example, an ester of the above-mentioned C-terminal and the like are used.

The partial peptides of the present invention include peptides in which the amino group of the N-terminal methionine residue is protected by a protecting group, those in which the N-terminal residue is cleaved in vivo and the glutamine residue is converted to pyroglutaminate, those in which substituents in amino acid side chains in the molecule are protected by appropriate protecting groups, or those in which sugar chains are bound, that is glycopeptides, as in the TGR5 mentioned above.

The salts of the TGR5 or partial peptides include physiologically acceptable salts formed with acids or bases, especially physiologically acceptable salts formed with acids are preferred. For examples, the salts formed with inorganic acids (e.g., hydrochloric acid, phosphoric acid, hydrobromic acid, sulfuric acid) and the salts formed with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid) are used.

TGR5, a partial peptide thereof and a salt thereof can be produced, purified and isolate according to the methods described in WO01/77325 and WO02/84286.

For the polynucleotide encoding TGR5, any polynucleotide containing the nucleotide sequence (DNA or RNA, preferably DNA) encoding TGR5 described above can be used. As the polynucleotide, DNA, RNA and the like having a nucleotide sequence encoding amino acid sequence of TGR5 can be mentioned, which may be double-stranded or single-stranded. When the polynucleotide is double-stranded, it may be double-stranded DNA, double-stranded RNA, or DNA:RNA hybrid. When the polynucleotide is single-stranded, it may be sense strand (i.e. coding strand) or antisense strand (i.e. non-coding strand).

The DNA encoding TGR5 may be any DNA of genomic DNA, genomic DNA library, cDNA and cDNA library derived from the cells and tissues described above, and synthetic DNA. For the vector used for library, bacteriophage, plasmid, cosmid, phagemid and the like may be used. The DNA may be directly amplified by Reverse Transcriptase Polymerase Chain Reaction (hereinafter to be abbreviated as RT-PCR method) using total RNA or mRNA fraction prepared from the cells and tissues described above.

Concretely, the DNA encoding TGR5 may be, for example, any DNA containing the nucleotide sequence shown by SEQ ID NO:1, SEQ ID NO:3, SEQ ID NO:5, SEQ ID NO:7, SEQ ID NO:9 or SEQ ID NO:11 or DNA having the nucleotide sequence that hybridize to the nucleotide sequence shown by SEQ ID NO:1, SEQ ID NO:3, SEQ ID NO:5, SEQ ID NO:7, SEQ ID NO:9 or SEQ ID NO:11 under a high stringent condition, and encoding the receptor protein having substantially same activity (e.g., ligand-binding activity, signal transduction activity and the like) as that of TGR5.

For the DNA that can hybridize to the nucleotide sequence shown by SEQ ID NO:1, SEQ ID NO:3, SEQ ID NO:5, SEQ ID NO:7, SEQ ID NO:9 or SEQ ID NO:11, for example, DNAs containing a nucleotide sequence that have about 70% or more homology, preferably about 80% or more homology, more preferably about 90% or more homology, most preferably about 95% or more homology to the nucleotide sequence shown by SEQ ID NO:1, SEQ ID NO:3, SEQ ID NO:5, SEQ ID NO:7, SEQ ID NO:9 or SEQ ID NO:11 and the like are used.

Hybridization can be performed using a known method or the method analogous thereto, for example, the method described in *Molecular Cloning,* 2nd ed. (J. Sambrook et al., Cold Spring Harbor Lab. Press, 1989) and the like. When a commercial library is used, hybridization may be performed according to a method described in the attached instruction. Preferably, hybridization may be performed according to a high stringent condition.

In the high stringent condition, for example, the sodium concentration is about 19 to 40 mM, preferably about 19 to 20 mM, and the temperature is about 50° C. to 70° C., preferably about 60° C. to 65° C. In the most preferred condition, the sodium concentration is about 19 mM and the temperature is about 65° C.

More concretely, for the DNA encoding human TGR5 containing an amino acid sequence shown by SEQ ID:2, the DNAs containing the nucleotide sequence shown by SEQ ID:1 and the like are used. As the DNA encoding mouse TGR5 containing an amino acid sequence shown by SEQ ID NO:4, a DNA containing a nucleotide sequence shown by SEQ ID NO:3 and the like are used. As the DNA encoding rat TGR5 containing an amino acid sequence shown by SEQ ID NO:6, a DNA containing a nucleotide sequence shown by SEQ ID NO:5 and the like are used. As the DNA encoding bovine TGR5 containing an amino acid sequence shown by SEQ ID NO:8, a DNA containing a nucleotide sequence shown by SEQ ID NO:7 and the like are used. As the DNA encoding rabbit TGR5 containing an amino acid sequence shown by SEQ ID NO:10, a DNA containing a nucleotide sequence shown by SEQ ID NO:9 and the like are used. As the DNA encoding guinea pig TGR5 containing an amino acid sequence shown by SEQ ID NO:12, a DNA containing a nucleotide sequence shown by SEQ ID NO:11 and the like are used.

The DNAs encoding the partial peptides of the present invention may be any DNA that contains a nucleotide sequence encoding the aforementioned partial peptide of the present invention, and may be genomic DNA, genomic DNA library, cDNA and cDNA library derived from the cells and tissues described above, and synthetic DNA. Vectors used for library may be bacteriophage, plasmid, cosmid, phagemid and the like. The DNA may be directly amplified using a mRNA fraction prepared from the cells and tissues described above by RT-PCR method.

Concretely, as the DNA encoding the partial peptides of the present invention, for example: (1) DNA containing a partial nucleotide sequence of the DNA shown by SEQ ID NO:1, SEQ ID NO:3, SEQ ID NO:5, SEQ ID NO:7, SEQ ID NO:9 or SEQ ID NO:11, and (2) DNA containing a partial nucleotide sequence of the DNA that contains a nucleotide sequence that hybridizes to the nucleotide sequence shown by SEQ ID NO:1, SEQ ID NO:3, SEQ ID NO:5, SEQ ID NO:7, SEQ ID NO:9 or SEQ ID NO:11 under a high stringent condition and encoding a receptor protein having substantially same activities (e.g., ligand binding activity, signal transduction activity and the like) as those of TGR5 and the like are used.

For the DNAs that-hybridize to the nucleotide sequence shown by SEQ ID NO:1, SEQ ID NO:3, SEQ ID NO:5, SEQ ID NO:7, SEQ ID NO:9 or SEQ ID NO:11, for example, DNAs containing about 70% or more, preferably about 80% or more, more preferably about 90% or more, most preferably about 95% or more homology to the nucleotide sequence shown by SEQ ID NO:1, SEQ ID NO:3, SEQ ID NO:5, SEQ ID NO:7, SEQ ID NO:9 or SEQ ID NO:11 and the like are used.

The above-mentioned DNA encoding TGR5 or partial peptides thereof can be cloned by the methods described in WO01/77325 and WO02/84286.

Conversion of the DNA nucleotide sequences can be performed by PCR or known methods such as ODA-LA PCR method, Gapped duplex method and Kunkel method or methods analogous thereto using a known kit such as Mutan™-super Express Km (TAKARA SHUZO CO., LTD.), Mutan™-K (TAKARA SHUZO CO., LTD.) and the like.

The cloned DNAs encoding TGR5 or a partial peptide thereof can be used without treatment or used after digestion with restriction enzymes or addition of linkers when desired.

Said DNA may contain the translational initiation codon ATG at the 5'-end and translational stop codon TAA, TGA, or TAG at the 3'-end. These translational initiation codon and stop codon can be added using an appropriate synthetic DNA adaptor.

Expression vectors for TGR5 or a partial peptide thereof can be manufactured, for example, as follows: (i) The objective DNA fragment is excised from the DNA encoding TGR5 or a partial peptide thereof, and (ii) the DNA fragment is ligated to downstream of the promoter in an appropriate vector.

For the vector, *Escherichia coli*-derived plasmid (e.g., pBR322, pBR325, pUC12, pUC13), *Bacillus subtilis*-derived plasmid (e.g., pUB110, pTP5, pC194), yeast-derived plasmid (e.g., pSH19, pSH15), bacteriophages such as λ phage, animal viruses such as retrovirus, vaccinia virus, baculovirus, and pA1-11, pXT1, pRC/CMV, pRC/RSV, pcDNAI/Neo and the like are used.

Any promoter that is appropriate and corresponds to the host used for the gene expression may be used as the promoter used in expression vector of the present invention. For example, when animal cells are used as the host, SRα promoter, SV40 promoter, LTR promoter, CMV promoter, HSV-TK promoter and the like are mentioned.

Among them, CMV promoter, SRα promoter and the like are preferred. When the host is bacteria of *Escherichia* genus, trp promoter, lac promoter, recA promoter, λP$_L$ promoter, 1pp promoter and the like are preferred. When the host is bacteria of *Bacillus* genus, SPO1 promoter, SPO2 promoter, penP promoter and the like are preferred. When the host is yeast, PHO5 promoter, PGK promoter, GAP promoter, ADH promoter and the like are preferred. When the host is insect cells, polyhedrin promoter, P10 promoter and the like are preferred.

In addition to the vectors described above, expression vectors containing enhancer, splicing signal, polyA addition signal, selection marker, SV40 replication origin (hereinafter sometimes to be abbreviated as SV40ori) and the like, may be used when desired. For the selection marker, for example, dihydrofolate reductase (hereinafter to be abbreviated as dhfr) gene [methotrexate (MTX)-resistant], ampicillin resistance gene (hereinafter sometimes to be abbreviated as Amp$^r$), neomycin resistance gene (hereinafter sometimes to be abbreviated as Neo$^r$, G418 resistant) and the like are used. Especially, when dhfr gene is used as a selection marker using a dhfr gene-deficient chinese hamster ovary [CHO(dhfr$^-$)] cell as a host, the objective gene can be selected using a thymidine-free medium.

Where necessary, moreover, a signal sequence appropriate for the host is added to the N-terminal of TGR5 (or substituted by native signal sequence). When the host is bacteria of *Escherichia* genus, PhoA signal sequence, OmpA signal sequence and the like can be used. When the host is bacteria of *Bacillus* genus, α-amylase signal sequence, subtilisin signal sequence and the like can be used. When the host is yeast, MFα signal sequence, SUC2 signal sequence and the like can be used. When the host is animal cells, insulin signal sequence, α-interferon signal sequence, the signal sequence of antibody molecule and the like can be used.

Using the vectors containing the DNA encoding TGR5 or a partial peptide thereof constructed as described above, transformants can be manufactured.

For the host, for example, *Escherichia* genus, *Bacillus* genus, yeast, insect cells, insects, animal cells and the like are used.

Specific examples of the host of *Escherichia* genus are *Escherichia coli* K12 DH1 *[Proceedings of the National*

Academy of Sciences of the USA (Proc. Natl. Acad. Sci. USA) Vol. 60, 160 (1968)], JM103 [Nucleic Acids Research Vol. 9, 309 (1981)], JA221 [Journal of Molecular Biology Vol. 120, 517 (1978)], HB101 [Journal of Molecular Biology Vol. 41, 459 (1969)], C600 [Genetics Vol. 39, 440 (1954)] and the like are used.

For the host of Bacillus genus, for example, Bacillus subtilis MI114 [Gene Vol. 24, 255 (1983)] 207-21 [Journal of Biochemistry Vol. 95, 87 (1984)] and the like are used.

For the host of yeast, for example, Saccharomyces cerevisiae AH22, AH22R⁻, NA87-11A, DKD-5D, 20B-12, Schizosaccharomyces pombe NCYC1913, NCYC2036, Pichia pastoris and the like are used.

For the host of insect cells, for example, when the virus is AcNPV, Spodoptera frugiperda cells (Sf cells), MG1 cells derived from-the middle gut of Trichoplusia ni, High Five™ cells derived from Trichoplusia ni eggs, Mamestra brassicae-derived cells, Estigmena acrea-derived cells and the like are used. When the virus is BmNPV, silkworm-derived cells Bombyx mori N (BmN cells) and the like are used. For said Sf cells, for example, SF9 cells (ATCC CRL1711), Sf21 cells (Vaughn, J. L. et al., In Vivo 13, 213-217 (1977)) and the like are used.

For the host of insect, for example, silkworm larvae and the like are used [Maeda et al., Nature, Vol. 315, 592 (1985)].

For the host of animal cells, for example, monkey COS-7 cells, Vero, chinese hamster ovary cell (hereinafter to be abbreviated as CHO cells), dhfr gene-deficient Chinese hamster ovary cell (hereinafter to be abbreviated as CHO (dhfr⁻) cells), mouse L cells, mouse AtT-20, mouse myeloma cells, rat GH3, human FL cells, human HEK293 cells and the like are used.

Bacteria of Escherichia genus can be transformed according to, for example, the methods described in Proc. Natl. Acad. Sci. USA Vol. 69, 2110 (1972), Gene Vol. 17, 107 (1982) and the like.

Bacteria of Bacillus genus can be transformed according to, for example, the methods described in Molecular & General Genetics Vol. 168, 111 (1979) and the like.

Yeast can be transformed according to, for example, the methods described in Methods in Enzymology Vol. 194, 182-187 (1991), Proc. Natl. Acad. Sci. USA Vol. 75, 1929 (1978) and the like.

Insect cells and insects can be transformed according to, for example, the methods described in Bio/Technology, 6, 47-55 (1988) and the like.

Animal cells can be transformed by, for example, the methods described in Cell Engineering (Saibo Kogaku) Separate Vol. 8, New Cell Engineering Experimental Protocol, 263-267 (1995) (Shujun-sha) and Virology Vol. 52, 456 (1973).

As described above, the transformants transformed by the expression vector containing the DNA encoding TGR5 or a partial peptide thereof can be obtained.

For the medium for culturing the transformants wherein the host is Escherichia or Bacillus host, liquid medium is suitable, in which carbon source, nitrogen source, inorganic compounds, and other substances necessary for the growth of the transformants are contained. The carbon source includes for example, glucose, dextrin, soluble starch, sucrose and the like. The nitrogen source includes for example, inorganic and organic compounds such as ammonium salts, nitrates, corn steep liquor, peptone, casein, meat extract, soybean cake, potato extract and the like. The inorganic compounds include for example, calcium chloride, sodium dihydrogen phosphate, magnesium chloride and the like. Yeast extract, vitamins, growth factors and the like may be added. The pH of about 5 to 8 is desirable for the culture.

For the culture medium for bacteria of Escherichia genus, for example, M9 medium containing glucose and casamino acids (Miller, Journal of Experiments in Molecular Genetics, 431-433, Cold Spring Harbor Laboratory, New York, 1972) is preferred. When more efficiency is required for the function of the promoter, reagent such as 3β-indolyl acrylate may be added. When the host is bacteria of Escherichia genus, the bacteria are generally cultured at about 15° C. to 43° C. for about 3 to 24 hrs, and aeration or agitation may be added to the culture, when necessary.

When the host is bacteria of Bacillus genus, the bacteria are generally cultured at about 30° C. to 40° C. for about 6 to 24 hrs, and aeration or agitation may be added to the culture, when necessary.

For the medium for culturing the transformant of yeast host, for example, Burkholder minimum medium [Bostian, K. L. et al., Proc. Natl. Acad. Sci. USA Vol. 77, 4505 (1980)] and SD medium containing 0.5% casamino acid [Bitter, G. A. et al., Proc. Natl. Acad. Sci. USA Vol. 81, 5330 (1984)] are used. The pH of the medium is preferably adjusted to about 5 to 8. The culture are generally performed at about 20° C. to 35° C. for about 24 to 72 hrs, and aeration or agitation may be added to the culture, when necessary.

When transformants of insect cell host or insect host are cultured, Grace's insect medium (Grace, T. C. C., Nature, 195, 788 (1962)) containing appropriate supplements such as inactivated 10% bovine serum is used as a medium. The pH of the medium is preferably adjusted to about 6.2 to 6.4. Usually, the culture is performed at about 27° C. for about 3 to 5 days, and aeration or agitation may be added to the culture, when necessary.

When the transformants of animal cell host are cultured, for example, MEM medium containing about 5 to 20% fetal calf serum [(Science Vol. 122, 501 (1952)), DMEM medium [Virology Vol. 8, 396 (1959)], RPMI 1640 medium [The Journal of the American Medical Association vol. 199, 519 (1967)], 199 medium [Proceeding of the Society for the Biological Medicine Vol. 73, 1 (1950)] and the like are used as the medium. The pH is preferably adjusted to about 6 to 8. Usually, the culture is performed at about 30° C. to 40° C. for about 15 to 60 hrs, and aeration or agitation may be added to the culture, when necessary.

As described above, TGR5 or a partial peptide thereof or a salt thereof can be produced intracellularly, on cell membrane or extracellularly of the transformants.

TGR5 or a partial peptide thereof or a salt thereof can be purified from the culture described above by, for example, the methods described below.

When TGR5 or a partial peptide thereof or a salt thereof is extracted from the cultured bacteria or cells, the bacteria or cells are collected after culture by a known method, and suspended in an appropriate buffer. The bacteria or cells are then disrupted using ultrasonication, lysozymes, and/or by freeze-thawing and the like, and the crude extract of receptor protein is obtained by centrifugation or filtration. The buffer may contain a protein denaturation agent such as urea, guanidine hydrochloride and the like. When TGR5 or a partial peptide thereof or a salt thereof is of a membrane binding type, the membrane fraction precipitated by centrifugation or filtration is solubilized with a surfactant such as TritonX-100™ and the like, and centrifuged to recover a supernatant. When TGR5 or a partial peptide thereof or a salt thereof is secreted into a culture medium, after the completion of the culture, the bacteria or cells and culture supernatant are separated by a known method and the culture supernatant is collected.

For purification of the TGR5 or a partial peptide thereof or a salt thereof contained in the thus-obtained culture supernatant, or a membrane solubilized fraction, known methods for separation and purification can be appropriately combined. These known methods for separation and purification include methods using solubility such as salting out and solvent precipitation, methods mainly using differences in molecular weight such as dialysis, ultrafiltration, gel filtration, and SDS-polyacrylamide gel electophoresis, methods using differences in electric charge such as ion-exchange chromatography, methods using specific affinity such as affinity chromatography, methods using differences in hydrophobicity such as reverse-phase high performance liquid chromatography, methods using differences in isoelectric point such as isoelectric focusing and the like.

When TGR5 or a partial peptide thereof thus obtained is in a free form, the free form can be converted to salts by known methods or methods analogous thereto. Conversely, when TGR5 or a partial peptide thereof is obtained in a salt form, the salt form can be converted to the free form or other salts by known methods or methods analogous thereto.

TGR5 or a partial peptide thereof produced by transformants can be optionally modified or partially removed a polypeptide from TGR5 or a partial peptide thereof by treating TGR5 or a partial peptide thereof with an appropriate protein-modifying enzyme before or after purification. For the protein-modifying enzyme, for example, trypsin, chymotrypsin, arginylendopeptidase, protein kinase, glycosidase and the like are used.

The activity of TGR5 or a partial peptide thereof or a salt thereof thus produced can be measured by binding assay using labeled ligands and by enzyme immunoassay using specific antibody and the like.

In the following, a screening method for a compound that changes the bindability between TGR5 and a cholesterol metabolism-related substance, which is a physiological ligand thereof (i.e., other ligand to TGR5, TGR5 agonist, TGR5 antagonist and the like) is described in detail.

As mentioned above, since the compound of the present invention has a TGR5 agonistic activity, TGR5 ligand, agonist or antagonist can be efficiently screened for from the test compound by the use of a binding assay system using TGR5 or a partial peptide thereof or a salt thereof (hereinafter sometimes to be comprehensively abbreviated as to be "TGR5") (including cells expressing recombinant or endogenous TGR5, cell membrane fraction thereof and the like) and the compound of the present invention as a surrogate ligand.

The TGR5 ligand and agonist are physiological and non-physiological compounds that bind with TGR5 to show a cell stimulating activity (e.g., increasing of intracellular CAMP production activity, activation of MAP kinase and the like) (hereinafter to be generally abbreviated as "TGR5 agonist"). As the cell stimulating activity, for example, activity to increase (1) intracellular CAMP production, (2) phosphorylation of intracellular protein (e.g., MAP kinase and the like), (3) extracellular pH reduction, (4) activation of low molecular weight G proteins such as Rho, Rac, Ras and the like, (5) transcription activation of reporter gene (e.g., luciferase and the like) placed downstream of transcription control CRE cis-element (cAMP responsive element), AP1, NFAT, SRE (serum responsive element) and the like, (6) intracellular calcium ion mobilization, (7) intracellular cGMP production, (8) inositol phosphate production and the like, can be mentioned.

The TGR5 antagonist is a compound that binds with TGR5 but does not show a cell stimulating activity, or shows an activity inverse to the cell stimulating activity (inverse agonistic activity). In the present specification, therefore, the "TGR5 antagonist" is used as a concept encompassing not only what is called neutral antagonists but also inverse agonists.

In addition, by the screening method of the present invention, a compound that potentiates binding avidity of cholesterol metabolism-related substance and TGR5, or a compound that decreases the binding avidity of cholesterol metabolism-related substance and TGR5 and the like can be screened for.

That is, the present invention provides a screening method of TGR5 agonist or TGR5 antagonist, which comprises comparing between (i) when TGR5 and the compound of the present invention are brought into contact and (ii) when TGR5, the compound of the present invention and a test compound are brought into contact.

The screening method of the present invention is characterized in that, for example, binding amount, cell stimulating activity and the like of the compound of the present invention relative to TGR5 in the cases of (i) and (ii) are determined and compared.

More specifically, the present invention provides (1) a screening method of TGR5 agonist or TGR5 antagonist, which is characterized in that the amounts of the labeled compound of the present invention bound to TGR5 in the cases of when a labeled compound of the present invention is brought into contact with TGR5 and when a labeled compound of the present invention and a test compound are brought into contact with TGR5 are determined and compared, (2) a screening method of TGR5 agonist or TGR5 antagonist, which is characterized in that the amounts of the labeled compound of the present invention bound to a cell or a membrane fraction in the cases of when a labeled compound of the present invention is brought into contact with the cell containing TGR5 or the membrane fraction of the cell and when a labeled compound of the present invention and a test compound are brought into contact with the cell containing TGR5 or the membrane fraction of the cell are determined and compared, (3) a screening method of TGR5 agonist or TGR5 antagonist, which is characterized in that the amount of the labeled compound of the present invention bound to TGR5 in the cases of when a labeled compound of the present invention is brought into contact with TGR5 expressed on a cell membrane by culture of a transformant containing TGR5 DNA and when a labeled compound of the present invention and a test compound are brought into contact with TGR5 expressed on a cell membrane by culture of a transformant containing TGR5 DNA are determined and compared, (4) a screening method of TGR5 agonist or TGR5 antagonist, which is characterized in that the cell stimulating activity via TGR5 in cells containing TGR5 are determined in the presence or absence of a test compound and compared, (5) a screening method of TGR5 agonist or TGR5 antagonist, which is characterized in that the cell stimulating activity via TGR5 expressed on a cell membrane by culture of a transformant containing TGR5 DNA are determined in the presence or absence of a test compound and compared, (6) a screening method of TGR5 agonist or TGR5 antagonist, which is characterized in that the cell stimulating activity via TGR5 in the cases of when a compound of the present invention is brought into contact with a cell containing TGR5-and when a compound of the present invention and a test compound are brought into contact with a cell containing TGR5 are determined and compared, and (7) a screening method of TGR5 agonist or TGR5 antagonist, which is characterized in that the cell stimulating activity via TGR5 in the cases of when a compound of the present invention is brought into contact with TGR5 expressed on a cell membrane by culture of a transformant containing TGR5 DNA and when a compound of the present invention and a test compound are brought into contact with TGR5 expressed on a cell membrane by culture of a transformant containing TGR5 DNA are determined and compared.

TGR5 or cells expressing TGR5 can be prepared using the above-mentioned method.

As the cell stimulating activities, for example, (1) intracellular cAMP production, (2) phosphorylation of intracellular protein (e.g., MAP kinase and the like), (3) extracellular pH reduction, (4) activation of low molecular weight G proteins such as Rho, Rac, Ras and the like, (5) activation of reporter gene (e.g., luciferase and the like) placed downstream of transcription element CRE (cAMP responsive element), AP1, NFAT, SRE (serum responsive element) and the like, (6) intracellular calcium ion mobilization, (7) intracellular cGMP production, (8) inositol phosphate production and the like can be mentioned.

As the test compound, for example, peptide, protein, non-peptidic compound, synthetic compound, fermentation product, cell extract, plant extract, animal tissue extract and the like are used and these compounds may be novel compounds or known compounds.

In the screening method of the present invention, when cells containing TGR5 are used, the cells may be fixed with glutaraldehyde, formalin, etc. The cells can be fixed by a known method.

The cells containing TGR5 are host cells that express the TGR5 (including cell endogenously expressing TGR5). For the host cells, *Escherichia coli, Bacillus subtilis*, yeast, insect cells, animal cells and the like are preferred.

The membrane fraction is a fraction containing the abundant cell membrane obtained after disruption of the above-mentioned cells containing TGR5 by a known method. The cell disruption methods include crushing the cells using a Potter-Elvehjem homogenizer, disruption using a Waring blender or polytron (Kinematica Co.), disruption by ultrasonication, and disruption by passing the cells through a narrow nozzle with compressing the cells using a French Press and the like. For the cell membrane fractionation, fractionation method based on centrifugal force such as centrifugation for fractionation and density gradient centrifugation are mainly used. For example, disrupted cell suspension is centrifuged at a low speed (500 to 3,000 rpm) for a short time (usually about 1 to 10 min), the supernatant is then centrifuged at a high speed (15,000 to 30,000 rpm) for usually 30 min to 2 hrs, and the obtained precipitate is used as the membrane fraction. The membrane fraction contains many membrane components such as the expressed TGR5, and phospholipids and membrane proteins derived from the cells.

The amount of receptor protein in the cells and membrane fractions containing TGR5 is preferably $10^3$ to $10^8$ molecules and suitably $10^5$ to $10^7$ molecules per cell. A higher expression amount enhances ligand binding activity (specific activity) per membrane fraction, which makes not only construction of a highly sensitive screening system but also assay of a large amount of specimen in a single lot possible.

To perform the above-mentioned screening methods (1) to (3), for example, a suitable TGR5-containing fraction and a labeled compound of the present invention are necessary.

As the TGR5-containing fraction, a TGR5 protein (peptide) preparation (when the assay system is a heterogeneous type requiring solid liquid (BF) separation, the preparation is desirably immobilized on a suitable solid phase such as a microplate, glass beads, magnetic particles and the like) isolated from TGR5 producing cells by a conventional method, or chemically synthesized or synthesized by a cell-free translation system, a TGR5-containing lipid bilayer (e.g., proteo-liposome) obtained by fusing TGR5 and a suitable lipid (e.g., mixed phospholipid, cholesterol etc.) and the like can be exemplified for (1), cells endogenously expressing TGR5 or a membrane fraction thereof can be exemplified for (2), and a transformant expressing a recombinant TGR5 (including mutants, partial peptides and the like) having an activity equivalent to endogenous TGR5, or a membrane fraction thereof and the like are preferably exemplified for (2) and (3). Here, the equivalent activity means the same level of ligand binding activity, signal transduction activity and the like.

As the labeled compound of the present invention, for example, a compound of the present invention labeled with radioisotope such as [$^3$H], [$^{125}$I], [$^{14}$C], [$^{35}$S] or the like, fluorescence substance, enzyme or the like, or the like is used.

Concretely, to perform screening for a TGR5 agonist or antagonist, firstly, TGR5 preparation is prepared by suspending cells or a cell membrane fraction (cell-derived or reconstructed membrane) containing TGR5 or a TGR5-immobilized solid phase into a buffer appropriate for the screening. As the buffer, any buffer that does not inhibit the binding of the compound of the present invention to TGR5 such as phosphate buffer and Tris-hydrochloride buffer and the like having pH 4 to 10 (preferably pH 6 to 8) can be used. To reduce non-specific binding, a surfactant such as CHAPS, Tween-80™ (Kao-Atras Co.), digitonin, deoxycholate and the like may be added to the buffer. Further, to inhibit degradation of TGR5 and the test compound (peptidic compound) by proteases, protease inhibitors such as PMSF, leupeptin, E-64 (Peptide Research Laboratory, CO.), and pepstatin may be added. To 0.01 to 10 ml of TGR5 suspension, a specified amount (e.g., 5,000 to 500,000 cpm in the case of RI labeling) of labeled compound of the present invention is added so that $10^{-4}$ M to $10^{-10}$ M of the test compound can exist simultaneously. To examine the amount of non-specific binding (NSB), reaction tubes containing a highly excessive amount of non-labeled compound of the present invention are also prepared. The reaction is performed at about 0° C. to 50° C., preferably about 4° C. to 37° C., for about 20 min to 24 hrs, preferably for about 30 min to 3 hrs. After the reaction, the reaction solution is filtered through a glass fiber filter and the like and the filter was washed with an appropriate amount of the buffer. The amount of labeling (e.g., radioactivity in the case of RI labeling, using a liquid scintillation counter or γ-counter) remaining on the glass fiber filter is measured. A test compound showing a specific binding amount (B-NSB) of, for example, not more than 50%, wherein a count ($B_0$-NSB) obtained by subtracting a non-specific binding amount (NSB) from a count ($B_0$) free of antagonistic substance is taken as 100%, can be selected as a candidate substance having an antagonistic inhibitory ability (agonist or antagonist).

When a binding between TGR5 and the compound of the present invention is measured using, for example, a surface plasmon resonance (SPR) method and the like, the compound of the present invention does not need to be labeled.

To perform the above-mentioned screening methods of TGR5 agonist or TGR5 antagonist (4) to (7), TGR5 mediated cell stimulating activity can be measured using a known method or commercial assay-kits.

Concretely, first, cells containing TGR5 are cultured in multiwell plates and the like. Before screening, the medium is exchanged to fresh medium or an appropriate buffer that exhibits no toxicity for the cells. After incubation of the cells by adding a test compound and the like for a specified time, the cells are extracted or the supernatant is collected, and the product is quantified according to the corresponding method. When detection of the production of a substance (e.g., transcription or translated product under the control of CAMP, CRE and the like) to be used as an index of cell stimulating activity is difficult due to catabolic enzymes contained in the cell, an inhibitor of the catabolic enzymes may be added before assay. As regards the activity of CAMP production inhibition and the like, it can be detected as a production inhibitory action on the cell made to show increased basic production amount with forskolin and the like.

For example, of the test compounds selected by the above-mentioned screening methods (1) to (3) (which antagonized the compound of the present invention with regard to the binding with TGR5), a test compound that increases the above-mentioned cell stimulating activity by not less than about 10%, preferably not less than about 20%, more preferably not less than about 50%, as compared to the absence of a test compound in the above-mentioned screening methods (4) to (5), can be selected as a TGR5 agonist.

On the other hand, of the test compounds selected by the above-mentioned screening methods (1) to (3), a test compound that does not increase (does not change or decreases) the above-mentioned cell stimulating activity as compared to the absence of a test compound in the above-mentioned screening methods (4) to (5), can be selected as a TGR5 antagonist.

In addition, a test compound that decreases the above-mentioned cell stimulating activity by about 10%, preferably not less than about 20%, more preferably not less than about 50%, as compared to the absence of a test compound in the above-mentioned screening methods (6) to (7), can be selected as a TGR5 antagonist. On the other hand, in the above-mentioned screening methods (6) to (7), when a partial agonist having a relatively low TGR5 agonistic activity is used as the compound of the present invention, a test compound capable of increasing the above-mentioned cell stimulating activity as compared to the absence of a test compound can be also selected as a full agonist having high TGR5 agonistic activity.

The screening kit for TGR5 agonist or TGR5 antagonist of present invention comprises TGR5, a cell containing TGR5 or a membrane fraction of a cell containing TGR5 and the compound of the present invention and the like.

The screening kit and use thereof of the present invention are exemplified by, but not limited to, the following examples.

1. Reagents for Screening (1) Buffers for Measurement and Washing

Hanks' Balanced Salt Solution (Gibco Co.) supplemented with 0.05% bovine serum albumin (Sigma Co.). The solution is sterilized by filtration through a 0.45 µm filter, and stored at 4° C. or may be prepared at use.

(2) Standard TGR5

CHO cells expressing TGR5 are passed in 12-well plates at a density of $5\times10^5$ cells/well and cultured at 37° C. under 5% $CO_2$ and 95% air for two days.

(3) Labeled Compound of the Present Invention (Hereinafter to be Abbreviated as labeled Compound)

The compound of the present invention labeled with commercial $[^3H]$, $[^{125}I]$, $[^{14}C]$, $[^{35}S]$ or the like. The compound in the form of aqueous solution is stored at 4° C. or −20° C., and the solution is diluted to 1 µM with measurement buffer at use.

(4) Standard Solution of the Compound of the Present Invention (Hereinafter to be Abbreviated as Non-labeled Compound Standard Solution)

The compound of the present invention is dissolved in PBS containing 0.1% bovine serum albumin (manufactured by SIGMA) to 1 mM and preserved at −20° C.

2. Measurement Methods (1) CHO cells expressing TGR5 are cultured in a 12-well tissue culture plate and washed twice with 1 ml of measurement buffer, and 490 µl of the measurement buffer is added to each well.

(2) A solution of a test compound (5 µl) at $10^{-3}$ to $10^{-10}$ M is added, 5 µl of labeled test compound is added, and the cell are reacted at room temperature for one hr. To measure the non-specific binding, 5 µl of the non-labeled compound standard solution ($10^{-3}$ M) is added in place of the test compound.

(3) The reaction solution is removed, and the wells are washed three times with 1 ml of washing buffer. The labeled compound bound to the cells is dissolved with 0.2N NaOH-1% SDS, and mixed with 4 ml of liquid scintillator A (Wako Pure Chemical Industries, Ltd.)

(4) The radioactivity is measured using a liquid scintillation counter (Beckman Co.), and Percent Maximum Binding (PMB) is determined by the following formula:

$$PMB=[(B-NSB)/(B_0-NSB)]\times 100$$

PMB: Percent Maximum Binding

B: value with addition of sample

NSB: Non-specific Binding (amount of non-specific binding)

$B_0$: maximum binding amount

The screening method of the present invention is characterized by screening for a TGR5 agonist or TGR5 antagonist using, TGR5 and the compound of the present invention, as a surrogate ligand. Use of such synthetic ligand is advantageous as compared to screening using an endogenous ligand, which is a naturally occurring substance, in that labeling of the ligand is easy and, binding activity to TGR5 is stronger than by an endogenous ligand, and the screening can be performed efficiently with a small amount of a ligand.

The compound obtained by the screening method or screening kit of the present invention, and a salt thereof are TGR5 agonists or TGR5 antagonists.

Since TGR5 agonist has an action similar to the physiological activity (ligand activity) that a cholesterol metabolism-related substance to TGR5 has, it is useful as a safe and low less pharmaceutical agent according to the cholesterol metabolism-related substance-like activity, such as a regulator (promoter) of physiological function in which TGR5 is involved, an agent for the prophylaxis or treatment of pathology or disease in which TGR5 is involved, and the like.

Since TGR5 antagonist can inhibit the physiological activity (ligand activity) to TGR5 that the cholesterol metabolism-related substance has, it is useful as a safe and less toxic pharmaceutical agent such as a regulator (suppressant) of physiological function in which TGR5 is involved, an agent for the prophylaxis or treatment of pathology or disease in which TGR5 is involved, and the like, based on the inhibitory activity.

Since a compound that potentiates the binding avidity between cholesterol metabolism-related substance and TGR5 can enhance the physiological activity (ligand activity) to TGR5 that the cholesterol metabolism-related substance has, it is useful as a safe and less toxic pharmaceutical agent such as a regulator (promoter) of physiological function in which TGR5 is involved, an agent for the prophylaxis or treatment of pathology or disease in which TGR5 is involved, and the like, based on the enhancing activity.

Since a compound that decreases the binding avidity between the cholesterol metabolism-related substance and TGR5 can decrease the physiological activity (ligand activity) to TGR5 that the cholesterol metabolism-related substance has, it is useful as a safe and less toxic pharmaceutical agent such as a regulator (suppressant) of physiological function in which TGR5 is involved, an agent for the prophylaxis or treatment of pathology or disease in which TGR5 is involved, and the like, based on the decreasing activity.

Here, as the physiological function of a "regulator of physiological function in which TGR5 is involved", cytokine production, immune reaction, GLP (glucagon-like peptide)-1 secretion, insulin secretion, appetite, pancreatic regeneration, pancreatic β cell differentiation, pancreatic β cell growth, insulin resistance and the like can be mentioned. As the regulator (promoter or suppressant) of the physiological function, for example, cytokine production regulator (promoter or suppressant), immunoregulator (promoter or suppressant), GLP-1 secretion promoter, insulin secretagogue, anorectic agent, pancreatic regenerator, pancreatic β cell differentiation promoter, pancreatic β cell growth promoter, insulin sensitizer and the like can be mentioned.

In addition, as the "pathology or disease in which TGR5 is involved", for example, cardiac failure, cardiac infarction, acute kidney failure, angina pectoris, arrhythmia, bronchial asthma, chronic obstructive pulmonary disease, arteriosclerosis, rheumatoid arthritis, diabetes (including type I diabetes, type II diabetes, gestational diabetes), obesity, insulin hyposecretion, pancreatic fatigue, gastric ulcer, ulcerative colitis, allergy, osteoarthritis, erythematosus, excessive immune reaction after transplantation, infectious disease and the like can be mentioned.

Furthermore, as the "pathology or disease in which TGR5 is involved", for example, Alzheimer's disease, dementia, eating disorder, hypertension, hypotension, cardiac hypertrophy, nonsmall cell lung cancer, ovarian cancer, prostate cancer, stomach cancer, bladder cancer, breast cancer, cervical cancer, colon cancer, rectal cancer, pneumonia, bronchitis, lung fibrosis, Crohn's disease, atopic dermatitis, immune deficiency, leukemia, liver cirrhosis, hepatitis, liver failure, cholestasis, calculus, gastrointestinal ulcer, enteritis, obesity, pain and the like can be mentioned.

Of these diseases, TGR5 agonist is particularly effective for the prophylaxis or treatment of diseases caused by promotion of immune function, macrophage function and the like (e.g., inflammatory disease, excessive immune reaction after transplantation and the like).

On the other hand, TGR5 antagonist is particularly effective for the prophylaxis or treatment of diseases caused by suppression of immune function, macrophage function and the like (e.g., immunodeficiency, infectious disease and the like).

When the TGR5 agonist or TGR5 antagonist obtained using the screening method or screening kit of the present invention is used as the above-mentioned pharmaceutical agent, they can be used as they are or by admixing with a pharmacologically acceptable carrier and the like to give a pharmaceutical composition.

Here, various organic or inorganic carriers conventionally used as materials for pharmaceutical preparations are used as a pharmacologically acceptable carrier, which are added as excipient, lubricant, binder, disintegrant for solid preparations; and solvent, dissolution aids, suspending agent, isotonicity agent, buffer, soothing agent and the like for liquid preparations. Where necessary, additives for pharmaceutical preparations such as preservative, antioxidant, coloring agent, sweetening agent and the like can be used. Specifically, as these carrier substances and additives for pharmaceutical preparations, those similar to the above-mentioned TGR5 receptor agonist containing the compound of the present invention are preferably shown.

The above-mentioned pharmaceutical composition can be produced according to a method conventionally used in the field of pharmaceutical preparation, such as the method described in Japan Pharmacopoeia (e.g., 13th Ed.) and the like. The content of the TGR5 agonist or TGR5 antagonist in the pharmaceutical composition is for example, about 0.1-100 wt % of the whole composition.

The dosage form of the aforementioned pharmaceutical composition is, for example, an oral agent such as tablets (inclusive of sublingual tablets and orally disintegrable tablets), capsules (inclusive of soft capsules and micro capsules), powders, granules, troches, syrups and the like; or a parenteral agent such as injections (e.g., subcutaneous injections, intravenous injections, intramuscular injections, intraperitoneal injections, drip infusions etc.), external agents (e.g., transdermal preparations, ointments etc.), suppositories (e.g., rectal suppositories, vaginal suppositories etc.), pellets, nasal preparations, pulmonary preparations (inhalations), ophthalmic preparations and the like. These agents may be controlled-release preparations such as rapid-release preparations and sustained-release preparations (e.g., sustained-release microcapsules).

Since the preparation obtained in this way is safe and low in toxicity, it can be administered to, for example, human and other mammals (e.g., rat, mouse, guinea pig, rabbit, sheep, pig, bovine, cat, dog, monkey etc.).

While the dose of the TGR5 agonist-containing preparation varies depending on the administration subject, administration route, disease and the like, for example, when the preparation is orally administered as an immunosuppressant to an adult (about 60 kg), it is about 0.1 to 100 mg, preferably about 1.0 to 50 mg, more preferably about 1.0 to 20 mg, based on TGR5 agonist, which is the active ingredient, per day. The dose may be given at once or in several portions. When the preparation is parenterally (e.g., intravenous injection) administered as an immunosuppressant to an adult (about 60 kg), the dose is about 0.01 to 30 mg, preferably about 0.1 to 20 mg, more preferably about 0.1 to 10 mg, based on TGR5 agonist, which is the active ingredient, per day. The dose may be given at once or in several portions. The amount calculated for 60 kg can be administered to other animals.

While the dose of the TGR5 antagonist-containing preparation varies depending on the administration subject, administration route, disease and the like, for example, when the preparation is orally administered to an adult (body weight about 60 kg) as an adjuvant, the daily dose is about 0.1 to about 100 mg, preferably about 1.0 to 50 mg, more preferably about 1.0 to 20 mg, based on the TGR5 antagonist, which is an active ingredient. The dose may be given at once or in several portions. In addition, when the preparation is parentearlly (e.g., intravenous injection) administered to an adult (body weight about 60 kg) as an adjuvant, the daily dose is about 0.01 to 30 mg, preferably about 0.1 to 20 mg, more preferably about 0.1 to 10 mg, based on the TGR5 antagonist, which is an active ingredient. The dose may be given at once or in several portions. The amount calculated for 60 kg can be administered to other animals.

When bases or amino acids are expressed in abbreviations in the present specification, the following abbreviations in accordance with IUPAC-IUB Commission on Biochemical Nomenclature or based on customary abbreviations in this field are used. If amino acids can occur as optical isomers, L-isomers are referred to unless otherwise specified.

| | |
|---|---|
| DNA | deoxyribonucleic acid |
| cDNA | complementary deoxyribonucleic acid |
| A | adenine |
| T | thymine |
| G | guanine |
| C | cytosine |
| RNA | ribonucleic acid |
| mRNA | messenger ribonucleic acid |
| dATP | deoxyadenosine triphosphate |
| dTTP | deoxythymidine triphosphate |
| dGTP | deoxyguanosine triphosphate |
| dCTP | deoxycytidine triphosphate |
| ATP | adenosine triphosphate |
| EDTA | ethylenediamine tetraacetic acid |
| SDS | sodium dodecyl sulfate |
| Gly | glycine |
| Ala | alanine |
| Val | valine |
| Leu | leucine |
| Ile | isoleucine |
| Ser | serine |
| Thr | threonine |
| Cys | cysteine |
| Met | methionine |
| Glu | glutamic acid |
| Asp | aspartic acid |
| Lys | lysine |
| Arg | arginine |
| His | histidine |
| Phe | phenylalanine |
| Tyr | tyrosine |
| Trp | tryptophan |
| Pro | proline |
| Asn | asparagine |
| Gln | glutamine |
| pGlu | pyroglutamic acid |

The substituent groups, protecting groups and reagents appearing frequently in the present specification are expressed in the following symbols.

| | |
|---|---|
| Me | methyl group |
| Et | ethyl group |
| Bu | butyl group |
| Ph | phenyl group |
| CHO | formyl |
| Bzl | benzyl |
| Z | benzyloxycarbonyl |
| Boc | t-butoxycarbonyl |
| Tr | trityl |
| Fmoc | N-9-fluorenylmethoxycarbonyl |
| HOBt | 1-hydroxybenztriazole |
| HOOBt | 3,4-dihydro-3-hydroxy-4-oxo-1,2,3-benzotriazine |
| HONB | 1-hydroxy-5-norbornene-2,3-dicarboxyimide |
| DCC | N,N'-dicyclohexylcarbodiimide |

Other abbreviations used in the present specification mean the following.

| | |
|---|---|
| s | singlet |
| d | doublet |
| t | triplet |
| q | quartet |
| dd | double doublet |
| ddd | double double doublet |
| dt | double triplet |
| br | broad |
| brs | broad singlet |
| J | coupling constant |
| Hz | Hertz |
| $CDCl_3$ | deuterated chloroform |
| DMSO-$d_6$ | deuterated dimethyl sulfoxide |
| $^1$H NMR | proton nuclear magnetic resonance |

The sequence numbers in the Sequence Listing in the present specification show the following sequences.

SEQ ID NO:1 shows the nucleotide sequence of cDNA encoding TGR5 derived from human.

SEQ ID NO:2 shows the amino acid sequence of TGR5 derived from human.

SEQ ID NO:3 shows the nucleotide sequence of cDNA encoding TGR5 derived from mouse heart.

SEQ ID NO:4 shows the amino acid sequence of TGR5 derived from mouse heart.

SEQ ID NO:5 shows the nucleotide sequence of cDNA encoding TGR5 derived from rat heart.

SEQ ID NO:6 shows the amino acid sequence of TGR5 derived from rat heart.

SEQ ID NO:7 shows the nucleotide sequence of cDNA encoding TGR5 derived from bovine.

SEQ ID NO:8 shows the amino acid sequence of TGR5 derived from bovine.

SEQ ID NO:9 shows the nucleotide sequence of cDNA encoding TGR5 derived from rabbit.

SEQ ID NO:10 shows the amino acid sequence of TGR5 derived from rabbit.

SEQ ID NO:11 shows the nucleotide sequence of cDNA encoding TGR5 derived from guinea pig.

SEQ ID NO:12 shows the amino acid sequence of TGR5 derived from guinea pig.

SEQ ID NO:13 shows the nucleotide sequence of primer using guinea pig spleen cDNA as a template.

SEQ ID NO:14 shows the nucleotide sequence of primer 2 using guinea pig spleen cDNA as a template.

The present invention is explained in detail by referring to the following Reference Examples, Examples, Formulation Examples and Experimental Examples, which are not to be construed as limitative and may be changed without departing from the scope of the present invention.

In the following, the yield is in mol/mol %, and other % means % by weight unless otherwise specified. In addition, room temperature means 1 to 30° C.

REFERENCE EXAMPLE 1

2-[3,5-trans-5-(3-aminophenyl)-7-chloro-1-neopentyl-2-oxo-1,2,3,5-tetrahydro-4,1-benzoxazepin-3-yl]-N-(2-fluorobenzyl)acetamide The title compound was synthesized according to the method described in Example 80 of JP-A-11-209356.

REFERENCE EXAMPLE 2

2-[3,5-trans-7-chloro-5-[3-([1,3]dioxolan-2-yl)phenyl]-1-neopentyl-2-oxo-1,2,3,5-tetrahydro-4,1-benzoxazepin-3-yl]-N-(2-fluorobenzyl)acetamide The title compound was synthesized according to the method described in Example 41(6) of JP-A-11-209356.

REFERENCE EXAMPLE 3

2-[3,5-trans-5-[3-(acetylaminomethyl)phenyl]-7-chloro-1-neopentyl-2-oxo-1,2,3,5-tetrahydro-4,1-benzoxazepin-3-yl]-N-(2-fluorobenzyl)acetamide The title compound was synthesized according to the method described in Example 112 of JP-A-11-209356.

REFERENCE EXAMPLE 4

2-[3,5-trans-7-chloro-5-[3-(methanesulfonylaminomethyl)phenyl]-1-neopentyl-2-oxo-1,2,3,5-tetrahydro-4,1-benzoxazepin-3-yl]-N-(2-fluorobenzyl)acetamide The title compound was synthesized according to the method described in Example 113 of JP-A-11-209356.

REFERENCE EXAMPLE 5

N-[3-[3,5-trans-7-chloro-3-[2-[(2-fluorobenzyl)amino]-2-oxoethyl]-1-neopentyl-2-oxo-1,2,3,5-tetrahydro-4,1-benzoxazepin-5-yl]benzyl]-2,2,2-trifluoroacetamide The title compound was synthesized according to the method described in Example 114 of JP-A-11-209356.

REFERENCE EXAMPLE 6 methyl [3-[3,5-trans-7-chloro-3-[2-[(2-fluorobenzyl)amino]-2-oxoethyl]-1-neopentyl-2-oxo-1,2,3,5-tetrahydro-4,1-benzoxazepin-5-yl]benzyl]carbamate The title compound was synthesized according to the method described in Example 115 of JP-A-11-209356.

REFERENCE EXAMPLE 7

2-[3,5-trans-7-chloro-5-[3-[[[(methylamino)carbonyl]amino]methyl]phenyl]-1-neopentyl-2-oxo-1,2,3,5-tetrahydro-4,1-benzoxazepin-3-yl]-N-(2-fluorobenzyl)acetamide The title compound was synthesized according to the method described in Example 116 of JP-A-11-209356.

REFERENCE EXAMPLE 8

2-[3,5-trans-7-chloro-5-(3-formylphenyl)-1-neopentyl-2-oxo-1,2,3,5-tetrahydro-4,1-benzoxazepin-3-yl]-N-(2-fluorobenzyl)acetamide The title compound was synthesized according to the method described in Example 41(7) of JP-A-11-209356.

REFERENCE EXAMPLE 9

2-[3,5-trans-7-chloro-5-[3-(hydroxymethyl)phenyl]-1-neopentyl-2-oxo-1,2,3,5-tetrahydro-4,1-benzoxazepin-3-yl]-N-(2-fluorobenzyl)acetamide The compound (0.1 g) obtained in Reference Example 8 was dissolved in methanol (1 ml), sodium borohydride (11 mg) was added under ice-cooling, and the mixture was stirred at room temperature for 30 min. The reaction mixture was concentrated, and water and ethyl acetate were added to the residue. The separated organic layer was washed with water and brine, and dried over sodium sulfate. The solvent was evaporated and the residue was purified by column chromatography [developing solvent:hexane-ethyl acetate (1:1)] to give the title compound (76 mg) as a colorless amorphous solid.

$^1$H-NMR (CDCl$_3$) δ: 0.92 (9H, s), 2.69 (1H, dd, J=6.2, 14.4 Hz), 2.88 (1H, dd, J=7.4, 14.4 Hz), 3.35 (1H, d, J=13.6 Hz), 4.39-4.59 (4H, m), 4.73 (2H, s), 6.00 (1H, s), 6.30 (1H, br), 6.58 (1H, d, J=2.2 Hz), 6.98-7.39 (10H, m).

EXAMPLE 1

N-[3-[3,5-trans-7-chloro-3-[2-[(2-fluorobenzyl)amino]-2-oxoethyl]-1-neopentyl-2-oxo-1,2,3,5-tetrahydro-4,1-benzoxazepin-5-yl]benzyl]propanamide To a solution of 2-[3,5-trans-5-[3-(aminomethyl)phenyl]-7-chloro-1-neopentyl-2-oxo-1,2,3,5-tetrahydro-4,1-benzoxazepin-3-yl]-N-(2-fluorobenzyl)acetamide hydrochloride (0.24 g) obtained in Example 6 of JP-A-11-209356 in pyridine (5 ml) were added propionic anhydride (0.12 g) and 4-dimethylaminopyridine (0.02 g), and the mixture was stirred at room temperature for 20 hrs. After evaporation of the solvent, ethyl acetate was added and the mixture was washed with water and dried over anhydrous MgSO$_4$. The solvent was evaporated, and the residue was purified by silica gel column chromatography, and recrystallized from diisopropyl ether-ethyl acetate to give the title compound (181 mg) as colorless crystals having a melting point of 164-165° C.

$^1$H-NMR (CDCl$_3$) δ: 0.91 (9H, s), 1.18 (3H, t, J=7.6 Hz), 2.26 (2H, q, J=7.6 Hz), 2.69 (1H, dd, J=5.7, 14.3 Hz), 2.88 (1H, dd, J=7.1, 14.3 Hz), 3.35 (1H, d, J=13.8 Hz), 4.37-4.51 (6H, m), 5.75 (1H, m), 5.98 (1H, s), 6.29 (1H, m), 6.57 (1H, d, J=2.2 Hz), 6.98-7.07 (2H, m), 7.19-7.40 (8H, m).

EXAMPLE 2

N-[3-[3,5-trans-7-chloro-3-[2-[(2-fluorobenzyl)amino]-2-oxoethyl]-1-neopentyl-2-oxo-1,2,3,5-tetrahydro-4,1-benzoxazepin-5-yl]benzyl]butanamide To a solution of 3,5-trans-5-[3-(aminomethyl)phenyl]-7-chloro-N-(2-fluorobenzyl)-1-neopentyl-2-oxo-1,2,3,5-tetrahydro-4,1-benzoxazepine-3-acetamide hydrochloride (0.25 g) obtained in Example 6 of JP-A-11-209356 in pyridine (5 ml) were added butyric anhydride (0.15 g) and 4-dimethylaminopyridine (0.03 g), and the mixture was stirred at room temperature for 16 hrs. After evaporation of the solvent, ethyl acetate was added and the mixture was washed with water and dried over anhydrous MgSO$_4$. The solvent was evaporated, and the residue was purified by silica gel column chromatography to give the title compound (174 mg) as a colorless amorphous solid.

$^1$H-NMR (CDCl$_3$) δ: 0.91 (9H, s), 0.93 (3H, t, J=7.3 Hz), 1.69 (2H, m), 2.20 (2H, t, J=7.4 Hz), 2.68 (1H, dd, J=5.7, 14.4 Hz), 2.88 (1H, dd, J=7.2, 14.4 Hz), 3.35 (1H, d, J=13.8 Hz), 4.37-4.56 (6H, m), 5.78 (1H, m), 5.97 (1H, s), 6.33 (1H, m), 6.55 (1H, d, J=2.1 Hz), 6.98-7.07 (2H, m), 7.20-7.40 (8H, m).

EXAMPLE 3 ethyl [3-[3,5-trans-7-chloro-3-[2-[(2-fluorobenzyl) amino]-2-oxoethyl]-1-neopentyl-2-oxo-1,2,3,5-tetrahydro-4,1-benzoxazepin-5-yl]benzyl]carbamate To a solution of 2-[3,5-trans-5-[3-(aminomethyl)phenyl]-7-chloro-1-neopentyl-2-oxo-1,2,3,5-tetrahydro-4,1-benzoxazepin-3-yl]-N-(2-fluorobenzyl)acetamide hydrochloride (0.25 g) obtained in Example 6 of JP-A-11-209356 in tetrahydrofuran (10 ml) were added ethyl chlorocarbonate (0.09 g) and triethylamine (0.13 g), and the mixture was stirred at room temperature for 6 hrs. After evaporation of the solvent, ethyl acetate was added and the mixture was washed with water and dried over anhydrous MgSO$_4$. The solvent was evaporated, and the residue was purified by silica gel column chromatography to give the title compound (178 mg) as a colorless amorphous solid.

$^1$H-NMR (CDCl$_3$) δ: 0.90 (9H, s), 1.23 (3H, t, J=7.1 Hz), 2.69 (1H, dd, J=5.8, 14.4 Hz), 2.88 (1H, dd, J=7.1, 14.4 Hz), 3.34 (1H, d, J=13.8 Hz), 4.13 (2H, q, J=7.1 Hz), 4.35-4.55 (6H, m), 5.11 (1H, m), 5.97 (1H, s), 6.48 (1H, m), 6.56 (1H, d, J=1.8 Hz), 7.00-7.05 (2H, m), 7.18-7.37 (8H, m).

REFERENCE EXAMPLE 10 ethyl 3,5-trans-5-[3-(acetylaminomethyl)phenyl]-7-chloro-1-neopentyl-2-oxo-1,2,3,5-tetrahydro-4,1-benzoxazepine-3-acetate To a solution of ethyl 3,5-trans-5-[3-(tert-butoxy carbonylaminomethyl)phenyl]-7-chloro-1-neopentyl-2-oxo-1,2,3,5-tetrahydro-4,1-benzoxazepine-3-acetate (1.4 g) obtained in Example 6-(1) of JP-A-11-209356 in ethyl acetate (15 ml) was added a 4N solution (15 ml) of hydrogen chloride in ethyl acetate, and the mixture was stirred at room temperature for 4 hrs. The solvent was evaporated to give ethyl 3,5-trans-5-[3-(aminomethyl)phenyl]-7-chloro-1-neopentyl-2-oxo-1,2,3,5-tetrahydro-4,1-benzoxazepine-3-acetate hydrochloride (1.2 g) as a colorless amorphous solid. To a solution of this compound (0.40 g) in pyridine (3 ml) were added acetic anhydride (0.13 g) and 4-dimethylaminopyridine (0.05 g), and the mixture was stirred at room temperature for 3 hrs. After evaporation of the solvent, ethyl acetate was added and the mixture was washed with water and dried over anhydrous MgSO$_4$. The solvent was evaporated, and the residue was purified by silica gel column chromatography and recrystallized from ethyl acetate to give the title compound (340 mg) as colorless crystals having a melting point of 172-173° C.

$^1$H-NMR (CDCl$_3$) δ: 0.92 (9H, s), 1.24 (3H, t, J=7.1 Hz), 2.04 (3H, s), 2.77 (1H, dd, J=5.8, 16.5 Hz), 3.04 (1H, dd, J=7.7, 16.5 Hz), 3.37 (1H, d, J=13.9 Hz), 4.10 (2H, m), 4.40 (1H, dd, J=5.8, 7.7 Hz), 4.47-4.52 (3H, m), 5.79 (1H, m), 6.00 (1H, s), 6.57 (1H, d, J=2.1 Hz), 7.22-7.43 (6H, m).

REFERENCE EXAMPLE 11

3,5-trans-5-[3-(acetylaminomethyl)phenyl]-7-chloro-1-neopentyl-2-oxo-1,2,3,5-tetrahydro-4,1-benzoxazepine-3-acetic acid The compound (0.56 g) obtained in Reference Example was dissolved in a mixed solvent of ethanol (5 ml) and tetrahydrofuran (5 ml), 1N aqueous sodium hydroxide solution (1.6 ml) was added thereto, and the mixture was stirred at room temperature for 8 hrs. After evaporation of the solvent, the residue was neutralized with aqueous potassium hydrogensulfate solution and extracted with ethyl acetate. The extract was washed with water and dried over anhydrous MgSO$_4$. The solvent was evaporated to give the title compound (484 mg) as a colorless amorphous solid.

$^1$H-NMR (DMSO-d$_6$) δ: 0.86 (9H, s), 1.86 (3H, s), 2.63 (1H, dd, J=5.8, 16.5 Hz), 2.81 (1H, dd, J=7.5, 16.5 Hz), 3.62 (1H, d, J=13.5 Hz), 4.21-4.30 (4H, m), 5.85 (1H, s), 6.42 (1H, d, J=2.2 Hz), 7.20-7.22 (2H, m), 7.31 (1H, d, J=7.4 Hz), 7.44 (1H, m), 7.56 (1H, m), 7.78 (1H, d, J=8.8 Hz), 8.38 (1H, m), 12.28 (1H, br).

EXAMPLE 4

2-[3,5-trans-5-[3-(acetylaminomethyl)phenyl]-7-chloro-1-neopentyl-2-oxo-1,2,3,5-tetrahydro-4,1-benzoxazepin-3-yl]-N-phenylacetamide To a solution of 3,5-trans-5-[3-(acetylaminomethyl)phenyl]-7-chloro-1-neopentyl-2-oxo-1,2,3,5-tetrahydro-4,1-benzoxazepine-3-acetic acid (0.30 g) obtained in Reference Example 11 in dimethylformamide (5 ml) were added aniline (0.08 g), 1-hydroxy-1H-benzotriazole (0.10 g) and 1-ethyl-3-(3-dimethylaminopropyl)carbodiimide hydrochloride (0.16 g), and the mixture was stirred at room temperature for 18 hrs. Ethyl acetate was added, and the mixture was washed with water and dried over anhydrous MgSO$_4$. The solvent was evaporated, and the residue was purified by silica gel column chromatography and recrystallized from chloroform to give the title compound (0.28 g) as colorless crystals.

$^1$H-NMR (CDCl$_3$) δ: 0.94 (9H, s), 2.01 (3H, s), 2.84 (1H, dd, J=5.9, 13.9 Hz), 3.00 (1H, dd, J=7.3, 13.9 Hz), 3.36 (1H, d, J=13.9 Hz), 4.40-4.55 (4H, m), 5.66 (1H, brs), 6.03 (1H, s), 6.57 (1H, d, J=2.2 Hz), 7.05-7.55 (11H, m), 7.82 (1H, s)

| Elemental analysis for C$_{31}$H$_{34}$N$_3$O$_4$Cl•0.5H$_2$O | |
|---|---|
| Calculated | C, 66.84; H, 6.33; N, 7.54 |
| Found | C, 66.58; H, 6.11; N, 7.46 |

In the same manner as in Example 4, 3,5-trans-5-[3-(acetylaminomethyl)phenyl]-7-chloro-1-neopentyl-2-oxo-1,2,3,5-tetrahydro-4,1-benzoxazepine-3-acetic acid and various amine were condensed to give the compounds of the following Examples 5 to 12.

EXAMPLE 5

2-[3,5-trans-5-[3-(acetylaminomethyl)phenyl]-7-chloro-1-neopentyl-2-oxo-1,2,3,5-tetrahydro-4,1-benzoxazepin-3-yl]-N-benzylacetamide $^1$H-NMR (CDCl$_3$) δ: 0.91 (9H, s), 2.03 (3H, s), 2.71 (1H, dd, J=5.8, 14.3 Hz), 2.88 (1H, dd, J=7.2, 14.3 Hz), 3.35 (1H, d, J=13.9 Hz), 4.34 (1H, dd, J=5.4, 15.0 Hz), 4.40-4.60 (5H, m), 5.75 (1H, brs), 5.99 (1H, s), 6.23 (1H, brs), 6.57 (1H, d, J=2.2 Hz), 7.15-7.45 (11H, m).

| Elemental analysis for C$_{32}$H$_{36}$N$_3$O$_4$Cl•0.5H$_2$O | |
|---|---|
| Calculated | C, 67.30; H, 6.53; N, 7.36 |
| Found | C, 67.01; H, 6.39; N, 7.27 |

EXAMPLE 6

2-[3,5-trans-5-[3-(acetylaminomethyl)phenyl]-7-chloro-1-neopentyl-2-oxo-1,2,3,5-tetrahydro-4,1-benzoxazepin-3-yl]-N-propylacetamide $^1$H-NMR (CDCl$_3$) δ: 0.85-0.92 (12H, m), 1.50 (2H, m), 2.04 (3H, s), 2.62 (1H, dd, J=5.7, 14.2 Hz), 2.82 (1H, dd, J=7.5, 14.2 Hz), 3.18 (2H, m), 3.35 (1H, d, J=13.9 Hz), 4.35-4.50 (4H, m), 5.75-5.90 (2H, m), 5.98 (1H, s), 6.56 (1H, s), 7.20-7.45 (6H, m).

| Elemental analysis for C$_{28}$H$_{36}$N$_3$O$_4$Cl | |
|---|---|
| Calculated | C, 65.42; H, 7.06; N, 8.17 |
| Found | C, 65.12; H, 7.11; N, 8.18 |

EXAMPLE 7

2-[3,5-trans-5-[3-(acetylaminomethyl)phenyl]-7-chloro-1-neopentyl-2-oxo-1,2,3,5-tetrahydro-4,1-benzoxazepin-3-yl]-N-benzyl-N-methylacetamide $^1$H-NMR (CDCl$_3$) δ: 0.93 (3.5H, s), 0.94 (5.5H, s), 2.02 (1.2H, s), 2.04 (1.8H, s), 2.78 (1H, dd, J=5.0, 15.8 Hz), 2.89 (1.2H, s), 2.97 (1.8H, s), 3.23 (1H, dd, J=8.3, 16.0 Hz), 3.39 (1H, d, J=13.9 Hz), 4.30-4.79 (6H, m), 5.72 (1H, brs), 5.99 (0.4H, s), 6.02 (0.6H, s), 6.58 (1H, s), 7.10-7.43 (11H, m)

| Elemental analysis for C$_{33}$H$_{38}$N$_3$O$_4$Cl•0.5AcOEt | |
|---|---|
| Calculated | C, 68.36; H, 6.98; N, 6.93 |
| Found | C, 68.31; H, 6.84; N, 7.20 |

EXAMPLE 8

2-[3,5-trans-5-[3-(acetylaminomethyl)phenyl]-7-chloro-1-neopentyl-2-oxo-1,2,3,5-tetrahydro-4,1-benzoxazepin-3-yl]-N-(2-pyridylmethyl)acetamide $^1$H-NMR (DMSO-d$_6$) δ: 0.85 (9H, s), 1.85 (3H, s), 2.63 (1H, dd, J=6.7, 15.1 Hz), 2.74 (1H, dd, J=6.6, 15.1 Hz), 3.59 (1H, d, J=13.9 Hz), 4.25-4.35 (6H, m), 5.85 (1H, s), 6.40 (1H, d, J=2.3 Hz), 7.15-7.80 (9H, m), 8.35-8.60 (3H, m).

| Elemental analysis for C$_{31}$H$_{35}$N$_4$O$_4$Cl | |
|---|---|
| Calculated | C, 66.12; H, 6.27; N, 9.95 |
| Found | C, 65.87; H, 6.34; N, 10.16 |

EXAMPLE 9

2-[3,5-trans-5-[3-(acetylaminomethyl)phenyl]-7-chloro-1-neopentyl-2-oxo-1,2,3,5-tetrahydro-4,1-benzoxazepin-3-yl]-N-(cyclohexylmethyl)acetamide $^1$H-NMR (CDCl$_3$) δ: 0.80-1.80 (11H, m), 0.92 (9H, s), 2.05 (3H, s), 2.63 (1H, dd, J=5.5, 14.1 Hz), 2.86 (1H, dd, J=5.8, 14.1 Hz), 3.00-3.10 (2H, m), 3.35 (1H, d, J=13.9 Hz), 4.35-4.50 (4H, m), 5.79 (1H, brs), 5.95 (1H, m), 5.98 (1H, s), 6.57 (1H, d, J=2.1 Hz), 7.25-7.45 (6H, m).

| Elemental analysis for C$_{32}$H$_{42}$N$_3$O$_4$Cl•0.5AcOEt | |
|---|---|
| Calculated | C, 67.26; H, 7.75; N, 7.02 |
| Found | C, 67.39; H, 7.49; N, 6.89 |

EXAMPLE 10

2-[3,5-trans-5-[3-(acetylaminomethyl)phenyl]-7-chloro-1-neopentyl-2-oxo-1,2,3,5-tetrahydro-4,1-benzoxazepin-3-yl]-N-(2-phenylethyl)acetamide $^1$H-NMR (CDCl$_3$) δ: 0.92 (9H, s), 2.03 (3H, s), 2.60 (1H, dd, J=5.9, 14.3 Hz), 2.75-2.85 (3H, m), 3.34 (1H, d, J=14.0 Hz), 3.35-3.60 (2H, m), 4.35-4.50 (4H, m), 5.74 (1H, brs), 5.86 (1H, m), 5.97 (1H, s), 6.57 (1H, d, J=2.0 Hz), 7.15-7.45 (11H, m).

| Elemental analysis for C$_{33}$H$_{38}$N$_3$O$_4$Cl•0.25H$_2$O | |
|---|---|
| Calculated | C, 68.26; H, 6.68; N, 7.24 |
| Found | C, 68.18; H, 6.76; N, 7.35 |

EXAMPLE 11

2-[3,5-trans-5-[3-(acetylaminomethyl)phenyl]-7-chloro-1-neopentyl-2-oxo-1,2,3,5-tetrahydro-4,1-benzoxazepin-3-yl]-N-(1-methyl-1-phenylethyl)acetamide $^1$H-NMR (CDCl$_3$) δ: 0.93 (9H, s), 1.66 (6H, d, J=5.0 Hz), 2.02 (3H, s), 2.67 (1H, dd, J=5.7, 14.5 Hz), 2.83 (1H, dd, J=7.0, 14.5 Hz), 3.35 (1H, d, J=13.8 Hz), 4.36-4.53 (4H, m), 5.72 (1H, brs), 6.00 (1H, s), 6.19 (1H, s), 6.55 (1H, d, J=2.1 Hz), 7.14-7.65 (11H, m).

EXAMPLE 12

2-[3,5-trans-5-[3-(acetylaminomethyl)phenyl]-7-chloro-1-neopentyl-2-oxo-1,2,3,5-tetrahydro-4,1-benzoxazepin-3-yl]-N-[4-(methylsulfonyl)benzyl]acetamide $^1$H-NMR (CDCl$_3$) δ: 0.85 (9H, s), 1.84 (3H, s), 2.63 (1H, dd, J=6.8, 15.2 Hz), 2.72 (1H, dd, J=6.8, 15.1 Hz), 3.17 (3H, s), 3.59 (1H, d, J=14.0 Hz), 4.24-4.35 (6H, m), 5.84 (1H, s), 6.40 (1H, d, J=2.1 Hz), 7.15-7.85 (10H, m), 8.36 (1H, t, J=5.9 Hz), 8.59 (1H, t, J=5.9 Hz).

REFERENCE EXAMPLE 12

Ethyl 3,5-trans-7-chloro-5-[3-(methoxycarbonylaminomethyl)phenyl]-1-neopentyl-2-oxo-1,2,3,5-tetrahydro-4,1-benzoxazepine-3-acetate Under ice-cooling, to a solution of ethyl 3,5-trans-5-[3-(aminomethyl)phenyl]-7-chloro-1-neopentyl-2-oxo-1,2,3,5-tetrahydro-4,1-benzoxazepine-3-acetate hydrochloride (6.74 g) obtained in Reference-Example 10 in tetrahydrofuran (150 ml) was added triethylamine (4.14 g). After stirring at the same temperature for 10 min., a solution (20 ml) of methyl chlorocarbonate (2.57 g) in tetrahydrofuran was added dropwise. After the completion of the dropwise addition, the reaction system was stirred for 8 hrs while allowing to warm gradually to room temperature. Saturated aqueous ammonium chloride solution was added to the reaction mixture, and the mixture was extracted with ethyl acetate and dried over anhydrous MgSO$_4$. The solvent was evaporated, and the residue was purified by silica gel column chromatography to give the title compound (5.04 g) as colorless crystals.

$^1$H-NMR (CDCl$_3$) δ: 0.92 (9H, s), 1.24 (3H, t, J=7.1 Hz), 2.77 (1H, dd, J=5.8, 16.5 Hz), 3.04 (1H, dd, J=7.8, 16.5 Hz), 3.36 (1H, d, J=13.9 Hz), 3.71 (3H, s), 4.07-4.18 (2H, m), 4.35-4.45 (3H, m), 4.50 (1H, d, J=13.9 Hz), 5.02 (1H, brs), 6.00 (1H, s), 6.58 (1H, d, J=1.8 Hz), 7.21-7.44 (6H, m).

REFERENCE EXAMPLE 13

3,5-trans-7-chloro-5-[3-(methoxycarbonylaminomethyl)phenyl]-1-neopentyl-2-oxo-1,2,3,5-tetrahydro-4,1-benzoxazepine-3-acetic acid The compound (1.62 g) obtained in Reference Example 12 was dissolved in a mixed solvent of methanol (20 ml) and tetrahydrofuran (20 ml), and 1N aqueous sodium hydroxide solution (3.5 ml) was added thereto. The mixture was stirred at room temperature for 8 hrs and concentrated. The residue was neutralized with aqueous potassium hydrogensulfate solution and extracted with ethyl acetate. The organic layer was washed with water, and dried over anhydrous magnesium sulfate. The solvent was evaporated to give the title compound (1.08 g) as colorless crystals.

$^1$H-NMR (CDCl$_3$) δ: 0.92 (9H, s), 2.80-3.04 (2H, m), 3.36 (1H, d, J=13.9 Hz), 3.72 (3H, s), 4.35-4.48 (3H, m), 4.52 (1H, d, J=13.9 Hz), 5.15 (1H, brs), 6.02 (1H, s), 6.56 (1H, s), 7.05-7.50 (7H, m).

REFERENCE EXAMPLE 14

2-[3,5-trans-5-[3-(aminomethyl)phenyl]-7-chloro-1-isobutyl-2-oxo-1,2,3,5-tetrahydro-4,1-benzoxazepin-3-yl]-N-(2-fluorobenzyl)acetamide hydrochloride (1) To a solution of tert-butyl [3-[(2-amino-5-chlorophenyl)(hydroxy)methyl]benzyl]carbamate (3.0 g) obtained by a method described in Example 1 of JP-A-11-209356, and acetic acid (1 ml) in methanol (80 ml) was added isobutylaldehyde (0.72 g), and the mixture was stirred at room temperature for 1 hr. Sodium cyanotrihydroborate (1.6 g) was added, and the mixture was stirred at room temperature for 24 hrs. The solvent was evaporated, water was added to the residue and the mixture was extracted with ethyl acetate. The organic layer was washed with water and dried over anhydrous MgSO$_4$. The solvent was evaporated to give tert-butyl [3-[[5-chloro-2-(isobutylamino)phenyl](hydroxy)methyl]benzyl]carbamate (3.4 g) as a colorless amorphous solid.

(2) To a mixture of the compound (3.4 g) obtained in the aforementioned (1) and sodium hydrogencarbonate (2.2 g) in ethyl acetate (120 ml) and water (20 ml) was added a solution of ethyl (E)-4-chloro-4-oxo-2-butenoate (1.7 g) in ethyl acetate (10 ml), and the mixture was stirred at room temperature for 2 hrs. The organic layer was washed with water and dried over anhydrous MgSO$_4$. The solvent was evaporated, and the residue was dissolved in ethanol (80 ml). Potassium carbonate (1.7 g) was added, and the mixture was stirred at 60° C. for 2 hrs. After evaporation of the solvent, water and ethyl acetate were added and the mixture was extracted. The organic layer was washed with water and dried over anhydrous MgSO$_4$. The solvent was evaporated, and the residue was purified by silica gel column chromatography to give ethyl [3,5-trans-5-[3-(tert-butoxy carbonylaminomethyl) phenyl]-7-chloro-1-isobutyl-2-oxo-1,2,3,5-tetrahydro-4,1-benzoxazepin-3-yl]acetate (2.1 g) as a colorless amorphous solid.

$^1$H-NMR (CDCl$_3$) δ: 0.91 (3H, d, J=6.6 Hz), 0.98 (3H, d, J=6.6 Hz), 1.24 (3H, t, J=7.1 Hz), 1.45 (9H, s), 2.06 (1H, m), 2.76 (1H, dd, J=5.6, 16.5 Hz), 3.06 (1H, dd, J=8.0, 16.5 Hz), 3.46 (1H, m), 4.12 (2H, q, J=7.1 Hz), 4.22-4.43 (4H, m), 4.86 (1H, m), 5.85 (1H, s), 6.58 (1H, d, J=2.1 Hz), 7.24-7.42 (6H, m).

(3) To a solution of the compound (1.9 g) obtained in the aforementioned (2) in a mixed solvent of ethanol (20 ml) and tetrahydrofuran (20 ml) was added 1N aqueous sodium hydroxide solution (7 ml), and the mixture was stirred at 60° C. for 2 hrs. The solvent was evaporated, and the residue was neutralized with aqueous KHSO$_4$ solution and extracted with ethyl acetate. The organic layer was separated, washed with water and dried over anhydrous MgSO$_4$. After evaporation of the solvent, the residue was dissolved in dimethylformamide (30 ml), and 2-fluorobenzylamine (0.69 g), 1-hydroxy-1H-benzotriazole (0.62 g) and 1-ethyl-3-(3-dimethylaminopropyl)carbodiimide hydrochloride (1.05 g) were added. The mixture was stirred at room temperature for 24 hrs. Ethyl acetate was added and the mixture was washed with water and dried over anhydrous MgSO$_4$. The solvent was evaporated, and the residue was purified by silica gel column chromatography to give tert-butyl [3-[3,5-trans-7-chloro-3-[2-[(2-fluorobenzyl)amino]-2-oxoethyl]-1-isobutyl-2-oxo-1,2,3,5-tetrahydro-4,1-benzoxazepin-5-yl]benzyl]carbamate (1.8 g) as a colorless amorphous solid.

$^1$H-NMR (CDCl$_3$) δ: 0.90 (3H, d, J=6.6 Hz), 0.97 (3H, d, J=6.6 Hz), 1.44 (9H, s), 2.03 (1H, m), 2.68 (1H, dd, J=5.8, 14.3 Hz), 2.89 (1H, dd, J=7.2, 14.3 Hz), 3.41 (1H, dd, J=6.3, 13.7 Hz), 4.23 (1H, dd, J=7.8, 13.7 Hz), 4.31 (2H, d, J=5.5 Hz), 4.40-4.50 (3H, m), 4.84 (1H, m), 5.83 (1H, s), 6.29 (1H, m), 6.57 (1H, d, J=2.2 Hz), 7.00-7.05 (2H, m), 7.19-7.37 (8H, m).

(4) To a solution of the compound (1.6 g) obtained in the aforementioned (3) in ethyl acetate (15 ml) was added a 4N solution (15 ml) of hydrogen chloride in ethyl acetate, and the mixture was stirred at room temperature for 1 hr. The solvent was evaporated, and the residue was recrystallized from diisopropyl ether-ethanol to give the title compound (1.2 g) as colorless crystals.

$^1$H-NMR (DMSO-d$_6$) δ: 0.87 (3H, d, J=6.6 Hz), 0.92 (3H, d, J=6.6 Hz), 1.91 (1H, m), 2.62 (1H, dd, J=6.4, 15.2 Hz), 2.77 (1H, dd, J=7.0, 15.2 Hz), 3.61 (1H, dd, J=6.1, 13.6 Hz), 4.03-4.13 (3H, m), 4.26-4.37 (3H, m), 5.76 (1H, s), 6.44 (1H, d, J=2.4 Hz), 7.13-7.67 (10H, m), 8.40 (3H, brs), 8.51 (1H, m).

The compounds of the following Reference Examples 15 and 16 were synthesized in the same manner as in Reference Example 14.

REFERENCE EXAMPLE 15

2-[3,5-trans-5-[3-(aminomethyl)phenyl]-7-chloro-2-oxo-1-propyl-1,2,3,5-tetrahydro-4,1-benzoxazepin-3-yl]-N-(2-fluorobenzyl)acetamide hydrochloride $^1$H-NMR (DMSO-d$_6$) δ: 0.89 (3H, t, J=7.3 Hz), 1.61 (2H, m), 2.61 (1H, dd, J=6.3, 15.1 Hz), 2.77 (1H, dd, J=7.0, 15.1 Hz), 3.70 (1H, m), 4.04-4.16 (3H, m), 4.26-4.36 (3H, m), 5.71

(1H, s), 6.43 (1H, d, J=2.1 Hz), 7.10-7.19 (2H, m), 7.27-7.37 (3H, m), 7.47-7.65 (5H, m), 8.41 (3H, brs), 8.53 (1H, m).

REFERENCE EXAMPLE 16

2-[3,5-trans-5-[3-(aminomethyl)phenyl]-7-chloro-2-oxo-1-(2-thienylmethyl)-1,2,3,5-tetrahydro-4,1-benzoxazepin-3-yl]-N-(2-fluorobenzyl)acetamide hydrochloride $^1$H-NMR (DMSO-$d_6$) δ: 2.65 (1H, dd, J=6.0, 15.4 Hz), 2.84 (1H, dd, J=7.4, 15.4 Hz), 4.01 (2H, m), 4.29 (2H, m), 4.39 (1H, dd, J=6.0, 7.4 Hz), 5.13 (1H, d, J=15.4 Hz), 5.45 (1H, s), 5.63 (1H, d, J=15.4 Hz), 6.38 (1H, d, J=2.2 Hz), 6.94-7.78 (13H, m), 8.56 (4H, m).

REFERENCE EXAMPLE 17 ethyl [5-[3-(tert-butoxycarbonylaminomethyl)phenyl]-7-chloro-1-(2,4-dimethoxybenzyl)-2-oxo-1,2,3,5-tetrahydro-4,1-benzoxazepin-3-yl]acetate In the same manner as in Reference Example 14-(1) and (2), the title compound was synthesized.

$^1$H-NMR (CDCl$_3$) δ: 1.22-1.28 (3H, m), 1.45 (9H, s), 2.72-2.91 (1H, m), 3.06-3.20 (1H, m), 3.59 (2.25H, s), 3.65 (0.75H, s), 3.76 (0.75H, s), 3.79 (2.25H, s), 3.95 (0.25H, m), 4.08-4.17 (2H, m), 4.30-4.32 (2H, m), 4.43 (1H, m), 4.64 (0.25H, m), 4.87-4.92 (1.75H, m), 5.33 (0.75H, d, J=14.7 Hz), 5.52 (0.75H, s), 5.87 (0.25H, s), 6.32-6.47 (3H, m), 7.03-7.42 (7H, m).

REFERENCE EXAMPLE 18 tert-butyl [3-[7-chloro-3-[2-[(2-fluorobenzyl)amino]-2-oxoethyl]-2-oxo-1,2,3,5-tetrahydro-4,1-benzoxazepin-5-yl]benzyl]carbamate (1) A solution of the compound (2.6 g) obtained in Reference Example 17 in trifluoroacetic acid (20 ml) was stirred at room temperature for 36 hrs. The solvent was evaporated, and the residue was neutralized with a saturated aqueous sodium hydrogencarbonate solution and extracted with ethyl acetate. The organic layer was separated, washed with water and dried over anhydrous MgSO$_4$. The solvent was evaporated, and the residue was dissolved in tetrahydrofuran (80 ml). Di-tert-butyl dicarbonate (1.8 g) was added, and the mixture was stirred at room temperature for 5 hrs. The solvent was evaporated, and the residue was purified by silica gel column chromatography to give ethyl [5-[3-(tert-butoxycarbonylaminomethyl)phenyl]-7-chloro-2-oxo-1,2,3,5-tetrahydro-4,1-benzoxazepin-3-yl]acetate (0.84 g) as a colorless amorphous solid.

$^1$H-NMR (CDCl$_3$) δ: 1.20-1.28 (3H, m), 1.45 (9H, s), 2.73-2.90 (1H, m), 3.00-3.06 (1H, m), 4.08-4.15 (2H, m), 4.33-4.35 (2H, m), 4.58 (0.75H, m), 4.86-5.00 (1.25H, m), 5.87 (0.25H, s), 5.93 (0.75H, s), 6.69 (0.75H, s), 6.81 (0.25H, s), 6.89 (0.25H, d, J=8.5 Hz), 7.00 (0.75H, d, J=8.4 Hz), 7.18-7.40 (5H, m), 7.90-8.04 (1H, m).

(2) To a solution of the compound (0.84 g) obtained in the aforementioned (1) in a mixed solvent of ethanol (10 ml) and tetrahydrofuran (10 ml) was added 1N aqueous sodium hydroxide solution (6 ml), and the mixture was stirred at 60° C. for 2 hrs. The solvent was evaporated, and the residue was neutralized with aqueous KHSO$_4$ solution and extracted with ethyl acetate. The organic layer was separated, washed with water and dried over anhydrous MgSO$_4$. After evaporation of the solvent, the residue was dissolved in dimethylformamide (8 ml). 2-Fluorobenzylamine (0.33 g), 1-hydroxy-1H-benzotriazole (0.30 g) and 1-ethyl-3-(3-dimethylaminopropyl)carbodiimide hydrochloride (0.50 g) were added, and the mixture was stirred at room temperature for 24 hrs. Ethyl acetate was added and the mixture was washed with water and dried over anhydrous MgSO$_4$. The solvent was evaporated, and the residue was purified by silica gel column chromatography, and recrystallized from hexane-tetrahydrofuran to give the title compound (0.40 g) as colorless crystals.

$^1$H-NMR (CDCl$_3$) δ: 1.44 (9H, s), 2.62-2.74 (1H, m), 2.84-2.91 (1H, m), 4.25-4.32 (2H, m), 4.42-4.51 (2H, m), 4.60 (0.75H, m), 4.81 (0.25H, m), 4.90 (0.25H, m), 5.01 (0.75H, m), 5.87 (0.25H, s), 5.90 (0.75H, s), 6.22 (1H, m), 6.66 (0.75H, s), 6.83 (0.5H, m), 6.96-7.38 (9.75H, m), 7.76 (0.25H, m), 7.95 (0.75H, m).

REFERENCE EXAMPLE 19 ethyl [3,5-trans-5-[3-(tert-butoxy carbonylaminomethyl)phenyl]-7-chloro-1-(2,2-dimethyl-3-hydroxypropyl)-2-oxo-1,2,3,5-tetrahydro-4,1-benzoxazepin-3-yl]acetate The title compound was synthesized in the same manner as in Reference Examples 14-(1) and (2).

$^1$H-NMR (CDCl$_3$) δ: 0.60 (3H, s), 1.04 (3H, S), 1.24 (3H, t, J=7.1 Hz), 1.45 (9H, s), 2.76 (1H, dd, J=5.2, 16.7 Hz), 3.03-3.15 (2H, m), 3.39 (1H, d, J=14.3 Hz), 3.51 (1H, m), 4.08-4.15 (3H, m), 4.34-4.40 (3H, m), 4.47 (1H, d, J=14.3 Hz), 4.87 (1H, m), 5.89 (1H, s), 6.60 (1H, s), 7.21-7.43 (6H, m).

REFERENCE EXAMPLE 20

[3,5-trans-1-(3-acetoxy-2,2-dimethylpropyl)-5-[3-(tert-butoxycarbonylaminomethyl)phenyl]-7-chloro-2-oxo-1,2,3,5-tetrahydro-4,1-benzoxazepin-3-yl] acetic acid To a solution of the compound (1.78 g) obtained in Reference Example 19 in a mixed solvent of ethanol (15 ml) and tetrahydrofuran (15 ml) was added 1N aqueous sodium hydroxide solution (4 ml), and the mixture was stirred at 60° C. for 1 hr. The solvent was evaporated, and the residue was neutralized with aqueous KHSO$_4$ solution and extracted with ethyl acetate. The organic layer was separated, washed with water and dried over anhydrous MgSO$_4$. The solvent was evaporated, and the residue was dissolved in tetrahydrofuran (20 ml). Acetyl chloride (0.60 g) and pyridine (0.98 g) were added, and the mixture was stirred at room temperature for 3 hrs. Water (15 ml) was further added, and the mixture was stirred at room temperature for 22 hrs. The solvent was evaporated, and the residue was extracted with ethyl acetate. The organic layer was separated, washed with water and dried over anhydrous MgSO$_4$. The solvent was evaporated to give the title compound (0.91 g) as a colorless amorphous solid.

$^1$H-NMR (DMSO-$d_6$) δ: 0.87 (6H, s), 1.35 (9H, s), 1.92 (3H, s), 2.60 (1H, m), 2.80 (1H, m), 3.71-3.76 (3H, m), 4.05-4.20 (3H, m), 4.31 (1H, m), 5.90 (1H, s), 6.40 (1H, s), 7.10-7.44 (5H, m), 7.56 (1H, m), 7.76 (1H, m), 12.29 (1H, brs).

REFERENCE EXAMPLE 21

3-[3,5-trans-5-[3-(aminomethyl)phenyl]-7-chloro-3-[2-[(2-fluorobenzyl)amino]-2-oxoethyl]-2-oxo-2,3-dihydro-4,1-benzoxazepin-1(5H)-yl]-2,2-dimethylpropyl acetate hydrochloride (1) To a solution of the compound (1.26 g) obtained in Reference Example 20 in dimethylformamide (20 ml) were added 2-fluorobenzylamine (0.43 g), 1-hydroxy-1H-benzotriazole (0.38 g) and 1-ethyl-3-(3-dimethylaminopropyl)carbodiimide hydrochloride (0.61 g), and the mixture was stirred at room temperature for 20 hrs. Ethyl acetate was added and the mixture was washed with water and dried over anhydrous $MgSO_4$. The solvent was evaporated, and the residue was purified by silica gel column chromatography to give 3-[3,5-trans-5-[3-(tert-butoxycarbonylaminomethyl)phenyl]-7-chloro-3-[2-[(2-fluorobenzyl)amino]-2-oxoethyl]-2-oxo-2,3-dihydro-4,1-benzoxazepin-1(5H)-yl]-2,2-dimethylpropyl acetate (1.19 g) as a colorless amorphous solid.

$^1$H-NMR (CDCl$_3$) δ: 0.94 (3H, s), 0.97 (3H, s), 1.44 (9H, s), 1.97 (3H, s), 2.68 (1H, dd, J=5.8, 14.4 Hz), 2.87 (1H, dd, J=7.1, 14.4 Hz), 3.52 (1H, d, J=15.1 Hz), 3.76 (2H, m), 4.32 (2H, m), 4.38-4.56 (4H, m), 4.94 (1H, m), 6.00 (1H, s), 6.24 (1H, m), 6.57 (1H, s), 6.99-7.13 (2H, m), 7.21-7.40 (8H, m).

(2) To a solution of the compound (0.95 g) obtained in the aforementioned (1) in ethyl acetate (10 ml) was added a 4N solution (10 ml) of hydrogen chloride in ethyl acetate, and the mixture was stirred at room temperature for 30 min. The solvent was evaporated, and the residue was recrystallized from diisopropyl ether-methanol to give the title compound (0.86 g) as a colorless solid.

$^1$H-NMR (DMSO-d$_6$) δ: 0.89 (3H, s), 0.90 (3H, s), 1.95 (3H, s), 2.61 (1H, dd, J=6.4, 15.1 Hz), 2.73 (1H, dd, J=6.8, 15.1 Hz), 3.71-3.76 (3H, m), 4.04 (2H, s), 4.20-4.35 (4H, m), 5.93 (1H, s), 6.40 (1H, d, J=2.1 Hz), 7.10-7.19 (2H, m), 7.27-7.34 (3H, m), 7.46-7.59 (4H, m) 7.76 (1H, d, J=8.8 Hz), 8.39 (3H, brs), 8.51 (1H, m).

REFERENCE EXAMPLE 22

3-[3,5-trans-5-[3-(tert-butoxycarbonylaminomethyl)phenyl]-7-chloro-2-oxo-3-[2-oxo-2-[[2-(trifluoromethyl)benzyl]amino]ethyl]-2,3-dihydro-4,1-benzoxazepin-1(5H)-yl]-2,2-dimethylpropyl acetate The title compound was synthesized by the same method as in Reference Example 21-(1) and using the compound obtained in Reference Example 20.

$^1$H-NMR (CDCl$_3$) δ: 0.94 (3H, s), 0.97 (3H, s), 1.44 (9H, s), 1.97 (3H, s), 2.69 (1H, dd, J=5.5, 14.4 Hz), 2.89 (1H, dd, J=7.3, 14.4 Hz), 3.52 (1H, d, J=14.1 Hz), 3.78 (2H, m), 4.32 (2H, d, J=5.3 Hz), 4.41 (1H, m), 4.49 (1H, d, J=14.1 Hz), 4.57-4.69 (2H, m), 4.94 (1H, m), 6.00 (1H, s), 6.27 (1H, m), 6.57 (1H, s), 7.22-7.52 (9H, m), 7.63 (1H, d, J=7.6 Hz).

REFERENCE EXAMPLE 23

2-[3,5-trans-7-chloro-5-(3-hydroxy-2-methoxyphenyl)-1-neopentyl-2-oxo-1,2,3,5-tetrahydro-4,1-benzoxazepin-3-yl]-N-(2-fluorobenzyl)acetamide (1) To a solution of 2,3-dihydroxybenzaldehyde (20.0 g) in dimethylsulfoxide (80 ml) was added sodium hydride (5.79 g), and the mixture was stirred at room temperature for 1 hr. Methyl iodide (9.0 ml) was added, and the mixture was further stirred at room temperature for 20 hrs. The obtained reaction mixture was partitioned between ethyl acetate (1000 ml) and water (500 ml). The aqueous layer was further extracted with ethyl acetate (1000 ml). The organic layers were combined, washed with saturated brine, dried over anhydrous magnesium sulfate, and concentrated under reduced pressure. The residue was purified by silica gel chromatography and crystallized from diisopropyl ether and hexane to give 3-hydroxy-2-methoxybenzaldehyde (11.5 g) as pale-brown crystals.

$^1$H-NMR (CDCl$_3$) δ: 3.98 (3H, s), 5.86 (1H, s), 7.12-7.40 (3H, m), 10.27 (1H, s).

(2) To a solution of the compound (11.4 g) obtained in the aforementioned (1), potassium carbonate (22.8 g) and potassium iodide (2.49 g) in DMF (130 ml) was added benzyl bromide (9.8 ml), and the mixture was stirred at room temperature for 17 hrs. The obtained reaction mixture was concentrated under reduced pressure, and the residue was partitioned between ethyl acetate (1500 ml) and water (1500 ml). The organic layer was washed successively with water and saturated brine, dried over anhydrous magnesium sulfate, and concentrated under reduced pressure. The residue was purified by silica gel chromatography and crystallized from diisopropyl ether and hexane to give 3-benzyloxy-2-methoxybenzaldehyde (13.7 g) as pale-yellow crystals.

$^1$H-NMR (CDCl$_3$) δ: 4.03 (3H, s), 5.16 (2H, s), 7.09-7.47 (8H, m), 10.45 (1H, d, J=0.66 Hz).

(3) To a solution of 4-chloroaniline (10.0 g) and triethylamine (16.4 ml) in acetonitrile (80 ml) was added dropwise pivaloyl chloride (14.5 ml) under ice-cooling. The mixture was allowed to warm to room temperature and stirred for 5 hrs. The obtained reaction mixture was concentrated under reduced pressure, and the residue was partitioned between ethyl acetate (1500 ml) and water (1500 ml). The organic layer was washed successively with water, saturated aqueous sodium hydrogencarbonate solution and saturated brine, dried over anhydrous magnesium sulfate, and concentrated under reduced pressure. The residue was crystallized from diethyl ether and hexane to give N-(4-chlorophenyl)-2,2-dimethylpropionamide (15.0 g) as colorless crystals.

$^1$H-NMR (CDCl$_3$) δ: 1.31 (9H, s), 7.26-7.50 (4H, m).

(4) A solution of the compound (11.5 g) obtained in the aforementioned (3) in tetrahydrofuran (120 ml) was purged with nitrogen, and a 1.6 M solution (72 ml) of n-butyllithium in hexane was gradually added dropwise at −50° C. under stirring. The reaction solution was allowed to warm to room temperature and stirred for 2.5 hrs. The reaction mixture was cooled to −50° C. again, and a solution of compound (14.5 g) obtained in the aforementioned (2) in tetrahydrofuran (50 ml) was added dropwise. The reaction mixture was allowed to warm to room temperature and stirred for 1 hr. The obtained reaction mixture was diluted with water, and extracted twice with ethyl acetate (1000 ml). The organic layers were combined, washed with saturated brine, dried over anhydrous magnesium sulfate, and concentrated under reduced pressure. The residue was purified by silica gel chromatography, and crystallized from diethyl ether and hexane to give N-{2-[(3-benzyloxy-2-methoxyphenyl)hydroxymethyl]-4-chlorophenyl}-2,2-dimethylpropionamide (19.3 g) as colorless crystals.

$^1$H-NMR (CDCl$_3$) δ: 1.12 (9H, s), 3.93 (3H, s), 4.29 (1H, d, J=4.5 Hz), 5.14 (2H, d, J=1.4 Hz), 5.99 (1H, d, J=4.5 Hz), 6.52 (1H, dd, J=7.1, 1.9 Hz), 6.94-7.02 (3H, m), 7.28-7.47 (6H, m), 8.17 (1H, d, J=8.7 Hz), 9.20 (1H, brs).

(5) To a solution of the compound (20.0 g) obtained in the aforementioned (4) in tetrahydrofuran (50 ml) was added 9N sulfuric acid (33.2 ml), and the mixture was heated under reflux for 5 hrs. The reaction solution was ice-cooled, and 4N aqueous sodium hydroxide solution (90 ml) was gradually added to basify the solution. The obtained reaction mixture was diluted with water, and extracted twice with ethyl acetate (1000 ml). The organic layers were combined, washed successively with water and saturated brine, dried over anhydrous magnesium sulfate, and concentrated under reduced pressure. The residue was purified by silica gel chromatography to give (2-amino-5-chlorophenyl)-(3-benzyloxy-2-methoxyphenyl)methanol (11.5 g) as colorless crystals.

$^1$H-NMR (CDCl$_3$) δ: 3.12 (1H, d, J=5.3 Hz), 3.87 (3H, s), 4.21 (2H, bs), 5.13 (2H, s), 6.03 (1H, d, J=5.2 Hz), 6.59 (1H, d, J=8.3 Hz), 6.86-7.10 (5H, m), 7.32-7.47 (5H, m).

(6) To a solution of the compound (9.5 g) obtained in the aforementioned (5), pivalaldehyde (2.35 g) and acetic acid (4.1 ml) in methanol (80 ml) was added sodium cyanotrihydroborate (2.26 g), and the mixture was stirred at room temperature for 2 hrs. The obtained reaction mixture was diluted with 5% aqueous potassium hydrogensulfate solution, and concentrated under reduced pressure. The residue was partitioned between ethyl acetate (1000 ml) and water (1000 ml), and the organic layer was washed successively with saturated aqueous sodium hydrogencarbonate solution and saturated brine, dried over anhydrous magnesium sulfate, and concentrated under reduced pressure. The residue was crystallized from diethyl ether and hexane to give (3-benzyloxy-2-methoxyphenyl)-[5-chloro-2-(2,2-dimethylpropylamino)phenyl]methanol (10.2 g) as colorless crystals.

$^1$H-NMR (CDCl$_3$) δ: 0.93 (9H, s), 2.83 (2H, d, J=4.5 Hz), 3.21 (1H, d, J=5.5 Hz), 3.87 (3H, s), 4.77-4.92 (1H, brs), 5.13 (2H, s), 5.99 (1H, d, J=5.1 Hz), 6.57 (1H, d, J=8.7 Hz), 6.78-7.16 (5H, m), 7.30-7.49 (5H, m).

(7) To a suspension of the compound (10.0 g) obtained in the aforementioned (6) and sodium hydrogencarbonate (5.35 g) in dichloromethane (200 ml) was added dropwise a solution of ethyl (E)-4-chloro-4-oxo-2-butenoate (4.25 g) in dichloromethane (30 ml), and the mixture was stirred at room temperature for 3 hrs. The obtained reaction mixture was filtered and the filtrate was concentrated under reduced pressure. The residue was partitioned between ethyl acetate (1000 ml) and water (1000 ml), and the organic layer was washed with saturated brine, dried over anhydrous magnesium sulfate, and concentrated under reduced pressure. The residue was purified by silica gel chromatography to give ethyl 3-[{2-[(3-benzyloxy-2-methoxyphenyl)hydroxymethyl]-4-chlorophenyl}(2,2-dimethylpropyl)carbamoyl]acrylate (12.2 g) as a colorless oil.

(8) A suspension of the compound (12.1 g) obtained in the aforementioned (7) and potassium carbonate (3.54 g) in ethanol (140 ml) was stirred at room temperature for 19 hrs, and the obtained reaction mixture was concentrated under reduced pressure. The residue was partitioned between ethyl acetate (1000 ml) and water (1000 ml), and the organic layer was washed with saturated brine, dried over anhydrous magnesium sulfate, and concentrated under reduced pressure. The residue was crystallized from diethyl ether and hexane to give ethyl [3,5-trans-5-(3-benzyloxy-2-methoxyphenyl)-7-chloro-1-neopentyl-2-oxo-1,2,3,5-tetrahydro-4,1-benzoxazepin-3-yl]acetate (10.7 g) as colorless crystals.

$^1$H-NMR (CDCl$_3$) δ: 0.94 (9H, s), 1.24 (3H, t, J=7.1 Hz), 2.77 (1H, dd, J=16.5, 6.0 Hz), 3.03 (1H, dd, J=16.4, 7.7 Hz), 3.37 (1H, d, J=13.9 Hz), 3.66 (3H, s), 4.04-4.22 (2H, m), 4.39 (1H, dd, J=7.6, 6.0 Hz), 4.51 (1H, d, J=13.9 Hz), 5.13 (2H, s), 6.28 (1H, s), 6.63 (1H, d, J=1.7 Hz), 6.99-7.49 (10H, m).

(9) To a solution of the compound (10.6 g) obtained in the aforementioned (8) in ethanol/tetrahydrofuran (125 ml/150 ml) was added 1N aqueous sodium hydroxide solution (45 ml), and the mixture was heated at 60° C. for 45 min. The reaction solution was cooled, neutralized with 1N hydrochloric acid (80 ml), and concentrated under reduced pressure. The residue was partitioned between ethyl, acetate (1000 ml) and water (1000 ml), and the organic layer was washed with saturated brine, dried over anhydrous magnesium sulfate, and concentrated under reduced pressure. The residue was crystallized from diethyl ether and hexane to give [3,5-trans-5-(3-benzyloxy-2-methoxyphenyl)-7-chloro-1-neopentyl-2-oxo-1,2,3,5-tetrahydro-4,1-benzoxazepin-3-yl]acetic acid (9.4 g) as colorless crystals.

$^1$H-NMR (CDCl$_3$) δ: 0.95 (9H, s), 2.84 (1H, dd, J=16.4, 5.4 Hz), 3.07 (1H, dd, J=16.4, 7.5 Hz), 3.38 (1H, d, J=13.8 Hz), 3.66 (3H, s), 4.34 (1H, dd, J=7.4, 5.4 Hz), 4.52 (1H, d, J=13.9 Hz), 5.13 (2H, s), 6.27 (1H, s), 6.65 (1H, d, J=2.0 Hz), 7.00-7.49 (10H, m).

(10) To a solution of the compound (9.3 g) obtained in the aforementioned (9), HOBt(2.80 g) and WSC (3.98 g) in DMF (150 ml) was added a solution of 2-fluorobenzylamine (2.60 g) in DMF (30 ml), and the mixture was stirred at room temperature for 2.5 hrs, and the reaction mixture was concentrated under reduced pressure. The residue was partitioned between ethyl acetate (1000 ml) and water (1000 ml). The organic layer was washed successively with saturated aqueous sodium hydrogencarbonate solution and saturated brine, dried over anhydrous magnesium sulfate, and concentrated under reduced pressure. The residue was crystallized from diethyl ether and hexane to give 2-[3,5-trans-5-(3-benzyloxy-2-methoxyphenyl)-7-chloro-1-neopentyl-2-oxo-1,2,3,5-tetrahydro-4,1-benzoxazepin-3-yl]-N-(2-fluorobenzyl)acetamide (10.7 g) as colorless crystals.

$^1$H-NMR (CDCl$_3$) δ: 0.93 (9H, s), 2.69 (1H, dd, J=14.3, 6.1 Hz), 2.87 (1H, dd, J=14.3, 6.9 Hz), 3.35 (1H, d, J=13.8 Hz), 3.65 (3H, s), 4.10-4.52 (4H, m), 5.13 (2H, s), 6.26 (1H, s), 6.30 (1H, br), 6.62 (1H, d, J=2.2 Hz), 6.99-7.49 (14H, m).

(11) To a suspension of the compound (9.3 g) obtained in the aforementioned (10) and 10% palladium carbon (1.0 g) in ethyl acetate (200 ml) was added 5N hydrochloric acid (10 ml), and the mixture was stirred under a hydrogen gas atmosphere at room temperature for 1.5 hrs. The reaction mixture was filtered through celite and the filtrate was concentrated under reduced pressure. The residue was partitioned between ethyl acetate (1000 ml) and water (1000 ml), and the organic layer was washed with saturated brine, dried over anhydrous magnesium sulfate, and concentrated under reduced pressure. The residue was crystallized from diethyl ether and hexane to give the title compound (8.8 g) as colorless crystals.

$^1$H-NMR (CDCl$_3$) δ: 0.94 (9H, s), 2.69 (1H, dd, J=14.4, 6.1 Hz), 2.87 (1H, dd, J=14.4, 6.8 Hz), 3.37 (1H, d, J=13.9 Hz), 3.58 (3H, s), 4.39-4.52 (4H, m), 5.51 (1H, s), 6.23 (1H, s), 6.29 (1H, br), 6.62 (1H, d, J=2.2 Hz), 6.96-7.41 (9H, m).

REFERENCE EXAMPLE 24 tert-butyl [3-[3,5-trans-7-chloro-3-[2-[(2-fluorobenzyl)amino]-2-oxoethyl]-1-neopentyl-2-oxo-1,2,3,5-tetrahydro-4,1-benzoxazepin-5-yl]-2-methoxyphenoxy]acetate To a solution of the compound (0.90 g) obtained in Reference Example 23 and potassium carbonate (0.34 g) in DMF (15 ml) was added a solution of tert-butyl bromoacetate (0.38 g) in DMF (5 ml), and the mixture was stirred at 80° C. for 2 hrs. The obtained reaction mixture was cooled and concentrated under reduced pressure. The residue was partitioned between ethyl acetate (100 ml) and water (100 ml). The organic layer was washed successively with water and saturated brine, dried over anhydrous magnesium sulfate, and concentrated under reduced pressure. The residue was crystallized from diethyl ether-hexane to give the title compound (1.0 g) as colorless crystals.

$^1$H-NMR (CDCl$_3$) δ: 0.94 (9H, s), 1.48 (9H, s), 2.69 (1H, dd, J=14.3, 6.1 Hz), 2.87 (1H, dd, J=14.3, 6.9 Hz), 3.35 (1H, d, J=13.8 Hz), 3.69 (3H, s), 4.37-4.57 (4H, m), 4.57 (2H, s), 6.26 (1H, s), 6.30 (1H, br), 6.58 (1H, d, J=2.1 Hz), 6.81-7.39 (9H, m).

REFERENCE EXAMPLE 25

[3-[3,5-trans-7-chloro-3-[2-[(2-fluorobenzyl)amino]-2-oxoethyl]-1-neopentyl-2-oxo-1,2,3,5-tetrahydro-4, 1-benzoxazepin-5-yl]-2-methoxyphenoxy]acetic acid A mixture of the compound (1.00 g) obtained in Reference Example 24 and a 4N solution (15 ml) of hydrochloric acid in ethyl acetate was stirred at room temperature for 2 hrs. The obtained reaction mixture was concentrated under reduced pressure, and the residue was crystallized from diethyl ether to give the title compound (0.81 g) as colorless crystals.

$^1$H-NMR (CDCl$_3$) δ: 0.93 (9H, m), 2.71 (1H, dd, J=14.3, 5.9 Hz), 2.88 (1H, dd, J=14.3, 6.9 Hz), 3.35 (1H, d, J=13.9 Hz), 3.67 (3H, s), 4.37-4.57 (4H, m), 4.71 (2H, s), 6.24 (1H, s), 6.47 (1H, br), 6.58 (1H, d, J=2.1 Hz), 6.86-7.40 (9H, m).

REFERENCE EXAMPLE 26

2-[3,5-trans-7-chloro-5-[3-(chloromethyl)phenyl]-1-neopentyl-2-oxo-1,2,3,5-tetrahydro-4,1-benzoxazepin-3-yl]-N-(2-fluorobenzyl)acetamide The compound (0.4 g) obtained in Reference Example 9 was dissolved in toluene (8 ml), and thionyl chloride (97 mg) and pyridine (0.01 ml) were added at room temperature, and the mixture was stirred at room temperature for 30 min. Ethyl acetate was added to the reaction mixture. The mixture was washed with 1N hydrochloric acid, saturated aqueous sodium hydrogencarbonate solution and brine, and dried over sodium sulfate. The solvent was evaporated to give the title compound (0.43 g) as a colorless amorphous solid.

$^1$H-NMR (CDCl$_3$) δ: 0.92 (9H, s), 2.69 (1H, dd, J=5.4, 14.2 Hz), 2.88 (1H, dd, J=6.8, 14.2 Hz), 3.35 (1H, d, J=14.0 Hz), 4.39-4.51 (4H, m), 4.60 (2H, s), 6.00 (1H, s), 6.25-6.35 (1H, br), 6.56 (1H, d, J=2.2 Hz), 7.02-7.43 (10H, m).

In the same manner as in Reference Example 14, the compounds of the following Reference Examples 27 to 31 were synthesized.

REFERENCE EXAMPLE 27

2-[3,5-trans-5-[3-(aminomethyl)phenyl]-7-chloro-1-(6-methoxy-2-naphthylmethyl)-2-oxo-1,2,3,5-tetrahydro-4,1-benzoxazepin-3-yl]-N-(2-fluorobenzyl) acetamide hydrochloride $^1$H-NMR (DMSO-d$_6$) δ: 2.70 (1H, dd, J=5.8, 15.4 Hz), 2.92 (1H, dd, J=7.6, 15.4 Hz), 3.87 (3H, s), 3.99 (2H, d, J=5.8 Hz), 4.33 (2H, m), 4.51 (1H, dd, J=5.8, 7.6 Hz), 5.22 (1H, d, J=15.8 Hz), 5.43 (1H, d, J=15.8 Hz), 5.63 (1H, s), 6.37 (1H, m), 7.04-7.61 (13H, m), 7.76-7.85 (3H, m), 8.55 (3H, brs), 8.64 (1H, m).

REFERENCE EXAMPLE 28

2-[3,5-trans-5-[3-(aminomethyl)phenyl]-7-chloro-2-oxo-1-(quinolin-2-ylmethyl)-1,2,3,5-tetrahydro-4,1-benzoxazepin-3-yl]-N-(2-fluorobenzyl)acetamide hydrochloride $^1$H-NMR (DMSO-d$_6$) δ: 2.73-2.82 (2H, m), 4.05 (2H, m), 4.31 (2H, m), 4.57 (1H, m), 5.63 (2H, m), 6.36 (1H, s), 6.45 (1H, d, J=2.6 Hz), 6.99-7.37 (6H, m), 7.51-7.78 (7H, m), 7.94 (1H, m), 8.10-8.21 (2H, m), 8.61-8.67 (4H, m).

REFERENCE EXAMPLE 29

2-[3,5-trans-5-[3-(aminomethyl)phenyl]-7-chloro-1-(9H-fluoren-2-ylmethyl)-2-oxo-1,2,3,5-tetrahydro-4, 1-benzoxazepin-3-yl]-N-(2-fluorobenzyl)acetamide hydrochloride $^1$H-NMR (DMSO-d$_6$) δ: 2.69 (1H, dd, J=6.2, 15.4 Hz), 2.90 (1H, dd, J=7.2, 15.4 Hz), 3.86 (2H, s), 3.95 (2H, m), 4.32 (2H, m), 4.50 (1H, dd, J=6.2, 7.2 Hz), 5.17 (1H, d, J=15.2 Hz), 5.39 (1H, d, J=15.2 Hz), 5.62 (1H, s), 6.39 (1H, s), 7.04-7.63 (15H, m), 7.88 (2H, m), 8.51 (3H, brs), 8.62 (1H, m).

REFERENCE EXAMPLE 30

2-[3,5-trans-5-[3-(aminomethyl)phenyl]-7-chloro-1-[5-(2-methoxyphenyl)-2-furylmethyl]-2-oxo-1,2,3,5-tetrahydro-4,1-benzoxazepin-3-yl]-N-(2-fluorobenzyl)acetamide hydrochloride $^1$H-NMR (DMSO-d$_6$) δ: 2.65 (1H, dd, J=5.8, 14.6 Hz), 2.84 (1H, dd, J=6.8, 14.6 Hz), 3.76 (2H, m), 3.90 (3H, s), 4.30 (2H, m), 4.41 (1H, dd, J=5.8, 6.8 Hz), 5.03 (1H, d, J=15.4 Hz), 5.58 (1H, d, J=15.4 Hz), 5.59 (1H, s), 6.34 (1H, s), 6.43 (1H, m), 6.79 (1H, m), 6.88-7.32 (10H, m), 7.49 (2H, m), 7.61 (1H, d, J=8.6 Hz), 7.77 (1H, d, J=8.6 Hz), 8.35 (3H, brs), 8.56 (1H, m).

REFERENCE EXAMPLE 31

2-[3,5-trans-5-[3-(aminomethyl)phenyl]-1-(2,3'-bithien-5-ylmethyl)-7-chloro-1-2-oxo-1,2,3,5-tetrahydro-4,1-benzoxazepin-3-yl]-N-(2-fluorobenzyl) acetamide hydrochloride $^1$H-NMR (DMSO-d$_6$) δ: 2.66 (1H, dd, J=6.1, 15.4 Hz), 2.85 (1H, dd, J=7.4, 15.4 Hz), 3.92 (2H, m), 4.31 (2H, m), 4.39 (1H, dd, J=6.1, 7.4 Hz), 5.13 (1H, d, J=15.4 Hz), 5.52 (1H, s), 5.56 (1H, d, J=15.4 Hz), 6.40 (1H, d, J=2.2 Hz), 6.95-7.44 (10H, m), 7.54-7.78 (5H, m), 8.51 (3H, brs), 8.60 (1H, m).

EXAMPLE 13

2-[3,5-trans-5-[3-(acetylaminomethyl)phenyl]-7-chloro-1-neopentyl-2-oxo-1,2,3,5-tetrahydro-4,1-benzoxazepin-3-yl]-N-(tetrahydrofuran-2-ylmethyl) acetamide To a solution of 3,5-trans-5-[3-(acetylaminomethyl)phenyl]-7-chloro-1-neopentyl-2-oxo-1,2,3,5-tetrahydro-4,1-benzoxazepine-3-acetic acid (0.30 g) obtained in Reference Example 11 in dimethylformamide (5 ml) were added tetrahydrofurfurylamine (0.10 g), 1-hydroxy-1H-benzotriazole (0.11 g) and 1-ethyl-3-(3-dimethylaminopropyl)carbodiimide hydrochloride (0.18 g), and the mixture was stirred at room temperature for 18 hrs. Ethyl acetate was added, and the organic layer was washed with water, and dried over anhydrous magnesium sulfate. The solvent was evaporated and the residue was purified by silica gel column chromatography to give the title compound as a colorless solid. This solid was recrystallized from chloroform to give the title compound (0.27 g) as colorless crystals.

$^1$H-NMR (CDCl$_3$) δ: 0.92 (9H, s), 1.45-1.60 (1H, m), 1.75-2.00 (3H, m), 2.04 (3H, s), 2.68 (1H, dd, J=6.3, 14.5 Hz), 2.78-2.90 (1H, m), 3.10-3.30 (1H, m), 3.35 (1H, d, J=13.9 Hz), 3.40-3.60 (1H, m), 3.65-3.90 (2H, m), 3.90-4.00 (1H, m), 4.38-4.52 (4H, m), 5.80-6.00 (1H, brs), 6.00 (1H, s), 6.18 (1H, brs), 6.57 (1H, s), 7.20-7.43 (6H, m).

By the same method as in Example 13, 3,5-trans-5-[3-(acetylaminomethyl)phenyl]-7-chloro-1-neopentyl-2-oxo-1,2,3,5-tetrahydro-4,1-benzoxazepine-3-acetic acid and various amine were condensed to give the compounds of the following Examples 14 to 27.

EXAMPLE 14

2-[3,5-trans-5-[3-(acetylaminomethyl)phenyl]-7-chloro-1-neopentyl-2-oxo-1,2,3,5-tetrahydro-4,1-benzoxazepin-3-yl]-N-[2-(trifluoromethyl)benzyl]acetamide $^1$H-NMR (CDCl$_3$) δ: 0.91 (9H, s), 2.03 (3H, s), 2.71 (1H, dd, J=5.2, 14.3 Hz), 2.90 (1H, dd, J=7.1, 14.3 Hz), 3.35 (1H, d, J=13.9 Hz), 4.40-4.70 (6H, m), 5.81 (1H, brs), 5.98 (1H, s), 6.37 (1H, brs), 6.57 (1H, s), 7.20-7.55 (9H, m), 7.63 (1H, d, J=7.2 Hz).

EXAMPLE 15 tert-butyl [2-[3,5-trans-5-[3-(acetylaminomethyl)phenyl]-7-chloro-1-neopentyl-2-oxo-1,2,3,5-tetrahydro-4,1-benzoxazepin-3-yl]acetylamino]acetate $^1$H-NMR (CDCl$_3$) δ: 0.92 (9H, s), 1.46 (9H, s), 2.04 (3H, s), 2.72 (1H, dd, J=5.8, 14.3 Hz), 2.91 (1H, dd, J=6.7, 15.4 Hz), 3.35 (1H, d, J=14.0 Hz), 3.84 (1H, dd, J=4.7, 18.5 Hz), 3.98 (1H, dd, J=4.6, 18.2 Hz), 4.38-4.58 (4H, m), 5.90 (1H, brs), 6.01 (1H, s), 6.31 (1H, brs), 6.58 (1H, s), 7.20-7.62 (6H, m).

EXAMPLE 16

2-[3,5-trans-5-[3-(acetylaminomethyl)phenyl]-7-chloro-1-neopentyl-2-oxo-1,2,3,5-tetrahydro-4,1-benzoxazepin-3-yl]-N-[3,5-bis(trifluoromethyl)benzyl]acetamide $^1$H-NMR (CDCl$_3$) δ: 0.92 (9H, s), 2.04 (3H, s), 2.74 (1H, dd, J=4.5, 13.7 Hz), 2.96 (1H, dd, J=8.8, 13.4 Hz), 3.35 (1H, d, J=13.8 Hz), 4.33-4.52 (5H, m), 4.72 (1H, dd, J=7.1, 15.8 Hz), 5.81 (1H, brs), 5.99 (1H, s), 6.58 (2H, brs), 7.20-7.42 (6H, m), 7.72-7.78 (3H, m).

EXAMPLE 17

2-[3,5-trans-5-[3-(acetylaminomethyl)phenyl]-7-chloro-1-neopentyl-2-oxo-1,2,3,5-tetrahydro-4,1-benzoxazepin-3-yl]-N-(cycloheptylmethyl)acetamide $^1$H-NMR (CDCl$_3$) δ: 0.92 (9H, s), 1.05-1.30 (2H, m), 1.30-1.80 (11H, m), 2.04 (3H, s), 2.63 (1H, dd, J=5.3, 14.0 Hz), 2.86 (1H, dd, J=7.6, 14.0 Hz), 3.00-3.20 (2H, m), 3.35 (1H, d, J=13.9 Hz), 4.35-4.60 (4H, m), 5.80 (1H, brs), 5.95 (1H, brs), 5.98 (1H, s), 6.57 (1H, d, J=2.1 Hz), 7.25-7.60 (6H, m).

EXAMPLE 18

2-[3,5-trans-5-[3-(acetylaminomethyl)phenyl]-7-chloro-1-neopentyl-2-oxo-1,2,3,5-tetrahydro-4,1-benzoxazepin-3-yl]-N-(cyclopropylmethyl)acetamide $^1$H-NMR (CDCl$_3$) δ: 0.14-0.20 (2H, m), 0.45-0.52 (2H, m) 0.92 (10H, s), 2.04 (3H, s), 2.64 (1H, dd, J=5.8, 14.2 Hz), 2.83 (1H, dd, J=7.3, 14.2 Hz), 2.95-3.20 (2H, m), 3.35 (1H, d, J=13.9 Hz), 4.39-4.50 (4H, m), 5.84 (1H, brs), 5.92-6.04 (1H, m), 5.97 (1H, m), 5.99 (1H, s), 7.25-7.43 (6H, m)

EXAMPLE 19

2-[3,5-trans-5-[3-(acetylaminomethyl)phenyl]-7-chloro-1-neopentyl-2-oxo-1,2,3,5-tetrahydro-4,1-benzoxazepin-3-yl]-N-[2-(methylsulfanyl)benzyl]acetamide $^1$H-NMR (CDCl$_3$) δ: 0.91 (9H, s), 2.02 (3H, s), 2.43 (3H, s), 2.70 (1H, dd, J=6.2, 14.6 Hz), 2.86 (1H, dd, J=6.8, 14.5 Hz), 3.34 (1H, d, J=13.9 Hz), 4.35-4.60 (6H, m), 5.82 (1H, brs), 5.98 (1H, s), 6.30-6.36 (1H, brs), 6.56 (1H, d, J=2.2 Hz), 7.00-7.40 (10H, m).

EXAMPLE 20

2-[3,5-trans-5-[3-(acetylaminomethyl)phenyl]-7-chloro-1-neopentyl-2-oxo-1,2,3,5-tetrahydro-4,1-benzoxazepin-3-yl]-N-[2-(methylsulfonyl)benzyl]acetamide $^1$H-NMR (CDCl$_3$) δ: 0.92 (9H, s), 2.01 (3H, s), 3.07 (1H, dd, J=7.0, 16.6 Hz), 3.20 (1H, dd, J=6.4, 16.6 Hz), 3.29-3.37 (2H, m), 3.34 (3H, s), 4.40-4.60 (5H, m), 6.05 (2H, brs), 6.56 (1H, s), 7.21-7.80 (11H, m).

EXAMPLE 21

2-[3,5-trans-5-[3-(acetylaminomethyl)phenyl]-7-chloro-1-neopentyl-2-oxo-1,2,3,5-tetrahydro-4,1-benzoxazepin-3-yl]-N-[3-(trifluoromethyl)benzyl]acetamide $^1$H-NMR (CDCl$_3$) δ: 0.91 (9H, s), 2.03 (3H, s), 2.72 (1H, dd, J=5.1, 14.1 Hz), 2.93 (1H, dd, J=8.0, 14.1 Hz), 3.35 (1H, d, J=13.9 Hz), 4.40-4.56 (6H, m), 5.79 (1H, brs), 5.98 (1H, s), 6.43 (1H, t, J=5.6 Hz), 6.58 (1H, d, J=2.3 Hz), 7.20-7.52 (10H, m).

EXAMPLE 22

2-[3,5-trans-5-[3-(acetylaminomethyl)phenyl]-7-chloro-1-neopentyl-2-oxo-1,2,3,5-tetrahydro-4,1-benzoxazepin-3-yl]-N-[4-(trifluoromethyl)benzyl]acetamide $^1$H-NMR (CDCl$_3$) δ: 0.91 (9H, s), 2.03 (3H, s), 2.74 (1H, dd, J=5.3, 14.3 Hz), 2.90 (1H, dd, J=7.5, 14.3 Hz), 3.35 (1H, d, J=13.9 Hz), 4.37-4.59 (6H, m), 5.77 (1H, brs), 5.98 (1H, s), 6.47 (1H, brs), 6.58 (1H, d, J=2.3 Hz), 7.19-7.52 (10H, m).

EXAMPLE 23

2-[3,5-trans-5-[3-(acetylaminomethyl)phenyl]-7-chloro-1-neopentyl-2-oxo-1,2,3,5-tetrahydro-4,1-benzoxazepin-3-yl]-N-(2-bromobenzyl)acetamide $^1$H-NMR (CDCl$_3$) δ: 0.91 (9H, s), 2.03 (3H, s), 2.71 (1H, dd, J=5.6, 14.4 Hz), 2.90 (1H, dd, J=7.1, 14.4 Hz), 3.35 (1H, d, J=13.9 Hz), 4.38-4.57 (6H, m), 5.77 (1H, brs), 5.99 (1H, s), 6.40 (1H, t, J=5.3 Hz), 6.57 (1H, d, J=2.1 Hz), 7.08-7.42 (9H, m), 7.52 (1H, d, J=7.7 Hz).

EXAMPLE 24

2-[3,5-trans-5-[3-(acetylaminomethyl)phenyl]-7-chloro-1-neopentyl-2-oxo-1,2,3,5-tetrahydro-4,1-benzoxazepin-3-yl]-N-(2-chlorobenzyl)acetamide $^1$H-NMR (CDCl$_3$) δ: 0.92 (9H, s), 2.04 (3H, s), 2.70 (1H, dd, J=5.6, 14.3 Hz), 2.90 (1H, dd, J=7.1, 14.4 Hz), 3.35 (1H, d, J=13.9 Hz), 4.38-4.59 (6H, m), 5.74 (1H, brs), 5.99 (1H, s), 6.36 (1H, t, J=5.6 Hz), 6.57 (1H, d, J=2.2 Hz), 7.14-7.42 (10H, m).

EXAMPLE 25

2-[3,5-trans-5-[3-(acetylaminomethyl)phenyl]-7-chloro-1-neopentyl-2-oxo-1,2,3,5-tetrahydro-4,1-benzoxazepin-3-yl]-N-(2-methoxybenzyl)acetamide $^1$H-NMR (CDCl$_3$) δ: 0.92 (9H, s), 2.02 (3H, s), 2.66 (1H, dd, J=6.3, 14.5 Hz), 2.83 (1H, dd, J=6.8, 14.4 Hz), 3.34 (1H, d, J=13.9 Hz), 3.80 (3H, s), 4.32-4.52 (6H, m), 5.78 (1H, brs), 5.98 (1H, s), 6.32 (1H, t, J=5.8 Hz), 6.55 (1H, d, J=2.3 Hz), 6.83-6.90 (2H, m), 7.15-7.39 (8H, m).

EXAMPLE 26

2-[3,5-trans-5-[3-(acetylaminomethyl)phenyl]-7-chloro-1-neopentyl-2-oxo-1,2,3,5-tetrahydro-4,1-benzoxazepin-3-yl]-N-(2,6-difluorobenzyl)acetamide $^1$H-NMR (CDCl$_3$) δ: 0.91 (9H, s), 2.04 (3H, s), 2.64 (1H, dd, J=5.8, 14.4 Hz), 2.83 (1H, dd, J=7.1, 14.5 Hz), 4.37-4.49 (5H, m), 4.59 (1H, dd, J=6.0, 14.5 Hz), 5.85 (1H, brs), 5.96 (1H, s), 6.26 (1H, t, J=5.5 Hz), 6.56 (1H, d, J=2.3 Hz), 6.86 (2H, t, J=7.7 Hz), 7.15-7.42 (8H, m).

EXAMPLE 27

2-[3,5-trans-5-[3-(acetylaminomethyl)phenyl]-7-chloro-1-neopentyl-2-oxo-1,2,3,5-tetrahydro-4,1-benzoxazepin-3-yl]-N-(2,2,2-trifluoroethyl)acetamide $^1$H-NMR (CDCl$_3$) δ: 0.92 (9H, s), 2.04 (3H, s), 2.73 (1H, dd, J=5.6, 14.4 Hz), 2.90 (1H, dd, J=7.1, 14.4 Hz), 3.67-3.88 (1H, m), 3.93-4.13 (1H, m), 4.35-4.51 (4H, m), 5.82 (1H, brs), 5.99 (1H, s), 6.44 (1H, t, J=6.4 Hz), 6.59 (1H, d, J=2.3 Hz), 7.18-7.45 (7H, m).

EXAMPLE 28

[2-[3,5-trans-5-[3-(acetylaminomethyl)phenyl]-7-chloro-1-neopentyl-2-oxo-1,2,3,5-tetrahydro-4,1-benzoxazepin-3-yl]acetylamino]acetic acid To a solution (3 ml) of the compound (0.10 g) obtained in Example 15 in dichloromethane was added trifluoroacetic acid (1.5 ml), and the mixture was stirred at room temperature for 2 hrs., and concentrated. The residual trifluoroacetic acid was removed by azeotrope with toluene and the residue was extracted with ethyl acetate. The organic layer was concentrated, and the solvent was evaporated. The residue was purified by silica gel column chromatography to give the title compound (0.066 g) as colorless crystals.

$^1$H-NMR (DMSO-d$_6$) δ: 0.84 (9H, s), 1.85 (3H, s), 2.57 (1H, dd, J=6.5, 15.1 Hz), 2.67 (1H, dd, J=6.4, 15.3 Hz), 3.58 (1H, d, J=13.9 Hz), 3.63-3.80 (2H, m), 4.20-4.35 (4H, m), 5.83 (1H, s), 6.38 (1H, d, J=2.1 Hz), 7.19 (2H, brs), 7.29 (1H, d, J=7.7 Hz), 7.41 (1H, t, 7.7 Hz), 7.54 (1H, dd, J=2.0, 8.5 Hz), 7.73 (1H, d, J=8.7 Hz), 8.29 (1H, t, J=5.7 Hz), 8.36 (1H, t, J=5.6 Hz).

In the same manner as in Example 13, condensation reactions of 3,5-trans-7-chloro-5-[3-(methoxycarbonylaminomethyl)phenyl]-1-neopentyl-2-oxo-1,2,3,5-tetrahydro-4,1-benzoxazepine-3-acetic acid obtained in Reference Example 13 with various amines were carried out to give the compounds of the following Examples 29 to 31.

EXAMPLE 29 methyl [3-[3,5-trans-7-chloro-1-neopentyl-2-oxo-3-[2-oxo-2-[[2-(trifluoromethyl)benzyl]amino]ethyl]-1,2,3,5-tetrahydro-4,1-benzoxazepin-5-yl]benzyl]carbamate $^1$H-NMR (CDCl$_3$) δ: 0.91 (9H, s), 2.71 (1H, dd, J=5.6, 14.4 Hz), 2.90 (1H, dd, J=7.3, 14.4 Hz), 3.35 (1H, d, J=13.9 Hz), 3.70 (3H, s), 4.35-4.50 (4H, m), 4.56 (1H, dd, J=6.0, 15.7 Hz), 4.66 (1H, dd, J=6.1 Hz, 15.3 Hz), 5.01 (1H, brs), 5.98 (1H, s), 6.32 (1H, t, J=6.0 Hz), 6.57 (1H, d, J=2.1 Hz), 7.15-7.53 (9H, m), 7.63 (1H, d, J=7.6 Hz).

EXAMPLE 30 methyl [3-[3,5-trans-7-chloro-3-[2-[(cyclohexylmethyl)amino]-2-oxoethyl]-1-neopentyl-2-oxo-1,2,3,5-tetrahydro-4,1-benzoxazepin-5-yl]benzyl]carbamate $^1$H-NMR (CDCl$_3$) δ: 0.80-1.00 (2H, m), 0.92 (9H, s), 1.10-1.80 (9H, m), 2.63 (1H, dd, J=5.4, 14.1 Hz), 2.85 (1H, dd, J=7.6, 14.1 Hz), 3.00-3.15 (2H, m), 3.35 (1H, d, J=13.9 Hz), 3.71 (3H, s), 4.35-4.50 (4H, m), 5.03 (1H, brs), 5.94 (1H, brs), 5.98 (1H, s), 6.56 (1H, d, J=2.1 Hz), 7.20-7.44 (6H, m).

EXAMPLE 31 methyl [3-[3,5-trans-7-chloro-3-[2-(3,4-dihydroisoquinolin-2(1H)-yl)-2-oxoethyl]-1-neopentyl-2-oxo-1,2,3,5-tetrahydro-4,1-benzoxazepin-5-yl]benzyl]carbamate $^1$H-NMR (CDCl$_3$) δ: 0.93 (9H, s), 2.75-2.95 (3H, m), 3.10-3.28 (1H, m), 3.38 (1H, d, J=14.0 Hz), 3.59-3.78 (1.5H, m), 3.70 (3H, s), 3.86-3.96 (0.5H, m), 4.37 (2H, d, J=5.1 Hz), 4.46-4.78 (4H, m), 4.99 (1H, brs), 6.01 (1H, s), 6.55 (1H, s), 7.00-7.39 (10H, m).

EXAMPLE 32

N-{[3,5-trans-5-[3-(acetylaminomethyl)phenyl]-7-chloro-1-neopentyl-2-oxo-1,2,3,5-tetrahydro-4,1-benzoxazepin-3-yl]methyl}-2-(2-fluorophenyl)acetamide (1) A solution of 3,5-trans-5-[3-(acetylaminomethyl)phenyl]-7-chloro-1-neopentyl-2-oxo-1,2,3,5-tetrahydro-4,1-benzoxazepine-3-acetic acid (1.00 g) obtained in Reference Example 11, diphenylphosphoryl azide (0.94 g) and triethylamine (0.27 g) in N,N-dimethylformamide (6 ml) was stirred at room temperature for 1 hr. Water was added to the reaction mixture and the mixture was extracted with ethyl acetate. The organic layer was washed with saturated aqueous sodium chloride solution, and dried over anhydrous magnesium sulfate, and the solvent was evaporated. To the obtained residue was added toluene (25 ml), and this solution was heated under reflux. Then, 9-fluorenylmethanol (0.43 g) was added, and the mixture was further heated under reflux for 3 hrs. Water was added to the reaction mixture, and the mixture was extracted with ethyl acetate. The organic layer was washed with saturated aqueous sodium chloride solution, and and dried over anhydrous magnesium sulfate. The solvent was evaporated and the residue was purified by silica gel column chromatography to give 9-fluorenylmethyl {3,5-trans-5-[3-(acetylaminomethyl)phenyl]-7-chloro-1-neopentyl-2-oxo-1,2,3,5-tetrahydro-4,1-benzoxazepin-3-yl}methylcarbamate (0.86 g) as a colorless oil.

$^1$H-NMR (CDCl$_3$) δ: 0.93 (9H, s), 2.03 (3H, s), 3.36 (1H, d, J=13.8 Hz), 3.60-3.70 (2H, m), 3.90-3.97 (1H, m), 4.08-4.25 (2H, m), 4.30-4.55 (4H, m), 5.30 (1H, brs), 5.81 (1H, brs), 5.99 (1H, s), 6.61. (1H, s), 7.20-7.45 (10H, m), 7.55 (2H, d, J=7.0 Hz), 7.75 (2H, d, J=7.4 Hz).

(2) A mixture of the compound (0.39 g) obtained in the aforementioned (1), piperidine (0.5 ml) and N,N-dimethylformamide (5 ml) was stirred at room temperature for 1 hr, water was added to the reaction mixture and the mixture was extracted with ethyl acetate. The organic layer was washed with saturated aqueous sodium chloride solution, and dried over anhydrous magnesium sulfate, and the solvent was evaporated. To the obtained residue were added 2-fluorophenylacetic acid (0.089 g), 1-hydroxy-1H-benzotriazole (0.10 g), 1-ethyl-3-(3-dimethylaminopropyl)carbodiimide hydrochloride (0.17 g) and N,N-dimethylformamide (5 ml), and the mixture was stirred at room temperature for 18 hrs. The solvent was evaporated, saturated aqueous sodium hydrogencarbonate solution was added to the obtained residue, and the mixture was extracted with ethyl acetate. The organic layer was washed with saturated aqueous sodium chloride solution, and dried over anhydrous magnesium sulfate. The solvent was evaporated and the residue was purified by silica gel column chromatography, and the obtained colorless amorphous solid was recrystallized from tetrahydrofuran to give the title compound (0.13 g) as colorless crystals.

$^1$H-NMR (CDCl$_3$) δ: 0.91 (9H, s), 2.05 (3H, s), 3.33 (1H, d, J=13.9 Hz), 3.53 (2H, s), 3.55-3.80 (2H, m), 3.92 (1H, t, J=5.3 Hz), 4.41-4.50 (3H, m), 5.89 (1H, brs), 5.92. (H, s), 6.15 (1H, t, J=6.2 Hz), 6.59 (1H, d, J=2.3 Hz), 6.95-7.43 (10H, m).

EXAMPLE 33

N-[3-[3,5-trans-7-chloro-3-[[[[(2-fluorobenzyl)amino]carbonyl]amino]methyl]-1-neopentyl-2-oxo-1,2,3,5-tetrahydro-4,1-benzoxazepin-5-yl]benzyl]acetamide A solution of 3,5-trans-5-[3-(acetylaminomethyl)phenyl]-7-chloro-1-neopentyl-2-oxo-1,2,3,5-tetrahydro-4,1-benzoxazepine-3-acetic acid (0.28 g) obtained in Reference Example 11, diphenylphosphoryl azide (0.26 g) and triethylamine (0.077 g) in N,N-dimethylformamide (3 ml) was stirred at room temperature for 1 hr. Water was added to the reaction mixture and the mixture was extracted with ethyl acetate. The organic layer was washed with saturated aqueous sodium chloride solution, and dried over anhydrous magnesium sulfate, and the solvent was evaporated. To the obtained residue was added toluene (8 ml), and this solution was heated under reflux for 3 hrs. 2-Fluorobenzylamine (0.078 g) was added, and the mixture was further heated under reflux for 2 hrs. Water was added to the reaction mixture and the mixture was extracted with ethyl acetate. The organic layer was washed with saturated aqueous sodium chloride solution, and dried over anhydrous magnesium sulfate. The solvent was evaporated and the residue was purified by silica gel column chromatography, and the obtained colorless amorphous solid was recrystallized from tetrahydrofuran to give the title compound (0.11 g) as colorless crystals.

$^1$H-NMR (CDCl$_3$) δ: 0.91 (9H, s), 1.95 (3H, s), 3.31 (1H, d, J=13.9 Hz), 3.43-3.58 (1H, m), 3.79-3.92.(1H, m), 3.93-4.00 (1H, m), 4.21 (1H, dd, J=5.8, 14.6 Hz), 4.41 (2H, d, J=4.9 Hz), 4.50 (1H, d, J=13.9 Hz), 4.61 (1H, dd, J=6.9, 14.6 Hz), 4.99-5.10 (1H, m), 5.94-6.10 (2H, m), 6.00 (1H, s), 6.56 (1H, d, J=2.3 Hz), 6.90-7.42 (9H, m), 7.74 (1H, s).

EXAMPLE 34

2-[3,5-trans-5-[3-(2-amino-2-oxoethoxy)-2-methoxyphenyl]-7-chloro-1-neopentyl-2-oxo-1,2,3,5-tetrahydro-4,1-benzoxazepin-3-yl]-N-(2-fluorobenzyl)acetamide To a solution of the compound (100 mg) obtained in Reference Example 25 and HONB (N-hydroxy-5-norbornene-2,3-dicarboximide)(44 mg) in acetonitrile (5 ml) was added WSC (63 mg), and the mixture was stirred at room temperature for 1.5 hrs. 28% Aqueous ammonia (0.1 ml) was added to the reaction mixture, and the mixture was further stirred at room temperature for 3 hrs. Water was added to the obtained reaction mixture and the mixture was extracted with ethyl acetate. The organic layer was washed successively with saturated aqueous sodium hydrogencarbonate, water and saturated brine, dried over anhydrous magnesium sulfate, and concentrated under reduced pressure. The residue was crystallized from diethyl ether-hexane to give the title compound (68 mg) as colorless crystals.

$^1$H-NMR (CDCl$_3$) δ: 0.95 (9H, s), 2.65-2.86 (2H, m), 3.41 (1H, d, J=11.4 Hz), 3.63 (3H, s), 4.34-4.57 (4H, m), 4.57 (2H, s), 6.24 (1H, s), 6.57 (1H, d, J=1.7 Hz), 6.97-7.39 (10H, m).

EXAMPLE 35

2-[3,5-trans-7-chloro-5-[3-[2-(dimethylamino)-2-oxoethoxy]-2-methoxyphenyl]-1-neopentyl-2-oxo-1,2,3,5-tetrahydro-4,1-benzoxazepin-3-yl]-N-(2-fluorobenzyl)acetamide To a solution of the compound (100 mg) obtained in Reference Example 25, HOBt (30 mg) and WSC (40 mg) in DMF (4 ml) were added dimethylamine hydrochloride (27 mg) and triethylamine (68 μl), and the mixture was stirred at room temperature for 3 hrs. The reaction mixture was concentrated under reduced pressure and the residue was partitioned between ethyl acetate (50 ml) and water (50 ml). The organic layer was washed successively with saturated aqueous sodium hydrogencarbonate solution and saturated brine, dried over anhydrous magnesium sulfate, and concentrated under reduced pressure. The residue was crystallized from diethyl ether and hexane to give the title compound (85 mg) as colorless crystals.

$^1$H-NMR (CD$_3$OD) δ: 0.95 (9H, s), 2.75 (2H, d, J=7.3 Hz), 2.98 (3H, s), 3.10 (3H, s), 3.57 (1H, d, J=14.0 Hz), 3.65 (3H, s), 4.31-4.51 (4H, m), 4.89 (2H, s), 6.24 (1H, s), 6.53 (1H, d, J=2.4 Hz), 6.94-7.66 (9H, m).

In the same manner as in Example 35, the compounds of the following Examples 36 and 37 were synthesized.

EXAMPLE 36

2-[3-(3,5-trans-7-chloro-3-{2-[(2-fluorobenzyl)amino]-2-oxoethyl}-1-neopentyl-2-oxo-1,2,3,5-tetrahydro-4,1-benzoxazepin-5-yl)-2-methoxyphenoxy]-N-(2-phenylethyl)acetamide $^1$H-NMR (CDCl$_3$) δ: 0.95 (9H, m), 2.63-2.92 (4H, m), 3.37 (1H, d, J=14.0 Hz), 3.40 (3H, s), 3.50-3.72 (2H, m), 4.35-4.65 (4H, m), 4.54 (2H, s), 6.21 (1H, s), 6.18-6.32 (1H, m), 6.55 (1H, d, J=2.0 Hz), 6.65-6.70 (1H, m), 6.86-7.41 (14H, m).

EXAMPLE 37

2-[3-[3,5-trans-7-chloro-3-[2-[(2-fluorobenzyl)amino]-2-oxoethyl]-1-neopentyl-2-oxo-1,2,3,5-tetrahydro-4,1-benzoxazepin-5-yl]-2-methoxyphenoxy]-N-[3-(1H-imidazol-1-yl)propyl]acetamide $^1$H-NMR (CDCl$_3$) δ: 0.94 (9H, s), 1.79-2.01 (2H, m), 2.65-2.88 (2H, m), 3.17-3.50 (2H, m), 3.37 (1H, d, J=14.1 Hz), 3.62 (3H, s), 4.33-4.61 (4H, m), 4.62 (2H, s), 6.26 (1H, s), 6.57 (1H, d, J=2.0 Hz), 6.79-7.43 (14H, m).

The compound obtained in Reference Example 3 was subjected to optical resolution under the conditions shown below to give the compounds of the following Reference Examples 32 and 33.

Conditions of Preparative HPLC

Column: CHIRALPAK AD 50 mmID×500 mml (Lot No. JG001)

Mobile phase: hexane/isopropanol=7/3

Flow rate: 70 ml/min

Temperature: 30° C.

Detection: UV 220 nm

REFERENCE EXAMPLE 32

(−)-2-[3,5-trans-5-[3-(acetylaminomethyl)phenyl]-7-chloro-1-neopentyl-2-oxo-1,2,3,5-tetrahydro-4,1-benzoxazepin-3-yl]-N-(2-fluorobenzyl)acetamide $[α]_D^{20}$=−171 (c=0.20, CHCl$_3$), retention time 11.0 min

REFERENCE EXAMPLE 33

(+)-2-[3,5-trans-5-[3-(acetylaminomethyl)phenyl]-7-chloro-1-neopentyl-2-oxo-1,2,3,5-tetrahydro-4,1-benzoxazepin-3-yl]-N-(2-fluorobenzyl)acetamide $[α]_D^{20}$=+195 (c=0.28, CHCl$_3$), retention time 14.9 min

EXAMPLE 38

2-[3,5-trans-5-[3-(acetylaminomethyl)phenyl]-7-chloro-2-oxo-1,2,3,5-tetrahydro-4,1-benzoxazepin-3-yl]-N-(2-fluorobenzyl)acetamide A solution of the compound (0.40 g) obtained in Reference Example 18 in trifluoroacetic acid (5 ml) was stirred at room temperature for 2 hrs. The solvent was evaporated, and the residue was dissolved in pyridine (5 ml). Acetic anhydride (0.30 g) and 4-dimethylaminopyridine (0.06 g) were added, and the mixture was stirred at room temperature for 24 hrs. After evaporation of the solvent, the residue was purified by silica gel column chromatography and recrystallized from diisopropyl ether-ethanol to give the title compound (0.05 g) as colorless crystals.

$^1$H-NMR (DMSO-d$_6$) δ: 1.86 (3H, s), 2.57 (1H, dd, J=7.0, 14.9 Hz), 2.71 (1H, dd, J=5.8, 14.9 Hz), 4.19-4.28 (4H, m), 4.46 (1H, m), 5.85 (1H, s), 6.51 (1H, s), 7.05-7.45 (10H, m), 8.33 (1H, m), 8.43 (1H, m), 10.50 (1H, s)

| Elemental analysis for C$_{27}$H$_{25}$N$_3$O$_4$FCl•0.25H$_2$O | |
| --- | --- |
| Calculated | C, 63.04; H, 5.00; N, 8.17 |
| Found | C, 63.08; H, 4.84; N, 7.98 |

EXAMPLE 39

2-[3,5-trans-5-[4-(acetylaminomethyl)phenyl]-7-chloro-1-neopentyl-2-oxo-1,2,3,5-tetrahydro-4,1-benzoxazepin-3-yl]-N-(2-fluorobenzyl)acetamide To a solution of 2-[3,5-trans-5-[4-(aminomethyl)phenyl]-7-chloro-1-neopentyl-2-oxo-1,2,3,5-tetrahydro-4,1-benzoxazepin-3-yl]-N-(2-fluorobenzyl)acetamide hydrochloride (0.05 g) obtained in Example 82 of JP-A-11-209356 in pyridine (3 ml) were added acetic anhydride (0.03 g) and 4-dimethylaminopyridine (0.01 g), and the mixture was stirred at room temperature for 24 hrs. After evaporation of the solvent, ethyl acetate was added, and the mixture was washed with water and dried over anhydrous MgSO$_4$. The solvent was evaporated, and the residue was purified by silica gel column chromatography to give the title compound (0.04 g) as colorless crystals.

$^1$H-NMR (CDCl$_3$) δ: 0.90 (9H, s), 2.06 (3H, s), 2.67 (1H, dd, J=6.0, 14.3 Hz), 2.86 (1H, dd, J=6.9, 14.3 Hz), 3.34 (1H, d, J=13.9 Hz), 4.37-4.56 (6H, m), 5.79 (1H, m), 5.97 (1H, s), 6.27 (1H, m), 6.57 (1H, d, J=2.2 Hz), 6.99-7.09 (2H, m), 7.24-7.37 (8H, m).

| Elemental analysis for $C_{32}H_{35}N_3O_4FCl \cdot 0.5H_2O$ | |
|---|---|
| Calculated | C, 65.24; H, 6.16; N, 7.13 |
| Found | C, 65.15; H, 5.96; N, 7.19 |

The compounds of the following Examples 40 to 42 were respectively synthesized by the same method as in Example 39 and using the compounds obtained in Reference Examples 14 to 16.

EXAMPLE 40

2-[3,5-trans-5-[3-(acetylaminomethyl)phenyl]-7-chloro-1-isobutyl-2-oxo-1,2,3,5-tetrahydro-4,1-benzoxazepin-3-yl]-N-(2-fluorobenzyl)acetamide $^1$H-NMR (CDCl$_3$) δ: 0.90 (3H, d, J=6.6 Hz), 0.97 (3H, d, J=6.6 Hz), 2.03 (3H, s), 2.04 (1H, m), 2.69 (1H, dd, J=5.8, 14.3 Hz), 2.88 (1H, dd, J=7.1, 14.3 Hz), 3.42 (1H, m), 4.23 (1H, dd, J=7.8, 13.7 Hz), 4.38-4.53 (5H, m), 5.78 (1H, m), 5.83 (1H, s), 6.31 (1H, m), 6.57 (1H, d, J=2.3 Hz), 7.02-7.07 (2H, m), 7.19-7.38 (8H, m).

| Elemental analysis for $C_{31}H_{33}N_3O_4FCl$ | |
|---|---|
| Calculated | C, 65.78; H, 5.88; N, 7.42 |
| Found | C, 65.62; H, 5.90; N, 7.71 |

EXAMPLE 41

2-[3,5-trans-5-[3-(acetylaminomethyl)phenyl]-7-chloro-2-oxo-1-propyl-1,2,3,5-tetrahydro-4,1-benzoxazepin-3-yl]-N-(2-fluorobenzyl)acetamide $^1$H-NMR (CDCl$_3$) δ: 0.95 (3H, t, J=7.3 Hz), 1.67 (2H, m) 2.02 (3H, s), 2.69 (1H, dd, J=5.8, 14.3 Hz), 2.89 (1H, dd, J=7.1, 14.3 Hz), 3.60 (1H, m), 4.19 (1H, m), 4.39-4.52 (5H, m), 5.73 (1H, s), 5.79 (1H, m), 6.32 (1H, m), 6.56 (1H, d, J=2.3 Hz), 7.02-7.06 (2H, m), 7.21-7.39 (8H, m).

| Elemental analysis for $C_{30}H_{31}N_3O_4FCl$ | |
|---|---|
| Calculated | C, 65.27; H, 5.66; N, 7.61 |
| Found | C, 65.21; H, 5.78; N, 7.35 |

EXAMPLE 42

2-[3,5-trans-5-[3-(acetylaminomethyl)phenyl]-7-chloro-2-oxo-1-(2-thienylmethyl)-1,2,3,5-tetrahydro-4,1-benzoxazepin-3-yl]-N-(2-fluorobenzyl)acetamide $^1$H-NMR (CDCl$_3$) δ: 2.02 (3H, s), 2.69 (1H, dd, J=5.7, 14.4 Hz), 2.92 (1H, dd, J=7.3, 14.4 Hz), 4.38-4.52 (5H, m), 4.86 (1H, d, J=15.1 Hz), 5.37 (1H, s), 5.67 (1H, d, J=15.1 Hz), 5.70 (1H, m), 6.27 (1H, m), 6.50 (1H, d, J=2.1 Hz), 6.91-7.05 (6H, m), 7.23-7.38 (7H, m).

| Elemental analysis for $C_{32}H_{29}N_3O_4SFCl$ | |
|---|---|
| Calculated | C, 63.41; H, 4.82; N, 6.93 |
| Found | C, 63.21; H, 4.86; N, 7.22 |

The compounds of the following Examples 43 and 44 were respectively synthesized by the same method as in Example 3 and using the compounds obtained in Reference Examples 14 and 15 and methyl chlorocarbonate.

EXAMPLE 43 methyl [3-[3,5-trans-7-chloro-3-[2-[(2-fluorobenzyl)amino]-2-oxoethyl]-1-isobutyl-2-oxo-1,2,3,5-tetrahydro-4,1-benzoxazepin-5-yl]benzyl]carbamate $^1$H-NMR (CDCl$_3$) δ: 0.90 (3H, d, J=6.6 Hz), 0.98 (3H, d, J=6.6 Hz), 2.04 (1H, m), 2.69 (1H, dd, J=5.8, 14.3 Hz), 2.89 (1H, dd, J=7.1, 14.3 Hz), 3.42 (1H, dd, J=6.4, 13.7 Hz), 3.70 (3H, s), 4.23 (1H, dd, J=7.8, 13.7 Hz), 4.37-4.50 (5H, m), 5.01 (1H, m), 5.83 (1H, s), 6.28 (1H, m), 6.57 (1H, d, J=2.1 Hz), 6.99-7.07 (2H, m), 7.19-7.40 (8H, m).

| Elemental analysis for $C_{31}H_{33}N_3O_5FCl$ | |
|---|---|
| Calculated | C, 63.97; H, 5.71; N, 7.22 |
| Found | C, 63.87; H, 5.82; N, 7.34 |

EXAMPLE 44 methyl [3-[3,5-trans-7-chloro-3-[2-[(2-fluorobenzyl)amino]-2-oxoethyl]-2-oxo-1-propyl-1,2,3,5-tetrahydro-4,1-benzoxazepin-5-yl]benzyl]carbamate $^1$H-NMR (CDCl$_3$) δ: 0.95 (3H, t, J=7.3 Hz), 1.68 (2H, m), 2.69 (1H, dd, J=5.9, 14.3 Hz), 2.89 (1H, dd, J=7.0, 14.3 Hz), 3.60 (1H, m), 3.70 (3H, s), 4.20 (1H, m), 4.36-4.53 (5H, m), 5.00 (1H, m), 5.73 (1H, s), 6.27 (1H, m), 6.56 (1H, d, J=2.1 Hz), 6.99-7.07 (2H, m), 7.22-7.40 (8H, m).

| Elemental analysis for $C_{30}H_{31}N_3O_5FCl$ | |
|---|---|
| Calculated | C, 63.43; H, 5.50; N, 7.40 |
| Found | C, 63.34; H, 5.54; N, 7.18 |

EXAMPLE 45

3-[3,5-trans-5-[3-(acetylaminomethyl)phenyl]-7-chloro-3-[2-[(2-fluorobenzyl)amino]-2-oxoethyl]-2-oxo-2,3-dihydro-4,1-benzoxazepin-1(5H)-yl]-2,2-dimethylpropyl acetate The title compound was synthesized by the same method as in Example 39 and using the compound obtained in Reference Example 21.

$^1$H-NMR (CDCl$_3$) δ: 0.97 (6H, s), 1.94 (3H, s), 2.02 (3H, s), 2.68 (1H, dd, J=5.8, 14.4 Hz), 2.87 (1H, dd, J=7.1, 14.4 Hz), 3.53 (1H, d, J=14.1 Hz), 3.75 (2H, s), 4.38-4.56 (6H, m), 5.93 (1H, m), 6.00 (1H, s), 6.25 (1H, m), 6.57 (1H, d, J=2.2 Hz), 7.02-7.08 (2H, m), 7.23-7.38 (8H, m).

| Elemental analysis for C₃₄H₃₇N₃O₆FCl•0.25H₂O | |
|---|---|
| Calculated | C, 63.55; H, 5.88; N, 6.54 |
| Found | C, 63.49; H, 5.87; N, 6.46 |

EXAMPLE 46

3-[3,5-trans-7-chloro-3-[2-[(2-fluorobenzyl)amino]-2-oxoethyl]-5-[3-(methoxycarbonylaminomethyl)phenyl]-2-oxo-2,3-dihydro-4,1-benzoxazepin-1(5H)-yl]-2,2-dimethylpropyl acetate The title compound was synthesized by the same method as in Example 3 and using the compound obtained in Reference Example 21 and methyl chlorocarbonate.

$^1$H-NMR (CDCl$_3$) δ: 0.96 (3H, s), 0.97 (3H, s), 1.97 (3H, s), 2.68 (1H, dd, J=5.8, 14.4 Hz), 2.87 (1H, dd, J=7.1, 14.4 Hz), 3.52 (1H, d, J=14.1 Hz), 3.69 (3H, s), 3.76 (2H, m), 4.39 (2H, d, J=6.0 Hz), 4.43-4.56 (4H, m), 5.15 (1H, m), 6.00 (1H, s), 6.24 (1H, m), 6.57 (1H, d, J=2.0 Hz), 7.02-7.08 (2H, m), 7.22-7.38 (8H, m).

| Elemental analysis for C₃₄H₃₇N₃O₇FCl•0.25H₂O | |
|---|---|
| Calculated | C, 62.00; H, 5.74; N, 6.38 |
| Found | C, 62.05; H, 5.64; N, 6.21 |

EXAMPLE 47

2-[3,5-trans-5-[3-(acetylaminomethyl)phenyl]-7-chloro-1-(3-hydroxy-2,2-dimethylpropyl)-2-oxo-1,2,3,5-tetrahydro-4,1-benzoxazepin-3-yl]-N-(2-fluorobenzyl)acetamide To a solution of 3-[3,5-trans-5-[3-(acetylaminomethyl)phenyl]-7-chloro-3-[2-[(2-fluorobenzyl)amino]-2-oxoethyl]-2-oxo-2,3-dihydro-4,1-benzoxazepin-1(5H)-yl]-2,2-dimethylpropyl acetate (0.22 g) obtained in Example 45 in a mixed solvent of ethanol (4 ml) and tetrahydrofuran (4 ml) was added 1N aqueous sodium hydroxide solution (0.7 ml), and the mixture was stirred at room temperature for 1 hr. The solvent was evaporated, and the residue was extracted with ethyl acetate. The organic layer was separated, washed with water and dried over anhydrous MgSO$_4$. The solvent was evaporated, and the residue was recrystallized from hexane-ethanol to give the title compound (0.11 g) as colorless crystals.

$^1$H-NMR (CDCl$_3$) δ: 0.59 (3H, s), 1.04 (3H, s), 2.03 (3H, s), 2.69 (1H, dd, J=5.6, 14.5 Hz), 2.89 (1H, dd, J=7.4, 14.5 Hz), 3.15 (1H, m), 3.37 (1H, d, J=14.3 Hz), 3.50 (1H, m), 4.09 (1H, m), 4.40-4.49 (6H, m), 5.80 (1H, m), 5.87 (1H, s), 6.20 (1H, m), 6.57 (1H, d, J=2.0 Hz), 7.00-7.09 (2H, m), 7.17-7.41 (8H, m).

| Elemental analysis for C₃₂H₃₅N₃O₅FCl•1.0H₂O | |
|---|---|
| Calculated | C, 62.59; H, 6.07; N, 6.84 |
| Found | C, 62.98; H, 6.18; N, 6.50 |

EXAMPLE 48 methyl [3-[3,5-trans-7-chloro-3-[2-[(2-fluorobenzyl)amino]-2-oxoethyl]-1-(3-hydroxy-2,2-dimethylpropyl)-2-oxo-1,2,3,5-tetrahydro-4,1-benzoxazepin-5-yl]benzyl]carbamate The title compound was synthesized by the same method as in Example 47 and using 3-[3,5-trans-7-chloro-3-[2-[(2-fluorobenzyl)amino]-2-oxoethyl]-5-[3-(methoxycarbonylaminomethyl)phenyl]-2-oxo-2,3-dihydro-4,1-benzoxazepin-1(5H)-yl]-2,2-dimethylpropyl acetate obtained in Example 46.

$^1$H-NMR (CDCl$_3$) δ: 0.60 (3H, s), 1.04 (3H, s), 2.69 (1H, dd, J=5.7, 14.5 Hz), 2.88 (1H, dd, J=7.3, 14.5 Hz), 3.15 (1H, m), 3.37 (1H, d, J=14.3 Hz), 3.52 (1H, d, J=11.8 Hz), 3.70 (3H, s), 4.08 (1H, m), 4.37-4.54 (6H, m), 5.02 (1H, m), 5.88 (1H, s), 6.18 (1H, m), 6.57 (1H, d, J=1.8 Hz), 7.00-7.10 (2H, m), 7.19-7.41 (8H, m).

| Elemental analysis for C₃₂H₃₅N₃O₆FCl | |
|---|---|
| Calculated | C, 62.79; H, 5.76; N, 6.87 |
| Found | C, 62.73; H, 5.87; N, 6.72 |

EXAMPLE 49

3-[3,5-trans-7-chloro-5-[3-(methoxycarbonylaminomethyl)phenyl]-2-oxo-3-[2-oxo-2-[[2-(trifluoromethyl)benzyl]amino]ethyl]-2,3-dihydro-4,1-benzoxazepin-1(5H)-yl]-2,2-dimethylpropyl acetate The title compound was synthesized by the same method as in Reference Example 14-(4) and Example 3 and using the compound obtained in Reference Example 22.

$^1$H-NMR (CDCl$_3$) δ: 0.95 (3H, s), 0.97 (3H, s), 1.96 (3H, s), 2.69 (1H, dd, J=5.6, 14.5 Hz), 2.89 (1H, dd, J=7.3, 14.5 Hz), 3.52 (1H, d, J=14.1 Hz), 3.69 (3H, s), 3.76 (2H, m), 4.38-4.43 (3H, m), 4.49 (1H, d, J=14.1 Hz), 4.53-4.70 (2H, m), 5.15 (1H, m), 6.00 (1H, s), 6.28 (1H, m), 6.58 (1H, d, J=1.9 Hz), 7.23-7.52 (9H, m), 7.63 (1H, d, J=7.5 Hz).

| Elemental analysis for C₃₅H₃₇N₃O₇F₃Cl | |
|---|---|
| Calculated | C, 59.70; H, 5.30; N, 5.97 |
| Found | C, 59.45; H, 5.30; N, 5.80 |

EXAMPLE 50 methyl [3-[3,5-trans-7-chloro-1-(3-hydroxy-2,2-dimethylpropyl)-2-oxo-3-[2-oxo-2-[[2-(trifluoromethyl)benzyl]amino]ethyl]-1,2,3,5-tetrahydro-4,1-benzoxazepin-5-yl]benzyl]carbamate The title compound was synthesized by the same method as in Example 47 and using the compound obtained in Example 49.

$^1$H-NMR (CDCl$_3$) δ: 0.60 (3H, s), 1.04 (3H, s), 2.71 (1H, dd, J=5.5, 14.6 Hz), 2.91 (1H, dd, J=7.5, 14.6 Hz), 3.15 (1H, m), 3.37 (1H, d, J=14.3 Hz), 3.49 (1H, dd, J=4.1, 11.9 Hz), 3.69 (3H, s), 4.06 (1H, m), 4.37-4.46 (4H, m), 4.61 (2H, d, J=6.0 Hz), 5.03 (1H, m), 5.87 (1H, s), 6.21 (1H, m), 6.58 (1H, d, J=2.0 Hz), 7.17-7.21 (2H, m), 7.32-7.41 (5H, m), 7.45-7.52 (2H, m), 7.64 (1H, d, J=7.7 Hz).

| Elemental analysis for C₃₃H₃₅N₃O₆F₃Cl | |
|---|---|
| Calculated | C, 59.86; H, 5.33; N, 6.35 |
| Found | C, 59.56; H, 5.38; N, 6.22 |

EXAMPLE 51

3-[3,5-trans-7-chloro-5-[3-(methoxycarbonylaminomethyl)phenyl]-2-oxo-3-[2-oxo-2-[[2-(trifluoromethyl)benzyl]amino]ethyl]-2,3-dihydro-4,1-benzoxazepin-1(5H)-yl]-2,2-dimethylpropyl methanesulfonate To a solution of methyl [3-[3,5-trans-7-chloro-1-(3-hydroxy-2,2-dimethylpropyl)-2-oxo-3-[2-oxo-2-[[2-(trifluoromethyl)benzyl]amino]ethyl]-1,2,3,5-tetrahydro-4,1-benzoxazepin-5-yl]benzyl]carbamate (0.25 g) obtained in Example 50 in dichloromethane (10 ml) were added methanesulfonyl chloride (0.17 g) and triethylamine (0.19 g), and the mixture was stirred at room temperature for 2 hrs. The solvent was evaporated, and the residue was purified by silica gel column chromatography, and recrystallized from hexane-ethyl acetate to give the title compound (0.22 g) as colorless crystals.

¹H-NMR (CDCl₃) δ: 0.97 (3H, s), 1.02 (3H, s), 2.69 (1H, dd, J=5.8, 14.6 Hz), 2.87 (1H, dd, J=7.1, 14.6 Hz), 2.92 (3H, s), 3.53 (1H, d, J=14.3 Hz), 3.69 (3H, s), 3.92-3.99 (2H, m), 4.38 (2H, d, J=5.9 Hz), 4.44 (1H, m), 4.49 (1H, d, J=14.3 Hz), 4.52-4.64 (2H, m), 5.10 (1H, m), 5.95 (1H, s), 6.23 (1H, m), 6.60 (1H, d, J=2.2 Hz), 7.22-7.51 (9H, m), 7.63 (1H, d, J=7.7 Hz).

| Elemental analysis for C₃₄H₃₇N₃O₈SF₃Cl | |
|---|---|
| Calculated | C, 55.17; H, 5.04; N, 5.68 |
| Found | C, 54.90; H, 5.12; N, 5.79 |

In the same manner as in Example 4, 3,5-trans-5-[3-(acetylaminomethyl)phenyl]-7-chloro-1-neopentyl-2-oxo-1,2,3,5-tetrahydro-4,1-benzoxazepine-3-acetic acid and various amines were condensed to give the following compounds of Examples 52 to 56.

EXAMPLE 52 methyl 4-trans-[[3,5-trans-5-[3-(acetylaminomethyl)phenyl]-7-chloro-1-neopentyl-2-oxo-1,2,3,5-tetrahydro-4,1-benzoxazepin-3-yl]acetylaminomethyl]cyclohexanecarboxylate ¹H-NMR (CDCl₃) δ: 0.85-0.95 (11H, m), 1.28-1.41 (3H, m) 1.76 (2H, m), 1.93 (2H, m), 2.04 (3H, s), 2.18 (1H, m), 2.66 (1H, dd, J=5.1, 14.1 Hz), 2.83 (1H, dd, J=7.5, 14.1 Hz), 3.03 (1H, m), 3.11 (1H, m), 3.35 (1H, d, J=13.8 Hz), 3.66 (3H, s), 4.37 (1H, m), 4.44-4.49 (3H, m), 5.97 (2H, m), 6.11 (1H, m), 6.58 (1H, d, J=2.0 Hz), 7.22-7.43 (6H, m).

EXAMPLE 53

2-[3,5-trans-5-[3-(acetylaminomethyl)phenyl]-7-chloro-1-neopentyl-2-oxo-1,2,3,5-tetrahydro-4,1-benzoxazepin-3-yl]-N-cyclohexylacetamide ¹H-NMR (CDCl₃) δ: 0.92 (9H, s), 1.10-1.36 (6H, m), 1.66-1.71 (2H, m), 1.83-1.89 (2H, m), 2.04 (3H, s), 2.59 (1H, dd, J=6.0, 14.1 Hz), 2.78 (1H, dd, J=7.0, 14.1 Hz), 3.35 (1H, d, J=13.8 Hz), 3.71 (1H, m), 4.39-4.50 (4H, m), 5.71 (1H, d, J=7.9 Hz), 5.79 (1H, m), 5.98 (1H, s), 6.56 (1H, d, J=2.1 Hz), 7.26-7.43 (6H, m).

| Elemental analysis for C₃₁H₄₀N₃O₄Cl•1.5H₂O | |
|---|---|
| Calculated | C, 64.07; H, 7.46; N, 7.23 |
| Found | C, 63.97; H, 7.27; N, 6.99 |

EXAMPLE 54

2-[3,5-trans-5-[3-(acetylaminomethyl)phenyl]-7-chloro-1-neopentyl-2-oxo-1,2,3,5-tetrahydro-4,1-benzoxazepin-3-yl]-N-(2-thienylmethyl) acetamide ¹H-NMR (CDCl₃) δ: 0.91 (9H, s), 2.03 (3H, s), 2.68 (1H, dd, J=5.7, 14.3 Hz), 2.78 (1H, dd, J=7.2, 14.3 Hz), 3.35 (1H, d, J=13.9 Hz), 4.40-4.54 (5H, m), 4.66 (1H, dd, J=5.9, 15.3 Hz), 5.78 (1H, m), 5.98 (1H, s), 6.29 (1H, m), 6.57 (1H, d, J=1.7 Hz), 6.91-6.93 (2H, m), 7.19-7.41 (7H, m).

| Elemental analysis for C₃₀H₃₄N₃O₄SCl•0.25H₂O | |
|---|---|
| Calculated | C, 62.92; H, 6.07; N, 7.34 |
| Found | C, 62.97; H, 6.07; N, 7.40 |

EXAMPLE 55

2-[3,5-trans-5-[3-(acetylaminomethyl)phenyl]-7-chloro-1-neopentyl-2-oxo-1,2,3,5-tetrahydro-4,1-benzoxazepin-3-yl]-N-(3-thienylmethyl)acetamide ¹H-NMR (CDCl₃) δ: 0.91 (9H, s), 2.03 (3H, s), 2.69 (1H, dd, J=5.7, 14.3 Hz), 2.86 (1H, dd, J=7.2, 14.3 Hz), 3.35 (1H, d, J=13.8 Hz), 4.33-4.51 (6H, m), 5.79 (1H, m), 5.98 (1H, s), 6.23 (1H, m), 6.57 (1H, d, J=2.1 Hz), 6.96 (1H, m), 7.11 (1H, m), 7.19-7.42 (7H, m).

| Elemental analysis for C₃₀H₃₄N₃O₄SCl | |
|---|---|
| Calculated | C, 63.42; H, 6.03; N, 7.40 |
| Found | C, 63.11; H, 6.21; N, 7.27 |

EXAMPLE 56

2-[3,5-trans-5-[3-(acetylaminomethyl)phenyl]-7-chloro-1-neopentyl-2-oxo-1,2,3,5-tetrahydro-4,1-benzoxazepin-3-yl]-N-(2-furylmethyl)acetamide ¹H-NMR (CDCl₃) δ: 0.91 (9H, s), 2.03 (3H, s), 2.68 (1H, dd, J=5.9, 14.4 Hz), 2.85 (1H, dd, J=7.1, 14.4 Hz), 3.35 (1H, d, J=13.9 Hz), 4.32 (1H, dd, J=5.1, 15.5 Hz), 4.40-4.53 (5H, m), 5.80 (1H, m), 5.98 (1H, s), 6.19-6.23 (2H, m), 6.30 (1H, m), 6.57 (1H, d, J=2.1 Hz), 7.20-7.42 (7H, m).

| Elemental analysis for $C_{30}H_{34}N_3O_5Cl$ | |
|---|---|
| Calculated | C, 65.27; H, 6.21; N, 7.61 |
| Found | C, 64.95; H, 6.48; N, 7.56 |

EXAMPLE 57

4-trans-[[3,5-trans-5-[3-(acetylaminomethyl)phenyl]-7-chloro-1-neopentyl-2-oxo-1,2,3,5-tetrahydro-4,1-benzoxazepin-3-yl]acetylaminomethyl]cyclohexanecarboxylic acid To a solution of methyl 4-trans-[[3,5-trans-5-[3-(acetylaminomethyl)phenyl]-7-chloro-1-neopentyl-2-oxo-1,2,3,5-tetrahydro-4,1-benzoxazepin-3-yl]acetylaminomethyl]cyclohexanecarboxylate (0.18 g) obtained in Example 52 in a mixed solvent of methanol (5 ml) and tetrahydrofuran (5 ml) was added 1N aqueous sodium hydroxide solution (0.44 ml), and the mixture was stirred at 60° C. for 18 hrs. The solvent was evaporated, and the residue was neutralized with 1N hydrochloric acid and extracted with ethyl acetate. The organic layer was separated, washed with water and dried over anhydrous $MgSO_4$. The solvent was evaporated, and the residue was crystallized from diethyl ether to give the title compound (0.14 g) as colorless crystals.

$^1$H-NMR (DMSO-$d_6$) δ: 0.85 (9H, s), 0.86 (2H, m), 1.20-1.28 (3H, m), 1.68 (2H, m), 1.85 (3H, s), 1.86 (2H, m), 2.09 (1H, m), 2.54-2.58 (2H, m), 2.81-2.93 (2H, m), 3.58 (1H, d, J=13.8 Hz), 4.27-4.29 (4H, m), 5.84 (1H, s), 6.39 (1H, s), 7.15 (1H, s), 7.20 (1H, m), 7.31 (1H, d, J=7.0 Hz), 7.42 (1H, m), 7.55 (1H, d, J=8.4 Hz), 7.75 (1H, d, J=8.7 Hz), 7.88 (1H, m), 8.36 (1H, m), 11.97 (1H, s).

| Elemental analysis for $C_{33}H_{42}N_3O_6Cl\cdot 0.5H_2O$ | |
|---|---|
| Calculated | C, 63.81; H, 6.98; N, 6.76 |
| Found | C, 64.11; H, 7.17; N, 6.82 |

EXAMPLE 58

2-[3,5-trans-5-[3-(acetylaminomethyl)phenyl]-1-neopentyl-2-oxo-1,2,3,5-tetrahydro-4,1-benzoxazepin-3-yl]-N-(2-fluorobenzyl)acetamide To a solution of 2-[3,5-trans-5-[3-(acetylaminomethyl)phenyl]-7-chloro-1-neopentyl-2-oxo-1,2,3,5-tetrahydro-4,1-benzoxazepin-3-yl]-N-(2-fluorobenzyl)acetamide (0.15 g) obtained in Reference Example 3 in methanol (10 ml) were added 10% palladium carbon (0.04 g) and ammonium formate (0.05 g), and the mixture was heated under reflux for 2 hrs. Palladium carbon was filtered off, and the filtrate was concentrated. The residue was purified by silica gel column chromatography, and the residue was recrystallized from hexane-ethyl acetate to give the title compound (0.07 g) as colorless crystals.

$^1$H-NMR (CDCl$_3$) δ: 0.91 (9H, s), 2.02 (3H, s), 2.69 (1H, dd, J=5.6, 14.2 Hz), 2.89 (1H, dd, J=7.3, 14.2 Hz), 3.42 (1H, d, J=13.8 Hz), 4.38-4.50 (6H, m), 5.76 (1H, m), 6.03 (1H, s), 6.38 (1H, m), 6.59 (1H, d, J=7.5 Hz), 7.00-7.05 (2H, m), 7.13 (1H, m), 7.21-7.38 (8H, m).

| Elemental analysis for $C_{32}H_{36}N_3O_4F$ | |
|---|---|
| Calculated | C, 70.44; H, 6.65; N, 7.70 |
| Found | C, 70.23; H, 6.74; N, 7.53 |

EXAMPLE 59

2-[3,5-trans-7-chloro-1-neopentyl-2-oxo-5-[3-(4H-1,2,4-triazol-4-ylmethyl)phenyl]-1,2,3,5-tetrahydro-4,1-benzoxazepin-3-yl]-N-(2-fluorobenzyl)acetamide To a solution of 2-[3,5-trans-5-[3-(aminomethyl)phenyl]-7-chloro-1-neopentyl-2-oxo-1,2,3,5-tetrahydro-4,1-benzoxazepin-3-yl]-N-(2-fluorobenzyl)acetamide hydrochloride (0.25 g) obtained in Example 6 of JP-A-11-209356 in pyridine (5 ml) was added N'-[(dimethylamino)methylene]-N,N-dimethylhydrazonoformamide (0.19 g), and the mixture was stirred with heating at 100° C. for 24 hrs. After evaporation of the solvent, the residue was purified by silica gel column chromatography to give the title compound (0.18 g) as a colorless amorphous solid.

$^1$H-NMR (CDCl$_3$) δ: 0.90 (9H, s), 2.68 (1H, dd, J=5.7, 14.5 Hz), 2.88 (1H, dd, J=7.2, 14.5 Hz), 3.35 (1H, d, J=13.9 Hz), 4.39-4.52 (4H, m), 5.20 (2H, s), 5.99 (1H, s), 6.26 (1H, m), 6.48 (1H, d, J=2.2 Hz), 7.01-7.44 (10H, m), 8.18 (2H, s).

| Elemental analysis for $C_{32}H_{33}N_5O_3FCl\cdot 0.5AcOEt$ | |
|---|---|
| Calculated | C, 64.40; H, 5.88; N, 11.04 |
| Found | C, 64.19; H, 5.94; N, 11.21 |

EXAMPLE 60

2-[3,5-trans-7-chloro-5-[3-(1H-imidazol-1-ylmethyl)phenyl]-1-neopentyl-2-oxo-1,2,3,5-tetrahydro-4,1-benzoxazepin-3-yl]-N-(2-fluorobenzyl)acetamide 2-[3,5-trans-7-Chloro-5-[3-(chloromethyl)phenyl]-1-neopentyl-2-oxo-1,2,3,5-tetrahydro-4,1-benzoxazepin-3-yl]-N-(2-fluorobenzyl)acetamide (0.3 g) obtained in Reference Example 26 was dissolved in N,N-dimethylformamide (3 ml), and potassium carbonate (0.11 g) and imidazole (44 mg) were added at room temperature. The mixture was stirred at 60° C. for 8 hrs. Ethyl acetate was added, and the reaction mixture was washed with 5% aqueous potassium hydrogensulfate solution, saturated aqueous sodium hydrogencarbonate solution and brine, and dried over sodium sulfate. The solvent was evaporated and the residue was purified by column chromatography [developing solvent: ethyl acetate-methanol (10:1)] to give the title compound (0.20 g) as a colorless amorphous solid.

| Elemental analysis for $C_{33}H_{34}N_4O_3ClF\cdot 0.5H_2O$ | |
|---|---|
| Calculated | C, 66.27; H, 5.90; N, 9.37. |
| Found | C, 66.19; H, 6.08; N, 9.07. |

The compounds of the following Examples 61 to 65 were respectively synthesized by the same method as in Example 39 and using the compounds obtained in Reference Examples 27 to 31.

EXAMPLE 61

2-[3,5-trans-5-[3-(acetylaminomethyl)phenyl]-7-chloro-1-(6-methoxy-2-naphthylmethyl)-2-oxo-1,2,3,5-tetrahydro-4,1-benzoxazepin-3-yl]-N-(2-fluorobenzyl)acetamide $^1$H-NMR (CDCl$_3$)δ: 1.99 (3H, s), 2.72 (1H, dd, J=5.7, 14.4 Hz), 2.94 (1H, dd, J=7.3, 14.4 Hz), 3.91 (3H, s), 4.29 (2H, d, J=5.6 Hz), 4.38-4.57 (3H, m), 4.95 (1H, d, J=14.7 Hz), 5.36 (1H, s), 5.57 (1H, d, J=14.7 Hz), 5.59 (1H, m), 6.25 (1H, m), 6.45 (1H, s), 6.74 (1H, brs), 6.94-7.04 (3H, m), 7.12-7.33 (9H, m), 7.61-7.69 (3H, m).

| Elemental analysis for C$_{39}$H$_{35}$N$_3$O$_5$FCl | |
|---|---|
| Calculated | C, 68.87; H, 5.19; N, 6.18 |
| Found | C, 68.64; H, 5.17; N, 6.02 |

EXAMPLE 62

2-[3,5-trans-5-[3-(acetylaminomethyl)phenyl]-7-chloro-2-oxo-1-(quinolin-2-ylmethyl)-1,2,3,5-tetrahydro-4,1-benzoxazepin-3-yl]-N-(2-fluorobenzyl)acetamide $^1$H-NMR (CDCl$_3$) δ: 2.00 (3H, s), 2.75 (1H, dd, J=5.7, 14.4 Hz), 2.93 (1H, dd, J=7.2, 14.4 Hz), 4.34-4.56 (4H, m), 4.62 (1H, m), 5.32 (1H, d, J=15.7 Hz), 5.52 (1H, d, J=15.7 Hz), 5.72 (1H, m), 6.28 (2H, m), 6.55 (1H, d, J=2.0 Hz), 6.95-7.00 (2H, m), 7.19-7.55 (10H, m), 7.67 (1H, m), 7.79 (1H, d, J=8.0 Hz), 7.97 (1H, d, J=8.4 Hz), 8.13 (1H, d, J=8.4 Hz).

| Elemental analysis for C$_{37}$H$_{32}$N$_4$O$_4$FCl | |
|---|---|
| Calculated | C, 68.25; H, 4.95; N, 8.60 |
| Found | C, 68.20; H, 4.74; N, 8.47 |

EXAMPLE 63

2-[3,5-trans-5-[3-(acetylaminomethyl)phenyl]-7-chloro-1-(9H-fluoren-2-ylmethyl)-2-oxo-1,2,3,5-tetrahydro-4,1-benzoxazepin-3-yl]-N-(2-fluorobenzyl)acetamide $^1$H-NMR (CDCl$_3$) δ: 1.92 (3H, s), 2.71 (1H, dd, J=5.9, 14.4 Hz), 2.93 (1H, dd, J=7.2, 14.4 Hz), 3.83 (2H, s), 4.12 (1H, dd, J=5.7, 14.7 Hz), 4.23 (1H, dd, J=5.9, 14.7 Hz), 4.42-4.56 (3H, m), 4.87 (1H, d, J=14.5 Hz), 5.31 (1H, s), 5.45 (1H, m), 5.53 (1H, d, J=14.5 Hz), 6.24 (1H, m), 6.46 (1H, d, J=1.6 Hz), 6.73 (1H, brs), 6.97-7.04 (3H, m), 7.19-7.38 (9H, m), 7.46 (1H, s), 7.53 (1H, d, J=7.3 Hz), 7.69 (1H, d, J=7.8 Hz), 7.77 (1H, d, J=7.3 Hz).

| Elemental analysis for C$_{41}$H$_{35}$N$_3$O$_4$FCl | |
|---|---|
| Calculated | C, 71.56; H, 5.13; N, 6.11 |
| Found | C, 71.41; H, 5.11; N, 5.95 |

EXAMPLE 64

2-[3,5-trans-5-[3-(acetylaminomethyl)phenyl]-7-chloro-1-[5-(2-methoxyphenyl)-2-furylmethyl]-2-oxo-1,2,3,5-tetrahydro-4,1-benzoxazepin-3-yl]-N-(2-fluorobenzyl)acetamide $^1$H-NMR (CDCl$_3$) δ: 1.95 (3H, s), 2.71 (1H, dd, J=6.0, 14.4 Hz), 2.91 (1H, dd, J=7.0, 14.4 Hz), 3.91 (3H, s), 4.09 (2H, d, J=5.6 Hz), 4.38-4.57 (3H, m), 4.73 (1H, d, J=15.3 Hz), 5.43 (1H, m), 5.56 (1H, s), 5.66 (1H, d, J=15.3 Hz), 6.27 (1H, m), 6.36 (1H, d, J=3.2 Hz), 6.49 (1H, s), 6.75 (1H, s), 6.83 (1H, d, J=3.2 Hz), 6.89-7.07 (5H, m), 7.20-7.27 (5H, m), 7.39-7.40 (2H, m), 7.50 (1H, m).

| Elemental analysis for C$_{39}$H$_{35}$N$_3$O$_6$FCl | |
|---|---|
| Calculated | C, 67.29; H, 5.07; N, 6.04 |
| Found | C, 67.07; H, 5.10; N, 5.93 |

EXAMPLE 65

2-[3,5-trans-5-[3-(acetylaminomethyl)phenyl]-1-(2,3'-bithien-5-ylmethyl)-7-chloro-2-oxo-1,2,3,5-tetrahydro-4,1-benzoxazepin-3-yl]-N-(2-fluorobenzyl)acetamide $^1$H-NMR (CDCl$_3$) δ: 1.93 (3H, s), 2.71 (1H, dd, J=5.9, 14.4 Hz), 2.92 (1H, dd, J=7.2, 14.4 Hz), 4.25 (2H, m), 4.40-4.52 (3H, m), 4.81 (1H, d, J=15.0 Hz), 5.42 (1H, s), 5.57 (1H, m), 5.65 (1H, d, J=15.0 Hz), 6.26 (1H, m), 6.52 (1H, d, J=2.1 Hz), 6.85 (1H, d, J=3.5 Hz), 6.90 (1H, s), 6.99-7.05 (4H, m), 7.23-7.40 (9H, m).

| Elemental analysis for C$_{36}$H$_{31}$N$_3$O$_4$S$_2$FCl | |
|---|---|
| Calculated | C, 62.83; H, 4.54; N, 6.11 |
| Found | C, 62.55; H, 4.56; N, 5.87 |

REFERENCE EXAMPLE 1B tert-butyl 3-(2-ethoxy-2-oxoethyl)-1-neopentyl-2-oxo-1,2,3,5-tetrahydro-4H-1,4-benzodiazepine-4-carboxylate (1) To a solution of 2-aminobenzylamine (16.2 g) in tetrahydrofuran (300 ml) was added a solution of di-tert-butyl dicarbonate (30.6 g) in tetrahydrofuran (100 ml) at 0° C., and the mixture was stirred at 0° C. for 1 hr. The solvent was evaporated, and the residue was recrystallized from hexane-chloroform to give tert-butyl 2-aminobenzylcarbamate (26.8 g) as colorless crystals.

$^1$H-NMR (CDCl$_3$) δ: 1.44 (9H, s), 4.24 (2H, d, J=6.2 Hz), 4.30 (2H, brs), 4.76 (1H, brs), 6.67-6.71 (2H, m), 7.03 (1H, d, J=7.7 Hz), 7.10 (1H, m).

(2) To a solution of the compound (12.0 g) obtained in the aforementioned (1) in methanol (80 ml) were added pivalaldehyde (4.8 g) and acetic acid (8 ml), and the mixture was stirred at room temperature for 1 hr. Further, sodium cyanotrihydroborate (10.2 g) was added, and the mixture was stirred at room temperature for 20 hrs. After evaporation of the solvent, ethyl acetate was added and the mixture was washed with water and dried over anhydrous $MgSO_4$. The solvent was evaporated, and the residue was purified by silica gel column chromatography to give tert-butyl 2-(neopentylamino)benzylcarbamate (14.8 g) as a colorless oil.

$^1$H-NMR ($CDCl_3$) δ: 1.03 (9H, s), 1.44 (9H, s), 2.90 (2H, s), 4.27 (2H, d, J=6.0 Hz), 4.50 (1H, brs), 4.66 (1H, brs), 6.60 (1H, m), 6.65 (1H, d, J=8.1 Hz), 7.02 (1H, d, J=7.2 Hz), 7.18 (1H, m).

(3) To a solution of the compound (14.8 g) obtained in the aforementioned (2) in tetrahydrofuran (250 ml) was added triethylamine (7.7 g), and then a solution of ethyl (E)-4-chloro-4-oxo-2-butenoate (8.6 g) in tetrahydrofuran (50 ml) was added, and the mixture was stirred at room temperature for 15 hrs. After evaporation of the solvent, ethyl acetate was added and the mixture was washed with water. The organic layer was further washed with 1N hydrochloric acid and saturated aqueous $NaHCO_3$ solution and dried over anhydrous $MgSO_4$. The solvent was evaporated, and the residue was dissolved in ethyl acetate (250 ml). A 4N solution (250 ml) of hydrogen chloride in ethyl acetate was added, and the mixture was stirred at room temperature for 2 hrs. After evaporation of the solvent, the residue was dissolved in ethanol (250 ml), and potassium carbonate (20.1 g) was added. The mixture was stirred at room temperature for 1 hr. After evaporation of the solvent, ethyl acetate was added and the mixture was washed with water and dried over anhydrous $MgSO_4$. The solvent was evaporated, and the residue was purified by silica gel column chromatography to give ethyl (1-neopentyl-2-oxo-2,3,4,5-tetrahydro-1H-1,4-benzodiazepin-3-yl)acetate (11.5 g) as brown crystals.

$^1$H-NMR ($CDCl_3$) δ: 0.81 (9H, s), 1.21 (3H, t, J=7.0 Hz), 1.95 (1H, brs), 2.55 (1H, dd, J=6.1, 16.7 Hz), 2.81 (1H, dd, J=7.0, 16.7 Hz), 3.33 (1H, d, J=13.8 Hz), 3.65 (1H, m), 3.85 (1H, d, J=12.2 Hz), 4.08 (2H, q, J=7.0 Hz), 4.20 (1H, d, J=12.2 Hz), 4.40 (1H, d, J=13.8 Hz), 7.21-7.36 (4H, m).

(4) To a solution of the compound (11.5 g) obtained in the aforementioned (3) in tetrahydrofuran (250 ml) was added di-tert-butyl dicarbonate (15.9 g), and the mixture was stirred at room temperature for 18 hrs. The solvent was evaporated, and the residue was purified by silica gel column chromatography to give the title compound (15.0 g) as colorless crystals.

$^1$H-NMR ($CDCl_3$) δ: 0.81 (9H, s), 1.20 (3H, t, J=7.0 Hz), 1.46 (9H, s), 1.90 (1H, m), 2.34 (1H, m), 3.60 (1H, m), 4.05 (2H, m), 4.21 (1H, m), 4.40 (1H, m), 4.83 (1H, m), 5.00 (1H, m), 7.22 (1H, m), 7.31-7.40 (3H, m).

REFERENCE EXAMPLE 2B

[4-(tert-butoxycarbonyl)-1-neopentyl-2-oxo-2,3,4,5-tetrahydro-1H-1,4-benzodiazepin-3-yl]acetic acid To a solution of the compound (15.0 g) obtained in Reference Example 1B in a mixed solvent of ethanol (160 ml) and tetrahydrofuran (160 ml) was added 2N aqueous sodium hydroxide solution (23 ml), and the mixture was stirred at room temperature for 4 hrs. The solvent was evaporated, and the residue was neutralized with 2N hydrochloric acid and extracted with ethyl acetate. The organic layer was separated, washed with water and dried over anhydrous $MgSO_4$. The solvent was evaporated to give the title compound (13.9 g) as a colorless amorphous solid.

$^1$H-NMR (DMSO-$d_6$) δ: 0.73 (9H, s), 1.41 (9H, s), 1.99 (2H, m), 3.71 (1H, m), 4.01 (1H, m), 4.27 (1H, m), 4.72-4.77 (2H, m), 7.27 (1H, m), 7.40-7.49 (2H, m), 7.56 (1H, m), 12.20 (1H, brs).

REFERENCE EXAMPLE 3B tert-butyl 3-[2-[(2-fluorobenzyl)amino]-2-oxoethyl]-1-neopentyl-2-oxo-1,2,3,5-tetrahydro-4H-1,4-benzodiazepine-4-carboxylate To a solution of the compound (13.9 g) obtained in Reference Example 2B in dimethylformamide (150 ml) were added 2-fluorobenzylamine (5.7 g), 1-hydroxy-1H-benzotriazole (5.7 g) and 1-ethyl-3-(3-dimethylaminopropyl)carbodiimide hydrochloride (10.4 g), and the mixture was stirred at room temperature for 20 hrs. Ethyl acetate was added to the reaction mixture and the mixture was washed with water and dried over anhydrous $MgSO_4$. The solvent was evaporated, and the residue was purified by silica gel column chromatography to give the title compound (16.3 g) as a colorless amorphous solid.

$^1$H-NMR ($CDCl_3$) δ: 0.79 (9H, s), 1.45 (9H, s), 1.93 (1H, m), 2.18 (1H, m), 3.49 (1H, m), 4.17 (1H, m), 4.34-4.43 (3H, m), 4.80 (1H, m), 5.02 (1H, m), 7.01-7.10 (2H, m), 7.20-7.38 (6H, m).

EXAMPLE 1B

N-(2-fluorobenzyl)-2-(4-isonicotinoyl-1-neopentyl-2-oxo-2,3,4,5-tetrahydro-1H-1,4-benzodiazepin-3-yl)acetamide (1) To a solution of the compound (16.3 g) obtained in Reference Example 3B in ethyl acetate (150 ml) was added a 4N solution (150 ml) of hydrogen chloride in ethyl acetate, and the mixture was stirred at room temperature for 3 hrs. The solvent was evaporated, and the residue was washed with diethyl ether to give N-(2-fluorobenzyl)-2-(1-neopentyl-2-oxo-2,3,4,5-tetrahydro-1H-1,4-benzodiazepin-3-yl)acetamide hydrochloride (13.4 g) as colorless crystals.

$^1$H-NMR (DMSO-$d_6$) δ: 0.75 (9H, s), 2.60 (1H, dd, J=3.7, 15.8 Hz), 3.04 (1H, dd, J=9.4, 15.8 Hz), 3.57 (1H, d, J=13.9 Hz), 3.83 (1H, m), 3.98 (1H, d, J=13.1 Hz), 4.17-4.25 (3H, m), 4.42 (1H, d, J=13.1 Hz), 7.12-7.18 (2H, m), 7.26-7.40 (3H, m), 7.51-7.60 (2H, m), 7.69 (1H, d, J=8.1 Hz), 8.72 (1H, m), 10.45 (1H, brs), 10.70 (1H, brs).

(2) To a solution of the compound (1.2 g) obtained in the aforementioned (1) in dimethylformamide (35 ml) were added isonicotinic acid (0.68 g), 1-hydroxy-1H-benzotriazole 0.48 g), triethylamine (0.42 g) and 1-ethyl-3-(3-dimethylaminopropyl)carbodiimide hydrochloride (1.0 g), and the mixture was stirred at room temperature for 40 hrs. Ethyl acetate was added to the reaction mixture and the mixture was washed with water and dried over anhydrous $MgSO_4$. The solvent was evaporated, and the residue was purified by silica gel column chromatography and recrystallized from hexane-tetrahydrofuran to give the title compound (1.2 g) as colorless crystals.

$^1$H-NMR ($CDCl_3$) δ: 0.80 (9H, s), 2.04 (1H, m), 2.50 (1H, m), 3.62 (1H, m), 4.15 (1H, m), 4.42-4.58 (4H, m), 5.18 (1H, m), 6.60 (1H, brs), 6.99-7.50 (10H, m), 8.75 (2H, d, J=4.8 Hz).

4.60-4.85 (2H, m), 5.20 (1H, m), 6.85 (1H, brs), 7.04-7.11 (3H, m), 7.18-7.43 (7H, m), 7.63 (1H, m).

| Elemental analysis for $C_{29}H_{31}N_4O_3F \cdot 0.5H_2O$ | |
| --- | --- |
| Calculated | C, 68.08; H, 6.41; N, 10.76 |
| Found | C, 67.90; H, 6.23; N, 10.61 |

In the same manner as in Example 1B, the compounds of the following Examples 2B to 17B and Reference Examples 4B to 5B were synthesized.

EXAMPLE 2B

N-(2-fluorobenzyl)-2-[1-neopentyl-2-oxo-4-(3-pyridylcarbonyl)-2,3,4,5-tetrahydro-1H-1,4-benzodiazepin-3-yl]acetamide $^1$H-NMR (CDCl$_3$) δ: 0.80 (9H, s), 2.00 (1H, m), 2.48 (1H, m), 3.66 (1H, m), 4.17 (1H, m), 4.42 (2H, d, J=4.5 Hz), 4.61 (2H, m), 5.20 (1H, m), 6.65 (1H, brs), 6.99-7.43 (9H, m), 7.81 (1H, m), 8.73 (2H, m).

| Elemental analysis for $C_{29}H_{31}N_4O_3F$ | |
| --- | --- |
| Calculated | C, 69.30; H, 6.22; N, 11.15 |
| Found | C, 69.16; H, 6.48; N, 10.91 |

EXAMPLE 3B

N-(2-fluorobenzyl)-2-[1-neopentyl-2-oxo-4-(2-pyridylcarbonyl)-2,3,4,5-tetrahydro-1H-1,4-benzodiazepin-3-yl]acetamide $^1$H-NMR (DMSO-d$_6$) δ: 0.75 (9H, s), 1.66 (1H, m), 2.40 (1H, m), 3.59 (1H, m), 4.07-4.16 (3H, m), 4.50 (1H, m), 4.80 (1H, m), 5.20 (1H, m), 7.11-7.30 (6H, m), 7.32-7.60 (3H, m), 7.69 (1H, m), 7.98 (1H, m), 8.12 (1H, m), 8.40-8.80 (1H, m).

| Elemental analysis for $C_{29}H_{31}N_4O_3F$ | |
| --- | --- |
| Calculated | C, 69.30; H, 6.22; N, 11.15 |
| Found | C, 69.21; H, 6.19; N, 10.86 |

EXAMPLE 4B

N-(2-fluorobenzyl)-2-[1-neopentyl-2-oxo-4-(4-quinolinylcarbonyl)-2,3,4,5-tetrahydro-1H-1,4-benzodiazepin-3-yl]acetamide $^1$H-NMR (DMSO-d$_6$) δ: 0.73 (9H, s), 1.78 (1H, m), 2.38 (1H, m), 3.56 (1H, m), 4.00-4.55 (5H, m), 5.28-5.50 (1H, m), 6.64 (1H, m), 7.14 (3H, m), 7.28 (2H, m), 7.46-7.70 (5H, m), 7.87 (1H, m), 8.14-8.29 (2H, m), 8.80-9.05 (1H, m).

EXAMPLE 5B

N-(2-fluorobenzyl)-2-[1-neopentyl-2-oxo-4-(3-thienylcarbonyl)-2,3,4,5-tetrahydro-1H-1,4-benzodiazepin-3-yl]acetamide $^1$H-NMR (CDCl$_3$) δ: 0.81 (9H, s), 2.00 (1H, m), 2.41 (1H, m), 3.58 (1H, m), 4.20 (1H, m), 4.42 (2H, d, J=5.5 Hz),

| Elemental analysis for $C_{28}H_{30}N_3O_3FS$ | |
| --- | --- |
| Calculated | C, 66.25; H, 5.96; N, 8.28 |
| Found | C, 66.06; H, 6.00; N, 8.35 |

EXAMPLE 6B

N-(2-fluorobenzyl)-2-[4-(3-furoyl)-1-neopentyl-2-oxo-2,3,4,5-tetrahydro-1H-1,4-benzodiazepin-3-yl]acetamide $^1$H-NMR (CDCl$_3$) δ: 0.82 (9H, s), 1.93 (1H, m), 2.31 (1H, m), 3.53 (1H, m), 4.23 (1H, m), 4.42 (2H, d, J=5.8 Hz), 4.70 (1H, m), 4.92 (1H, m), 5.25 (1H, m), 6.65 (1H, m), 7.02-7.11 (2H, m), 7.17-7.48 (8H, m), 7.83 (1H, s).

| Elemental analysis for $C_{28}H_{30}N_3O_4F$ | | | |
| --- | --- | --- | --- |
| Calculated | C, 68.42; | H, 6.15; | N, 8.55 |
| Found | C, 68.35; | H, 5.98; | N, 8.34 |

EXAMPLE 7B 2-(4-benzoyl-1-neopentyl-2-oxo-2,3,4,5-tetrahydro-1H-1,4-benzodiazepin-3-yl)-N-(2-fluorobenzyl)acetamide $^1$H-NMR (CDCl$_3$) δ: 0.80 (9H, s), 2.00 (1H, m), 2.43 (1H, m), 3.62 (1H, m), 4.20 (1H, m), 4.43 (2H, d, J=4.6 Hz), 4.60 (2H, m), 5.21 (1H, m), 6.95 (1H, brs), 6.98-7.11 (3H, m), 7.17-7.24 (2H, m), 7.32-7.47 (8H, m).

| Elemental analysis for $C_{30}H_{32}N_3O_3F$ | | | |
| --- | --- | --- | --- |
| Calculated | C, 71.84; | H, 6.43; | N, 8.38 |
| Found | C, 71.51; | H, 6.20; | N, 8.15 |

EXAMPLE 8B

N-(2-fluorobenzyl)-2-[1-neopentyl-2-oxo-4-(2-pyrazinylcarbonyl)-2,3,4,5-tetrahydro-1H-1,4-benzodiazepin-3-yl]acetamide $^1$H-NMR (DMSO-d$_6$) δ: 0.74 (9H, s), 1.68 (1H, m), 2.27 (1H, m), 3.58 (1H, m), 4.09-4.14 (3H, m), 4.51 (1H, m), 4.82 (1H, m), 5.25 (1H, m), 7.14-7.40 (6H, m), 7.48-7.51 (2H, m), 8.13 (1H, brs), 8.50-8.80 (2H, m), 8.91 (1H, m).

| Elemental analysis for $C_{28}H_{30}N_5O_3F$ | | | |
| --- | --- | --- | --- |
| Calculated | C, 66.78; | H, 6.00; | N, 13.91 |
| Found | C, 66.61; | H, 5.95; | N, 13.75 |

EXAMPLE 9B

N-(2-fluorobenzyl)-2-[1-neopentyl-2-oxo-4-(1H-pyrrol-2-ylcarbonyl)-2,3,4,5-tetrahydro-1H-1,4-benzodiazepin-3-yl]acetamide $^1$H-NMR (CDCl$_3$) δ: 0.83 (9H, s), 1.92 (1H, m), 2.26 (1H, m), 3.50 (1H, m), 4.28 (1H, m), 4.42 (2H, m), 4.80 (1H, m), 5.22 (1H, d, J=13.0 Hz), 5.43 (1H, m), 6.31 (1H, m), 6.75 (1H, m), 6.96-7.08 (3H, m), 7.19-7.43 (6H, m), 7.48 (1H, m), 9.51 (1H, brs).

| Elemental analysis for C$_{28}$H$_{31}$N$_4$O$_3$F | | | |
|---|---|---|---|
| Calculated | C, 68.55; | H, 6.37; | N, 11.42 |
| Found | C, 68.25; | H, 6.34; | N, 11.42 |

EXAMPLE 10B

2-[4-[(2,4-dimethyl-1,3-thiazol-5-yl)carbonyl]-1-neopentyl-2-oxo-2,3,4,5-tetrahydro-1H-1,4-benzodiazepin-3-yl]-N-(2-fluorobenzyl)acetamide $^1$H-NMR (CDCl$_3$) δ: 0.80 (9H, s), 2.00 (1H, m), 2.44 (3H, s), 2.48 (1H, m), 2.71 (3H, s), 3.68 (1H, m), 4.10 (1H, m), 4.43 (2H, d, J=5.5 Hz), 4.65 (2H, m), 5.13 (1H, m), 6.50 (1H, m), 7.02-7.11 (3H, m), 7.20-7.42 (5H, m).

| Elemental analysis for C$_{29}$H$_{33}$N$_4$O$_3$FS•0.5H$_2$O | | | |
|---|---|---|---|
| Calculated | C, 63.83; | H, 6.28; | N, 10.27 |
| Found | C, 63.82; | H, 6.35; | N, 9.99 |

EXAMPLE 11B

N-(2-fluorobenzyl)-2-[1-neopentyl-2-oxo-4-(4-pyridylacetyl)-2,3,4,5-tetrahydro-1H-1,4-benzodiazepin-3-yl]acetamide $^1$H-NMR (DMSO-d$_6$) δ: 0.73 (9H, s), 1.46 (1H, m), 1.98 (1H, m), 3.33 (1H, m), 3.56 (1H, m), 3.80-4.25 (5H, m), 4.43 (1H, m), 4.94 (1H, m), 5.23 (1H, m), 7.10-7.30 (7H, m), 7.46-7.50 (2H, m), 8.11 (1H, m), 8.51 (2H, m).

| Elemental analysis for C$_{30}$H$_{33}$N$_4$O$_3$F•0.5H$_2$O | | | |
|---|---|---|---|
| Calculated | C, 68.55; | H, 6.52; | N, 10.66 |
| Found | C, 68.79; | H, 6.27; | N, 10.41 |

EXAMPLE 12B

N-(2-fluorobenzyl)-2-[1-neopentyl-2-oxo-4-(3-pyridylacetyl)-2,3,4,5-tetrahydro-1H-1,4-benzodiazepin-3-yl]acetamide $^1$H-NMR (CDCl$_3$) δ: 0.79 (9H, s), 1.66 (1H, m), 1.80-2.20 (1H, m), 3.22-3.48 (1H, m), 3.88 (2H, m), 4.31-4.40 (3H, m), 4.60 (1H, m), 5.10-5.40 (2H, m), 6.78 (1H, m), 7.01-7.42 (9H, m), 7.59 (1H, m), 8.51 (2H, m).

| Elemental analysis for C$_{30}$H$_{33}$N$_4$O$_3$F•0.5H$_2$O | | | |
|---|---|---|---|
| Calculated | C, 68.55; | H, 6.52; | N, 10.66 |
| Found | C, 68.71; | H, 6.28; | N, 10.59 |

EXAMPLE 13B

2-[4-(2-chloroisonicotinoyl)-1-neopentyl-2-oxo-2,3,4,5-tetrahydro-1H-1,4-benzodiazepin-3-yl]-N-(2-fluorobenzyl)acetamide $^1$H-NMR (CDCl$_3$) δ: 0.80 (9H, s), 2.03 (1H, m), 2.48 (1H, m), 3.63 (1H, m), 4.18 (1H, m), 4.42-4.57 (4H, m), 5.15 (1H, m), 6.44 (1H, m), 7.00-7.13 (3H, m), 7.22-7.44 (7H, m), 8.53 (1H, m).

| Elemental analysis for C$_{29}$H$_{30}$N$_4$O$_3$FCl | | | |
|---|---|---|---|
| Calculated | C, 64.86; | H, 5.63; | N, 10.43 |
| Found | C, 64.79; | H, 5.71; | N, 10.30 |

EXAMPLE 14B

N-(2-fluorobenzyl)-2-[4-(2-methylisonicotinoyl)-1-neopentyl-2-oxo-2,3,4,5-tetrahydro-1H-1,4-benzodiazepin-3-yl]acetamide $^1$H-NMR (CDCl$_3$) δ: 0.80 (9H, s), 2.00 (1H, m), 2.42 (1H, m), 2.64 (3H, s), 3.60 (1H, m), 4.20 (1H, m), 4.41-4.57 (4H, m), 5.20 (1H, m), 6.40 (1H, m), 6.99-7.43 (10H, m), 8.63 (1H, d, J=4.7 Hz).

| Elemental analysis for C$_{30}$H$_{33}$N$_4$O$_3$F | | | |
|---|---|---|---|
| Calculated | C, 69.75; | H, 6.44; | N, 10.85 |
| Found | C, 69.66; | H, 6.49; | N, 11.00 |

EXAMPLE 15B

4-[[3-[2-[(2-fluorobenzyl)amino]-2-oxoethyl]-1-neopentyl-2-oxo-1,2,3,5-tetrahydro-4H-1,4-benzodiazepin-4-yl]carbonyl]-2-pyridinecarboxamide $^1$H-NMR (CDCl$_3$) δ: 0.80 (9H, s), 1.91 (1H, m), 2.48 (1H, m), 3.70 (1H, m), 4.10-4.60 (4H, m), 5.20 (1H, m), 5.72 (1H, m), 6.50 (1H, m), 6.98-7.46 (8H, m), 7.56 (1H, m), 7.82 (1H, m), 8.25 (1H, m), 8.72 (1H, d, J=4.7 Hz).

| Elemental analysis for C$_{30}$H$_{32}$N$_5$O$_4$F•0.5H$_2$O | | | |
|---|---|---|---|
| Calculated | C, 64.99; | H, 6.00; | N, 12.63 |
| Found | C, 65.21; | H, 6.05; | N, 12.35 |

EXAMPLE 16B

2-[4-[4-(acetylamino)benzoyl]-1-neopentyl-2-oxo-2,3,4,5-tetrahydro-1H-1,4-benzodiazepin-3-yl]-N-(2-fluorobenzyl)acetamide $^1$H-NMR (CDCl$_3$) δ: 0.80 (9H, s), 2.15 (1H, m), 2.17 (3H, s), 2.50 (1H, m), 3.68 (1H, m), 4.10 (1H, m), 4.42 (2H, m), 4.61 (2H, m), 5.13 (1H, m), 6.98-7.38 (11H, m), 7.56 (2H, d, J=8.1 Hz), 7.91 (1H, m).

| Elemental analysis for C$_{32}$H$_{35}$N$_4$O$_4$F | | | |
|---|---|---|---|
| Calculated | C, 68.80; | H, 6.31; | N, 10.03 |
| Found | C, 68.59; | H, 6.30; | N, 10.17 |

REFERENCE EXAMPLE 4B

2-[4-[3-(acetylamino)propanoyl]-1-neopentyl-2-oxo-2,3,4,5-tetrahydro-1H-1,4-benzodiazepin-3-yl]-N-(2-fluorobenzyl)acetamide $^1$H-NMR (CDCl$_3$) δ: 0.79 (9H, s), 1.86 (1H, m), 1.94 (3H, s), 2.10 (1H, m), 2.67 (2H, m), 3.35-3.62 (3H, m), 4.20-4.70 (5H, m), 5.10-5.34 (1H, m), 6.10-6.50 (1H, m), 6.90-7.11 (3H, m), 7.21-7.45 (6H, m).

| Elemental analysis for C$_{28}$H$_{35}$N$_4$O$_4$F•0.25H$_2$O | | | |
|---|---|---|---|
| Calculated | C, 65.29; | H, 6.95; | N, 10.88 |
| Found | C, 65.19; | H, 6.97; | N, 10.89 |

REFERENCE EXAMPLE 5B

2-[4-[(acetylamino)acetyl]-1-neopentyl-2-oxo-2,3,4,5-tetrahydro-1H-1,4-benzodiazepin-3-yl]-N-(2-fluorobenzyl)acetamide $^1$H-NMR (CDCl$_3$) δ: 0.79 (9H, s), 1.79 (1H, m), 2.04 (3H, s), 2.06 (1H, m), 3.45 (1H, m), 4.02-4.65 (7H, m), 5.10-5.40 (1H, m), 6.53 (2H, m), 6.99-7.11 (2H, m), 7.21-7.44 (6H, m).

| Elemental analysis for C$_{27}$H$_{33}$N$_4$O$_4$F•0.5H$_2$O | | | |
|---|---|---|---|
| Calculated | C, 64.14; | H, 6.78; | N, 11.08 |
| Found | C, 64.40; | H, 6.93; | N, 11.07 |

EXAMPLE 17B

2-[4-[(1-acetyl-4-piperidinyl)carbonyl]-1-neopentyl-2-oxo-2,3,4,5-tetrahydro-1H-1,4-benzodiazepin-3-yl]-N-(2-fluorobenzyl)acetamide $^1$H-NMR (CDCl$_3$) δ: 0.80 (9H, s), 1.40-2.00 (6H, m), 2.09 (3H, s), 2.50-2.82 (1H, m), 2.90-3.50 (3H, m), 3.86 (1H, m), 4.33-4.70 (5H, m), 5.00-5.30 (2H, m), 6.85-7.49 (9H, m).

| Elemental analysis for C$_{31}$H$_{39}$N$_4$O$_4$F•0.5H$_2$O | | | |
|---|---|---|---|
| Calculated | C, 66.53; | H, 7.20; | N, 10.01 |
| Found | C, 66.61; | H, 7.03; | N, 10.29 |

REFERENCE EXAMPLE 6B 2-(4-acetyl-1-neopentyl-2-oxo-2,3,4,5-tetrahydro-1H-1,4-benzodiazepin-3-yl)-N-(2-fluorobenzyl)acetamide To a solution of the compound (0.15 g) obtained in Example 1B (1) in pyridine (6 ml) were added acetic anhydride (0.20 g) and 4-dimethylaminopyridine (0.05 g), and the mixture was stirred at room temperature for 14 hrs. The solvent was evaporated, and the residue was purified by silica gel column chromatography and recrystallized from hexane-ethyl acetate to give the title compound (0.11 g) as colorless crystals.

$^1$H-NMR (CDCl$_3$) δ: 0.80 (9H, s), 1.83 (1H, m), 2.08 (1H, m), 2.22 (3H, s), 3.23-3.50 (1H, m), 4.15-4.63 (5H, m), 5.18 (1H, m), 5.32 (1H, m), 7.03-7.12 (3H, m), 7.20-7.43 (5H, m).

| Elemental analysis for C$_{25}$H$_{30}$N$_3$O$_3$F | | | |
|---|---|---|---|
| Calculated | C, 68.32; | H, 6.88; | N, 9.56 |
| Found | C, 68.27; | H, 6.97; | N, 9.79 |

EXAMPLE 18B cl N-(2-fluorobenzyl)-2-[1-neopentyl-4-(1-oxidoisonicotinoyl)-2-oxo-2,3,4,5-tetrahydro-1H-1,4-benzodiazepin-3-yl]acetamide To a solution of N-(2-fluorobenzyl)-2-(4-isonicotinoyl-1-neopentyl-2-oxo-2,3,4,5-tetrahydro-1H-1,4-benzodiazepin-3-yl)acetamide (0.50 g) obtained in Example 1B (2) in chloroform (10 ml) was added 3-chloroperbenzoic acid (0.44 g), and the mixture was stirred at room temperature for 15 hrs. The solvent was evaporated, and the residue was purified by silica gel column chromatography and recrystallized from methanol to give the title compound (0.50 g) as colorless crystals.

$^1$H-NMR (CDCl$_3$) δ: 0.80 (9H, s), 2.18 (1H, m), 2.50 (1H, m), 3.70 (1H, m), 4.05 (1H, m), 4.37-4.44 (2H, m), 4.56-4.70 (2H, m), 5.05 (1H, m), 6.60 (1H, m), 7.01-7.13 (3H, m), 7.18-7.43 (7H, m), 8.23 (2H, d, J=6.8 Hz).

| Elemental analysis for C$_{29}$H$_{31}$N$_4$O$_4$F•0.5H$_2$O | | | |
|---|---|---|---|
| Calculated | C, 66.02; | H, 6.11; | N, 10.62 |
| Found | C, 66.31; | H, 6.13; | N, 10.57 |

EXAMPLE 19B

2-[4-(2-cyanoisonicotinoyl)-1-neopentyl-2-oxo-2,3,4,5-tetrahydro-1H-1,4-benzodiazepin-3-yl]-N-(2-fluorobenzyl)acetamide To a solution of the compound (0.36 g) obtained in Example 18B in acetonitrile (10 ml) were added trimethylsilylnitrile (0.34 g) and N,N-dimethylcarbamoyl chloride (0.23 g), and the mixture was stirred at room temperature for 170 hrs. The solvent was evaporated, and the residue was purified by silica gel column chromatography and recrystallized from hexane-ethyl acetate to give the title compound (0.31 g) as a colorless amorphous solid.

$^1$H-NMR (CDCl$_3$) δ: 0.80 (9H, s), 2.00 (1H, m), 2.50 (1H, m), 3.62 (1H, m), 4.15 (1H, m), 4.30-4.58 (4H, m), 5.07 (1H, m), 6.40 (1H, m), 7.01-7.15 (3H, m), 7.24-7.36 (4H, m), 7.45 (1H, m), 7.55 (1H, m), 7.71 (1H, m), 8.84 (1H, m).

| Elemental analysis for C$_{30}$H$_{30}$N$_5$O$_3$F•0.25AcOEt | | | |
|---|---|---|---|
| Calculated | C, 67.74; | H, 5.87; | N, 12.74 |
| Found | C, 67.77; | H, 5.73; | N, 12.75 |

In the same manner as in Reference Examples 1B to 3B, the compounds of the following Reference Examples 7B and 8B were syntheseized.

REFERENCE EXAMPLE 7B tert-butyl 3-[2-[(2-fluorobenzyl)amino]-2-oxoethyl]-1-isobutyl-2-oxo-1,2,3,5-tetrahydro-4H-1,4-benzodiazepine-4-carboxylate $^1$H-NMR (CDCl$_3$) δ: 0.81 (3H, d, J=6.7 Hz), 0.85 (3H, d, J=6.7 Hz), 1.45 (9H, s), 1.91 (1H, m), 2.04 (1H, m), 2.26 (1H, m), 3.50 (1H, m), 3.98 (1H, m), 4.30 (1H, d, J=13.8 Hz), 4.40 (2H, m), 4.72 (1H, d, J=13.8 Hz), 5.00 (1H, m), 6.33 (1H, brs), 7.01-7.11 (2H, m), 7.20-7.42 (6H, m).

REFERENCE EXAMPLE 8B tert-butyl 1-(2,4-dimethoxybenzyl)-3-[2-[(2-fluorobenzyl)amino]-2-oxoethyl]-2-oxo-1,2,3,5-tetrahydro-4H-1,4-benzodiazepine-4-carboxylate $^1$H-NMR (CDCl$_3$) δ: 1.43 (9H, s), 2.16 (1H, m), 2.32 (1H, m), 3.56 (3H, s), 3.75 (3H, s), 4.12 (1H, m), 4.40-4.45 (2H, m), 4.56 (1H, d, J=13.7 Hz), 4.85 (1H, d, J=15.0 Hz), 5.03 (1H, m), 5.13 (1H, d, J=15.0 Hz), 6.31 (1H, d, J=2.2 Hz), 6.39 (1H, dd, J=2.2, 8.3 Hz), 6.40 (1H, brs), 7.01-7.32 (9H, m).

REFERENCE EXAMPLE 9B

[4-(tert-butoxycarbonyl)-1-(3-hydroxy-2,2-dimethylpropyl)-2-oxo-2,3,4,5-tetrahydro-1H-1,4-benzodiazepin-3-yl]acetic acid In the same manner as in Reference Examples 1B and 2B, the title compound was synthesized.

$^1$H-NMR (DMSO-d$_6$) δ: 0.64 (3H, s), 0.65 (3H, s), 1.41 (9H, s), 2.00 (2H, m), 2.97 (2H, m), 3.72 (1H, m), 4.02 (1H, m), 4.26 (1H, m), 4.45 (1H, m), 4.71-4.79 (2H, m), 7.27 (1H, m), 7.39-7.55 (3H, m), 12.15 (1H, brs).

REFERENCE EXAMPLE 10B tert-butyl 1-(3-acetoxy-2,2-dimethylpropyl)-3-[2-[(2-fluorobenzyl)amino]-2-oxoethyl]-2-oxo-1,2,3,5-tetrahydro-4H-1,4-benzodiazepine-4-carboxylate (1) To a solution of the compound (1.23 g) obtained in Reference Example 9B in tetrahydrofuran (30 ml) were added acetyl chloride (0.74 g) and pyridine (1.19 g), and the mixture was stirred at room temperature for 5 hrs. Water (10 ml) was added, and the mixture was further stirred at room temperature for 16 hrs. Ethyl acetate was added, and the mixture was washed with water and 1N hydrochloric acid and dried over anhydrous MgSO$_4$. The solvent was evaporated to give [1-(3-acetoxy-2,2-dimethylpropyl)-4-(tert-butoxycarbonyl)-2-oxo-2,3,4,5-tetrahydro-1H-1,4-benzodiazepin-3-yl]acetic acid (1.35 g) as a colorless amorphous solid.

$^1$H-NMR (DMSO-d$_6$) δ: 0.76 (3H, s), 0.79 (3H, s), 1.41 (9H, s), 1.91 (3H, s), 1.92-2.02 (2H, m), 3.52 (2H, m), 3.78 (1H, m), 4.06 (1H, m), 4.27 (1H, m), 4.70-4.79 (2H, m), 7.27 (1H, m), 7.39-7.49,(2H, m), 7.56 (1H, m), 12.18 (1H, brs).

(2) To a solution of the compound (0.73 g) obtained in the aforementioned (1) in dimethylformamide (15 ml) were added 2-fluorobenzylamine (0.41 g), 1-hydroxy-1H-benzotriazole (0.33 g) and 1-ethyl-3-(dimethylaminopropyl)carbodiimide hydrochloride (0.62 g), and the mixture was stirred at room temperature for 15 hrs. Ethyl acetate was added and the mixture was washed with water and dried over anhydrous MgSO$_4$. The solvent was evaporated, and the residue was purified by silica gel column chromatography to give the title compound (0.85 g) as a colorless amorphous solid.

$^1$H-NMR (CDCl$_3$); δ: 0.87 (3H, s), 0.88 (3H, s), 1.45 (9H, s), 1.90 (1H, m), 1.94 (3H, s), 2.16 (1H, m), 3.55 (2H, m), 3.70 (1H, m), 4.25 (1H, m), 4.34-4.42 (3H, m), 4.80 (1H, m), 5.01 (1H, m), 7.01-7.11 (2H, m), 7.21-7.38 (7H, m).

REFERENCE EXAMPLE 11B tert-butyl 1-(3-acetoxy-2,2-dimethylpropyl)-2-oxo-3-[2-oxo-2-[[2-(trifluoromethyl)benzyl]amino]ethyl]-1,2,3,5-tetrahydro-4H-1,4-benzodiazepine-4-carboxylate The title compound was synthesized by the same method as in Reference Example 10B and using 2-(trifluoromethyl)benzylamine instead of 2-fluorobenzylamine.

$^1$H-NMR (CDCl$_3$) δ: 0.87 (6H, s), 1.45 (9H, s), 2.04 (3H, s), 2.22 (1H, m), 3.55 (2H, m), 3.70 (1H, m), 4.20 (1H, m), 4.38 (1H, m), 4.44-4.63 (3H, m), 4.80 (1H, m), 5.00 (1H, m), 7.19-7.40 (6H, m), 7.51 (2H, m), 7.62 (1H, m).

The compounds of the following Examples 20B to 29B were respectively synthesized by the same method as in Example 1B and using the compounds obtained in Reference Examples 3B, 7B, 8B, 10B and 11B.

EXAMPLE 20B

2-[4-[3,5-bis(trifluoromethyl)benzoyl]-1-neopentyl-2-oxo-2,3,4,5-tetrahydro-1H-1,4-benzodiazepin-3-yl]-N-(2-fluorobenzyl)acetamide $^1$H-NMR (CDCl$_3$) δ: 0.80 (9H, s), 2.08 (1H, m), 2.52 (1H, m), 3.65 (1H, m), 4.17 (1H, m), 4.42-4.60 (4H, m), 5.16 (1H, m), 6.40 (1H, m), 7.00-7.12 (3H, m), 7.22-7.44 (5H, m), 7.94 (2H, s), 8.01 (1H, s).

| Elemental analysis for C$_{32}$H$_{30}$N$_3$O$_3$F$_7$ | | | |
|---|---|---|---|
| Calculated | C, 60.28; | H, 4.74; | N, 6.59 |
| Found | C, 60.30; | H, 4.62; | N, 6.42 |

EXAMPLE 21B

N-(2-fluorobenzyl)-2-(1-isobutyl-4-isonicotinoyl-2-oxo-2,3,4,5-tetrahydro-1H-1,4-benzodiazepin-3-yl)acetamide $^1$H-NMR (CDCl$_3$) δ: 0.83 (3H, d, J=6.8 Hz), 0.85 (3H, d, J=6.8 Hz), 1.94 (1H, m), 2.13 (1H, m), 2.52 (1H, m), 3.61 (1H, m), 3.96 (1H, dd, J=7.7, 13.6 Hz), 4.42-4.47 (4H, m), 5.16 (1H, m), 6.42 (1H, brs), 6.99-7.12 (3H, m), 7.20-7.44 (7H, m), 8.76 (2H, d, J=5.7 Hz).

| Elemental analysis for C$_{28}$H$_{29}$N$_4$O$_3$F | | |
|---|---|---|
| Calculated | C, 68.84; | H, 5.98; | N, 11.47 |
| Found | C, 68.75; | H, 6.01; | N, 11.31 |

EXAMPLE 22B

2-[1-(2,4-dimethoxybenzyl)-4-isonicotinoyl-2-oxo-2,3,4,5-tetrahydro-1H-1,4-benzodiazepin-3-yl]-N-(2-fluorobenzyl)acetamide $^1$H-NMR (CDCl$_3$) δ: 2.25 (1H, m), 2.55 (1H, m), 3.51 (3H, s), 3.75 (3H, s), 4.23 (1H, d, J=13.7 Hz), 4.30 (1H, m), 4.45 (2H, d, J=5.8 Hz), 4.93 (1H, d, J=14.9 Hz), 5.15 (1H, d, J=14.9 Hz), 5.20 (1H, m), 6.29 (1H, d, J=2.3 Hz), 6.41 (1H, dd, J=2.3, 8.3 Hz), 6.42 (1H, m), 6.87 (1H, m), 7.08-7.37 (10H, m), 8.73 (2H, m).

| Elemental analysis for C$_{33}$H$_{31}$N$_4$O$_5$F | | |
|---|---|---|
| Calculated | C, 68.03; | H, 5.36; | N, 9.62 |
| Found | C, 67.91; | H, 5.52; | N, 9.53 |

EXAMPLE 23B

N-(2-fluorobenzyl)-2-[1-isobutyl-4-(2-methylisonicotinoyl)-2-oxo-2,3,4,5-tetrahydro-1H-1,4-benzodiazepin-3-yl]acetamide $^1$H-NMR (CDCl$_3$) δ: 0.83 (3H, d, J=6.7 Hz), 0.86 (3H, d, J=6.7 Hz), 1.94 (1H, m), 2.12 (1H, m), 2.51 (1H, m), 2.63 (3H, s), 3.60 (1H, m), 3.98 (1H, dd, J=7.7, 13.5 Hz), 4.42-4.47 (4H, m), 5.17 (1H, m), 6.43 (1H, brs), 6.99-7.12 (4H, m), 7.20-7.32 (5H, m), 7.44 (1H, m), 8.63 (1H, d, J=4.9 Hz).

| Elemental analysis for C$_{29}$H$_{31}$N$_4$O$_3$F | | |
|---|---|---|
| Calculated | C, 69.30; | H, 6.22; | N, 11.15 |
| Found | C, 69.11; | H, 6.45; | N, 10.94 |

EXAMPLE 24B

3-[3-[2-[(2-fluorobenzyl)amino]-2-oxoethyl]-4-isonicotinoyl-2-oxo-2,3,4,5-tetrahydro-1H-1,4-benzodiazepin-1-yl]-2,2-dimethylpropyl acetate $^1$H-NMR (CDCl$_3$) δ: 0.86 (3H, s), 0.89 (3H, s), 1.95 (3H, s), 1.97 (1H, m), 2.50 (1H, m), 3.53-3.62 (2H, m), 3.76 (1H, m), 4.26 (1H, m), 4.42-4.60 (4H, m), 5.22 (1H, m), 6.55 (1H, m), 7.00-7.12 (3H, m), 7.21-7.42 (7H, m), 8.76 (2H, m).

| Elemental analysis for C$_{31}$H$_{33}$N$_4$O$_5$F•0.25AcOEt | | |
|---|---|---|
| Calculated | C, 65.97; | H, 6.05; | N, 9.62 |
| Found | C, 66.01; | H, 5.90; | N, 9.45 |

EXAMPLE 25B

3-[4-(2-chloroisonicotinoyl)-3-[2-[(2-fluorobenzyl)amino]-2-oxoethyl]-2-oxo-2,3,4,5-tetrahydro-1H-1,4-benzodiazepin-1-yl]-2,2-dimethylpropyl acetate $^1$H-NMR (CDCl$_3$) δ: 0.85 (3H, s), 0.89 (3H, s), 1.96 (3H, s), 1.97 (1H, m), 2.45 (1H, m), 3.53-3.63 (2H, m), 3.73 (1H, m), 4.27 (1H, m), 4.41-4.60 (4H, m), 5.18 (1H, m), 6.43 (1H, m), 7.00-7.12 (3H, m), 7.20-7.46 (7H, m), 8.53 (1H, m).

| Elemental analysis for C$_{31}$H$_{32}$N$_4$O$_5$FCl | | |
|---|---|---|
| Calculated | C, 62.57; | H, 5.42; | N, 9.42 |
| Found | C, 62.45; | H, 5.33; | N, 9.15 |

EXAMPLE 26B

3-[4-isonicotinoyl-2-oxo-3-[2-oxo-2-[[2-(trifluoromethyl)benzyl]amino]ethyl]-2,3,4,5-tetrahydro-1H-1,4-benzodiazepin-1-yl]-2,2-dimethylpropyl acetate $^1$H-NMR (CDCl$_3$) δ: 0.86 (3H, s), 0.89 (3H, s), 1.94 (1H, m), 1.95 (3H, s), 2.51 (1H, m), 3.57 (2H, m), 3.75 (1H, m), 4.28 (1H, m), 4.57-4.61 (4H, m), 5.24 (1H, m), 6.47 (1H, m), 7.01 (1H, m), 7.21 (1H, m), 7.35-7.44 (5H, m) 7.52 (2H, m), 7.63 (1H, d, J=7.7 Hz), 8.78 (2H, m).

| Elemental analysis for C$_{32}$H$_{33}$N$_4$O$_5$F$_3$•0.25H$_2$ | | |
|---|---|---|
| Calculated | C, 62.48; | H, 5.49; | N, 9.11 |
| Found | C, 62.59; | H, 5.35; | N, 8.80 |

EXAMPLE 27B

3-[4-(2-chloroisonicotinoyl)-2-oxo-3-[2-oxo-2-[[2-(trifluoromethyl)benzyl]amino]ethyl]-2,3,4,5-tetrahydro-1H-1,4-benzodiazepin-1-yl]-2,2-dimethylpropyl acetate $^1$H-NMR (CDCl$_3$) δ: 0.85 (3H, s), 0.89 (3H, s), 1.96 (1H, m), 1.96 (3H, s), 2.50 (1H, m), 3.59 (2H, m), 3.76 (1H, m), 4.27 (1H, m), 4.45-4.62 (4H, m), 5.20 (1H, m), 6.32 (1H, m), 7.02 (1H, m), 7.20-7.45 (6H, m), 7.52 (2H, m), 7.63 (1H, d, J=7.7 Hz), 8.78 (1H, d, J=4.6 Hz).

| Elemental analysis for C$_{32}$H$_{32}$N$_4$O$_5$ClF$_3$ | | |
|---|---|---|
| Calculated | C, 59.58; | H, 5.00; | N, 8.69 |
| Found | C, 59.44; | H, 5.00; | N, 8.81 |

EXAMPLE 28B

2-[4-[2-(acetylamino)isonicotinoyl]-1-neopentyl-2-oxo-2,3,4,5-tetrahydro-1H-1,4-benzodiazepin-3-yl]-N-(2-fluorobenzyl)acetamide $^1$H-NMR (DMSO-d$_6$) δ: 0.75 (9H, s), 1.75 (1H, m), 2.12 (3H, s), 2.15 (1H, m), 3.60 (1H, m), 4.07-4.16 (3H, m), 4.44 (1H, m), 4.52 (1H, m), 5.11 (1H, m), 7.11-7.30 (7H, m), 7.45-7.55 (2H, m), 8.11 (1H, m), 8.12 (1H, m), 8.42 (1H, brs), 10.74 (1H, s).

EXAMPLE 29B

N-(2,6-dichloropyridin-4-yl)-3-[2-[(2-fluorobenzyl)amino]-2-oxoethyl]-1-neopentyl-2-oxo-1,2,3,5-tetrahydro-4H-1,4-benzodiazepine-4-carboxamide To a solution of compound (0.20 g) obtained in Example 1B (1) in tetrahydrofuran (15 ml) were added 2,6-dichloropyridine-4-isocyanate (0.19 g) and potassium carbonate (0.12 g), and the mixture was stirred at room temperature for 3 hrs. Ethyl acetate was added, and the mixture was washed with water and dried over anhydrous MgSO$_4$. The solvent was evaporated, and the residue was purified by silica gel column chromatography and recrystallized from hexane-chloroform to give the title compound (0.22 g) as colorless crystals.

$^1$H-NMR (CDCl$_3$) δ: 0.83 (9H, s), 1.42 (1H, dd, J=9.1, 16.8 Hz), 2.28 (1H, d, J=16.8 Hz), 3.35 (1H, d, J=13.8 Hz), 4.37-4.42 (4H, m), 4.85 (1H, d, J=13.3 Hz), 5.17 (1H, d, J=8.7 Hz), 5.70 (1H, m), 7.03-7.11 (2H, m), 7.23-7.48 (8H, m), 10.54 (1H, s).

| Elemental analysis for C$_{29}$H$_{30}$N$_5$O$_3$FCl$_2$ | | | |
|---|---|---|---|
| Calculated | C, 59.39; | H, 5.16; | N, 11.94 |
| Found | C, 59.38; | H, 5.25; | N, 11.81 |

EXAMPLE 30B

N-(2-fluorobenzyl)-2-[1-neopentyl-2-oxo-4-(pyridin-4-ylmethyl)-2,3,4,5-tetrahydro-1H-1,4-benzodiazepin-3-yl]acetamide To a solution of the compound (0.36 g) obtained in Example 1B (1) in dimethylformamide (15 ml) were added 4-(bromomethyl)pyridine hydrobromide (0.92 g) and potassium carbonate (0.87 g), and the mixture was stirred at room temperature for 20 hrs. Ethyl acetate was added, and the mixture was washed with water and dried over anhydrous MgSO$_4$. The solvent was evaporated, and the residue was purified by silica gel column chromatography and recrystallized from hexane-chloroform to give the title compound (0.15 g) as colorless crystals.

$^1$H-NMR (CDCl$_3$) δ: 0.79 (9H, s), 2.64 (1H, m), 2.80 (1H, m), 3.30-3.48 (4H, m), 3.69-3.80 (2H, m), 4.35 (1H, m), 4.41 (1H, dd, J=5.5, 15.0 Hz), 4.56 (1H, dd, J=6.3, 15.0 Hz), 7.02-7.10 (3H, m), 7.19-7.39 (8H, m), 8.53 (2H, m).

| Elemental analysis for C$_{29}$H$_{33}$N$_4$O$_2$F | | | |
|---|---|---|---|
| Calculated | C, 71.29; | H, 6.81; | N, 11.47 |
| Found | C, 70.97; | H, 6.88; | N, 11.51 |

EXAMPLE 31B

N-(2-fluorobenzyl)-2-(4-isonicotinoyl-2-oxo-2,3,4,5-tetrahydro-1H-1,4-benzodiazepin-3-yl)acetamide (1) To a solution of the compound (5.3 g) obtained in Reference Example 8B in ethyl acetate (40 ml) was added a 4N solution (40 ml) of hydrogen chloride in ethyl acetate, and the mixture was stirred at room temperature for 3 hrs. The solvent was evaporated, and the residue was recrystallized from diisopropyl ether-methanol to give 2-[1-(2,4-dimethoxybenzyl)-2-oxo-2,3,4,5-tetrahydro-1H-1,4-benzodiazepin-3-yl]-N-(2-fluorobenzyl)acetamide hydrochloride as colorless crystals (3.7 g).

$^1$H-NMR (DMSO-d$_6$) δ: 2.61 (1H, dd, J=3.8, 15.7 Hz), 3.08 (1H, dd, J=9.5, 15.7 Hz), 3.61 (3H, s), 3.69 (3H, s), 3.80 (1H, m), 3.92 (1H, m), 4.21-4.27 (3H, m), 4.83 (1H, d, J=15.0 Hz), 5.13 (1H, d, J=15.0 Hz), 6.36 (1H, dd, J=2.0, 8.3 Hz), 6.45 (1H, d, J=2.0 Hz), 7.08-7.18 (3H, m), 7.26-7.32 (3H, m), 7.42-7.54 (3H, m), 8.74 (1H, m), 10.34 (1H, brs), 10.45 (1H, brs).

(2) A solution of the compound (0.50 g) obtained in the forementioned (1) in trifluoroacetic acid (5 ml) was heated under reflux for 6 hrs. The solvent was evaporated, and the residue was neutralized with saturated aqueous sodium hydrogencarbonate solution and extracted with ethyl acetate. The organic layer was separated, washed with water and dried over anhydrous MgSO$_4$. The solvent was evaporated and recrystallized from hexane-tetrahydrofuran to give N-(2-fluorobenzyl)-2-(2-oxo-2,3,4,5-tetrahydro-1H-1,4-benzodiazepin-3-yl)acetamide (0.23 g) as colorless crystals.

$^1$H-NMR (DMSO-d$_6$) δ: 2.31 (1H, dd, J=6.0, 15.2 Hz), 2.64 (1H, dd, J=-7.1, 15.2 Hz), 3.50-3.84 (4H, m), 4.23-4.26 (2H, m), 7.01 (1H, d, J=7.9 Hz), 7.07-7.20 (3H, m), 7.24-7.35 (4H, m), 8.37 (1H, m), 9.84 (1H, s).

(3) To a solution of the compound (0.20 g) obtained in the aforementioned (2) in dimethylformamide (6 ml) were added isonicotinic acid (0.15 g), 1-hydroxy-1H-benzotriazole (0.12 g) and 1-ethyl-3-(3-dimethylaminopropyl)carbodiimide hydrochloride (0.24 g), and the mixture was stirred at room temperature for 24 hrs. Ethyl acetate was added and the mixture was washed with water and dried over anhydrous MgSO$_4$. The solvent was evaporated, and the residue was purified by silica gel column chromatography and recrystallized from hexane-ethanol to give the title compound (0.17 g) as colorless crystals.

$^1$H-NMR (CDCl$_3$) δ: 3.06 (1H, m), 3.20 (1H, m), 4.43-4.55 (3H, m), 4.72 (1H, m), 5.38 (1H, m), 6.40 (1H, m), 6.55 (1H, m), 6.91 (1H, d, J=7.9 Hz), 6.98-7.27 (7H, m), 7.36 (1H, m), 7.93 (1H, m), 8.65 (2H, d, J=5.5 Hz).

| Elemental analysis for C$_{24}$H$_{21}$N$_4$O$_3$F•0.25H$_2$O | | | |
|---|---|---|---|
| Calculated | C, 65.97; | H, 4.96; | N, 12.82 |
| Found | C, 66.25; | H, 4.98; | N, 12.63 |

REFERENCE EXAMPLE 1C (2-chloro-4-phenylpyridin-3-yl)methanol

To a solution of 2-chloro-4-phenylnicotinic acid (22.4 g) in tetrahydrofuran (200 ml) was added thionyl chloride (21 ml), and the mixture was heated under reflux for 3 hrs. The solvent was evaporated under reduced pressure, and the precipitated solid was collected by filtration and washed with hexane. The obtained powdery solid was dissolved in tetrahydrofuran (200 ml), and lithium aluminum hydride (4.5 g) was added by small portions while cooling in a dry ice-acetone bath. The mixture was stirred under cooling for 5 min. and water was added to quench the reaction. The precipitated solid was filtered off, and the filtrate was concentrated and extracted with ethyl acetate. The organic layer was washed successively with water, saturated aqueous sodium hydrogencarbonate and saturated brine, and dried over anhydrous magnesium sulfate, and the solvent was evaporated under reduced pressure to give the title compound (15.1 g) as a colorless oil.

$^1$H-NMR (CDCl$_3$) δ 3.15-3.45 (1H, br), 4.67 (2H, s), 7.20 (1H, d, J=5.2 Hz), 7.35-7.60 (5H, m), 8.30 (1H, dd, J=5.2, 1.0 Hz).

REFERENCE EXAMPLE 2C 2-chloro-3-(chloromethyl)-4-phenylpyridine hydrochloride To a solution of (2-chloro-4-phenylpyridin-3-yl)methanol (15.1 g) obtained in Reference Example 1C in tetrahydrofuran (150 ml) was added thionyl chloride (10 ml), and the mixture was heated under reflux for 30 min. The solvent was evaporated under reduced pressure and the obtained residue was washed with diethyl ether to give the title compound (12.6 g) as a pale-yellow powder.

$^1$H-NMR (CDCl$_3$) δ 4.65 (2H, s), 7.40-7.70 (5H, m), 7.67 (1H, d, J=4.2 Hz), 8.71 (1H, d, J=4.2 Hz).

REFERENCE EXAMPLE 3C

2-[(2-chloro-4-phenylpyridin-3-yl)methylamino] ethanol

To a suspension of 2-chloro-3-(chloromethyl)-4-phenylpyridine hydrochloride (12.6 g) obtained in Reference Example 2C in tetrahydrofuran (150 ml) was added ethanolamine (14 ml), and the mixture was heated under reflux for 6 hrs. After cooling the reaction solution, water was added and the mixture was extracted with ethyl acetate. The organic layer was washed successively with water and saturated brine, and dried over anhydrous magnesium sulfate, and the solvent was evaporated under reduced pressure to give the title compound (13.4 g) as a colorless oil.

$^1$H-NMR (CDCl$_3$) δ 2.00-2.50 (2H, br), 2.65 (2H, t, J=5.2 Hz), 3.51 (2H, t, J=5.2 Hz), 3.82 (2H, s), 7.17 (1H, d, J=5.0 Hz), 7.30-7.60 (5H, m), 8.32 (1H, d, J=5.0 Hz).

REFERENCE EXAMPLE 4C

3-[(2-chloro-4-phenylpyridin-3-yl)methylamino]-1-propanol

The title compound (12.9 g) was obtained as a colorless oil by a similar operation as in Reference Example 3C and using 2-chloro-3-(chloromethyl)-4-phenylpyridine hydrochloride (12.0 g) obtained in Reference Example 2C and 3-amino-1-propanol (16.0 g).

$^1$H-NMR (CDCl$_3$) δ 1.55-1.70 (2H, m), 2.01-3.20 (2H, br), 2.72 (2H, t, J=5.8 Hz), 3.74 (2H, t, J=5.4 Hz), 3.81 (2H, s), 7.17 (1H, d, J=5.0 Hz), 7.30-7.60 (5H, m), 8.33 (1H, d, J=5.0 Hz).

REFERENCE EXAMPLE 5C 6-phenyl-2,3,4,5-tetrahydropyrido[3,2-f][1,4]oxazepine hydrochloride To a solution of 2-[(2-chloro-4-phenylpyridin-3-yl)methylamino]ethanol (13.4 g) obtained in Reference Example 3C in tetrahydrofuran (250 ml) was added sodium hydride (60% in oil) (4.1 g), and the mixture was heated under reflux for 6 hrs. The solvent was evaporated under reduced pressure, and 2N hydrochloric acid (100 ml) was added to the obtained residue. The mixture was washed with diethyl ether. To the aqueous layer was added 6N aqueous sodium hydroxide (50 ml), and the mixture was extracted 5 times with ethyl acetate-tetrahydrofuran (1/1). The organic layer was dried over anhydrous sodium sulfate, and the solvent was evaporated to give a free basic form of the title compound as a colorless oil (11.1 g). Further, a 4N solution of hydrogen chloride in ethyl acetate (50 ml) was added, and the mixture was recrystallized from methanol-ethyl acetate to give the title compound (10.2 g) as colorless crystals having a melting point of 168-170° C.

$^1$H-NMR (free basic form; CDCl$_3$) δ 1.90-2.40 (1H, br), 2.26 (2H, t, J=4.8 Hz), 3.90 (2H, s), 4.27 (2H, t, J=4.8 Hz), 6.97 (1H, d, J=5.2 Hz), 7.20-7.60. (5H, m), 8.15 (1H, d, J=5.2 Hz).

REFERENCE EXAMPLE 6C 7-phenyl-3,4,5,6-tetrahydro-2H-pyrido[2,3-b][1,5]oxazocine hydrochloride The title compound (5.48 g) was obtained as colorless crystals by a similar operation as in Reference Example 5C and using 3-[(2-chloro-4-phenylpyridin-3-yl)methylamino] propan-1-ol (12.9 g) obtained in Reference Example 4C.

$^1$H-NMR (free basic form; CDCl$_3$) δ 1.60-2.00 (3H, m), 3.05-3.15 (2H, m), 3.89 (2H, s), 4.40 (2H, t, J=5.8 Hz), 7.04 (1H, d, J=5.2 Hz), 7.30-7.55 (5H, m), 8.28 (1H, d, J=5.2 Hz).

REFERENCE EXAMPLE 7C

4-[(2-chloro-4-phenylpyridin-3-yl)methylamino]butan-1-ol

The title compound (3.49 g) was obtained as a colorless oil by a similar operation as in Reference Example 3C and using a powder obtained from (2-chloro-4-phenylpyridin-3-yl)methanol (2.6 g) obtained in Reference Example 1C as a starting material by a similar operation as in Reference Example 2C and 4-amino-1-butanol (2.63 g).

$^1$H-NMR (CDCl$_3$) δ: 1.41-1.53 (2H, m), 1.54-1.65 (2H, m), 2.50 (2H, t, J=5.8 Hz), 3.53 (2H, t, J=5.5 Hz), 3.82 (2H, s), 7.16 (1H, d, J=5.0 Hz), 7.32-7.55 (5H, m), 8.32 (1H, d, J=4.9 Hz)

REFERENCE EXAMPLE 8C 8-phenyl-2,3,4,5,6,7-hexahydropyrido[2,3-b][1,5]oxazocine The title compound (1.20 g) was obtained as colorless crystals by a similar operation as in Reference Example 5C and using 4-[(2-chloro-4-phenylpyridin-3-yl)methylamino]butan-1-ol (3.49 g) obtained in Reference Example 7C.

$^1$H-NMR (CDCl$_3$) δ: 1.57-1.74 (4H, m), 3.02-3.08 (2H, m), 3.84 (2H, s), 4.60-4.66 (2H, m), 6.90 (1H, d, J=5.1 Hz), 7.26-7.47 (5H, m), 8.18 (1H, d, J=5.1 Hz).

REFERENCE EXAMPLE 9C

[2-chloro-4-(4-fluorophenyl)pyridin-3-yl]methanol

The title compound (6.25 g) was obtained as colorless crystals by a similar operation as in Reference Example 1C and using 2-chloro-4-(4-fluorophenyl)nicotinic acid (8.4 g).

$^1$H-NMR (CDCl$_3$) δ: 2.33 (1H, t, J=6.6 Hz), 4.67 (2H, d, J=6.6 Hz), 7.07-7.25 (3H, m), 7.39-7.56 (2H, m), 8.36 (1H, d, J=5.1 Hz).

REFERENCE EXAMPLE 10C

2-[[2-chloro-4-(4-fluorophenyl)pyridin-3-yl]methylamino]ethanol

The title compound (1.73 g) was obtained as a colorless oil by a similar operation as in Reference Example 3C and using the powder, which was obtained from [2-chloro-4-(4-fluorophenyl)pyridin-3-yl]methanol (2.0 g) obtained in Reference Example 9C as a starting material by a similar operation as in Reference Example 2C, and ethanolamine (4.0 ml).

$^1$H-NMR (CDCl$_3$) δ: 2.71 (2H, dt, J=5.2, 4.4 Hz), 3.56 (2H, dt, J=5.2, 4.3 Hz), 3.79 (2H, s), 7.12-7.21 (3H, m), 7.38-7.51 (2H, m), 8.32 (1H, d, J=5.0 Hz).

REFERENCE EXAMPLE 11C

3-[[2-chloro-4-(4-fluorophenyl)pyridin-3-yl]methylamino]propan-1-ol

The title compound (1.01 g) was obtained as a colorless oil by a similar operation as in Reference Example 3C and using the powder, which was obtained from [2-chloro-4-(4-fluorophenyl)pyridin-3-yl]methanol (0.8 g) obtained in Reference Example 9C as a starting material by a similar operation as in Reference Example 2C, and 3-amino-1-propanol (1.3 ml).

$^1$H-NMR (CDCl$_3$) δ: 1.59-1.68 (2H, m), 2.75 (2H, t, J=5.8 Hz), 3.73-3.78 (4H, m), 7.12-7.44 (5H, m), 8.32 (1H, d, J=5.0 Hz).

REFERENCE EXAMPLE 12C

4-[[2-chloro-4-(4-fluorophenyl)pyridin-3-yl]Methylamino]butan-1-ol

The title compound (1.93 g) was obtained as a colorless oil by a similar operation as in Reference Example 3C and using the powder, which was obtained from [2-chloro-4-(4-fluorophenyl)pyridin-3-yl]methanol (2.0 g) obtained in Reference Example 9C as a starting material by a similar operation as in Reference Example 2C, and 4-amino-1-butanol (1.36 g).

$^1$H-NMR (CDCl$_3$) δ: 1.46-1.57 (2H, m), 1.58-1.67 (2H, m), 2.55 (2H, t, J=5.9 Hz), 3.55 (2H, t, J=5.5 Hz), 3.77 (2H, s); 7.12-7.22 (3H, m), 7.37-7.51 (2H, m), 8.32 (1H, d, J=5.0 Hz).

REFERENCE EXAMPLE 13C 6-(4-fluorophenyl)-2,3,4,5-tetrahydropyrido[3,2-f][1,4]oxazepine The title compound (0.91 g) was obtained as colorless crystals by a similar operation as in Reference Example 5C and using 2-[[2-chloro-4-(4-fluorophenyl)pyridin-3-yl]methylamino]ethanol (1.7 g) obtained in Reference Example 10C.

$^1$H-NMR (CDCl$_3$) δ: 3.24-3.30 (2H, m), 3.88 (2H, s), 4.24-4.31 (2H, m), 6.93 (1H, d, J=5.1 Hz), 7.07-7.23 (2H, m), 7.25-7.35 (2H, m), 8.15 (1H, d, J=5.1 Hz).

REFERENCE EXAMPLE 14C 7-(4-fluorophenyl)-3,4,5,6-tetrahydro-2H-pyrido[2,3-b][1,5]oxazocine The title compound (0.90 g) was obtained as colorless crystals by a similar operation as in Reference Example 5C and using 3-[[2-chloro-4-(4-fluorophenyl)pyridin-3-yl]methylamino]propan-1-ol (1.0 g) obtained in Reference Example 1C.

$^1$H-NMR (CDCl$_3$) δ: 1.70-1.79 (2H, m), 3.08-3.12 (2H, m), 3.87 (2H, s), 4.40 (2H, t, J=5.8 Hz), 7.02 (1H, d, J=5.1 Hz), 7.10-7.18 (2H, m), 7.40-7.47 (2H, m), 8.28 (1H, d, J=5.2 Hz).

REFERENCE EXAMPLE 15C 8-(4-fluorophenyl)-2,3,4,5,6,7-hexahydropyrido[2,3-b][1,5]oxazonine The title compound (0.47 g) was obtained as colorless crystals by a similar operation as in Reference Example 5C and using 4-[[2-chloro-4-(4-fluorophenyl)pyridin-3-yl]methylamino]butan-1-ol (1.93 g) obtained in Reference Example 12C.

$^1$H-NMR (CDCl$_3$) δ: 1.56-1.74 (4H, m), 3.02-3.09 (2H, m), 3.82 (2H, s), 4,60-4.66 (2H, m), 6.87 (1H, d, J=5.1 Hz), 7.08-7.17 (2H, m), 7.23-7.32 (2H, m), 8.18 (1H, d, J=5.1 Hz).

REFERENCE EXAMPLE 16C 6-(3-fluorophenyl)-2,3,4,5-tetrahydropyrido[3,2-f][1,4]oxazepine hydrochloride (1) To a solution of 2-chloro-4-(3-fluorophenyl)nicotinic acid (8.37 g) in tetrahydrofuran (70 ml) was added thionyl chloride (11.9 g), and the mixture was heated under reflux for 2.5 hrs. The reaction mixture was concentrated and the obtained residue was dissolved in tetrahydrofuran (50 ml). This solution was added dropwise to an ice-cooled aqueous sodium borohydride (4.58 g) solution, and the mixture was stirred at room temperature for 3 hrs. The reaction mixture was extracted with ethyl acetate, and the organic layer was washed with saturated aqueous sodium hydrogencarbonate solution and saturated aqueous sodium chloride solution, and dried over anhydrous magnesium sulfate. The solvent was evaporated and the residue was purified by silica gel column chromatography to give [2-chloro-4-(3-fluorophenyl)pyridin-3-yl]methanol (3.07 g) as a colorless oil.

$^1$H-NMR (CDCl$_3$) δ: 2.26 (1H, t, J=6.7 Hz), 4.68 (2H, d, J=6.6 Hz), 7.10-7.38 (4H, m), 7.40-7.50 (1H, m), 8.38 (1H, d, J=5.0 Hz).

(2) To a solution of [2-chloro-4-(3-fluorophenyl)pyridin-3-yl]methanol (1.47 g) obtained in the aforementioned (1) in tetrahydrofuran (25 ml) was added thionyl chloride (1.84 g), and the mixture was heated under reflux for 2 hrs. The reaction mixture was concentrated and tetrahydrofuran (15 ml) and ethanolamine (3 ml) were added to the obtained residue. The mixture was heated under reflux for 4 hrs. The reaction mixture was allowed to cool to room temperature, water was then added, and the mixture was extracted with ethyl acetate. The organic layer was washed successively with water and saturated brine, and dried over anhydrous magnesium sulfate, and the solvent was evaporated to give 2-[[2-chloro-4-(3-fluorophenyl)pyridin-3-yl]methylamino]ethanol (1.54 g) as a colorless solid.

$^1$H-NMR (CDCl$_3$) δ: 2.71 (2H, t, J=5.3 Hz), 3.56 (2H, t, J=5.3 Hz), 3.80 (2H, s), 7.10-7.27 (4H, m), 7.40-7.50 (1H, m), 8.34 (1H, d, J=5.0 Hz).

(3) To a solution of 2-[[2-chloro-4-(3-fluorophenyl)pyridin-3-yl]methylamino]ethanol (1.47 g) obtained in the aforementioned (2) in tetrahydrofuran (60 ml) was added sodium hydride (60% in oil) (0.42 g), and the mixture was heated under reflux for 4 hrs. The reaction mixture was concentrated and saturated aqueous sodium hydrogencarbonate solution was added to the obtained residue. The mixture was extracted with ethyl acetate, and the organic layer was washed successively with water and saturated aqueous sodium chloride solution, and dried over anhydrous sodium sulfate, and the solvent was evaporated to give a free basic form of the title compound as a colorless oil. Further, a 4N solution of hydrogen chloride in ethyl acetate (30 ml) was added, and the mixture was recrystallized from methanol-ethyl acetate to give the title compound (1.45 g) as colorless crystals.

$^1$H-NMR (DMSO-d$_6$) δ: 3.50 (2H, s), 4.12 (2H, s), 4.43 (2H, s), 7.19 (1H, d, J=5.0 Hz), 7.28-7.41 (2H, m), 7.47 (1H, d, J=9.7 Hz), 7.50-7.66 (1H. m), 8.27 (1H, d, J=5.1 Hz), 9.91 (2H, brs).

REFERENCE EXAMPLE 17C 7-(3-fluorophenyl)-3,4,5,6-tetrahydro-2H-pyrido[2,3-b][1,5]oxazocine hydrochloride (1) 3-[[2-Chloro-4-(3-fluorophenyl)pyridin-3-yl]methylamino]propan-1-ol (1.29 g) was obtained as a colorless oil by a similar method as in Reference Example 16C(2) and using [2-chloro-4-(3-fluorophenyl)pyridin-3-yl]methanol (1.20 g) obtained in Reference Example 16C(1) and 3-amino-1-propanol (1.88 g).

$^1$H-NMR (CDCl$_3$) δ: 1.57-1.67 (2H, m), 2.74 (2H, t, J=5.8 Hz), 3.70-3.78 (4H, m), 7.10-7.23 (4H, m), 7.40-7.50 (1H, m), 8.33 (1H, d, J=5.0 Hz).

(2) The title compound (0.81 g) was obtained as colorless crystals by a similar method as in Reference Example 16C(3) and using the compound (1.29 g) obtained in the aforementioned (1).

$^1$H-NMR (free basic form; CDCl$_3$) δ: 1.68-1.94 (2H, m), 3.05-3.23 (2H, m), 3.87 (2H, s), 4.40 (2H, t, J=5.7 Hz), 7.03 (1H, d, J=5.1 Hz), 7.06-7.57 (4H, m), 8.29 (1H, d, J=5.1 Hz).

REFERENCE EXAMPLE 18C

[2-chloro-4-(4-chlorophenyl)pyridin-3-yl]methanol

To a solution of 2-chloro-4-(4-chlorophenyl)nicotinic acid (2.4 g) in tetrahydrofuran (60 ml) was added thionyl chloride (3.2 g), and the mixture was heated under reflux for 3 hrs. The solvent was evaporated under reduced pressure, and the residue was dissolved in tetrahydrofuran (60 ml). Sodium borohydride (1.5 g) was added by small portions at 0° C., and the mixture was allowed to warm gradually and stirred at room temperature for 2 hrs. Water was added to quench the reaction and the mixture was extracted with ethyl acetate. The organic layer was washed successively with water and saturated brine, and dried over anhydrous magnesium sulfate, and the solvent was evaporated under reduced pressure to give the title compound (1.9 g) as a colorless oil.

$^1$H-NMR (CDCl$_3$) δ: 2.27 (1H, t, J=6.6 Hz), 4.66 (2H, d, J=6.6 Hz), 7.19 (1H, d, J=5.0 Hz), 7.41-7.48 (4H, m), 8.37 (1H, d, J=5.0 Hz).

REFERENCE EXAMPLE 19C 7-(4-chlorophenyl)-3,4,5,6-tetrahydro-2H-pyrido[2,3-b][1,5]oxazocine The title compound was obtained as a free basic form by a similar operation as in Reference Example 16C (2) and (3) and using, as a starting material, [2-chloro-4-(4-chlorophenyl)pyridin-3-yl]methanol (1.9 g) obtained in Reference Example 18C.

$^1$H-NMR (CDCl$_3$) δ: 1.97 (2H, m), 2.80 (2H, t, J=6.5 Hz), 3.73 (2H, s), 4.39 (2H, t, J=5.3 Hz), 6.78 (1H, d, J=5.2 Hz), 7.43 (4H, m), 8.05 (1H, d, J=5.2 Hz).

REFERENCE EXAMPLE 20C 6-(4-chlorophenyl)-2,3,4,5-tetrahydropyrido[3,2-f][1,4]oxazepine dihydrochloride (1) To a solution of [2-chloro-4-(4-chlorophenyl)pyridin-3-yl]methanol (1.02 g) obtained in Reference Example 18C in tetrahydrofuran (30 ml) was added thionyl chloride (1.00 g), and the mixture was heated under reflux for 2 hrs. The reaction mixture was concentrated, and to the obtained residue were added tetrahydrofuran (50 ml) and ethanolamine (1.30 g). The mixture was heated under reflux for 18 hrs. The reaction mixture was allowed to cool to room temperature, and water was added. The mixture was extracted with ethyl acetate, and the organic layer was washed successively with water and saturated brine, and dried over anhydrous magnesium sulfate, and the solvent was evaporated to give 2-[[2-chloro-4-(4-chlorophenyl)pyridin-3-yl]methylamino]ethanol (1.18 g) as a colorless oil.

$^1$H-NMR (CDCl$_3$) δ: 2.10 (1H, brs), 2.71 (2H, t, J=5.2 Hz), 3.56 (2H, t, J=5.2 Hz), 3.77 (2H, s), 7.14 (1H, d, J=5.0 Hz), 7.39-7.48 (4H, m), 8.33 (1H, d, J=5.0 Hz).

(2) To a solution of 2-[[2-chloro-4-(4-chlorophenyl)pyridin-3-yl]methylamino]ethanol (1.18 g) obtained in the aforementioned (1) in tetrahydrofuran (40 ml) was added sodium hydride (60% in oil) (0.33 g), and the mixture was heated under reflux for 4 hrs. The reaction mixture was concentrated, water was added to the obtained residue, and the mixture was extracted with ethyl acetate. The organic layer was washed successively with water and saturated aqueous sodium chloride solution, and dried over anhydrous sodium sulfate, and the solvent was evaporated to give a free basic form of the title compound as a colorless oil. Furthermore, a 4N solution of hydrogen chloride in ethyl acetate (30 ml) was added, and the mixture was recrystallized from methanol-ethyl acetate to give the title compound (1.07 g) as colorless crystals.

$^1$H-NMR (DMSO-d$_6$) δ: 3.50 (2H, s), 4.11 (2H, s), 4.45 (2H, m), 7.18 (1H, d, J=5.0 Hz), 7.57-7.64 (4H, m), 8.28 (1H, d, J=5.0 Hz), 10.09 (2H, m).

| Elemental analysis for C₁₄H₁₃N₂OCl•2HCl•H₂O | | | |
|---|---|---|---|
| Calculated | C, 47.82; | H, 4.87; | N, 7.97 |
| Found | C, 47.73; | H, 4.83; | N, 7.95 |

REFERENCE EXAMPLE 21C

[2-chloro-4-(4-methylphenyl)pyridin-3-yl]methanol

The title compound was obtained by a similar operation as in Reference Example 18C and using 2-chloro-4-(4-methylphenyl)nicotinic acid as a starting material.

¹H NMR (CDCl₃) δ: 2.23 (1H, t, J=6.7 Hz), 2.42 (3H, s), 4.69 (2H, d, J=6.7 Hz), 7.20 (1H, d, J=4.9 Hz), 7.29 (2H, d, J=8.1 Hz), 7.35 (2H, d, J=8.1 Hz), 8.34 (1H, d, J=4.9 Hz).

REFERENCE EXAMPLE 22C 6-(4-methylphenyl)-2,3,4,5-tetrahydropyrido[3,2-f][1,4]oxazepine dihydrochloride The title compound was obtained by a similar operation as in Reference Example 20C and using [2-chloro-4-(4-methylphenyl)pyridin-3-yl]methanol obtained in Reference Example 21C as a starting material.

¹H-NMR (DMSO-d₆) δ: 2.39 (3H, s), 3.50 (2H, s), 4.16 (2H, s), 4.45 (2H, m), 5.81 (1H, brs), 7.16 (1H, dd, J=1.0, 5.0 Hz), 7.35 (2H, d, J=7.8 Hz), 7.43 (2H, d, J=7.8 Hz), 8.26 (1H, dd, J=1.0, 5.0 Hz), 9.98 (2H, m).

EXAMPLE 1C 4-(4-fluorobenzyl)-6-phenyl-2,3,4,5-tetrahydropyrido[3,2-f][1,4]oxazepine hydrochloride A mixture of the compound (301 mg) obtained in Reference Example 5C, saturated aqueous potassium carbonate (1 ml) and 4-fluorobenzyl chloride (0.205 ml) in ethanol (10 ml) was heated under reflux for 6 hrs. The solvent was evaporated under reduced pressure, water was then added, and the mixture was extracted with ethyl acetate. The organic layer was dried over anhydrous magnesium sulfate, and the solvent was evaporated to give a crude product of a free basic form of the title compound as a pale-yellow oil. Furthermore, a 4N solution of hydrogen chloride in ethyl acetate (3 ml) was added, and the mixture was crystallized from methanol-diethyl ether to give the title compound (310 mg) as colorless crystals having a melting point of 171-174° C.

¹H-NMR (DMSO-d₆) δ: 4.00-4.20 (2H, m), 4.25-4.40 (2H, m), 5.05 (4H, s), 7.05-7.40 (8H, m), 7.50-7.65 (2H, m), 8.27 (1H, d, J=5.0 Hz), 12.2-12.6 (1H, br).

EXAMPLE 2C 4-benzyl-6-phenyl-2,3,4,5-tetrahydropyrido[3,2-f][1,4]oxazepine hydrochloride The title compound (306 mg) was obtained as colorless crystals (melting point: 189-191° C.) by a similar operation as in Example 1C and using a free basic form (730 mg) of the compound obtained in Reference Example 5C and benzyl bromide (0.76 ml).

¹H-NMR (DMSO-d₆) δ: 3.60-3.80 (2H, m), 4.05-4.80 (6H, m), 7.10 (1H, d, J=4.8 Hz), 7.15-7.60 (10H, m), 8.27 (1H, d, J=5.4 Hz), 12.1-12.4 (1H, br).

EXAMPLE 3C 4-(3-methoxybenzyl)-6-phenyl-2,3,4,5-tetrahydropyrido[3,2-f][1,4]oxazepine hydrochloride The title compound (325 mg) was obtained as colorless crystals (melting point: 134-136° C.) by a similar operation as in Example 1C and using the compound (312 mg) obtained in Reference Example 5C and 3-methoxybenzyl chloride (0.26 ml).

¹H-NMR (DMSO-d₆) δ: 3.60-3.80 (2H, m), 3.77 (3H, s), 4.10-4.80 (6H, m), 6.90-7.00 (2H, m), 7.09 (1H, d, J=5.1 Hz), 7.25-7.35 (7H, m), 8.27 (1H, d, J=5.1 Hz), 12.0-12.3 (1H, br).

EXAMPLE 4C 4-(3,5-dimethoxybenzyl)-6-phenyl-2,3,4,5-tetrahydropyrido[3,2-f][1,4]oxazepine hydrochloride The title compound (304 mg) was obtained as colorless crystals (melting point: 170-173° C.) by a similar operation as in Example 1C and using the compound (321 mg) obtained in Reference Example 5C and 3,5-dimethoxybenzyl methanesulfonate (450 mg).

¹H-NMR (DMSO-d₆) δ: 3.73 (6H, s), 4.00-4.35 (2H, m), 4.40-4.80 (2H, m), 4.91 (4H, s), 6.47 (1H, t, J=2.2 Hz), 6.76 (2H, d, J=2.2 Hz), 7.10 (1H, d, J=5.2 Hz), 7.15-7.40 (5H, m), 8.27 (1H, d, J=5.2 Hz), 12.1-12.4 (1H, br).

EXAMPLE 5C 6-phenyl-4-(3,4,5-trimethoxybenzyl)-2,3,4,5-tetrahydropyrido[3,2-f][1,4]oxazepine The title compound (432 mg) was obtained as colorless crystals (melting point: 139-140° C.) by a similar operation as in Example 1C and using a free basic form (750 mg) of the compound obtained in Reference Example 5C and 3,4,5-trimethoxybenzyl chloride (1.43 g).

¹H-NMR (CDCl₃) δ: 2.95-3.05 (2H, m), 3.50 (2H, s), 3.67 (2H, s), 3.81 (6H, s), 3.86 (3H, s), 4.25-4.35 (2H, m), 6.46 (2H, s), 6.96 (1H, d, J=5.0 Hz), 7.15-7.40 (5H, m), 8.17 (1H, d, J=5.0 Hz).

EXAMPLE 6C 4-(2-chlorobenzyl)-6-phenyl-2,3,4,5-tetrahydropyrido[3,2-f][1,4]oxazepine hydrochloride The title compound (371 mg) was obtained as colorless crystals (melting point: 173-175° C.) by a similar operation as in Example 1C and using a free basic form (311 mg) of the compound obtained in Reference Example 5C and 2-chlorobenzyl chloride (0.22 ml).

¹H-NMR (DMSO-d₆) δ: 3.75-3.90 (2H, m), 4.00-4.80 (6H, m), 7.10 (1H, d, J=5.1 Hz), 7.15-7.60 (8H, m), 7.90-8.00 (1H, m), 8.27 (1H, d, J=4.8 Hz), 12.00-12.40 (1H, br).

EXAMPLE 7C 4-(3,4-dichlorobenzyl)-6-phenyl-2,3,4,5-tetrahydropyrido[3,2-f][1,4]oxazepine hydrochloride The title compound (201 mg) was obtained as colorless crystals (melting point: 133-134° C.) by a similar operation as in Example 1C and using a free basic form (284 mg) of the compound obtained in Reference Example 5C and 3,4-dichlorobenzyl chloride (1.17 ml).

$^1$H-NMR (free basic form; CDCl$_3$) δ: 2.90-3.05 (2H, m), 3.47 (2H, s), 3.59 (2H, s), 4.20-4.35 (2H, m), 6.93 (1H, d, J=5.2 Hz), 7.00 (1H, dd, J=8.2, 1.6 Hz), 7.05-7.40 (7H, m), 8.16 (1H, d, J=5.2 Hz).

EXAMPLE 8C 4-(2,6-dichlorobenzyl)-6-phenyl-2,3,4,5-tetrahydropyrido[3,2-f][1,4]oxazepine hydrochloride The title compound (313 mg) was obtained as colorless crystals (melting point: 146-148° C.) by a similar operation as in Example 1C and using the compound (305 mg) obtained in Reference Example 5C and 2,6-dichlorobenzyl chloride (350 mg).

$^1$H-NMR (DMSO-d$_6$) δ: 3.40-5.00 (8H, m), 7.14 (1H, d, J=5.4 Hz), 7.25-7.65 (8H, m), 8.26 (1H, d, J=5.4 Hz), 10.40-11.60 (1H, br).

EXAMPLE 9C

4-[3,5-bis(trifluoromethyl)benzyl]-6-phenyl-2,3,4,5-tetrahydropyrido[3,2-f][1,4]oxazepine The title compound (82 mg) was obtained as colorless crystals (melting point: 134-135° C.) by a similar operation as in Example 1C and using a free basic form (264 mg) of the compound obtained in Reference Example 5C and 3,5-bis(trifluoromethyl)benzyl methanesulfonate (450 mg).

$^1$H-NMR (CDCl$_3$) δ: 3.00-3.10 (2H, m), 3.63 (2H, s), 3.66 (2H, s), 4.25-4.40 (2H, m), 6.92 (1H, d, J=5.2 Hz), 7.00-7.35 (5H, m), 7.64 (2H, s), 7.70 (1H, s), 8.17 (1H, d, J=5.2 Hz).

EXAMPLE 10C 4-(2-nitrobenzyl)-6-phenyl-2,3,4,5-tetrahydropyrido[3,2-f][1,4]oxazepine hydrochloride The title compound (298 mg) was obtained as colorless crystals (melting point: 152-154° C.) by a similar operation as in Example 1C and using the compound (303 mg) obtained in Reference Example 5C and 2-nitrobenzyl bromide (374 mg).

$^1$H-NMR (DMSO-d$_6$) δ: 3.60-3.80 (2H, m), 4.00-4.90 (6H, m), 7.13 (1H, d, J=5.1 Hz), 7.20-7.45 (5H, m), 7.60-7.90 (3H, m), 8.00-8.15 (1H, m), 8.28 (1H, d, J=5.1 Hz), 11.50-12.20 (1H, br).

EXAMPLE 11C 4-(3.5-dinitrobenzyl)-6-phenyl-2,3,4,5-tetrahydropyrido[3,2-f][1,4]oxazepine The title compound (443 mg) was obtained as colorless crystals (melting point: 159-161° C.) by a similar operation as in Example 1C and using a free basic form (811 mg) of the compound obtained in Reference Example 5C and 3,5-dinitrobenzyl chloride (1.55 g).

$^1$H-NMR (DMSO-d$_6$) δ: 3.05-3.15 (2H, m), 3.61 (2H, s), 3.76 (2H, s), 4.20-4.30 (2H, m), 6.96 (1H, d, J=6.0 Hz), 7.00-7.20 (5H, m), 8.13 (1H, d, J=5.7 Hz), 8.30-8.40 (2H, m), 8.60-8.65 (1H, m).

EXAMPLE 12C 6-phenyl-4-(2-phenylethyl)-2,3,4,5-tetrahydropyrido[3,2-f][1,4]oxazepine hydrochloride The title compound (298 mg) was obtained as colorless crystals (melting point: 183-185° C.) by a similar operation as in Example 1C and using the compound (331 mg) obtained in Reference Example 5C and (2-bromoethyl)benzene(0.258 ml).

$^1$H-NMR (DMSO-d$_6$) δ: 2.65-2.80 (1H, m), 3.00-3.45 (3H, m), 3.60-3.80 (2H, m), 4.20-4.75 (4H, m), 7.10-7.40 (6H, m), 7.50-7.75 (5H, m), 8.33 (1H, d, J=4.8 Hz), 12.20-12.40 (1H, br).

REFERENCE EXAMPLE 23C 4-ethyl-6-phenyl-2,3,4,5-tetrahydropyrido[3,2-f][1,4]oxazepine hydrochloride The title compound (628 mg) was obtained as colorless crystals (melting point: 142-143° C.) by a similar operation as in Example 1C and using a free basic form (875 mg) of the compound obtained in Reference Example 5C and iodoethane (0.50 ml).

$^1$H-NMR (DMSO-d$_6$) δ: 1.00-1.20 (3H, m), 2.90-3.35 (2H, m), 3.50-3.75 (2H, m), 4.00-4.35 (2H, m), 4.40-4.75 (2H, m), 7.20-7.25 (1H, m), 7.30-7.80 (5H, m), 8.25-8.40 (1H, m), 12.10-12.35 (1H, br).

EXAMPLE 13C

4-[3,5-bis(trifluoromethyl)benzyl]-8-methyl-6-phenyl-2,3,4,5-tetrahydropyrido[3,2-f][1,4]oxazepine hydrochloride To a solution of 4-[3,5-bis(trifluoromethyl)benzyl]-8-methyl-6-phenyl-3,4-dihydropyrido[3,2-f][1,4]oxazepin-5 (2H)-one (500 mg) obtained in WO 99/47132 in tetrahydrofuran (15 ml) was added lithium aluminum hydride (100 mg) at room temperature, and the mixture was heated under reflux and stirred for 3 hrs. Water was added to the reaction mixture, and the separate solid was filtered off and washed with tetrahydrofuran. The filtrate was concentrated, aqueous potassium carbonate was added, and the mixture was extracted with ethyl acetate. The organic layer was washed successively with water, saturated aqueous sodium hydrogencarbonate and saturated brine, and dried over anhydrous magnesium sulfate. The solvent was evaporated under reduced pressure and the obtained residue was purified by silica gel chromatography (developing solvent; ethyl acetate-acetone (4:1)) to give a free basic form of the title compound as a colorless oil. Furthermore, hydrogen chloride-ethanol solution was added to give the title compound (100 mg) as colorless crystals having a melting point of 175-177° C.

$^1$H-NMR (DMSO-d$_6$) δ: 2.43 (3H, s), 3.60-3.85 (2H, m), 3.90-4.80 (6H, m), 7.00 (1H, s), 7.05-7.35 (5H, m), 7.70 (2H, s), 7.83 (1H, s), 12.10-12.35 (1H, br).

EXAMPLE 14C

4-[3,5-bis(trifluoromethyl)benzoyl]-6-phenyl-2,3,4, 5-tetrahydropyrido[3,2-f][1,4]oxazepine To a solution of the free basic form (400 mg) of the compound obtained in Reference Example 5C in tetrahydrofuran (20 ml) were added a solution of 3,5-bis(trifluoromethyl) benzoyl chloride (730 mg) in tetrahydrofuran (5 ml) and triethylamine (0.50 ml) at room temperature, and the mixture was stirred for 30 min. The solvent was evaporated under reduced pressure, aqueous potassium carbonate was added to the obtained residue and the mixture was extracted with ethyl acetate. The organic layer was washed successively with water, saturated aqueous sodium hydrogencarbonate and saturated brine, and dried over anhydrous magnesium sulfate, and the solvent was evaporated under reduced pressure to give the title compound (430 mg) as colorless crystals having a melting point of 179-180° C.

$^1$H-NMR (CDCl$_3$) δ: 3.70-4.25 (2H, m), 4.40-4.90 (4H, m), 6.70-8.00 (9H, m), 8.23 (1H, d, J=5.0 Hz).

EXAMPLE 15C

5-benzyl-7-phenyl-3,4,5,6-tetrahydro-2H-pyrido[2,3-b][1,5]oxazocine ½sulfate The title compound (91 mg) was obtained as a colorless amorphous powder by a similar operation as in Example 1C and using the compound (300 mg) obtained in Reference Example 6C and benzyl bromide (0.19 ml).

$^1$H-NMR (free basic form; CDCl$_3$) δ: 1.65-1.80 (2H, m), 2.75-2.85 (2H, m), 3.53 (2H, s), 3.76 (2H, s), 4.32 (2H, t, J=5.6 Hz), 7.05-7.50 (9H, m), 7.55-7.65 (2H, m), 8.31 (1H, d, J=5.0 Hz).

EXAMPLE 16C

5-(3,5-dimethoxybenzyl)-7-phenyl-3,4,5,6-tetrahydro-2H-pyrido[2,3-b][1,5]oxazocine ½sulfate The title compound (248 mg) was obtained as colorless crystals (melting point: 182-184° C.) by a similar operation as in Example 1C and using the compound (305 mg) obtained in Reference Example 6C and 3,5-dimethoxybenzyl chloride (310 mg).

$^1$H-NMR (free basic form; CDCl$_3$) δ: 1.65-1.80 (2H, m), 2.75-2.85 (2H, m), 3.46 (2H, s), 3.77 (8H, s), 4.32 (2H, t, J=5.6 Hz), 6.34 (1H, t, J=2.2 Hz), 6.46 (2H, d, J=2.2 Hz), 7.10 (1H, d, J=5.0 Hz), 7.30-7.45 (3H, m), 7.60-7.65 (2H, m), 8.31 (1H, d, J=5.0 Hz).

EXAMPLE 17C

5-(3,4-dichlorobenzyl)-7-phenyl-3,4,5,6-tetrahydro-2H-pyrido[2,3-b][1,5]oxazocine hydrochloride The title compound (366 mg) was obtained as colorless crystals (melting point: 136-138° C.) by a similar operation as in Example 1C and using the compound (303 mg) obtained in Reference Example 6C and 3,4-dichlorobenzyl chloride (0.23 ml).

$^1$H-NMR (free basic form; CDCl$_3$) δ: 1.65-1.80 (2H, m), 2.75-2.85 (2H, m), 3.43 (2H, s), 3.77 (2H, s), 4.33 (2H, t, J=5.6 Hz), 7.01 (1H, dd, J=8.3, 2.0 Hz), 7.07 (1H, d, J=5.2 Hz), 7.20-7.55 (7H, m), 8.31 (1H, d, J=5.2 Hz).

EXAMPLE 18C

5-[3,5-bis(trifluoromethyl)benzyl]-7-phenyl-3,4,5,6-tetrahydro-2H-pyrido[2,3-b][1,5]oxazocine ½sulfate The title compound (380 mg) was obtained as colorless crystals (melting point: 190-192° C.) by a similar operation as in Example 1C and using the compound (305 mg) obtained in Reference Example 6C and 3,5-bis(trifluoromethyl)benzyl methanesulfonate (536 mg).

$^1$H-NMR (free basic form; CDCl$_3$) δ: 1.65-1.80 (2H, m), 2.80-2.90 (2H, m), 3.53 (2H, s), 3.89 (2H, s), 4.36 (2H, t, J=5.6 Hz), 7.07 (1H, d, J=5.0 Hz), 7.20-7.50 (5H, m), 7.63 (2H, s), 7.69 (1H, s), 8.32 (1H, d, J=5.0 Hz).

EXAMPLE 19C

5-[3,5-bis(trifluoromethyl)benzoyl]-7-phenyl-3,4,5, 6-tetrahydro-2H-pyrido[2,3-b][1,5]oxazocine The title compound was obtained as colorless crystals by a similar operation as in Example 14C and using a free basic form of the compound obtained in Reference Example 6C and 3,5-bis(trifluoromethyl)benzoyl chloride.

$^1$H-NMR(CDCl$_3$) δ: 1.74-1.95 (2H×⅖, br), 2.09-2.31 (2H×⅗, br), 3.45-3.63 (2H×⅖, br), 3.80-4.00 (2H×⅗, br), 4.36-4.61 (2H, m), 4.73 (2H×⅗, brs), 4.88 (2H×⅖, brs), 6.75-7.97 (9H, m), 8.23-8.42 (1H, br).

EXAMPLE 20C

4-{[3,5-bis(trifluoromethyl)phenyl]acetyl}-6-phenyl-2,3,4,5-tetrahydropyrido[3,2-f][1,4]oxazepine To a solution of the free basic form (100 mg) of the compound obtained in Reference Example 5C, HOBt (72 mg) and WSC (102 mg) in DMF (5 ml) was added 3,5-bis(trifluoromethyl)phenylacetic acid (144 mg), and the mixture was stirred at room temperature for 20 hrs. Water was added to the obtained reaction solution and the mixture was extracted with ethyl acetate. The organic layer was washed successively with saturated aqueous sodium hydrogencarbonate and saturated brine, and dried over anhydrous magnesium sulfate. The solvent was evaporated under reduced pressure, and the obtained residue was purified by silica gel column chromatography to give the title compound (127 mg) as a colorless amorphous powder.

$^1$H-NMR(CDCl$_3$) δ: 3.15 (2H×¾, s), 3.81 (2H×¼, s), 3.90-4.07 (2H, m), 4.36-4.51 (2H, m), 4.66 (2H×¾, s), 4.70 (2H×¼, s), 6.94-7.75 (9H, m), 8.15-8.29 (1H, m).

EXAMPLE 21C

5-{[3,5-bis(trifluoromethyl)phenyl]acetyl}-7-phenyl-3,4,5,6-tetrahydro-2H-pyrido[2,3-b][1,5]oxazocine The title compound was obtained as a colorless amorphous powder by a similar operation as in Example 20C and using a free basic form of the compound obtained in Reference Example 6C and 3,5-bis(trifluoromethyl)phenylacetic acid.

$^1$H-NMR(CDCl$_3$) δ: 1.82-2.10 (2H, m), 3.05 (2H×⅘, s), 3.72 (2H×⅕, s), 3.64-3.88 (2H, m), 4.40-4.48 (2H, m), 4.71

(2H×⅕, s), 4.73 (2H×⅘, s), 6.99-7.14 (1H, m), 7.18-7.80 (8H, m), 8.26 (1H×⅕, d, J=5.1 Hz), 8.35 (1H×⅘, d, J=6.0 Hz).

EXAMPLE 22C

4-{[3,5-bis(trifluoromethyl)phenyl]sulfonyl}-6-phenyl-2,3,4,5-tetrahydropyrido[3,2-f][1,4]oxazepine The title compound (98 mg) was obtained as colorless crystals by a similar operation as in Example 14C and using a free basic form (100 mg) of the compound obtained in Reference Example 5C and 3,5-bis(trifluoromethyl)benzenesulfonyl chloride (166 mg).

$^1$H-NMR(CDCl$_3$) δ: 3.87 (2H, t, J=5.1 Hz), 4.39 (2H, t, J=5.1 Hz), 4.52 (2H, s), 6.96 (1H, d, J=5.0 Hz), 7.27-7.34 (2H, m), 7.46-7.54 (3H, m), 7.88 (2H, s), 7.96 (1H, s), 8.07 (1H, d, J=5.1 Hz).

EXAMPLE 23C

5-{[3,5-bis(trifluoromethyl)phenyl]sulfonyl}-7-phenyl-3,4,5,6-tetrahydro-2H-pyrido[2,3-b][1,5]oxazocine The title compound was obtained as colorless crystals by a similar operation as in Example 14C and using a free basic form of the compound obtained in Reference Example 6C and 3,5-bis(trifluoromethyl)benzenesulfonyl chloride.

$^1$H-NMR(CDCl$_3$) δ: 1.93-2.04 (2H, m), 3.67 (2H, dt, J=5.9, 5.0 Hz), 4.42 (2H, s), 4.46 (2H, t, J=6.2 Hz), 7.10 (1H, d, J=5.1 Hz), 7.28-7.36 (2H, m), 7.44-7.52 (3H, m), 7.82 (2H, s), 8.00 (1H, s), 8.33 (1H, d, J=5.1 Hz).

EXAMPLE 24C 4-(4-chlorobenzoyl)-6-phenyl-2,3,4,5-tetrahydropyrido[3,2-f][1,4]oxazepine The title compound (77 mg) was obtained as a colorless amorphous powder by a similar operation as in Example 14C and using a free basic form (90 mg) of the compound obtained in Reference Example 5C and 4-chlorobenzoyl chloride (85 mg).

$^1$H-NMR(CDCl$_3$) δ: 3.62-4.89 (6H, m), 6.69-7.66 (10H, m), 8.20 (1H, d, J=5.0 Hz).

EXAMPLE 25C 4-(4-nitrobenzoyl)-6-phenyl-2,3,4,5-tetrahydropyrido[3,2-f][1,4]oxazepine The title compound (97 mg) was obtained as a colorless amorphous powder by a similar operation as in Example 14C and using a free basic form (90 mg) of the compound obtained in Reference Example 5C and 4-nitrobenzoyl chloride (90 mg).

$^1$H-NMR(CDCl$_3$) δ: 3.77 (2H×⅓, br), 4.10-4.24 (2H×⅔, br), 4.32-4.87 (4H, m), 6.75-7.63 (9H, m), 7.90 (1H, d, J=8.2 Hz), 8.23 (1H, d, J=5.0 Hz).

EXAMPLE 26C 4-(3-methylbenzoyl)-6-phenyl-2,3,4,5-tetrahydropyrido[3,2-f][1,4]oxazepine The title compound (53 mg) was obtained as a colorless amorphous powder by a similar operation as in Example 14C and using a free basic form (90 mg) of the compound obtained in Reference Example 5C and 3-methylbenzoyl chloride (75 mg).

$^1$H-NMR(CDCl$_3$) δ: 2.07-2.46 (3H, br), 3.74-4.89 (6H, m), 6.62-7.62 (10H, m), 8.19 (1H, d, J=5.0 Hz).

EXAMPLE 27C 4-(1-naphthoyl)-6-phenyl-2,3,4,5-tetrahydropyrido[3,2-f][1,4]oxazepine The title compound (88 mg) was obtained as a colorless amorphous powder by a similar operation as in Example 14C and using a free basic form (90 mg) of the compound obtained in Reference Example 5C and 1-naphthoyl chloride (92 mg).

$^1$H-NMR(CDCl$_3$) δ: 3.59-5.04 (6H, m), 6.13-6.32 (1H, m), 6.51 (1H, d, J=5.0 Hz), 6.90-7.94 (11H, m), 8.07-8.26 (1H, m).

EXAMPLE 28C 4-(1-benzothien-2-ylcarbonyl)-6-phenyl-2,3,4,5-tetrahydropyrido[3,2-f][1,4]oxazepine The title compound (85 mg) was obtained as a colorless amorphous powder by a similar operation as in Example 14C and using a free basic form (90 mg) of the compound obtained in Reference Example 5C and 1-benzothiophene-2-carbonyl chloride (95 mg).

$^1$H-NMR(CDCl$_3$) δ: 4.13-4.17 (2H, m), 4.46-4.65 (2H, m), 4.86 (2H, brs), 6.91-7.83 (11H, m), 8.21 (1H, d, J=5.0 Hz).

EXAMPLE 29C 6-phenyl-4-[3-(trifluoromethyl)benzoyl]-2,3,4,5-tetrahydropyrido[3,2-f][1,4]oxazepine The title compound (46 mg) was obtained as a colorless amorphous powder by a similar operation as in Example 14C and using a free basic form (90 mg) of the compound obtained in Reference Example 5C and 3-(trifluoromethyl)benzoyl chloride (100 mg).

$^1$H-NMR(CDCl$_3$) δ: 3.70-4.91 (6H, m), 6.70-7.77 (10H, m), 8.21 (1H, d, J=5.0 Hz).

EXAMPLE 30C 6-phenyl-4-[4-(trifluoromethyl)benzoyl]-2,3,4,5-tetrahydropyrido[3,2-f][1,4]oxazepine The title compound (109 mg) was obtained as a colorless amorphous powder by a similar operation as in Example 14C and using a free basic form (90 mg) of the compound obtained in Reference Example 5C and 4-(trifluoromethyl)benzoyl chloride (100 mg).

¹H-NMR(CDCl₃) δ: 3.66-4.92 (6H, m), 6.72-7.79 (10H, m), 8.21 (1H, d, J=5.0 Hz).

EXAMPLE 31C 4-(3-chlorobenzoyl)-6-phenyl-2,3,4,5-tetrahydropyrido[3,2-f][1,4]oxazepine The title compound (68 mg) was obtained as a colorless amorphous powder by a similar operation as in Example 14C and using a free basic form (90 mg) of the compound obtained in Reference Example 5C and 3-chlorobenzoyl chloride (84 mg).

¹H-NMR(CDCl₃) δ: 3.70-4.91 (6H, m), 6.73-7.64 (10H, m), 8.21 (1H, d, J=5.0 Hz).

EXAMPLE 32C 4-(3,5-dichlorobenzoyl)-6-phenyl-2,3,4,5-tetrahydropyrido[3,2-f][1,4]oxazepine The title compound (77 mg) was obtained as a colorless amorphous powder by a similar operation as in Example 14C and using a free basic form (90 mg) of the compound obtained in Reference Example 5C and 3,5-dichlorobenzoyl chloride (100 mg).

¹H-NMR(CDCl₃) δ: 3.69-4.25 (2H, m), 4.29-4.86 (4H, m), 6.72-7.60 (9H, m), 8.22 (1H, d, J=4.8 Hz).

EXAMPLE 33C

4-{1-[3,5-bis(trifluoromethyl)phenyl]ethyl}-6-phenyl-2,3,4,5-tetrahydropyrido[3,2-f][1,4]oxazepine hydrochloride To a solution of a free basic form (250 mg) of 6-phenyl-2,3,4,5-tetrahydropyrido[3,2-f][1,4]oxazepine obtained in Reference Example 5C and potassium carbonate (305 mg) in DMF (5 ml) was added 1-[3,5-bis(trifluoromethyl)phenyl]ethyl methanesulfonate, and the mixture was stirred at 80° C. for 5 hrs. Water was added to the obtained reaction mixture and the mixture was extracted with ethyl acetate. The organic layer was washed successively with saturated aqueous sodium hydrogencarbonate, water and saturated brine, and dried over anhydrous magnesium sulfate. The solvent was evaporated under reduced pressure, and the obtained residue was purified by silica gel column chromatography and crystallized from diisopropyl ether to give a free basic form (178 mg) of the title compound as colorless crystals. The obtained free basic form (135 mg) was dissolved in ethyl acetate (2 ml), and a 4N solution (0.2 ml) of hydrochloric acid in ethyl acetate was added. The solvent was evaporated under reduced pressure, and the obtained residue was precipitated from methanol-diethyl ether to give the title compound (124 mg) as a colorless amorphous powder.

¹H-NMR (free basic form; CDCl₃) δ: 1.25 (3H, d, J=6.7 Hz), 2.96-3.18 (2H, m), 3.64 (2H, s), 3.78 (1H, q, J=6.7 Hz), 4.23-4.41 (2H, m), 6.88 (1H, d, J=5.0 Hz), 6.99-7.03 (2H, m), 7.19-7.28 (3H, m), 7.60 (2H, s), 7.65 (1H, s), 8.15 (1H, d, J=5.0 Hz).

The compounds of the following Examples 34C to 43C were synthesized by the same method as in Example 14C and using 6-phenyl-2,3,4,5-tetrahydropyrido[3,2-f][1,4]oxazepine obtained in Reference Example 5C.

EXAMPLE 34C 4-(3,5-dimethylbenzoyl)-6-phenyl-2,3,4,5-tetrahydropyrido[3,2-f][1,4]oxazepine ¹H-NMR (CDCl₃) δ: 2.14 (3h, brs), 2.28 (3H, brs), 3.72-4.89 (6H, m), 6.38-7.67 (9H, m), 8.18 (1H, d, J=5.0 Hz).

EXAMPLE 35C 6-phenyl-4-[2-(trifluoromethyl)benzoyl]-2,3,4,5-tetrahydropyrido[3,2-f][1,4]oxazepine ¹H-NMR (CDCl₃) δ: 3.45-3.74 (1H, m), 3.92-4.09 (1H×½, m), 4.20-4.73 (4H, m), 5.01-5.08 (1H×½, m), 6.64-6.90 (2H, m), 6.97-7.77 (8H, m), 8.10-8.30 (1H, m).

EXAMPLE 36C 4-(2-naphthoyl)-6-phenyl-2,3,4,5-tetrahydropyrido[3,2-f][1,4]oxazepine ¹H-NMR (CDCl₃) δ: 3.74-4.95 (6H, m), 6.30-7.99 (13H, m), 8.20 (1H, d, J=5.0 Hz).

EXAMPLE 37C 4-(1,3-benzodioxol-5-ylcarbonyl)-6-phenyl-2,3,4,5-tetrahydropyrido[3,2-f][1,4]oxazepine ¹H-NMR (CDCl₃) δ: 3.81-4.20 (2H, br), 4.31-4.63 (2H, br), 4.69 (2H, brs), 5.97 (2H, s), 6.30-7.63 (9H, m), 8.20 (1H, d, J=5.0 Hz)

EXAMPLE 38C 6-phenyl-4-(pyridin-3-ylcarbonyl)-2,3,4,5-tetrahydropyrido[3,2-f][1,4]oxazepine ¹H-NMR (CDCl₃) δ: 3.70-4.98 (6H, m), 6.64-7.83 (8H, m), 8.21 (1H, d, J=5.0 Hz), 8.37-8.78 (2H, m).

EXAMPLE 39C

3-[(6-phenyl-2,3-dihydropyrido[3,2-f][1,4]oxazepin-4(5H)-yl)carbonyl]benzonitrile ¹H-NMR (CDCl₃) δ: 3.69-4.92 (6H, m), 6.81-7.83 (10H, m), 8.14-8.30 (1H, br).

EXAMPLE 40C

4-[(6-phenyl-2,3-dihydropyrido[3,2-f][1,4]oxazepin-4(5H)-yl)carbonyl]indan-1-one ¹H-NMR (CDCl₃) δ: 2.36-3.15 (4H, m), 3.61-4.92 (6H, m), 6.55-7.88 (9H, m), 8.20 (1H, d, J=4.9 Hz).

EXAMPLE 41C

4-[(3,5-dichlorophenyl)sulfonyl]-6-phenyl-2,3,4,5-tetrahydropyrido[3,2-f][1,4]oxazepine ¹H-NMR (CDCl₃) δ: 3.79 (2H, t, J=4.9 Hz), 4.36 (2H, t, J=4.9 Hz), 4.45 (2H, s), 7.00 (1H, d, J=5.0 Hz), 7.31-7.59 (8H, m), 8.14 (1H, d, J=5.0 Hz).

EXAMPLE 42C 4-(1-naphthylsulfonyl)-6-phenyl-2,3,4,5-tetrahydropyrido[3,2-f][1,4]oxazepine ¹H-NMR (CDCl₃) δ: 3.87 (2H, t, J=4.6 Hz), 4.32 (2H, s), 4.34-4.39 (2H, m), 6.94 (1H, d, J=5.0 Hz), 7.13-7.61 (8H, m), 7.76 (1H, dd, J=7.4, 1.2 Hz), 7.82-7.92 (1H, m), 7.97-8.02 (1H, m), 8.14 (1H, d, J=5.0 Hz), 8.29-8.42 (1H, m).

EXAMPLE 43C 6-phenyl-4-(quinolin-8-ylsulfonyl)-2,3,4,5-tetrahydropyrido[3,2-f][1,4]oxazepine ¹H-NMR (CDCl₃) δ: 3.97 (2H, t, J=4.6 Hz), 4.35-4.42 (2H, m), 4.59 (2H, s), 6.95 (1H, d, J=5.0 Hz), 7.30-7.60 (7H, m), 7.92-8.03 (1H, m), 8.08-8.25 (3H, m), 8.82-8.87 (1H, m).

EXAMPLE 44C 4-(3-[3,5-bis(trifluoromethyl)phenyl]propanoyl)-6-phenyl-2,3,4,5-tetrahydropyrido[3,2-f][1,4]oxazepine The title compound (84 mg) was obtained as colorless crystals by the same method as in Example 20C and using a free basic form (90 mg) of 6-phenyl-2,3,4,5-tetrahydropyrido[3,2-f][1,4]oxazepine obtained in Reference Example 5C and 3,5-bis(trifluoromethyl)phenylpropionic acid (138 mg).

¹H-NMR (CDCl₃) δ: 1.86-1.94 (2H×¾, m), 2.60-2.68 (2H×¼, m), 2.80 (2H×¾, t, J=7.9 Hz), 3.04 (2H×¼, t, J=7.8 Hz), 3.84 (2H×¼, t, J=5.1 Hz), 4.03 (2H×¾, t, J=4.7 Hz), 4.23-4.52 (2H, m), 4.59 (2H×¾, s), 4.66 (2H×¼, s), 6.95 (1H×¼, d, J=5.0 Hz), 6.98 (1H×¾, d, J=5.1 Hz), 7.10-7.76 (8H, m), 8.12-8.25 (1H, m).

EXAMPLE 45C

4-{2-[3,5-bis(trifluoromethyl)phenyl]ethyl}-6-phenyl-2,3,4,5-tetrahydropyrido[3,2-f][1,4]oxazepine hydrochloride To 4-{[3,5-bis(trifluoromethyl)phenyl]acetyl}-6-phenyl-2,3,4,5-tetrahydropyrido[3,2-f][1,4]oxazepine (70 mg) obtained in Example 20C in tetrahydrofuran (3 ml) was added lithium aluminum hydride (17 mg) under ice-cooling, and the mixture was stirred at room temperature for 20 hrs. The reaction mixture was cooled, water was added, and the mixture was extracted with ethyl acetate. The organic layer was washed successively with saturated aqueous sodium hydrogencarbonate and saturated brine, and dried over anhydrous magnesium sulfate. The solvent was evaporated under reduced pressure, and the obtained residue was purified by silica gel column chromatography to give a free basic form of the title compound as a colorless oil. The obtained oil was dissolved in ethyl acetate (2 ml), and a 4N solution (0.5 ml) of hydrochloric acid in ethyl acetate was added. The solvent was evaporated under reduced pressure, and the obtained residue was precipitated from ethyl acetate-diisopropyl ether to give the title compound (16 mg) as a colorless amorphous powder.

¹H-NMR (free basic form; CDCl₃) δ: 2.59-2.73 (4H, m), 3.08 (2H, dt, J=4.7, 4.5 Hz), 3.72 (2H, s), 4.27 (2H, dt, J=4.6, 4.4 Hz), 6.99 (1H, d, J=5.0 Hz), 7.23-7.31 (2H, m), 7.36-7.46 (3H, m), 7.49 (2H, s), 7.70 (1H, s), 8.18 (1H, d, J=5.0 Hz).

EXAMPLE 46C

N-[3,5-bis(trifluoromethyl)phenyl]-6-phenyl-2,3-dihydropyrido[3,2-f][1,4]oxazepine-4(5H)-carboxamide To a solution of a free basic form (90 mg) of 6-phenyl-2,3,4,5-tetrahydropyrido[3,2-f][1,4]oxazepine obtained in Reference Example 5C in pyridine (5 ml) was added 3,5-bis(trifluoromethyl)phenylisocyanate (255 mg), and the mixture was stirred at room temperature for 18 hrs. The reaction mixture was evaporated under reduced pressure, water was added to the obtained residue and the mixture was extracted with ethyl acetate. The organic layer was washed successively with saturated aqueous sodium hydrogencarbonate and saturated brine, and dried over anhydrous magnesium sulfate. The solvent was evaporated under reduced pressure, and the obtained residue was purified by silica gel column chromatography and crystallized from diethyl ether to give the title compound (120 mg) as colorless crystals.

¹H-NMR (CDCl₃) δ: 4.05 (2H, t, J=4.4 Hz), 4.33 (2H, t, J=4.5 Hz), 4.74 (2H, s), 5.77 (1H, s), 7.06 (1H, d, J=5.1 Hz), 7.31-7.51 (5H, m), 7.55-7.64 (3H, m), 8.29 (1H, d, J=5.1 Hz).

EXAMPLE 47C

4-[3,5-bis(trifluoromethyl)benzoyl]-6-phenyl-2,3,4,5-tetrahydropyrido[3,2-f][1,4]oxazepine 9-oxide To a solution of 4-[3,5-is(trifluoromethyl)benzoyl]-6-phenyl-2,3,4,5-tetrahydropyrido[3,2-f][1,4]oxazepine (90 mg) obtained in Example 14C in ethyl acetate (5 ml) was added mCPBA (67 mg), and the mixture was stirred at room temperature for 2 days. The solvent was evaporated under reduced pressure, and the obtained residue was purified by silica gel column chromatography and crystallized from diisopropyl ether to give the title compound (67 mg) as colorless crystals.

¹H-NMR (CDCl₃) δ: 3.79-4.38 (2H, br), 4.48-4.98 (4H, br), 6.62-8.07 (9H, m), 8.23 (1H, d, J=6.7 Hz).

EXAMPLE 48C

5-{1-[3,5-bis(trifluoromethyl)phenyl]ethyl}-7-phenyl-3,4,5,6-tetrahydro-2H-pyrido[2,3-b][1,5]oxazocine hydrochloride The title compound was synthesized by the same method as in Example 33C and using 7-phenyl-3,4,5,6-tetrahydro-2H-pyrido[2,3-b][1,5]oxazocine obtained in Reference Example 6C and 1-[3,5-bis(trifluoromethyl)phenyl]ethyl methanesulfonate.

¹H-NMR (free basic form; CDCl₃) δ: 1.27 (3H, d, J=6.8 Hz), 1.58-1.88 (2H, m), 2.55-2.73 (1H, m), 2.77-2.95 (1H, m), 3.67 (1H, d, J=12.2 Hz), 3.72-3.85 (1H, m), 3.88 (1H, d, J=12.3 Hz), 4.23-4.40 (2H, m), 7.08 (1H, d, J=5.1 Hz), 7.32-7.51 (5H, m), 7.72 (3H, s), 8.32 (1H, d, J=5.0 Hz).

The compounds of the following Examples 49C to 52C were synthesized by the same method as in Example 14C or Example 33C and using 8-phenyl-2,3,4,5,6,7-hexahydropyrido[2,3-b][1,5]oxazonine obtained in Reference Example 8C.

EXAMPLE 49C

6-[3,5-bis(trifluoromethyl)benzyl]-8-phenyl-2,3,4,5,6,7-hexahydropyrido[2,3-b][1,5]oxazonine $^1$H-NMR (CDCl$_3$) δ: 1.57-1.67 (2H, m), 1.70-1.80 (2H, m), 3.20 (2H, t, J=5.7 Hz), 3.54 (2H, s), 3.83 (2H, s), 4.69 (2H, t, J=5.1 Hz), 6.75 (1H, d, J=5.1 Hz), 6.85-6.91 (2H, m), 7.19-7.32 (5H, m), 7.63 (1H, s), 8.15 (1H, d, J=5.2 Hz).

EXAMPLE 50C

6-{1-[3,5-bis(trifluoromethyl)phenyl]ethyl}-8-phenyl-2,3,4,5,6,7-hexahydropyrido[2,3-b][1,5]oxazonine $^1$H-NMR (CDCl$_3$) δ: 1.10 (3H, d, J=6.8 Hz), 1.55-1.87 (4H, m), 3.08-3.32 (2H, m), 3.65 (1H, q, J=6.8 Hz), 3.73 (2H, s), 4.61-4.79 (2H, m), 6.75 (1H, d, J=5.1 Hz), 6.88-6.94 (2H, m), 7.26-7.65 (3H, m), 7.33 (2H, s), 7.63 (1H, s), 8.14 (1H, d, J=5.1 Hz).

EXAMPLE 51C

6-[3,5-bis(trifluoromethyl)benzoyl]-8-phenyl-2,3,4,5,6,7-hexahydropyrido[2,3-b][1,5]oxazonine $^1$H-NMR (CDCl$_3$) δ: 1.15-1.31 (2H×⅓, m), 1.53-1.60 (2H×⅓, m), 1.71-1.81 (2H×⅔, m), 2.08-2.28 (2H×⅔, m), 3.78-4.02 (2H, m), 4.54 (2H×⅔, s), 4.64 (2H×⅓, s), 4.66-4.79 (2H, m), 6.69-7.90 (9H, m), 8.20-8.24 (1H, m).

EXAMPLE 52C

6-{[3,5-bis(trifluoromethyl)phenyl]sulfonyl}-8-phenyl-2,3,4,5,6,7-hexahydropyrido[2,3-b][1,5]oxazonine $^1$H-NMR (CDCl$_3$) δ: 1.70-1.80 (2H, m), 1.97-2.08 (2H, m), 3.64 (2H, t, J=6.1 Hz), 4.17 (2H, s), 4.73 (2H, t, J=4.7 Hz), 6.99 (1H, d, J=5.1 Hz), 7.28-7.34 (2H, m), 7.46-7.54 (3H, m), 7.64 (2H, s), 8.00 (1H, s), 8.25 (1H, d, J=5.2 Hz).

The compounds of the following Examples 53C to 56C were synthesized by the same method as in Example 14C or Example 33C and using 6-(4-fluorophenyl)-2,3,4,5-tetrahydropyrido[3,2-f][1,4]oxazepine obtained in Reference Example 13C.

EXAMPLE 53C

4-[3,5-bis(trifluoromethyl)benzyl]-6-(4-fluorophenyl)-2,3,4,5-tetrahydropyrido[3,2-f][1,4]oxazepine $^1$H-NMR (CDCl$_3$) δ: 3.07 (2H, dt, J=4.8, 4.5 Hz), 3.62 (2H, s), 3.63 (2H, S), 4.31 (2H, dt, J=4.7, 4.6 Hz), 6.82-6.93 (3H, m), 6.96-7.05 (2H, m), 7.64 (2H, s), 7.74 (1H, s), 8.17 (1H, d, J=5.1 Hz).

EXAMPLE 54C

4-{1-[3,5-bis(trifluoromethyl)phenyl]ethyl}-6-(4-fluorophenyl)-2,3,4,5-tetrahydropyrido[3,2-f][1,4]oxazepine $^1$H-NMR (CDCl$_3$) δ: 1.27 (3H, d, J=6.7 Hz), 2.95-3.27 (2H, m), 3.62 (2H, s), 3.78 (1H, q, J=6.7 Hz), 4.24-4.47 (2H, m), 6.84 (1H, d, J=5.0 Hz), 6.88-7.02 (4H, m), 7.61 (2H, s), 7.68 (1H, s), 8.15 (1H, d, J=5.0 Hz).

EXAMPLE 55C

4-[3,5-bis(trifluoromethyl)benzoyl]-6-(4-fluorophenyl)-2,3,4,5-tetrahydropyrido[3,2-f][1,4]oxazepine $^1$H-NMR (CDCl$_3$) δ: 3.71-4.29 (2H, br), 4.32-4.86 (4H, m), 6.67-7.59 (6H, m), 7.68-8.04 (2H, m), 8.22 (1H, d, J=5.1 Hz).

EXAMPLE 56C

4-{[3,5-bis(trifluoromethyl)phenyl]sulfonyl}-6-(4-fluorophenyl)-2,3,4,5-tetrahydropyrido[3,2-f][1,4]oxazepine $^1$H-NMR (CDCl$_3$) δ: 3.84 (2H, t, J=5.0 Hz), 4.39 (2H, t, J=5.0 Hz), 4.48 (2H, s), 6.94 (1H, d, J=5.1 Hz), 7.16-7.31 (4H, m), 7.89 (2H, m), 7.98 (1H, s), 8.08 (1H, d, J=5.0 Hz).

The compounds of the following Examples 57C to 60C were synthesized by the same method as in Example 14C or Example 33C and using 7-(4-fluorophenyl)-3,4,5,6-tetrahydro-2H-pyrido[2,3-b][1,5]oxazocine obtained in Reference Example 14C.

EXAMPLE 57C

5-[3,5-bis(trifluoromethyl)benzyl]-7-(4-fluorophenyl)-3,4,5,6-tetrahydro-2H-pyrido[2,3-b][1,5]oxazocine $^1$H-NMR (CDCl$_3$) δ: 1.71-1.79 (2H, m), 2.85-2.89 (2H, m), 3.58 (2H, s), 3.85 (2H, s), 4.36 (2H, t, J=5.6 Hz), 6.96-7.06 (3H, m), 7.37-7.45 (2H, m), 7.64 (2H, s), 7.73 (1H, s), 8.32 (1H, d, J=5.1 Hz).

EXAMPLE 58C

5-{1-[3,5-bis(trifluoromethyl)phenyl]ethyl}-7-(4-fluorophenyl)-3,4,5,6-tetrahydro-2H-pyrido[2,3-b][1,5]oxazocine $^1$H-NMR (CDCl$_3$) δ: 1.32 (3H, d, J=6.8 Hz), 1.60-1.88 (2H, m), 2.58-2.99 (2H, m), 3.59-3.88 (2H, m), 3.78-3.91 (1H, m), 4.20-4.42 (2H, m), 7.02-7.12 (3H, m), 7.42-7.51 (2H, m), 7.72 (2H, s), 7.73 (1H, s), 8.31 (1H, d, J=5.0 Hz).

EXAMPLE 59C

5-[3,5-bis(trifluoromethyl)benzoyl]-7-(4-fluorophenyl)-3,4,5,6-tetrahydro-2H-pyrido[2,3-b][1,5]oxazocine $^1$H-NMR (CDCl$_3$) δ: 1.76-1.89 (1H, br), 2.09-2.21 (1H, br), 3.48-3.63 (1H, br), 3.81-3.98 (1H, br), 4.39-4.57 (2H, br), 4.68-4.91 (2H, br), 6.73-7.90 (8H, m), 8.24-8.38 (1H, br).

EXAMPLE 60C

5-{[3,5-bis(trifluoromethyl)phenyl]sulfonyl}-7-(4-fluorophenyl)-3,4,5,6-tetrahydro-2H-pyrido[2,3-b][1,5]oxazocine $^1$H-NMR (CDCl$_3$) δ: 1.94-2.02 (2H, m), 3.64-3.68 (2H, m), 4.40 (2H, s), 4.44 (2H, t, J=6.2 Hz), 7.07 (1H, d, J=5.1 Hz), 7.15-7.35 (4H, m), 7.85 (2H, s), 8.03 (1H, s), 8.32 (1H, d, J=5.1 Hz).

The compounds of the following Examples 61C to 64C were synthesized by the same method as in Example 14C or Example 33C and using 8-(4-fluorophenyl)-2,3,4,5,6,7-hexahydropyrido[2,3-b][1,5]oxazonine obtained in Reference Example 15C.

EXAMPLE 61C

6-[3,5-bis(trifluoromethyl)benzyl]-8-(4-fluorophenyl)-2,3,4,5,6,7-hexahydropyrido[2,3-b][1,5]oxazonine $^1$H-NMR (CDCl$_3$) δ: 1.58-1.69 (2H, m), 1.72-1.82 (2H, m), 3.20 (2H, t, J=5.7 Hz), 3.57 (2H, s), 3.80 (2H, s), 4.69 (2H, t, J=5.1 Hz), 6.70 (1H, d, J=5.2 Hz), 6.79-6.98 (4H, m), 7.25 (2H, s), 7.65 (1H, s), 8.14 (1H, d, J=5.2 Hz).

EXAMPLE 62C

6-{1-[3,5-bis(trifluoromethyl)phenyl]ethyl}-8-(4-fluorophenyl)-2,3,4,5,6,7-hexahydropyrido[2,3-b][1,5]oxazonine $^1$H-NMR (CDCl$_3$) δ: 1.14 (3H, d, J=6.8 Hz), 1.58-1.70 (2H, m), 1.73-1.84 (2H, m), 3.11-3.34 (2H, m), 3.62-3.77 (1H, m), 3.70 (2H, s), 4.62-4.80 (2H, m), 6.70 (1H, d, J=5.2 Hz), 6.82-7.02 (4H, m), 7.29 (2H, s), 7.64 (1H, s), 8.13 (1H, d, J=5.2 Hz).

EXAMPLE 63C

6-[3,5-bis(trifluoromethyl)benzoyl]-8-(4-fluorophenyl)-2,3,4,5,6,7-hexahydropyrido[2,3-b][1,5]oxazonine $^1$H-NMR (CDCl$_3$) δ: 1.14-1.28 (2H×2/5, m), 1.42-1.55 (2H×2/5, m), 1.70-1.81 (2H×3/5, m), 2.09-2.25 (2H×3/5, m), 3.79-4.00 (2H, m), 4.52 (2H×3/5, s), 4.61 (2H×2/5, s), 4.69 (2H×2/5, t, J=4.8 Hz), 4.76 (2H×3/5, t, J=5.0 Hz), 6.71-6.96 (3H, m), 7.11-7.41 (2H, m), 7.20 (2H×3/5, s), 7.69 (2H×2/5, s), 7.72 (1H×3/5, s), 7.85 (1H×2/5, s), 8.19-8.25 (1H, m).

EXAMPLE 64C

6-{[3,5-bis(trifluoromethyl)phenyl]sulfonyl}-8-(4-fluorophenyl)-2,3,4,5,6,7-hexahydropyrido[2,3-b][1,5]oxazonine $^1$H-NMR (CDCl$_3$) δ: 1.70-1.80 (2H, m), 1.97-2.08 (2H, m), 3.64 (2H, t, J=6.0 Hz), 4.13 (2H, s), 4.73 (2H, t, J=4.7 Hz), 6.94 (1H, d, J=5.1 Hz), 7.16-7.33 (4H, m), 7.68 (2H, s), 8.01 (1H, s), 8.24 (1H, d, J=5.2 Hz).

EXAMPLE 65C

4-[3,5-bis(trifluoromethyl)benzoyl]-6-(3-fluorophenyl)-2,3,4,5-tetrahydropyrido[3,2-f][1,4]oxazepine To a solution of 6-(3-fluorophenyl)-2,3,4,5-tetrahydropyrido[3,2-f][1,4]oxazepine (0.20 g) obtained in Reference Example 16C in tetrahydrofuran (8 ml) were added triethylamine (0.18 g) and 3,5-bis(trifluoromethyl)benzoyl chloride (0.24 g), and the mixture was stirred at room temperature for 20 hrs. Water was added to the reaction mixture, and the mixture was extracted with ethyl acetate. The organic layer was washed successively with saturated aqueous sodium hydrogencarbonate solution and saturated aqueous sodium chloride solution, and dried over anhydrous magnesium sulfate. The solvent was evaporated and the residue was purified by silica gel column chromatography to give the title compound as a colorless solid. This solid was recrystallized from ethyl acetate to give the title compound (0.20 g) as colorless crystals.

$^1$H-NMR (CDCl$_3$) δ: 3.82 (1H, m), 4.18 (1H, m), 4.35-4.85 (4H, m), 6.40-6.72 (1H, m), 6.75-8.00 (7H, m), 8.23 (1H, d, J=5.0 Hz).

EXAMPLE 66C

4-[3,5-bis(trifluoromethyl)benzenesulfonyl]-6-(3-fluorophenyl)-2,3,4,5-tetrahydropyrido[3,2-f][1,4]oxazepine The title compound (0.21 g) was obtained as colorless crystals by a similar method as in Example 65C and using 6-(3-fluorophenyl)-2,3,4,5-tetrahydropyrido[3,2-f][1,4]oxazepine (0.20 g) obtained in Reference Example 16C and 3,5-bis(trifluoromethyl)benzenesulfonyl chloride (0.27 g).

$^1$H-NMR (CDCl$_3$) δ: 3.83-3.88 (2H, m), 4.36-4.43 (2H, m), 4.49 (2H, s), 6.95 (1H, d, J=5.0 Hz), 7.00-7.60 (4H, m), 7.90 (2H, s), 7.97 (1H, s), 8.10 (1H, d, J=5.0 Hz).

EXAMPLE 67C

4-[3,5-bis(trifluoromethyl)benzyl]-6-(3-fluorophenyl)-2,3,4,5-tetrahydropyrido[3,2-f][1,4]oxazepine To a solution of 6-(3-fluorophenyl)-2,3,4,5-tetrahydropyrido[3,2-f][1,4]oxazepine (0.20 g) obtained in Reference Example 16C in N,N-dimethylformamide (10 ml) were added 3,5-bis(trifluoromethyl)benzyl bromide (0.28 g) and potassium carbonate (0.65 g), and the mixture was stirred at 80° C. for 20 hrs. The reaction mixture was concentrated, and water was added to the obtained residue. The mixture was extracted with ethyl acetate, and the organic layer was washed with saturated aqueous sodium chloride solution and dried over anhydrous magnesium sulfate. The solvent was evaporated and the residue was purified by silica gel column chromatography to give the title compound (0.24 g) as colorless crystals.

$^1$H-NMR (CDCl$_3$) δ: 3.00-3.13 (2H, m), 3.64 (4H, s), 4.22-4.36 (2H, m), 6.74-7.19 (5H, m), 7.64 (2H, s), 7.72 (1H, s), 8.18 (1H, d, J=5.1 Hz).

EXAMPLE 68C

5-[3,5-bis(trifluoromethyl)benzoyl]-7-(3-fluorophenyl)-3,4,5,6-tetrahydro-2H-pyrido[2,3-b][1,5]oxazocine The title compound (0.12 g) was obtained as colorless crystals by a similar method as in Example 65C and using 7-(3-fluorophenyl)-3,4,5,6-tetrahydro-2H-pyrido[2,3-b][1,5]oxazocine hydrochloride (0.23 g) obtained in Reference Example 17C and 3,5-bis(trifluoromethyl)benzoyl chloride (0.20 g).

$^1$H-NMR (CDCl$_3$) δ: 1.84 (1H, brs), 2.18 (1H, brs), 3.56 (1H, brs), 3.91 (1H, brs), 4.35-4.60 (2H, m), 4.74 (1H, brs), 4.87 (1H, brs), 6.58 (1H, dd, 7.7 Hz, 24.9 Hz), 6.78-7.98 (7H, m), 8.32 (1H, brs).

EXAMPLE 69C

5-[3,5-bis(trifluoromethyl)benzenesulfonyl]-7-(3-fluorophenyl)-3,4,5,6-tetrahydro-2H-pyrido[2,3-b][1,5]oxazocine The title compound (0.16 g) was obtained as colorless crystals by a similar method as in Example 65C and using 7-(3-fluorophenyl)-3,4,5,6-tetrahydro-2H-pyrido[2,3-b][1,5]oxazocine hydrochloride (0.23 g) obtained in Reference Example 17C and 3,5-bis(trifluoromethyl)benzenesulfonyl chloride (0.22 g).

$^1$H-NMR (CDCl$_3$) δ: 1.94-2.04 (2H, m), 3.63-3.69 (2H, m), 4.40-4.49 (4H, m), 7.02-7.50 (5H, m), 7.85 (2H, s), 8.02 (1H, s), 8.34 (1H, d, J=5.1 Hz).

EXAMPLE 70C

5-[3,5-bis(trifluoromethyl)benzyl]-7-(3-fluorophenyl)-3,4,5,6-tetrahydro-2H-pyrido[2,3-b][1,5]oxazocine The title compound (0.24 g) was obtained as a colorless oil by a similar method as in Example 67C and using the compound (0.23 g) obtained in Reference Example 17C and 3,5-bis(trifluoromethyl)benzyl bromide (0.24 g).

$^1$H-NMR (CDCl$_3$) δ: 1.70-1.79 (2H, m), 2.80-2.86 (2H, m), 3.60 (2H, s), 3.85 (2H, s), 4.35 (2H, t, J=5.6 Hz), 7.03 (1H, td, J=8.3, 5.1 Hz), 7.07 (1H, d, J=5.2 Hz), 7.18-7.38 (3H, m), 7.68 (2H, s), 7.73 (1H, s), 8.33 (1H, d, J=5.1 Hz).

EXAMPLE 71C

4-{1-[3,5-bis(trifluoromethyl)phenyl]ethyl}-6-(3-fluorophenyl)-2,3,4,5-tetrahydropyrido[3,2-f][1,4]oxazepine To a solution of 6-(3-fluorophenyl)-2,3,4,5-tetrahydropyrido[3,2-f][1,4]oxazepine hydrochloride (0.50 g) obtained in Reference Example 16C and potassium carbonate (0.74 g) in DMF (20 ml) was added 1-[3,5-bis(trifluoromethyl)phenyl]ethyl methanesulfonate (0.6 g), and the mixture was stirred at 80° C. The addition of the same ester was repeated 3 times in 2 hrs. The reaction solution was allowed to cool, and the solvent was evaporated under reduced pressure. Water was added to the obtained residue, and the mixture was extracted with ethyl acetate. The organic layer was dried over anhydrous magnesium sulfate, and the solvent was evaporated under reduced pressure. The obtained residue was purified by silica gel column chromatography to give the title compound (0.059 g) as a white powder.

$^1$H-NMR (CDCl$_3$) δ: 1.28 (3H, d, J=6.7 Hz), 2.94-3.08 (1H, m), 3.12-3.24 (1H, m), 3.61 (2H, s), 3.79 (1H, q, J=6.7 Hz), 4.26-4.44 (2H, m), 6.68-6.80 (2H, m), 6.85 (1H, d, J=5.1 Hz), 6.93-7.03 (1H, m), 7.15-7.26 (1H, m), 7.61 (2H, s), 7.68 (1H, s), 8.16 (1H, d, J=5.0 Hz).

EXAMPLE 72C tert-butyl 3-{[6-(4-fluorophenyl)-2,3-dihydropyrido[3,2-f][1,4]oxazepin-4(5H)-yl]carbonyl}benzylcarbamate To a solution of 6-(4-fluorophenyl)-2,3,4,5-tetrahydropyrido[3,2-f][1,4]oxazepine (0.20 g) obtained in Reference Example 13C, 1-hydroxy-1H-benzotriazole (0.15 g), triethylamine (0.083 g) and 3-(tert-butoxycarbonylaminomethyl)benzoic acid (0.205 g) in acetonitrile (10 ml) was added 1-ethyl-3-(3-dimethylaminopropyl)carbodiimide hydrochloride (0.314 g), and the mixture was stirred at room temperature for 20 hrs. Ethyl acetate was added to the reaction mixture, and the mixture was washed with water, and dried over anhydrous magnesium sulfate. The solvent was evaporated and the residue was purified by silica gel column chromatography to give the title compound (0.35 g) as a colorless amorphous powder.

$^1$H-NMR (CDCl$_3$) δ: 1.45 (9H, s), 3.75-4.90 (9H, m), 6.70-7.50 (9H, m), 8.19 (1H, d, J=5.0 Hz).

EXAMPLE 73C

3-{[6-(4-fluorophenyl)-2,3-dihydropyrido[3,2-f][1,4]oxazepin-4(5H)-yl]carbonyl}benzylamine hydrochloride To tert-butyl 3-{[6-(4-fluorophenyl)-2,3-dihydropyrido[3,2-f][1,4]oxazepin-4(5H)-yl]carbonyl}benzylcarbamate (0.32 g) obtained in Example 72C was added a 4N solution (10 ml) of hydrochloric acid in ethyl acetate, and the mixture was stirred at room temperature for 30 min. The reaction mixture was concentrated and the residue was dissolved in a small amount of isopropanol. Ethyl acetate was added and the resulting crystals were collected by filtration to give the title compound (0.25 g) as colorless crystals.

$^1$H-NMR (DMSO-d$_6$) δ: 3.70-4.05 (4H, m), 4.40-4.90 (4H, m), 6.70-7.60 (9H, m), 8.15 (1H, m), 8.20-8.50 (3H, m). MS: 378 (M+1).

The compounds of the following Examples 74C and 75C were synthesized by the same method as in Example 14C and using 6-(4-chlorophenyl)-2,3,4,5-tetrahydropyrido[3,2-f][1,4]oxazepine dihydrochloride obtained in Reference Example 20C.

EXAMPLE 74C

4-[[3,5-bis(trifluoromethyl)phenyl]sulfonyl]-6-(4-chlorophenyl)-2,3,4,5-tetrahydropyrido[3,2-f][1,4]oxazepine $^1$H-NMR (CDCl$_3$) δ: 3.84 (2H, t, J=4.9 Hz), 4.39 (2H, t, J=4.9 Hz), 4.49 (2H, s), 6.93 (1H, t, J=5.0 Hz), 7.27 (2H, m), 7.51 (2H, m), 7.90 (2H, s), 7.98 (1H, s), 8.08 (1H, d, J=5.0 Hz).

EXAMPLE 75C

4-[3,5-bis(trifluoromethyl)benzoyl]-6-(4-chlorophenyl)-2,3,4,5-tetrahydropyrido[3,2-f][1,4]oxazepine $^1$H-NMR (CDCl$_3$) δ: 3.82 (1H, m), 4.17 (1H, m), 4.42-4.52 (2H, m), 4.64-4.75 (2H, m), 6.73 (1H, m), 6.82 (0.5H, m), 6.98 (0.5H, m), 7.17 (1H, m), 7.39-7.46 (3H, m), 7.78-7.81 (1.5H, m), 7.92 (0.5H, m), 8.22 (1H, d, J=5.0 Hz).

EXAMPLE 76C

4-[3,5-bis(trifluoromethyl)benzyl]-6-(4-chlorophenyl)-2,3,4,5-tetrahydropyrido[3,2-f][1,4]oxazepine To a solution of 6-(4-chlorophenyl)-2,3,4,5-tetrahydropyrido[3,2-f][1,4]oxazepine dihydrochloride (200 mg) obtained in Reference Example 20C and potassium carbonate (185 mg) in dimethylformamide (10 ml) was added 3,5-bis(trifluoromethyl)benzyl bromide (323 mg), and the mixture was stirred at 80° C. for 24 hrs. Water was added to the reaction mixture and the mixture was extracted with ethyl acetate. The organic layer was dried over anhydrous magnesium sulfate. After evaporation of the solvent, the obtained residue was purified by silica gel column chromatography and recrystallized from hexane-ethyl acetate to give the title compound (115 mg) as colorless crystals.

$^1$H-NMR (CDCl$_3$) δ: 3.06 (2H, m), 3.62 (2H, s), 3.63 (2H, s), 4.30 (2H, m), 6.88 (1H, d, J=5.0 Hz), 6.97 (2H, m), 7.15 (2H, m), 7.64 (2H, s), 7.75 (1H, s), 8.17 (1H, d, J=5.0 Hz).

EXAMPLE 77C

4-[1-[3,5-bis(trifluoromethyl)phenyl]ethyl]-6-(4-chlorophenyl)-2,3,4,5-tetrahydropyrido[3,2-f][1,4]oxazepine The title compound was obtained by the same method as in Example 76C and using 6-(4-chlorophenyl)-2,3,4,5-tetrahydropyrido[3,2-f][1,4]oxazepine dihydrochloride obtained in Reference Example 20C.

$^1$H-NMR (CDCl$_3$) δ: 1.27 (3H, d, J=6.6 Hz), 3.00 (1H, m), 3.15 (1H, m), 3.62 (2H, m), 3.77 (1H, q, J=6.6 Hz), 4.32 (2H, m), 6.83 (1H, d, J=5.0 Hz), 6.95 (2H, d, J=8.4 Hz), 7.21 (2H, d, J=8.4 Hz), 7.61 (2H, s), 7.69 (1H, s), 8.15 (1H, d, J=5.0 Hz).

The compounds of the following Examples 78C and 79C were synthesized by the same method as in Example 14C and using 7-(4-chlorophenyl)-3,4,5,6-tetrahydro-2H-pyrido[2,3-b][1,5]oxazocine obtained in Reference Example 19C.

EXAMPLE 78C

5-[[3,5-bis(trifluoromethyl)phenyl]sulfonyl]-7-(4-chlorophenyl)-3,4,5,6-tetrahydro-2H-pyrido[2,3-b][1,5]oxazocine $^1$H-NMR (CDCl$_3$) δ: 1.96 (2H, m), 3.65 (2H, m), 4.41-4.46 (4H, m), 7.06 (1H, d, J=5.1 Hz), 7.28 (2H, d, J=8.4 Hz), 7.47 (2H, d, J=8.4 Hz), 7.87 (2H, s), 8.03 (1H, s), 8.33 (1H, d, J=5.1 Hz).

EXAMPLE 79C

5-[3,5-bis(trifluoromethyl)benzoyl]-7-(4-chlorophenyl)-3,4,5,6-tetrahydro-2H-pyrido[2,3-b][1,5]oxazocine $^1$H-NMR (CDCl$_3$) δ: 1.81 (1H, m), 2.15 (1H, m), 3.57 (1H, m), 3.93 (1H, m), 4.46-4.53 (2H, m), 4.77-4.85 (2H, m), 6.77 (1H, d, J=7.2 Hz), 6.83 (0.5H, m), 7.06 (0.5H, m), 7.18 (1H, d, J=7.2 Hz), 7.30 (1H, d, J=7.2 Hz), 7.45 (1H, d, J=7.2 Hz), 7.50 (1H, s), 7.68 (1H, s), 7.75 (0.5H, m), 7.88 (0.5H, m), 8.31 (1H, m).

EXAMPLE 80C

5-[3,5-bis(trifluoromethyl)benzyl]-7-(4-chlorophenyl)-3,4,5,6-tetrahydro-2H-pyrido[2,3-b][1,5]oxazocine The title compound was obtained by the same method as in Example 76C and using 7-(4-chlorophenyl)-3,4,5,6-tetrahydro-2H-pyrido[2,3-b][1,5]oxazocine obtained in Reference Example 19C.

$^1$H-NMR (CDCl$_3$) δ: 1.74 (2H, m), 2.87 (2H, m), 3.58 (2H, s), 3.84 (2H, s), 4.36 (2H, t, J=5.6 Hz), 7.03 (1H, d, J=5.1 Hz), 7.28 (2H, d, J=8.4 Hz), 7.35 (2H, d, J=8.4 Hz), 7.63 (2H, s), 7.74 (1H, s), 8.32 (1H, d, J=5.1 Hz).

EXAMPLE 81C

5-[[3,5-bis(trifluoromethyl)phenyl]sulfonyl]-7-(4-chlorophenyl)-3,4,5,6-tetrahydro-2H-pyrido[2,3-b][1,5]oxazocine 10-oxide The title compound was obtained by the same method as in Example 47C and using 5-[[3,5-bis(trifluoromethyl)phenyl]sulfonyl]-7-(4-chlorophenyl)-3,4,5,6-tetrahydro-2H-pyrido[2,3-b][1,5]oxazocine obtained in Example 78C.

$^1$H-NMR (CDCl$_3$) δ: 2.08 (2H, m), 3.67 (2H, t, J=5.2 Hz), 4.34 (2H, s), 4.66 (2H, t, J=6.2 Hz), 7.04 (1H, d, J=6.7 Hz), 7.25 (2H, d, J=8.3 Hz), 7.49 (2H, d, J=8.3 Hz), 7.86 (2H, s), 8.05 (1H, s), 8.24 (1H, d, J=6.7 Hz).

EXAMPLE 82C

4-[1-[3,5-bis(trifluoromethyl)phenyl]ethyl]-6-(4-methylphenyl)-2,3,4,5-tetrahydropyrido[3,2-f][1,4]oxazepine dihydrochloride The title compound was obtained by the same method as in Example 76C and using 6-(4-methylphenyl)-2,3,4,5-tetrahydropyrido[3,2-f][1,4]oxazepine dihydrochloride obtained in Reference Example 22C.

$^1$H-NMR (DMSO-d$_6$) δ: 1.56-1.65 (3H, m), 2.29 (3H, s), 3.43 (0.5H, m), 3.65 (1H, m), 3.97 (0.5H, m), 4.16 (0.5H, m), 4.32 (1.5H, m), 4.59 (1.5H, m), 4.79 (1.5H, m), 6.97-7.41 (6H, m), 8.04-8.40 (4H, m), 12.39 (1H, m).

| Elemental analysis for C$_{25}$H$_{22}$N$_2$OF$_6$·2HCl | | | |
|---|---|---|---|
| Calculated | C, 54.26; | H, 4.37; | N, 5.06 |
| Found | C, 54.09; | H, 4.51; | N, 4.78 |

EXAMPLE 83C

4-[(2,2-difluoro-1,3-benzodioxol-4-yl)carbonyl]-6-phenyl-2,3,4,5-tetrahydropyrido[3,2-f][1,4]oxazepine The title compound was synthesized by the same method as in Example 14C and using 6-phenyl-2,3,4,5-tetrahydropyrido[3,2-f][1,4]oxazepine obtained in Reference Example 5C.

$^1$H-NMR (CDCl$_3$) δ: 3.72-3.98 (2H×⅖, br), 4.08-4.32 (2H×⅗, br), 4.36-4.61 (2H, m), 4.66 (2H×⅗, brs), 4.79 (2H×⅖, brs), 6.69-7.61 (9H, m), 8.11-8.33 (1H, m).

EXAMPLE 84C

4-[1-[3,5-bis(trifluoromethyl)phenyl]propyl]-6-phenyl-2,3,4,5-tetrahydropyrido[3,2-f][1,4]oxazepine hydrochloride The title compound was obtained as colorless amorphous powder by the same method as in Example 33C and using the free basic form of the compound obtained in Reference Example 5C and 1-[3,5-bis(trifluoromethyl)phenyl]propyl methanesulfonate.

$^1$H-NMR (free basic form; CDCl$_3$) δ: 0.63 (3H, t, J=7.3 Hz), 1.40-1.82 (2H, m), 2.90-3.18 (2H, m), 3.48-3.55 (1H, m), 3.57-3.71 (2H, m), 4.23-4.42 (2H, m), 6.90 (1H, d, J=5.1 Hz), 7.06-7.13 (2H, m), 7.28-7.35 (3H, m), 7.47 (2H, s), 7.67 (1H, s), 8.14 (1H, d, J=5.0 Hz).

FORMULATION EXAMPLE 1

| | | |
|---|---|---|
| 1) compound of Reference Example 3 | 30 mg | |
| 2) microcrystalline cellulose | 10 mg | |
| 3) lactose | 19 mg | |
| 4) magnesium stearate | 1 mg | |
| total | 60 mg | |

The above-mentioned 1), 2), 3) and 4) are mixed and packed in a gelatin capsule.

FORMULATION EXAMPLE 2

| | | |
|---|---|---|
| 1) compound of Reference Example 3 | 30 g | |
| 2) lactose | 50 g | |
| 3) corn starch | 15 g | |
| 4) carboxymethylcellulose calcium | 44 g | |
| 5) magnesium stearate | 1 g | |
| total of 1000 tablets | 140 g | |

The total amount of the above-mentioned 1), 2) and 3) and 30 g of 4) are kneaded with water, vacuum dried and granulated. The resulting granules were mixed with 14 g of 4) and 1 g of 5) and tableted with a punching machine. In this way, 1000 tablets containing 30 mg of the compound of Reference Example 3 per tablet are obtained.

EXPERIMENTAL EXAMPLE 1 cAMP Production Increasing Activity of the Compounds of the Present Invention in Human TGR5 Expressing CHO Cells Human TGR5 expressing CHO cells prepared by the method described in WO 02/84286 were seeded in a 96 well plate at a concentration of 4×10$^4$ cells/well, cultured overnight at 37° C., and used for the measurement of the cAMP production amount. As the assay buffer, Hank's balanced salt solution (HBSS, Invitrogen) supplemented with 0.1% bovine serum albumin (BSA, Sigma) and 0.5 mM 3-isobutyl-1-methylxanthine (IBMX, Sigma) was used. A test compound sample (1 μM) diluted with the assay buffer was added to the cells. The cells were incubated at 37° C. for 30 min. and the supernatant was suctioned. The intracellular cAMP amount increased by the stimulation of the test compound was quantitatively determined using a HitHunter™ EFC Cyclic AMP Chemiluminescence Assay Kit (ABI) kit.

The cAMP amount in the test compound addition well was determined as a relative value (control %), wherein the cAMP amount of the well added with lithocholic acid (LCA), which is a TGR5 agonist, to a concentration of 1 μM was 100% and the cAMP amount of the well free of the addition was 0%. The results are shown in Table 1. In the Table, the data show an average of 3 groups.

TABLE 1 cAMP production increasing activity of test compounds in human TGR5 expressing CHO cells

| test compounds | cAMP production increasing activity (control %) |
|---|---|
| Reference Example 1 | 97 |
| Reference Example 2 | 108 |
| Reference Example 3 | 85 |
| Reference Example 4 | 80 |
| Reference Example 5 | 116 |
| Reference Example 6 | 98 |
| Reference Example 9 | 128 |
| Example 1B | 113 |
| Example 9C | 96 |
| Example 14C | 100 |
| Example 18C | 112 |
| lithocholic acid | 100 |

Therefrom it is clear that the compounds of the present invention have a cAMP production increasing activity and are superior agonists for human TGR5.

EXPERIMENTAL EXAMPLE 2 cAMP Production Increasing Activity of the Compounds of the Present Invention in Mock CHO Cells Free of Human TGR5 Expression Mock CHO cells free of human TGR5 expression, prepared by the method described in WO 02/84286, were seeded in a 96 well plate at a concentration of 2×10$^4$ cells/well, incubated overnight at 37° C. under 5% CO$_2$, and used for the measurement of the cAMP production amount. As the assay buffer, Hank's balanced salt solution (HBSS, Invitrogen) supplemented with 0.1% bovine serum albumin (BSA, Sigma) and 0.2 mM 3-isobutyl-1-methylxanthine (IBMX, Sigma) was used. The cells were washed twice with the assay buffer and preincubated at 37° C. for 30 min. The cells were washed twice, and test compound samples (10 μM) diluted with the assay buffer to various concentrations were added. The cells were incubated at 37° C. for 20 min. The culture supernatant was discarded, and the cAMP production amount was measured using a cAMP Screen System (ABI). In addition, using Forskolin (reagent capable of nonspecifically increasing cAMP production) (2 μM) and lithocholic acid (TGR5 agonist) (10 μM) instead of the test compound, a similar test was performed. The results are shown in Table 2. In the Table, the data show an average of 3 groups, and Base shows non-addition of the compound.

TABLE 2 cAMP production increasing activity of test compounds in mock CHO cells

| test compounds (Reference Example No) | cAMP production increasing activity (pmol) |
|---|---|
| Base | 0.85 |
| Forskolin | 4.02 |
| lithocholic acid | 0.90 |
| 1 | 0.84 |
| 2 | 0.89 |
| 3 | 0.67 |
| 4 | 0.79 |
| 5 | 0.99 |
| 6 | 0.88 |
| 7 | 0.86 |
| 9 | 0.85 |

It is clear that the compounds of the present invention are human TGR5 specific agonists, because increased cAMP production confirmed in Experimental Example 1 was not observed in mock CHO cells free of TGR5 expression.

EXPERIMENTAL EXAMPLE 3 cAMP Production Increasing Activity of the Compounds of the Present Invention in Rabbit TGR5 Expressing CHO Cells Rabbit TGR5 expressing CHO cells prepared by the method described in WO 02/84286 were seeded in a 96 well plate at concentration of $2 \times 10^4$ cells/well, incubated overnight at 37° C. under 5% $CO_2$, and used for the measurement of the cAMP production amount. As the assay buffer, Hank's balanced salt solution (HBSS, Invitrogen) supplemented with 0.1% bovine serum albumin (BSA, Sigma) and 0.2 mM 3-isobutyl-1-methylxanthine (IBMX, Sigma) was used. The cells were washed twice with the assay buffer and preincubated at 37° C. for 30 min. The cells were washed twice and test compound samples (2 μM) diluted with the assay buffer were added. The cells were incubated at 37° C. for 20 min. The culture supernatant was discarded, and the cAMP production amount was measured using a cAMP Screen System (ABI).

The cAMP amount in the test compound addition well was determined as a relative value (control %), wherein the cAMP amount of the well added with lithocholic acid (LCA), which is a TGR5 agonist, to a concentration of 10 μM was 100% and the cAMP amount of the well free of the addition was 0%. The results are shown in Table 3. In the Table, the data show an average of 3 groups.

TABLE 3 cAMP production increasing activity of test compounds in rabbit TGR5 expressing CHO cells

| test compounds (Reference Example No) | cAMP production increasing activity (control %) |
|---|---|
| 1 | 84 |
| 2 | 71 |
| 3 | 97 |
| 4 | 57 |
| 5 | 95 |
| 6 | 100 |
| 7 | 104 |
| 9 | 95 |
| lithocholic acid (2 μM) | 65 |
| lithocholic acid (10 μM) | 100 |

Therefrom it is clear that the compounds of the present invention have a cAMP production increasing activity and are superior agonists for rabbit TGR5.

EXPERIMENTAL EXAMPLE 4 cAMP Production Increasing Activity of the Compounds of the Present Invention in Mock CHO Cells Free of Human TGR5 Expression In the same manner as in Experimental Example 2, the cAMP production increasing activity of the test compounds (2 μM) was determined. The results are shown in Table 4. In the Table, the data show an average of 3 groups, and Base shows non-addition of the compound.

TABLE 4 cAMP production increasing activity of test compounds in mock CHO cells

| test compound (Example No) | cAMP production increasing activity (pmol) |
|---|---|
| Base | 0.28 |
| Forskolin | 5.68 |
| 1B | 0.23 |

It is clear that the compounds of the present invention are human TGR5 specific agonists, because increased cAMP production confirmed in Experimental Example 1 was not observed in mock CHO cells free of TGR5 expression.

EXPERIMENTAL EXAMPLE 5 cAMP Production Increasing Activity of the Compounds of the Present Invention in Mock CHO Cells Free of Human TGR5 Expression In the same manner as in Experimental Example 2, the cAMP production increasing activity of the test compounds (2 μM) was determined. The results are shown in Table 5. In the Table, the data show an average of 3 groups, and Base shows non-addition of the compound.

TABLE 5 cAMP production increasing activity of test
compounds in mock CHO cells

| test compounds (Example No) | cAMP production increasing activity (pmol) |
|---|---|
| Base | 0.19 |
| Forskolin | 3.01 |
| 9C | 0.2 |
| 14C | 0.17 |
| 18C | 0.17 |

It is clear that the compounds of the present invention are human TGR5 specific agonists, because increased cAMP production confirmed in Experimental Example 1 was not observed in mock CHO cells free of TGR5 expression.

EXPERIMENTAL EXAMPLE 6 cAMP Production Increasing Activity of the Compounds of the Present Invention in Rabbit TGR5 Expressing CHO Cells In the same manner as in Experimental Example 3, the cAMP production increasing activity of the test compounds (2 μM) was determined. The results are shown in Table 6. In the Table, the data show an average of 3 groups.

TABLE 6 cAMP production increasing activity of test
compounds in rabbit TGR5 expressing CHO cells

| test compounds (Example No) | cAMP production increasing activity (control %) |
|---|---|
| 1B | 71.2 |
| 9C | 99 |
| 14C | 116 |
| 18C | 106 |
| lithocholic acid (2 μM) | 60.6 |
| lithocholic acid (10 μM) | 100 |

It is clear that the compounds of the present invention have a cAMP production increasing activity and are superior agonists for rabbit TGR5.

EXPERIMENTAL EXAMPLE 7

Suppressing Effect of Test Compounds on Lipopolysaccharide (LPS) Induced Tumor Necrosis Factor (TNF) α Secretion in THP-TGR5 Cells TGR5 high expression cells were established by introducing TGR5 gene into human macrophage cells line THP-1. According to a conventional method, pcDNA-TGR5 incorporating cDNA of human TGR5 in pcDNA3.1 (Invitrogen) was prepared. Then, THP-1 was cultured in a medium (RPMI1640 10% FBS), and pcDNA-TGR5 was introduced thereinto using lipofectamine (Gibco BRL) according to conventional methods. Thereafter, G418 (Gibco BRL) was added to the medium to select resistant strains, and cells line, THP-TGR5 that expresses TGR5 stably and highly was established.

THP-TGR5 thus obtained was diluted to a concentration of $1 \times 10^5$/well and cultured overnight in a 96 well plate in the presence of $10^{-8}$M phorbol ester (Wako Pure Chemical Industries, Ltd.). THP-TGR5 after culture was cultured for 1 hr in a medium containing a test compound or a control medium (0.1 ml) free of a test compound, 0.1 ml of a medium containing the same concentration of the test compound or a control medium free of the test compound, each of which containing LPS for induction of TNF α secretion was added (concentration at the time of addition 50 ng/ml) and the mixture was incubated at 37° C. under 5% $CO_2$ for 14 hrs. The culture supernatant was collected and the TNF α content was measured with the growth suppressing effect on the TNF sensitive cell line L929 (RIKEN Institute) as an index.

L929 cells were seeded in a 96 well plate at $1.2 \times 10^4$/well and incubated overnight at 37° C. under 5% $CO_2$. The obtained culture product was cultured overnight in a medium (phenol red free Dulbecco's Modified Eagle Medium (Invitrogen) supplemented with 10% fetal bovine serum (Invitrogen), 100 U/ml penicillin and 100 μg/ml streptomycin), which contained the aforementioned THP-TGR5-containing culture supernatant and 2 μg/ml Actinomycin D (Wako Pure Chemical Industries, Ltd.). The TNF α content was determined by measuring the growth of the L929 cells in the obtained culture product using a Cell Counting Kit-8 (Wako Pure Chemical Industries, Ltd.). As the standard sample, human recombinant TNF α (Genzyme) was used. The results are shown in Table 7.

TABLE 7 suppressing effect of test compound on
lipopolysaccharide induced tumor necrosis factor (TNF) α
secretion in THP-TGR5 cells

| LPS | test compounds (Example No) | | TNF α (ng/ml) |
|---|---|---|---|
| − | non-addition | | 2.7 |
| + | non-addition | | 11 |
| + | LCA | 50 μM | 1.1 |
| + | TLCA | 50 μM | 0.22 |
| + | Reference Example 3 | 10 μM | 0.33 |
| + | Reference Example 6 | 10 μM | 0.32 |
| + | Reference Example 1B | 10 μM | 0.63 |

As shown in Table 7, bile acids [TLCA (taurolithocholic acid), LCA (lithocholic acid)], which are endogenous agonists for TGR5, and the compounds of the present invention showed a remarkable suppressing activity on TNF α secretion in THP-TGR5. From these results, the compounds of the present invention were confirmed to have a suppressing effect on TNF α secretion via TGR5 in macrophage, and that TGR5 is involved in the control of immune function in living organisms.

EXPERIMENTAL EXAMPLE 8

Confirmation of TGR5 Expression in NCI-H716 Cells

TGR5 expression was analyzed according to the method described in WO 02/084286, Example 17.

Human colorectal cancer-derived cell line NCI-H716 (ATCC) was cultured in a medium (Dulbecco's Modified Eagle Medium (DMEM, Invitrogen) supplemented with 10% fetal bovine serum (Invitrogen), 100 U/ml penicillin, 100 μg/ml streptomycin). The cells were collected, and total RNA was extracted by Isogen (NIPPON GENE CO., LTD.). For quantitation of the expression amount of mRNA, ABI PRISM 7700 SequenceDetector (Applied Biosystems) was used. The primer and probe used for the quantitation of the expression amount were designed using PrimerExpress (Applied Biosystems), a software exclusively for ABI PRISM 7700 SequenceDetector, based on the nucleotide sequence of human TGR5 (SEQ ID NO:1). The cDNA to be the template was synthesized from 1 µg of polyA+RNA derived from various human tissues (Clontech) using a random primer at 42° C. For reverse transcription reaction, SuperScriptII reverse transcription enzyme (GIBCO BRL) was used and the reaction was carried out according to the attached protocol. The reaction mixture for the ABI PRISM 7700 Sequence Detector was prepared according to the manual of TaqMan Universal PCR Master Mix (Applied Biosystems). To be specific, a master mix (12.5 µl), a primer (0.9 µM), a probe (0.25 µM) and a cDNA solution of each sample (1 µl) were mixed and distilled water was added to the total amount of 25 µl. For the reaction by the ABI PRISM 7700 SequenceDetector, a cycle of 50° C. 2 min, 95° C. 10 min, 95° C. 15 sec and 60° C. 1 min was repeated 40 times.

As a result, expression of 6508 copies was observed per total RNA 25 ng of NCI-H716 cells.

EXPERIMENTAL EXAMPLE 9

Intracellular cAMP Production Increasing Action in NCI-H716 Cells

NCI-H716 (ATCC) was suspended in a medium (Dulbecco's Modified Eagle Medium (DMEM, Invitrogen) supplemented with 10% fetal bovine serum (Invitrogen), 100 U/ml penicillin and 100 µg/ml streptomycin), seeded in a 96 well plate, cultured for 2 days and used for cAMP production assay. As a cAMP assay buffer, modified Krebs-Ringer bicarbonate buffer (KRBH, 116 mM NaCl, 4.7 mM KCl, 1.2 mM $KH_2PO_4$, 1.2 MM $MgSO_4$, 2.5 mM $CaCl_2$, 25 mM $NaHCO_3$, 24 mM HEPES pH 7.3), supplemented with glucose 5.5 mM, bovine serum albumin (BSA) 0.1%, and 3-isobutyl-1-methylxanthine (IBMX, Sigma) 1 mM, was used. The cells were washed once with cAMP assay buffer. Bile acids (50 µM) diluted with cAMP assay buffer or the compounds of the present invention (10 µM) were added thereto and the cells were incubated for 2 hrs. The culture supernatant was discarded, and the cAMP production amount was measured by cAMP Screen System (ABI). The results are shown in Table 8. In the Table, Base means non-addition of a test compound.

TABLE 8

Intracellular cAMP production increasing action of test compounds in NCI-H716 cells

| test compounds (Example No) | | cAMP production increasing activity* (%) |
|---|---|---|
| Base | | 11 |
| Example 9C | 10 µM | 109 |
| Example 14 | 10 µM | 104 |
| Example 22C | 10 µM | 100 |
| Example 46 | 10 µM | 112 |
| TLCA | 50 µM | 100 |
| LCA | 50 µM | 107 |

*Production amount in TLCA (50 µM) was 100%.

As shown in Table 8, bile acids [TLCA (taurolithocholic acid), LCA (lithocholic acid)], which are endogenous agonists for TGR5 and the compounds of he present invention showed a cAMP production increasing action. From these results, it was shown that endogenous agonists for TGR5 and the compounds of the resent invention increase cAMP production in NCI-H716 cells via TGR5.

EXPERIMENTAL EXAMPLE 10

Increasing Effect on GLP-1 Secretion from NCI-H716 Cell Line

NCI-H716 cells secrete Glucagon-like peptide-1 (GLP-1). GLP-1 is a peptide useful for controlling blood glucose level because it acts on the pancreas to cause secretion of insulin and the like. In the same manner as in Experimental Example 9, NCI-H716 (ATCC) was seeded in a 96 well plate and, after incubation for 2 days, used for the following secretion test. As a buffer for secretion test, modified Krebs-Ringer bicarbonate buffer (KRBH, 116 mM NaCl, 4.7 mM KCl, 1.2 mM $KH_2PO_4$, 1.2 mM $MgSO_4$, 2.5 mM $CaCl_2$, 25 mM $NaHCO_3$, 24 mM HEPES, pH 7.3) supplemented with glucose 5.5 mM and BSA 0.1% was used. The cells were washed once with the buffer for secretion test, preincubated at 37° C. under 5% $CO_2$, bile acid diluted with the buffer for secretion test was added and the cells were cultured at 37° C. under 5% $CO_2$ for 2 hrs. The cell culture supernatant was collected, cryopreserved and the GLP-1 content in the supernatant was measured using a GLP-1 measurement EIA kit (Linco) The results are shown in Table 9. In the Table, Base means non-addition of a test compound.

TABLE 9

Increasing effect of test compounds on GLP-1 secretion from NCI-H716 cell line

| test compounds (Example No) | | GLP-1 secretion increase** (%) |
|---|---|---|
| Base | | 100 |
| Example 14 | 5 µM | 157 |
| Example 22C | 5 µM | 127 |
| Example 46 | 5 µM | 165 |
| TLCA | 25 µM | 124 |
| LCA | 25 µM | 121 |

**Secretion amount in Base was 100%.

As shown in Table 9, bile acids [TLCA (taurolithocholic acid), LCA (lithocholic acid)], which are endogenous agonists for TGR5, and the compounds of the present invention increased GLP-1 secretion. From these results, it was shown that endogenous agonists for TGR5 and the compounds of the present invention increased GLP-1 in NCI-H716 cells via TGR5.

EXPERIMENTAL EXAMPLE 11 cAMP Production Increasing Activity of the Compounds of the Present Invention in Guinea Pig TGR5-Expressing CHO Cells First, cloning of cDNA encoding guinea pig-derived TGR5 and determination of its nucleotide sequence were performed.

PCR was performed using guinea pig spleen cDNA as a template and primer (SEQ ID NO: 13) and primer 2 (SEQ ID NO: 14). PCR was performed using GC melt DNA Polymerase (Clonetech) under 1) 95° C. 2 min, 2) 35 cycles of 98° C. 10 sec, 63° C. 20 sec and 72° C. 1 min, and then elongation reaction at 72° C. 7 min. After the reaction, the amplification product was cleaved with restriction enzymes SalI and SpeI and cloned into pAKKO111H. This was introduced into

*Escherichia coli* DH5alpha (Toyobo) and the clones having the plasmid were selected from LB agar medium containing ampicillin. By the analysis of the nucleotide sequence of each clone, a cDNA sequence (SEQ ID NO: 11) encoding a novel G protein coupled receptor protein was obtained. A novel protein containing an amino acid sequence (SEQ ID NO: 12) derived from the cDNA was named as guinea pig TGR5. In addition, the transformant was named as *Escherichia coli* DH5alpha/pAKKO guinea pig TGR5. Using the transformant, guinea pig type TGR5 expressing CHO cells were prepared according to the method described in WO02/84286.

The guinea pig type TGR5 expressing CHO cells were seeded in one 150 cm$^2$ flask at 1×10$^7$ cells, and cultured overnight at 37° C., 5% $CO_2$. After culture, the cells were detached with 0.5 mM EDTA/PBS, washed with PBS, and suspended in Buffer 1 (HBSS+0.1% BSA, 25 mM HEPES pH 7.3, 0.5 mM IBMX) at a density of 1×10$^7$ cells/ml. The obtained cell suspension (460 µl), anti-cAMP acceptor beads (23 µl) of AlphaScreen cAMP assay kit (Perkin Elmer) and Buffer 1 (667 µl) were mixed and dispensed to a white 96 well plate (Costar) by 10 µl. Then, a test compound diluted with Buffer 1 was added to each well by 10 µl. At this time, one row of the plate was free of the cell suspension but added with anti-cAMP acceptor beads (9 µl) and Buffer 1 (441 µl) alone, and serial dilutions of cAMP were added instead of the test compound and used as the standard. A mixture of the cell suspension and the test compound contained in the plate was allowed to react at room temperature for 30 min. After 30 min, a mixture of Buffer 2 (HBSS+0.1% BSA, 25 mM HEPES pH 7.3, 1.5% Tween 20, 13.2 ml), Biotinyl cAMP (22 µl), and Streptavin donor beads (90.2 µl) of AlphaScreen cAMP assay kit was added to all wells of the plate by 30 µl. The plate was shaken at room temperature for 2.5 hrs and fluorescence intensity was measured by Fusion α (Parkin Elmer), and the cAMP concentration of each well was calculated using the cAMP standard on each plate.

The cAMP production amount by the test compound (2 µM) was shown in a relative value (control %) to the cAMP production amount with the addition achieving 10 µM of lithocholic acid (LCA), as 100%. The results are shown in Table 10. In the Table, the data show an average of 3 groups.

TABLE 10 cAMP production increasing activity of test compounds in guinea pig TGR5 expressing CHO cells

| test compounds (Example No.) | cAMP producing activity (control %) |
|---|---|
| LCA (lithocholic acid) | 100 |
| Example 14 | 76 |
| Example 30 | 86 |
| Example 43 | 82 |
| Example 46 | 77 |
| Example 22C | 101 |
| Example 23C | 119 |
| Example 32C | 89 |
| Example 33C | 111 |
| Example 42C | 104 |

Therefrom it is clear that the compounds of the present invention have a cAMP production increasing activity and are superior agonists for guinea pig TGR5.

EXPERIMENTAL EXAMPLE 12

Suppressing Activity on TNF and IL-6 Secretion in LPS-Stimulated Guinea Pig Peripheral Blood Mononuclear Cells The peripheral blood was taken from guinea pig, and mononuclear cell fraction was obtained by a density separation method using Ficoll-Paque PLUS (Amersham Pharmacia). The fraction at a concentration of 1×10$^5$/well was cultured for 16 hrs in the presence of 30 mg/ml LPS in a 96-well plate upon addition of bile acid or a test compound. The culture supernatant was collected and TNF and IL-6 in the supernatant were quantitated.

The TNF secretion amount in the culture supernatant was measured in the same manner as in Experimental Example 7.

The quantitation of IL-6 in the culture supernatant was performed using IL-6 dependent cell line 7TD1 (RIKEN Institute) with its growth promoting action as an index. First, 7TD1 cells were suspended in a basic medium (RPMI1640 (Invitrogen) supplemented with 1% non-essential amino acid (Invitrogen) and 55 µM 2-mercaptoethanol (Invitrogen)) and seeded in a 96-well plate at a concentration of 2×10$^3$/well. Immediately after seeding, peripheral blood mononuclear cell culture supernatant diluted with a dilution medium (the above-mentioned basic medium supplemented with 10% FBS) was added and the cells were cultured for 2 days. The IL-6 content was determined by measuring the growth of the 7TD1 cells in the obtained culture product using a CellTiter-Glo (Promega). As the standard sample, human recombinant IL-6 (Genzyme) was used. The results are shown in Tables 11 and 12.

TABLE 11

TNF secretion suppressing action of test compounds in LPS-stimulated guinea pig peripheral blood mononuclear cells

| LPS | test compounds (Example No.) | | $TNF_\alpha$ (pg/ml) |
|---|---|---|---|
| − | non-addition | | 13 |
| + | non-addition | | 160 |
| + | TLCA | 50 µM | 60 |
| + | Example 22C | 10 µM | 66 |
| + | Example 14 | 10 µM | 83 |

TABLE 12

IL-6 secretion suppressing action of test compounds in LPS-stimulated guinea pig peripheral blood mononuclear cells

| LPS | test compounds (Example No.) | | IL-6 (pg/ml) |
|---|---|---|---|
| − | non-addition | | 32 |
| + | non-addition | | 520 |
| + | TLCA | 50 µM | 260 |
| + | Example 22C | 10 µM | 170 |
| + | Example 14 | 10 µM | 260 |

As shown in Tables 11 and 12, bile acids [TLCA (taurolithocholic acid)], which are endogenous agonists for TGR5, and the compounds of the present invention showed a remarkable suppressing activity on TNF α and IL-6 secretion in LPS-stimulated guinea pig peripheral blood mononuclear cells. From these results, it was shown that the compounds of the present invention have a TNFα and IL-6 secretion suppressing action via TGR5 and that TGR5 is involved in the control of immune function in living organisms.

EXPERIMENTAL EXAMPLE 13 cAMP Production Increasing Activity of the Compounds of the Present Invention in Rat Type TGR5 Expressing CHO Cells The rat type TGR5 expressing CHO cells prepared according to the method described in WO02/84286 were seeded in one 150 cm² flask at 1×10⁷ cells, and cultured overnight at 37° C., 5% $CO_2$. After culture, the cells were detached with 0.5 mM EDTA/PBS, washed with PBS, and suspended in Buffer 1 (HBSS+0.1% BSA, 25 mM HEPES pH 7.3, 0.5 mM IBMX) at a density of 1×10⁷ cells/ml. The obtained cell suspension (460 μl), anti-cAMP acceptor beads (23 μl) of AlphaScreen cAMP assay kit (Perkin Elmer) and Buffer 1 (667 μl) were mixed and dispensed to a white 96 well plate (Costar) by 10 μl. Then, a test compound diluted with Buffer 1 was added to each well by 10 μl. At this time, one row of the plate was free of the cell suspension but added with anti-cAMP acceptor beads (9 μl) and Buffer 1 (441 μl) alone, and serial dilutions of cAMP were added instead of the test compound and used as the standard. A mixture of the cell suspension and the test compound contained in the plate was allowed to react at room temperature for 30 min. After 30 min, a mixture of Buffer 2 (HBSS+0.1% BSA, 25 mM HEPES pH 7.3, 1.5% Tween 20, 13.2 ml), Biotinyl cAMP (22 μl), and Streptavin donor beads (90.2 μl) of AlphaScreen cAMP assay kit was added to all wells of the plate by 30 μl. The plate was shaken at room temperature for 2.5 hrs and fluorescence intensity was measured by Fusion α (Parkin Elmer), and the cAMP concentration of each well was calculated using the cAMP standard on each plate.

The cAMP production amount by each of the test compounds (2 μM) was shown in a relative value (control %) to the cAMP production amount with the addition achieving 10 μM of lithocholic acid (LCA) as 100%. The results are shown in Table 13. In the Table, the data show an average of 3 groups.

TABLE 13 cAMP production increasing activity of test compounds in rat TGR5 expressing CHO cells

| test compounds | cAMP producing activity (control %) |
|---|---|
| LCA (lithocholic acid) | 100 |
| TDCA (taurodeoxycholic acid) | 140 |
| Reference Example 33 | 92 |
| Example 17 | 107 |
| Example 30 | 114 |
| Example 46 | 104 |
| Example 30B | 108 |
| Example 9C | 112 |
| Example 23C | 148 |
| Example 33C | 149 |
| Example 61C | 101 |

Therefrom it is clear that the compounds of the present invention have a cAMP production increasing activity and are superior agonists for rat TGR5.

EXPERIMENTAL EXAMPLE 14 cAMP Production Increasing Activity of the Compounds of the Present Invention in Human TGR5 Expressing CHO Cells In the same manner as in Experimental Example 1, cAMP production increasing activity of the test compound was measured. The cAMP production amount by the test compound was shown in a relative value (control %) to the cAMP production amount with the addition achieving 1 μM of lithocholic acid (LCA) as 100%, and the concentration ($EC_{50}$ value) necessary to make the cAMP production amount of the test compound 50% was calculated. As a result, the $EC_{50}$ value (nM) was 300-600 for lithocholic acid, and those of the compounds of Reference Example 33, Example 14, Example 17, Example 30, Example 43, Example 46, Example 60, Example 23B, Example 30B, Example 33C, Example 42C, Example 45C, Example 60C and Example 61C were less than 100.

Therefrom it is clear that the compounds of the present invention have a superior cAMP production increasing activity and are superior agonists for human TGR5.

EXPERIMENTAL EXAMPLE 15

GLP-1 Secretion from Guinea Pig Intestine Primary Culture Cells

Colon mucous membrane of guinea pig (Hartley, male, Charles River Japan, Inc.) was removed and subjected to an enzyme treatment to give a cell dispersion according to the following method.

The enzyme solution used was obtained by dissolving 5 mg/ml Collagenase (Sigma), 5 mg/ml Hyaluronidase (Sigma) and 0.5 mg/ml DNaseI (Sigma) in a medium. The medium used was Dulbecco's Modified Eagle Medium (DMEM, Invitrogen) supplemented with 4.5 g/l Glucose, 5% FBS (Invitrogen), 100 units/ml Penicillin (Invitrogen), 100 μg/ml Streptomycin (Invitrogen), 50 μg/ml Gentamicin (Invitrogen) and 20 mM Hepes (pH 7.3). After digestion by the enzyme solution at 37° C., the tissue sections were prepared into dispersed cells by passing through a pipette 4 times and the cells were collected. The collected cells were washed with a buffer (incubation buffer) obtained by adding 5.5 mM Glucose and 0.1% BSA to a modified Krebs-Ringer bicarbonate buffer (KRBH, 116 mM NaCl, 4.7 mM KCl, 1.2 mM $KH_2PO_4$, 1.2 MM $MgSO_4$, 2.5 mM $CaCl_2$, 25 mM $NaHCO_3$, 24 mM HEPES, pH 7.3), and preincubated at 37° C. under 5% $CO_2$ for 30 min. 0.1 μM Phorbol ester (Wako), 1% DPPIV inhibitor (Linco) and a test compound were added to the above-mentioned incubation buffer, and the obtained buffer was added to the cells after the aforementioned preincubation and incubated for 90 min. The culture supernatant was collected and cryopreserved. The concentration of GLP-1 released in the culture supernatant was measured using an ELISA kit (Linco). The results are shown in Table 14.

TABLE 14

GLP-1 secretion from guinea pig intestine
primary culture cells by test compounds

| test compounds (Example No.) | | GLP-1 (% relative to non-addition) |
|---|---|---|
| non-addition | | 100 |
| TLCA | 50 μM | 400 |
| LCA | 50 μM | 333 |
| Example 22C | 10 μM | 313 |
| Example 14 | 10 μM | 167 |

Therefrom it has been made clear that bile acids [TLCA (taurolithocholic acid), LCA (lithocholic acid)], which are endogenous agonists for TGR5, and the compounds of the present invention promote GLP-1 secretion from guinea pig intestine primary culture cells.

EXPERIMENTAL EXAMPLE 16

GLP-1 Secretion from Rat Intestine Primary Culture Cells

Terminal ileum and colon mucous membrane were removed from rat (Wistar, male, Charles River Japan, Inc.) and subjected to an enzyme treatment to give a cell dispersion according to the following method.

The enzyme solution used was obtained by dissolving 5 mg/ml Collagenase (Sigma), 5 mg/ml Hyaluronidase (Sigma) and 0.5 mg/ml DNaseI (Sigma) in a medium. The medium used was Dulbecco's Modified Eagle Medium (DMEM, Invitrogen) supplemented with 4.5 g/l Glucose, 5% FBS (Invitrogen), 100 units/ml Penicillin (Invitrogen), 100 μg/ml Streptomycin (Invitrogen), 50 μg/ml Gentamicin (Invitrogen) and 20 mM Hepes (pH 7.3). After digestion by the enzyme solution at 37° C., the tissue sections were prepared into dispersed cells by passing through a pipette 7 times and the cells were collected. The collected cells were washed with a buffer (incubation buffer) obtained by adding 5.5 mM Glucose and 0.1% BSA to a modified Krebs-Ringer bicarbonate buffer (KRBH, 116 mM NaCl, 4.7 mM KCl, 1.2 mM $KH_2PO_4$, 1.2 mM $MgSO_4$, 2.5 mM $CaCl_2$, 25 mM $NaHCO_3$, 24 mM HEPES, pH 7.3), and preincubated at 37° C. under 5% $CO_2$ for 30 min. 0.1 μM Phorbol ester (Wako), 1% DPPIV inhibitor (Linco) and a test compound were added to the above-mentioned incubation buffer, and the obtained buffer was added to the cells after the aforementioned preincubation and incubated for 150 min. The culture supernatant was collected and cryopreserved. The concentration of GLP-1 released in the culture supernatant was measured using an ELISA kit (Linco). The results are shown in Table 15.

TABLE 15

GLP-1 secretion from rat intestine primary
culture cells by test compounds

| test compounds (Example No.) | | GLP-1 (% relative to non-addition) |
|---|---|---|
| non-addition | | 100 |
| TLCA | 100 μM | 290 |
| LCA | 100 μM | 219 |
| Example 23C | 20 μM | 133 |
| Reference Example 33 | 20 μM | 201 |
| Example 33C | 20 μM | 214 |

Therefrom it was confirmed that bile acids [TDCA (taurodeoxycholic acid), LCA (lithocholic acid)], which are endogenous agonists for TGR5, and the compounds of the present invention have a promoting activity on GLP-1 secretion from rat intestine primary culture cells.

INDUSTRIAL APPLICABILITY

The TGR5 receptor agonist of the present invention has a superior TGR5 receptor activating action and is useful for the treatment of various diseases.

In addition, by the use of the compound of the present invention and TGR5, TGR5 ligand, agonist or antagonist can be efficiently screened for.

The invention claimed is:
1. A compound represented by the formula

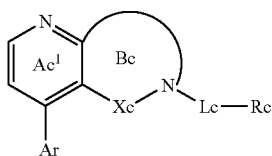
(IC')

wherein
ring $Ac^1$ is a pyridine ring optionally having 1 to 4 substituents selected from the following Group A:
[Group A]
  a halogen atom,
  an optionally halogenated $C_{1-6}$ alkyl group,
  an amino-$C_{1-6}$ alkyl group,
  a $C_{1-6}$ alkoxy-carbonylamino-$C_{1-6}$ alkyl group,
  a $C_{2-6}$ alkenyl group,
  a $C_{2-6}$ alkynyl group,
  a $C_{3-8}$ cycloalkyl group,
  a heterocyclic group selected from a monocyclic heterocyclic group, a bi- or tricyclic fused heterocyclic group and a reduced form thereof,
  a $C_{7-14}$ aralkyl group,
  an optionally halogenated $C_{1-6}$ alkoxy group,
  a $C_{6-14}$ aryloxy group,
  a heterocyclyloxy group,
  a $C_{7-14}$ aralkyloxy group,
  a formyloxy group,
  a $C_{1-6}$ alkyl-carbonyloxy group,
  an optionally halogenated $C_{1-6}$ alkylthio group,
  a $C_{1-6}$ alkylsulfinyl group,
  a hydroxy group,
  a mercapto group,
  a cyano group,
  a nitro group,
  a carboxyl group,
  a formyl group,
  an optionally halogenated $C_{1-6}$ alkyl-carbonyl group,
  a $C_{6-14}$ aryl-carbonyl group,
  a heterocyclyl-carbonyl group,
  a $C_{1-6}$ alkoxy-carbonyl group,
  a $C_{6-14}$ aryloxy-carbonyl group,
  an amino group,
  a mono- or di-$C_{1-6}$ alkylamino group,
  a formylamino group,
  an optionally halogenated $C_{1-6}$ alkyl-carbonylamino group,
  a $C_{1-6}$ alkoxy-carbonylamino group,
  an ureido group,
  a mono-, di- or tri-$C_{1-6}$ alkyl-ureido group,
  an optionally halogenated $C_{1-6}$ alkyl-sulfonylamino group,
  a carbamoyl group,
  a mono- or di-$C_{1-6}$ alkyl-carbamoyl group,
  a sulfo group,
  an optionally halogenated $C_{1-6}$ alkylsulfonyl group,
  a $C_{6-14}$ arylsulfonyl group,
  a heterocyclyl-sulfonyl group,
  a sulfamoyl group,
  a mono- or di-$C_{1-6}$ alkyl-sulfamoyl group,
  a $C_{6-14}$ aryl-carbonyl-$C_{1-6}$ alkoxy group,
  a hydroxy-$C_{1-6}$ alkoxy group,
  a $C_{1-6}$ alkoxy-carbonyl-$C_{1-6}$ alkoxy group,
  a $C_{3-14}$ cycloalkyl-$C_{1-6}$ alkoxy group,
  a heterocyclyl-$C_{1-6}$ alkoxy group,
  a $C_{7-14}$ aralkyloxy-carbonyl-$C_{1-6}$ alkoxy group,
  a hydroxyphenyl-$C_{1-6}$ alkoxy group,
  a $C_{7-14}$ aralkyloxy-carbonyl group,
  a mono- or di-$C_{1-6}$ alkylamino-$C_{1-6}$ alkoxy,
  a mono- or di-$C_{1-6}$ alkylamino-carbonyloxy, and
  a $C_{6-14}$ aryl group optionally having 1 to 4 substituents selected from a halogen atom, a nitro group, a cyano group, a $C_{1-6}$ alkyl group, an amino group optionally mono- or di-substituted by a $C_{1-6}$ alkyl group, a hydroxy group and a $C_{1-6}$ alkoxy group;
ring Bc is

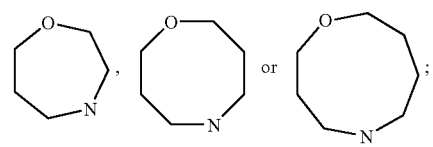

Xc is a methylene group;
Ar is a $C_{6-14}$ aryl group optionally having 1 to 4 substituents selected from a halogen atom, a nitro group, a cyano group, a $C_{1-6}$ alkyl group, an amino group optionally mono- or di-substituted by a $C_{1-6}$ alkyl group, a hydroxy group and a $C_{1-6}$ alkoxy group;
Rc is a cyclic group selected from
(a) a 5- or 6-membered monocyclic heterocyclic group having, as ring-constituting atom(s) besides a carbon atom, 1 to 4 hetero atoms selected from a nitrogen atom, an oxygen atom and a sulfur atom,
(b) a bi- or tricyclic fused heterocyclic group, and
(c) a $C_{6-14}$ aryl group,
each of (a) to (c) optionally having 1 to 4 substituents selected from the above mentioned Group A; and
Lc is
(a) a $C_{1-3}$ alkylene group optionally having 1 to 3 substituents selected from a halogen atom,
a nitro group,
a cyano group,
an amino group optionally mono- or di-substituted by a $C_{1-6}$ alkyl group,
a hydroxy group,
an optionally halogenated $C_{1-6}$ alkoxy group,
an oxo group, a thioxo group,
a $C_{6-14}$ aryl group, and
a heterocyclic group,
(b) —CONH—, or
(c) —SO$_2$—,
or a salt thereof.

2. The compound of claim 1, wherein the cyclic group for Rc is a phenyl group.

3. The compound of claim 1, wherein Rc is a 3,5-bis(trifluoromethyl)phenyl group.

4. The compound of claim 1, wherein Lc is a $C_{1-3}$ alkylene group optionally substituted by an oxo group, or —SO$_2$—.

5. The compound of claim 1, wherein Ar is a phenyl group optionally having 1 to 4 substituents selected from a halogen atom, a nitro group, a cyano group, a $C_{1-6}$ alkyl group, an amino group optionally mono- or di-substituted by a $C_{1-6}$ alkyl group, a hydroxy group and a $C_{1-6}$ alkoxy group.

6. A pharmaceutical composition comprising an effective amount of the compound of claim 1 and a pharmaceutically acceptable carrier.

7. The compound of claim 1, wherein
ring $Ac^1$ is a pyridine ring optionally having 1 to 4 $C_{1-6}$ alkyl groups;
Ar is a $C_{6-14}$ aryl group optionally having 1 to 4 substituents selected from a halogen atom and a $C_{1-6}$ alkyl group;
Rc is a cyclic group selected from
(a) a 5- or 6-membered monocyclic heterocyclic group having, as ring-constituting atom(s) besides a carbon atom, 1 to 4 hetero atoms selected from a nitrogen atom, an oxygen atom and a sulfur atom,
(b) a bicyclic fused heterocyclic group, and
(c) a $C_{6-14}$ aryl group, each of (a) to (c) optionally having 1 to 4 substituents selected from
a halogen atom,
an optionally halogenated $C_{1-6}$ alkyl group,
an amino-$C_{1-6}$ alkyl group,
a $C_{1-6}$ alkoxy-carbonylamino-$C_{1-6}$ alkyl group,
an optionally halogenated $C_{1-6}$ alkoxy group,
a cyano group, and
a nitro group; and
Lc is
(a) a $C_{1-3}$ alkylene group optionally substituted by an oxo group,
(b) —CONH—, or
(c) —SO$_2$—.

* * * * *

SEQUENCE LISTING

```
<160> NUMBER OF SEQ ID NOS: 14

<210> SEQ ID NO 1
<211> LENGTH: 990
<212> TYPE: DNA
<213> ORGANISM: Homo sapiens
<220> FEATURE:
<221> NAME/KEY: CDS
<222> LOCATION: (1)..(990)
<223> OTHER INFORMATION:

<400> SEQUENCE: 1 atg acg ccc aac agc act ggc gag gtg ccc agc ccc att ccc aag ggg      48
Met Thr Pro Asn Ser Thr Gly Glu Val Pro Ser Pro Ile Pro Lys Gly
1               5                   10                  15 gct ttg ggg ctc tcc ctg gcc ctg gca agc ctc atc atc acc gcg aac      96
Ala Leu Gly Leu Ser Leu Ala Leu Ala Ser Leu Ile Ile Thr Ala Asn
                20                  25                  30 ctg ctc cta gcc ctg ggc atc gcc tgg gac cgc cgc ctg cgc agc cca     144
Leu Leu Leu Ala Leu Gly Ile Ala Trp Asp Arg Arg Leu Arg Ser Pro
            35                  40                  45
```

| | | |
|---|---|---|
| cct gct ggc tgc ttc ttc ctg agc cta ctg ctg gct ggg ctg ctc acg<br>Pro Ala Gly Cys Phe Phe Leu Ser Leu Leu Leu Ala Gly Leu Leu Thr<br>50                          55                      60 | 192 |
| ggt ctg gca ttg ccc aca ttg cca ggg ctg tgg aac cag agt cgc cgg<br>Gly Leu Ala Leu Pro Thr Leu Pro Gly Leu Trp Asn Gln Ser Arg Arg<br>65                        70                    75                      80 | 240 |
| ggt tac tgg tcc tgc ctc ctc gtc tac ttg gct ccc aac ttc tcc ttc<br>Gly Tyr Trp Ser Cys Leu Leu Val Tyr Leu Ala Pro Asn Phe Ser Phe<br>                      85                    90                      95 | 288 |
| ctc tcc ctg ctt gcc aac ctc ttg ctg gtg cac ggg gag cgc tac atg<br>Leu Ser Leu Leu Ala Asn Leu Leu Leu Val His Gly Glu Arg Tyr Met<br>                100                   105                  110 | 336 |
| gca gtc ctg agg cca ctc cag ccc cct ggg agc att cgg ctg gcc ctg<br>Ala Val Leu Arg Pro Leu Gln Pro Pro Gly Ser Ile Arg Leu Ala Leu<br>      115                      120                    125 | 384 |
| ctc ctc acc tgg gct ggt ccc ctg ctc ttt gcc agt ctg ccc gct ctg<br>Leu Leu Thr Trp Ala Gly Pro Leu Leu Phe Ala Ser Leu Pro Ala Leu<br>130                        135                    140 | 432 |
| ggg tgg aac cac tgg acc cct ggt gcc aac tgc agc tcc cag gct atc<br>Gly Trp Asn His Trp Thr Pro Gly Ala Asn Cys Ser Ser Gln Ala Ile<br>145                        150                    155                  160 | 480 |
| ttc cca gcc ccc tac ctg tac ctc gaa gtc tat ggg ctc ctg ctg ccc<br>Phe Pro Ala Pro Tyr Leu Tyr Leu Glu Val Tyr Gly Leu Leu Leu Pro<br>                      165                    170                  175 | 528 |
| gcc gtg ggt gct gct gcc ttc ctc tct gtc cgc gtg ctg gcc act gcc<br>Ala Val Gly Ala Ala Ala Phe Leu Ser Val Arg Val Leu Ala Thr Ala<br>                180                   185                  190 | 576 |
| cac cgc cag ctg cag gac atc tgc cgg ctg gag cgg gca gtg tgc cgc<br>His Arg Gln Leu Gln Asp Ile Cys Arg Leu Glu Arg Ala Val Cys Arg<br>      195                      200                    205 | 624 |
| gat gag ccc tcc gcc ctg gcc cgg gcc ctt acc tgg agg cag gca agg<br>Asp Glu Pro Ser Ala Leu Ala Arg Ala Leu Thr Trp Arg Gln Ala Arg<br>210                        215                    220 | 672 |
| gca cag gct gga gcc atg ctg ctc ttc ggg ctg tgc tgg ggg ccc tac<br>Ala Gln Ala Gly Ala Met Leu Leu Phe Gly Leu Cys Trp Gly Pro Tyr<br>225                        230                    235                  240 | 720 |
| gtg gcc aca ctg ctc ctc tca gtc ctg gcc tat gag cag cgc ccg cca<br>Val Ala Thr Leu Leu Leu Ser Val Leu Ala Tyr Glu Gln Arg Pro Pro<br>                      245                    250                  255 | 768 |
| ctg ggg cct ggg aca ctg ttg tcc ctc ctc cta gga agt gcc agt<br>Leu Gly Pro Gly Thr Leu Leu Ser Leu Leu Ser Leu Gly Ser Ala Ser<br>                  260                    265                  270 | 816 |
| gca gcg gca gtg ccc gta gcc atg ggg ctg ggc gat cag cgc tac aca<br>Ala Ala Ala Val Pro Val Ala Met Gly Leu Gly Asp Gln Arg Tyr Thr<br>            275                      280                    285 | 864 |
| gcc ccc tgg agg gca gcc gcc caa agg tgc ctg cag ggg ctg tgg gga<br>Ala Pro Trp Arg Ala Ala Ala Gln Arg Cys Leu Gln Gly Leu Trp Gly<br>290                        295                    300 | 912 |
| aga gcc tcc cgg gac agt ccc ggc ccc agc att gcc tac cac cca agc<br>Arg Ala Ser Arg Asp Ser Pro Gly Pro Ser Ile Ala Tyr His Pro Ser<br>305                        310                    315                  320 | 960 |
| agc caa agc agt gtc gac ctg gac ttg aac<br>Ser Gln Ser Ser Val Asp Leu Asp Leu Asn<br>                      325                    330 | 990 |

<210> SEQ ID NO 2
<211> LENGTH: 330
<212> TYPE: PRT
<213> ORGANISM: Homo sapiens

<400> SEQUENCE: 2

```
Met Thr Pro Asn Ser Thr Gly Glu Val Pro Ser Pro Ile Pro Lys Gly
1               5                   10                  15

Ala Leu Gly Leu Ser Leu Ala Leu Ala Ser Leu Ile Ile Thr Ala Asn
            20                  25                  30

Leu Leu Leu Ala Leu Gly Ile Ala Trp Asp Arg Arg Leu Arg Ser Pro
        35                  40                  45

Pro Ala Gly Cys Phe Phe Leu Ser Leu Leu Ala Gly Leu Leu Thr
    50                  55                  60

Gly Leu Ala Leu Pro Thr Leu Pro Gly Leu Trp Asn Gln Ser Arg Arg
65                  70                  75                  80

Gly Tyr Trp Ser Cys Leu Leu Val Tyr Leu Ala Pro Asn Phe Ser Phe
                85                  90                  95

Leu Ser Leu Leu Ala Asn Leu Leu Val His Gly Glu Arg Tyr Met
                100                 105                 110

Ala Val Leu Arg Pro Leu Gln Pro Pro Gly Ser Ile Arg Leu Ala Leu
            115                 120                 125

Leu Leu Thr Trp Ala Gly Pro Leu Leu Phe Ala Ser Leu Pro Ala Leu
        130                 135                 140

Gly Trp Asn His Trp Thr Pro Gly Ala Asn Cys Ser Ser Gln Ala Ile
145                 150                 155                 160

Phe Pro Ala Pro Tyr Leu Tyr Leu Glu Val Tyr Gly Leu Leu Leu Pro
                165                 170                 175

Ala Val Gly Ala Ala Ala Phe Leu Ser Val Arg Val Leu Ala Thr Ala
            180                 185                 190

His Arg Gln Leu Gln Asp Ile Cys Arg Leu Glu Arg Ala Val Cys Arg
            195                 200                 205

Asp Glu Pro Ser Ala Leu Ala Arg Ala Leu Thr Trp Arg Gln Ala Arg
            210                 215                 220

Ala Gln Ala Gly Ala Met Leu Leu Phe Gly Leu Cys Trp Gly Pro Tyr
225                 230                 235                 240

Val Ala Thr Leu Leu Leu Ser Val Leu Ala Tyr Glu Gln Arg Pro Pro
                245                 250                 255

Leu Gly Pro Gly Thr Leu Leu Ser Leu Leu Ser Leu Gly Ser Ala Ser
            260                 265                 270

Ala Ala Ala Val Pro Val Ala Met Gly Leu Gly Asp Gln Arg Tyr Thr
            275                 280                 285

Ala Pro Trp Arg Ala Ala Gln Arg Cys Leu Gln Gly Leu Trp Gly
            290                 295                 300

Arg Ala Ser Arg Asp Ser Pro Gly Pro Ser Ile Ala Tyr His Pro Ser
305                 310                 315                 320

Ser Gln Ser Ser Val Asp Leu Asp Leu Asn
                325                 330
```

<210> SEQ ID NO 3
<211> LENGTH: 987
<212> TYPE: DNA
<213> ORGANISM: Mus musculus
<220> FEATURE:
<221> NAME/KEY: CDS
<222> LOCATION: (1)..(987)
<223> OTHER INFORMATION:

<400> SEQUENCE: 3

```
atg atg aca ccc aac agc act gag ctg tcg gcc att ccc atg ggg gtt      48
Met Met Thr Pro Asn Ser Thr Glu Leu Ser Ala Ile Pro Met Gly Val
1               5                   10                  15
```

-continued

```
ctg ggg ctt tcc ttg gcc ctg gca agc ctc atc gtc atc gcc aac ctg      96
Leu Gly Leu Ser Leu Ala Leu Ala Ser Leu Ile Val Ile Ala Asn Leu
         20                  25                  30 ctc ctg gcc cta ggc atc gcc ctg gac cgc cac ttg cgc agc cca cct     144
Leu Leu Ala Leu Gly Ile Ala Leu Asp Arg His Leu Arg Ser Pro Pro
 35                  40                  45 gct ggc tgc ttc ttc cta agc cta cta cta gcc ggg ctg ctc aca ggg     192
Ala Gly Cys Phe Phe Leu Ser Leu Leu Leu Ala Gly Leu Leu Thr Gly
 50                  55                  60 ctg gca ctg ccc atg ctg cct ggg cta tgg agc cgg aac cat cag ggc     240
Leu Ala Leu Pro Met Leu Pro Gly Leu Trp Ser Arg Asn His Gln Gly
65                   70                  75                  80 tac tgg tcc tgc ctc ctt ctc cac ttg acc ccc aac ttt tgt ttc ctt     288
Tyr Trp Ser Cys Leu Leu Leu His Leu Thr Pro Asn Phe Cys Phe Leu
                 85                  90                  95 tcc ctg ctt gcc aat ctg ctg ctg gtg cat ggg gaa cgc tac atg gca     336
Ser Leu Leu Ala Asn Leu Leu Leu Val His Gly Glu Arg Tyr Met Ala
            100                 105                 110 gtg ttg cag cca ctc cgg ccc cat gga agt gtg cgg cta gcc ctg ttc     384
Val Leu Gln Pro Leu Arg Pro His Gly Ser Val Arg Leu Ala Leu Phe
        115                 120                 125 ctc acc tgg gtc agc tcc ctg ttc ttt gcc agc ctg cct gct ctg ggc     432
Leu Thr Trp Val Ser Ser Leu Phe Phe Ala Ser Leu Pro Ala Leu Gly
130                 135                 140 tgg aac cat tgg agc cct gat gcc aac tgc agc tcc caa gct gtc ttc     480
Trp Asn His Trp Ser Pro Asp Ala Asn Cys Ser Ser Gln Ala Val Phe
145                 150                 155                 160 cca gcc ccc tac ctc tac ctg gaa gtt tat ggc ctc ctg ttg cct gcc     528
Pro Ala Pro Tyr Leu Tyr Leu Glu Val Tyr Gly Leu Leu Leu Pro Ala
                165                 170                 175 gtg ggg gcc act gcc ctt ctc tct gtc cgc gtg ttg gcc act gcc cac     576
Val Gly Ala Thr Ala Leu Leu Ser Val Arg Val Leu Ala Thr Ala His
            180                 185                 190 cgc cag ctg tgt gag atc cgc cga ctg gag cgg gca gtg tgc cgc gat     624
Arg Gln Leu Cys Glu Ile Arg Arg Leu Glu Arg Ala Val Cys Arg Asp
        195                 200                 205 gta ccc tca acc ctg gct agg gct ctc acc tgg agg cag gct agg gca     672
Val Pro Ser Thr Leu Ala Arg Ala Leu Thr Trp Arg Gln Ala Arg Ala
210                 215                 220 cag gca gga gcc aca ctg ctc ttc ttg ctg tgt tgg ggg ccc tat gtg     720
Gln Ala Gly Ala Thr Leu Leu Phe Leu Leu Cys Trp Gly Pro Tyr Val
225                 230                 235                 240 gcc aca ttg ctc ctg tca gtc ttg gcc tat gag cgt cgc cca cca cta     768
Ala Thr Leu Leu Leu Ser Val Leu Ala Tyr Glu Arg Arg Pro Pro Leu
                245                 250                 255 ggg cct gga act ctg tta tcg ctc atc tca ttg ggc agc acc agt gct     816
Gly Pro Gly Thr Leu Leu Ser Leu Ile Ser Leu Gly Ser Thr Ser Ala
            260                 265                 270 gcc gct gtg cct gtg gcc atg ggg ctg ggt gat cag cgc tac aca gcc     864
Ala Ala Val Pro Val Ala Met Gly Leu Gly Asp Gln Arg Tyr Thr Ala
        275                 280                 285 ccc tgg agg aca gct gcc caa agg tgt cta cga gtg ctt cga gga aga     912
Pro Trp Arg Thr Ala Ala Gln Arg Cys Leu Arg Val Leu Arg Gly Arg
290                 295                 300 gcc aag agg gac aat cca ggc ccc agc act gcc tac cac acc agt agc     960
Ala Lys Arg Asp Asn Pro Gly Pro Ser Thr Ala Tyr His Thr Ser Ser
305                 310                 315                 320 caa tgc agc att gac ctg gac ttg aat                                 987
Gln Cys Ser Ile Asp Leu Asp Leu Asn
```

<210> SEQ ID NO 4
<211> LENGTH: 329
<212> TYPE: PRT
<213> ORGANISM: Mus musculus

<400> SEQUENCE: 4

Met Met Thr Pro Asn Ser Thr Glu Leu Ser Ala Ile Pro Met Gly Val
1               5                   10                  15

Leu Gly Leu Ser Leu Ala Leu Ala Ser Leu Ile Val Ile Ala Asn Leu
            20                  25                  30

Leu Leu Ala Leu Gly Ile Ala Leu Asp Arg His Leu Arg Ser Pro Pro
        35                  40                  45

Ala Gly Cys Phe Phe Leu Ser Leu Leu Leu Ala Gly Leu Leu Thr Gly
    50                  55                  60

Leu Ala Leu Pro Met Leu Pro Gly Leu Trp Ser Arg Asn His Gln Gly
65                  70                  75                  80

Tyr Trp Ser Cys Leu Leu Leu His Leu Thr Pro Asn Phe Cys Phe Leu
                85                  90                  95

Ser Leu Leu Ala Asn Leu Leu Leu Val His Gly Glu Arg Tyr Met Ala
            100                 105                 110

Val Leu Gln Pro Leu Arg Pro His Gly Ser Val Arg Leu Ala Leu Phe
        115                 120                 125

Leu Thr Trp Val Ser Ser Leu Phe Phe Ala Ser Leu Pro Ala Leu Gly
    130                 135                 140

Trp Asn His Trp Ser Pro Asp Ala Asn Cys Ser Ser Gln Ala Val Phe
145                 150                 155                 160

Pro Ala Pro Tyr Leu Tyr Leu Glu Val Tyr Gly Leu Leu Leu Pro Ala
                165                 170                 175

Val Gly Ala Thr Ala Leu Leu Ser Val Arg Val Leu Ala Thr Ala His
            180                 185                 190

Arg Gln Leu Cys Glu Ile Arg Arg Leu Glu Arg Ala Val Cys Arg Asp
        195                 200                 205

Val Pro Ser Thr Leu Ala Arg Ala Leu Thr Trp Arg Gln Ala Arg Ala
    210                 215                 220

Gln Ala Gly Ala Thr Leu Leu Phe Leu Leu Cys Trp Gly Pro Tyr Val
225                 230                 235                 240

Ala Thr Leu Leu Leu Ser Val Leu Ala Tyr Glu Arg Arg Pro Pro Leu
                245                 250                 255

Gly Pro Gly Thr Leu Leu Ser Leu Ile Ser Leu Gly Ser Thr Ser Ala
            260                 265                 270

Ala Ala Val Pro Val Ala Met Gly Leu Gly Asp Gln Arg Tyr Thr Ala
        275                 280                 285

Pro Trp Arg Thr Ala Ala Gln Arg Cys Leu Arg Val Leu Arg Gly Arg
    290                 295                 300

Ala Lys Arg Asp Asn Pro Gly Pro Ser Thr Ala Tyr His Thr Ser Ser
305                 310                 315                 320

Gln Cys Ser Ile Asp Leu Asp Leu Asn
                325

<210> SEQ ID NO 5
<211> LENGTH: 987
<212> TYPE: DNA
<213> ORGANISM: Rattus norvegicus
<220> FEATURE:

```
<221> NAME/KEY: CDS
<222> LOCATION: (1)..(987)
<223> OTHER INFORMATION:

<400> SEQUENCE: 5
```

| | | | | | | | | | | | | | | | | |
|---|---|---|---|---|---|---|---|---|---|---|---|---|---|---|---|---|
| atg | atg | tca | cac | aac | acc | act | gag | ctg | tca | gcc | att | ccc | aga | ggg | gtt | 48 |
| Met | Met | Ser | His | Asn | Thr | Thr | Glu | Leu | Ser | Ala | Ile | Pro | Arg | Gly | Val | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| cag | gag | ctt | tcc | ctg | gtc | ctg | gca | agc | ctc | atc | gtc | atc | gcc | aac | ctg | 96 |
| Gln | Glu | Leu | Ser | Leu | Val | Leu | Ala | Ser | Leu | Ile | Val | Ile | Ala | Asn | Leu | |
| | | | 20 | | | | | 25 | | | | | 30 | | | |

| | | | | | | | | | | | | | | | | |
|---|---|---|---|---|---|---|---|---|---|---|---|---|---|---|---|---|
| ctc | ctg | gcc | cta | ggc | att | gtc | ctg | gac | cgc | cac | tta | cgc | agc | cca | cct | 144 |
| Leu | Leu | Ala | Leu | Gly | Ile | Val | Leu | Asp | Arg | His | Leu | Arg | Ser | Pro | Pro | |
| | | 35 | | | | | 40 | | | | | 45 | | | | |

| | | | | | | | | | | | | | | | | |
|---|---|---|---|---|---|---|---|---|---|---|---|---|---|---|---|---|
| gct | ggc | tgc | ttc | ttt | cta | agc | cta | cta | cta | gct | ggg | cta | ctc | aca | ggg | 192 |
| Ala | Gly | Cys | Phe | Phe | Leu | Ser | Leu | Leu | Leu | Ala | Gly | Leu | Leu | Thr | Gly | |
| | 50 | | | | | 55 | | | | | 60 | | | | | |

| | | | | | | | | | | | | | | | | |
|---|---|---|---|---|---|---|---|---|---|---|---|---|---|---|---|---|
| ttg | gca | ctg | ccc | acg | ctg | cct | ggg | cta | tgg | aat | agg | agc | cat | cag | ggg | 240 |
| Leu | Ala | Leu | Pro | Thr | Leu | Pro | Gly | Leu | Trp | Asn | Arg | Ser | His | Gln | Gly | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| tac | tgg | tcc | tgc | ctc | ctt | ctc | cac | ttg | gcc | ccc | aac | ttt | tgt | ttc | ctc | 288 |
| Tyr | Trp | Ser | Cys | Leu | Leu | Leu | His | Leu | Ala | Pro | Asn | Phe | Cys | Phe | Leu | |
| | | | 85 | | | | | 90 | | | | | 95 | | | |

| | | | | | | | | | | | | | | | | |
|---|---|---|---|---|---|---|---|---|---|---|---|---|---|---|---|---|
| tcc | ctg | ctt | gcc | aat | ctg | ctg | ctg | gtg | cat | ggg | gaa | cgc | tac | atg | gca | 336 |
| Ser | Leu | Leu | Ala | Asn | Leu | Leu | Leu | Val | His | Gly | Glu | Arg | Tyr | Met | Ala | |
| | | | 100 | | | | | 105 | | | | | 110 | | | |

| | | | | | | | | | | | | | | | | |
|---|---|---|---|---|---|---|---|---|---|---|---|---|---|---|---|---|
| gtg | ttg | cag | cca | ctc | cgg | ccc | cat | ggg | agt | gtg | cgg | cta | gcc | ctg | ttc | 384 |
| Val | Leu | Gln | Pro | Leu | Arg | Pro | His | Gly | Ser | Val | Arg | Leu | Ala | Leu | Phe | |
| | | | 115 | | | | | 120 | | | | | 125 | | | |

| | | | | | | | | | | | | | | | | |
|---|---|---|---|---|---|---|---|---|---|---|---|---|---|---|---|---|
| ctc | acc | tgg | atc | agc | tcc | ctg | ctc | ttt | gcc | agc | ctg | cct | gct | ctg | ggc | 432 |
| Leu | Thr | Trp | Ile | Ser | Ser | Leu | Leu | Phe | Ala | Ser | Leu | Pro | Ala | Leu | Gly | |
| | | 130 | | | | | 135 | | | | | 140 | | | | |

| | | | | | | | | | | | | | | | | |
|---|---|---|---|---|---|---|---|---|---|---|---|---|---|---|---|---|
| tgg | aac | cac | tgg | agt | cct | ggt | gcc | aac | tgc | agc | tcc | cag | gct | atc | ttc | 480 |
| Trp | Asn | His | Trp | Ser | Pro | Gly | Ala | Asn | Cys | Ser | Ser | Gln | Ala | Ile | Phe | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| cca | gcc | ccc | tac | ctt | tac | ctc | gaa | gtc | tat | ggg | ctc | ctg | ctc | ccc | gct | 528 |
| Pro | Ala | Pro | Tyr | Leu | Tyr | Leu | Glu | Val | Tyr | Gly | Leu | Leu | Leu | Pro | Ala | |
| | | | 165 | | | | | 170 | | | | | 175 | | | |

| | | | | | | | | | | | | | | | | |
|---|---|---|---|---|---|---|---|---|---|---|---|---|---|---|---|---|
| gtg | ggg | gcc | act | gcc | ctt | ctc | tct | gtc | cga | gtg | ttg | gcc | act | gcc | cac | 576 |
| Val | Gly | Ala | Thr | Ala | Leu | Leu | Ser | Val | Arg | Val | Leu | Ala | Thr | Ala | His | |
| | | | 180 | | | | | 185 | | | | | 190 | | | |

| | | | | | | | | | | | | | | | | |
|---|---|---|---|---|---|---|---|---|---|---|---|---|---|---|---|---|
| cac | cag | ctg | cgg | gag | atc | cgc | aga | ctg | gag | cgg | gcg | gtg | tgc | cgt | gat | 624 |
| His | Gln | Leu | Arg | Glu | Ile | Arg | Arg | Leu | Glu | Arg | Ala | Val | Cys | Arg | Asp | |
| | | | 195 | | | | | 200 | | | | | 205 | | | |

| | | | | | | | | | | | | | | | | |
|---|---|---|---|---|---|---|---|---|---|---|---|---|---|---|---|---|
| gca | ccc | tca | acc | cta | gcg | agg | gct | ctc | acc | tgg | agg | cag | gct | agg | gca | 672 |
| Ala | Pro | Ser | Thr | Leu | Ala | Arg | Ala | Leu | Thr | Trp | Arg | Gln | Ala | Arg | Ala | |
| | | 210 | | | | | 215 | | | | | 220 | | | | |

| | | | | | | | | | | | | | | | | |
|---|---|---|---|---|---|---|---|---|---|---|---|---|---|---|---|---|
| cag | gca | gga | gcc | aca | ctg | ctc | ttt | ttg | ctg | tgt | tgg | ggg | ccc | tat | gtg | 720 |
| Gln | Ala | Gly | Ala | Thr | Leu | Leu | Phe | Leu | Leu | Cys | Trp | Gly | Pro | Tyr | Val | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| gcc | aca | ttg | ctc | ctg | tca | gtc | ttg | gcc | tat | gag | cgg | cgg | cca | cca | cta | 768 |
| Ala | Thr | Leu | Leu | Leu | Ser | Val | Leu | Ala | Tyr | Glu | Arg | Arg | Pro | Pro | Leu | |
| | | | 245 | | | | | 250 | | | | | 255 | | | |

| | | | | | | | | | | | | | | | | |
|---|---|---|---|---|---|---|---|---|---|---|---|---|---|---|---|---|
| ggg | cct | gta | act | ctg | tta | tct | ctc | atc | tca | ttg | ggc | agt | gcc | agt | gct | 816 |
| Gly | Pro | Val | Thr | Leu | Leu | Ser | Leu | Ile | Ser | Leu | Gly | Ser | Ala | Ser | Ala | |
| | | | 260 | | | | | 265 | | | | | 270 | | | |

| | | | | | | | | | | | | | | | | |
|---|---|---|---|---|---|---|---|---|---|---|---|---|---|---|---|---|
| gca | gtt | gtg | cct | gtg | gcc | atg | ggt | ctg | ggt | gat | cag | cgc | tac | acg | gcc | 864 |
| Ala | Val | Val | Pro | Val | Ala | Met | Gly | Leu | Gly | Asp | Gln | Arg | Tyr | Thr | Ala | |
| | | 275 | | | | | 280 | | | | | 285 | | | | |

| | | | | | | | | | | | | | | | | |
|---|---|---|---|---|---|---|---|---|---|---|---|---|---|---|---|---|
| ccc | tgg | agg | aca | gct | gcc | caa | agg | tgg | cta | caa | gtg | ctt | cga | gga | aga | 912 |

```
Pro Trp Arg Thr Ala Ala Gln Arg Trp Leu Gln Val Leu Arg Gly Arg
    290                 295                 300 ccc aag agg gcc aat cca ggc ccc agc act gcc tac cac tcc agt agc      960
Pro Lys Arg Ala Asn Pro Gly Pro Ser Thr Ala Tyr His Ser Ser Ser
305                 310                 315                 320 caa tgc agc act gac ttg gac ttg aat                                  987
Gln Cys Ser Thr Asp Leu Asp Leu Asn
                325

<210> SEQ ID NO 6
<211> LENGTH: 329
<212> TYPE: PRT
<213> ORGANISM: Rattus norvegicus

<400> SEQUENCE: 6

Met Met Ser His Asn Thr Thr Glu Leu Ser Ala Ile Pro Arg Gly Val
1               5                   10                  15

Gln Glu Leu Ser Leu Val Leu Ala Ser Leu Ile Val Ile Ala Asn Leu
                20                  25                  30

Leu Leu Ala Leu Gly Ile Val Leu Asp Arg His Leu Arg Ser Pro Pro
            35                  40                  45

Ala Gly Cys Phe Phe Leu Ser Leu Leu Leu Ala Gly Leu Leu Thr Gly
        50                  55                  60

Leu Ala Leu Pro Thr Leu Pro Gly Leu Trp Asn Arg Ser His Gln Gly
65                  70                  75                  80

Tyr Trp Ser Cys Leu Leu Leu His Leu Ala Pro Asn Phe Cys Phe Leu
                85                  90                  95

Ser Leu Leu Ala Asn Leu Leu Leu Val His Gly Glu Arg Tyr Met Ala
                100                 105                 110

Val Leu Gln Pro Leu Arg Pro His Gly Ser Val Arg Leu Ala Leu Phe
            115                 120                 125

Leu Thr Trp Ile Ser Ser Leu Leu Phe Ala Ser Leu Pro Ala Leu Gly
        130                 135                 140

Trp Asn His Trp Ser Pro Gly Ala Asn Cys Ser Ser Gln Ala Ile Phe
145                 150                 155                 160

Pro Ala Pro Tyr Leu Tyr Leu Glu Val Tyr Gly Leu Leu Leu Pro Ala
                165                 170                 175

Val Gly Ala Thr Ala Leu Leu Ser Val Arg Val Leu Ala Thr Ala His
            180                 185                 190

His Gln Leu Arg Glu Ile Arg Arg Leu Glu Arg Ala Val Cys Arg Asp
        195                 200                 205

Ala Pro Ser Thr Leu Ala Arg Ala Leu Thr Trp Arg Gln Ala Arg Ala
    210                 215                 220

Gln Ala Gly Ala Thr Leu Leu Phe Leu Leu Cys Trp Gly Pro Tyr Val
225                 230                 235                 240

Ala Thr Leu Leu Leu Ser Val Leu Ala Tyr Glu Arg Arg Pro Pro Leu
                245                 250                 255

Gly Pro Val Thr Leu Leu Ser Leu Ile Ser Leu Gly Ser Ala Ser Ala
            260                 265                 270

Ala Val Val Pro Val Ala Met Gly Leu Gly Asp Gln Arg Tyr Thr Ala
        275                 280                 285

Pro Trp Arg Thr Ala Ala Gln Arg Trp Leu Gln Val Leu Arg Gly Arg
    290                 295                 300

Pro Lys Arg Ala Asn Pro Gly Pro Ser Thr Ala Tyr His Ser Ser Ser
305                 310                 315                 320
```

Gln Cys Ser Thr Asp Leu Asp Leu Asn
                325

<210> SEQ ID NO 7
<211> LENGTH: 987
<212> TYPE: DNA
<213> ORGANISM: Bos taurus
<220> FEATURE:
<221> NAME/KEY: CDS
<222> LOCATION: (1)..(987)
<223> OTHER INFORMATION:

<400> SEQUENCE: 7

```
atg aca tcc aac agc acc agg gag gtg ccc agc ccc gtt cct gca ggg    48
Met Thr Ser Asn Ser Thr Arg Glu Val Pro Ser Pro Val Pro Ala Gly
1               5                   10                  15 gcc ctg ggg ctc tcc ctg gcc ctg gca agc ctc atc gtc gct gcc aac    96
Ala Leu Gly Leu Ser Leu Ala Leu Ala Ser Leu Ile Val Ala Ala Asn
            20                  25                  30 ctc ctc ctg gcc gtg ggt atc gcc ggg gac cgc cgc ctg cgc agc ccg   144
Leu Leu Leu Ala Val Gly Ile Ala Gly Asp Arg Arg Leu Arg Ser Pro
        35                  40                  45 ccc gct ggc tgc ttc ttc ctg agt ctt ctg ctg gca ggg ctg ctc acg   192
Pro Ala Gly Cys Phe Phe Leu Ser Leu Leu Leu Ala Gly Leu Leu Thr
    50                  55                  60 ggg ctg gcg ctg ccc gcg ctg ccc gtc cta tgg agc cag agc cgc cgg   240
Gly Leu Ala Leu Pro Ala Leu Pro Val Leu Trp Ser Gln Ser Arg Arg
65                  70                  75                  80 ggc tac tgg tcc tgc ctc ttc ctc tac ttg gct ccc aac ttc tgc ttc   288
Gly Tyr Trp Ser Cys Leu Phe Leu Tyr Leu Ala Pro Asn Phe Cys Phe
                85                  90                  95 ctc tcc ctg ctc gcc aac ctc cta ctg gtg cac ggg gag cgc tac atg   336
Leu Ser Leu Leu Ala Asn Leu Leu Leu Val His Gly Glu Arg Tyr Met
            100                 105                 110 gcc gtg ctg cgg ccc ctg cgg ccc cgt ggg agc atg cgg ctg gcc ctg   384
Ala Val Leu Arg Pro Leu Arg Pro Arg Gly Ser Met Arg Leu Ala Leu
        115                 120                 125 ctc ctc acc tgg gct gcc ccc ttg ctc ttt gcc agc ctg cct gcc ctg   432
Leu Leu Thr Trp Ala Ala Pro Leu Leu Phe Ala Ser Leu Pro Ala Leu
    130                 135                 140 ggc tgg aac cac tgg gcc cct ggt ggc aac tgc agc tcc cag gcc gtc   480
Gly Trp Asn His Trp Ala Pro Gly Gly Asn Cys Ser Ser Gln Ala Val
145                 150                 155                 160 ttc cca gcc ccc tac ctc tac ctc gaa atc tat ggg ctc ctg ctg ccg   528
Phe Pro Ala Pro Tyr Leu Tyr Leu Glu Ile Tyr Gly Leu Leu Leu Pro
                165                 170                 175 gct gtg ggc gcg gcc gcc ctc ctc tcg gtc cgc gtg ctg gtc act gcg   576
Ala Val Gly Ala Ala Ala Leu Leu Ser Val Arg Val Leu Val Thr Ala
            180                 185                 190 cac cgc cag ctg cag gac atc cgc cgg ctg gag cgg gcc gtg tgc cgc   624
His Arg Gln Leu Gln Asp Ile Arg Arg Leu Glu Arg Ala Val Cys Arg
        195                 200                 205 ggg gcg ccc tcg gcc ctg gcc cga gcc ctc acc tgg cgg cag gcc agg   672
Gly Ala Pro Ser Ala Leu Ala Arg Ala Leu Thr Trp Arg Gln Ala Arg
    210                 215                 220 gcg cag gct ggg gcc acg ttg ctc ttt ggg ctg tgc tgg ggc ccc tac   720
Ala Gln Ala Gly Ala Thr Leu Leu Phe Gly Leu Cys Trp Gly Pro Tyr
225                 230                 235                 240 gtg gcc acc ctg ctg ctc tct gtc ctg gcc ttt gag cag cgc ccg cca   768
Val Ala Thr Leu Leu Leu Ser Val Leu Ala Phe Glu Gln Arg Pro Pro
                245                 250                 255
```

```
cta ggg ccc gga act ctg ctg tcc ctc atc tca ctg ggc agc gcc agt     816
Leu Gly Pro Gly Thr Leu Leu Ser Leu Ile Ser Leu Gly Ser Ala Ser
        260                 265                 270 gcg gcg gcc gtg ccc gtg gcc atg ggg ctg ggt gat cag cgc tat aca     864
Ala Ala Ala Val Pro Val Ala Met Gly Leu Gly Asp Gln Arg Tyr Thr
        275                 280                 285 ggc ccc tgg agg gtg gcc gcc cag aag tgg ctc cgg atg ctg cgg ggc     912
Gly Pro Trp Arg Val Ala Ala Gln Lys Trp Leu Arg Met Leu Arg Gly
290                 295                 300 aga ccg cag agc agt cct ggt ccc agc acc gcc tac cat acc agc agc     960
Arg Pro Gln Ser Ser Pro Gly Pro Ser Thr Ala Tyr His Thr Ser Ser
305                 310                 315                 320 caa agc agc gtg gac ctt gac ttg aac                                 987
Gln Ser Ser Val Asp Leu Asp Leu Asn
                325
```

<210> SEQ ID NO 8
<211> LENGTH: 329
<212> TYPE: PRT
<213> ORGANISM: Bos taurus

<400> SEQUENCE: 8

```
Met Thr Ser Asn Ser Thr Arg Glu Val Pro Ser Pro Val Pro Ala Gly
1               5                   10                  15

Ala Leu Gly Leu Ser Leu Ala Leu Ala Ser Leu Ile Val Ala Ala Asn
            20                  25                  30

Leu Leu Leu Ala Val Gly Ile Ala Gly Asp Arg Arg Leu Arg Ser Pro
        35                  40                  45

Pro Ala Gly Cys Phe Phe Leu Ser Leu Leu Ala Gly Leu Leu Thr
    50                  55                  60

Gly Leu Ala Leu Pro Ala Leu Pro Val Leu Trp Ser Gln Ser Arg Arg
65                  70                  75                  80

Gly Tyr Trp Ser Cys Leu Phe Leu Tyr Leu Ala Pro Asn Phe Cys Phe
                85                  90                  95

Leu Ser Leu Leu Ala Asn Leu Leu Val His Gly Glu Arg Tyr Met
            100                 105                 110

Ala Val Leu Arg Pro Leu Arg Pro Arg Gly Ser Met Arg Leu Ala Leu
        115                 120                 125

Leu Leu Thr Trp Ala Ala Pro Leu Leu Phe Ala Ser Leu Pro Ala Leu
    130                 135                 140

Gly Trp Asn His Trp Ala Pro Gly Gly Asn Cys Ser Ser Gln Ala Val
145                 150                 155                 160

Phe Pro Ala Pro Tyr Leu Tyr Leu Glu Ile Tyr Gly Leu Leu Leu Pro
                165                 170                 175

Ala Val Gly Ala Ala Leu Leu Ser Val Arg Val Leu Val Thr Ala
            180                 185                 190

His Arg Gln Leu Gln Asp Ile Arg Arg Leu Glu Arg Ala Val Cys Arg
        195                 200                 205

Gly Ala Pro Ser Ala Leu Ala Arg Ala Leu Thr Trp Arg Gln Ala Arg
    210                 215                 220

Ala Gln Ala Gly Ala Thr Leu Leu Phe Gly Leu Cys Trp Gly Pro Tyr
225                 230                 235                 240

Val Ala Thr Leu Leu Leu Ser Val Leu Ala Phe Glu Gln Arg Pro Pro
                245                 250                 255

Leu Gly Pro Gly Thr Leu Leu Ser Leu Ile Ser Leu Gly Ser Ala Ser
            260                 265                 270
```

-continued

```
Ala Ala Ala Val Pro Val Ala Met Gly Leu Gly Asp Gln Arg Tyr Thr
            275                 280                 285

Gly Pro Trp Arg Val Ala Ala Gln Lys Trp Leu Arg Met Leu Arg Gly
        290                 295                 300

Arg Pro Gln Ser Ser Pro Gly Pro Ser Thr Ala Tyr His Thr Ser Ser
305                 310                 315                 320

Gln Ser Ser Val Asp Leu Asp Leu Asn
                325
```

<210> SEQ ID NO 9
<211> LENGTH: 990
<212> TYPE: DNA
<213> ORGANISM: Oryctolagus cuniculus
<220> FEATURE:
<221> NAME/KEY: CDS
<222> LOCATION: (1)..(990)
<223> OTHER INFORMATION:

<400> SEQUENCE: 9

```
atg aca ccc aac agc acc ggg gag gtg cct ggc ccc atc ccc agg ggc      48
Met Thr Pro Asn Ser Thr Gly Glu Val Pro Gly Pro Ile Pro Arg Gly
1               5                   10                  15 gcc ctg gag ctg tca ctg gcc ctg gca agc ctc atc atc gca gcc aac      96
Ala Leu Glu Leu Ser Leu Ala Leu Ala Ser Leu Ile Ile Ala Ala Asn
                20                  25                  30 ctg ctc ctg gcg ctg ggc atc gcc tgc gac cgc cgc ctt cgc agc cca     144
Leu Leu Leu Ala Leu Gly Ile Ala Cys Asp Arg Arg Leu Arg Ser Pro
            35                  40                  45 ccg gcc ggc tgc ttc ttc ctg agc ctg ttg ctg gcc ggg ctg ctt acg     192
Pro Ala Gly Cys Phe Phe Leu Ser Leu Leu Leu Ala Gly Leu Leu Thr
        50                  55                  60 ggg ctg gca ctg ccc act ctg cca ggg ctc tgg aga cag agc cac cgg     240
Gly Leu Ala Leu Pro Thr Leu Pro Gly Leu Trp Arg Gln Ser His Arg
65                  70                  75                  80 ggc tat tgg tcc tgc ctg ctc gtc tac ttg gct ccc aac ttc tcc ttc     288
Gly Tyr Trp Ser Cys Leu Leu Val Tyr Leu Ala Pro Asn Phe Ser Phe
                85                  90                  95 ctc tcc ctg ctc gcc aac ctg ctg gtg cac ggg gag cgc tat gtg           336
Leu Ser Leu Leu Ala Asn Leu Leu Val His Gly Glu Arg Tyr Val
            100                 105                 110 gcg gtg ctg cgg cca ctc cag cct ccg ggg agc atc cgg ctg gcc ctg     384
Ala Val Leu Arg Pro Leu Gln Pro Pro Gly Ser Ile Arg Leu Ala Leu
        115                 120                 125 ctc ctc acc tgg acc ggc ccc ctg ctc ttt gcc agc ctg ccg gcc ctg     432
Leu Leu Thr Trp Thr Gly Pro Leu Leu Phe Ala Ser Leu Pro Ala Leu
130                 135                 140 ggc tgg aac cac tgg ggc cct gag gcc aac tgc agc tcc cag acc atc     480
Gly Trp Asn His Trp Gly Pro Glu Ala Asn Cys Ser Ser Gln Thr Ile
145                 150                 155                 160 ttc cca gcg ccc tac ctc tac ctc gaa gtc tac ggg ctc ctg ctg ccg     528
Phe Pro Ala Pro Tyr Leu Tyr Leu Glu Val Tyr Gly Leu Leu Leu Pro
                165                 170                 175 gcc gtg ggg gcc gcg gcc ctt ctc tcg gct cac gtg ctg ctg gcc gcc     576
Ala Val Gly Ala Ala Ala Leu Leu Ser Ala His Val Leu Leu Ala Ala
            180                 185                 190 cac cgc cag ctg cag gac atc cgc cgg ctg gag cgg gcc gtg tgc cgc     624
His Arg Gln Leu Gln Asp Ile Arg Arg Leu Glu Arg Ala Val Cys Arg
        195                 200                 205 gac gcg ccc tcc gcc ctg gcc cgg gcc ctt acc tgg agg cag gcg cgg     672
Asp Ala Pro Ser Ala Leu Ala Arg Ala Leu Thr Trp Arg Gln Ala Arg
210                 215                 220
```

```
gcg cag gct gga gcc acg ctg ctc ttt ggg ctg tgc tgg ggg ccc tat      720
Ala Gln Ala Gly Ala Thr Leu Leu Phe Gly Leu Cys Trp Gly Pro Tyr
225                 230                 235                 240 gtg gcc acg ctg ttc ctg tcg gtc ctg gcc tat gag cag cgc cca cct      768
Val Ala Thr Leu Phe Leu Ser Val Leu Ala Tyr Glu Gln Arg Pro Pro
                245                 250                 255 cta ggg ccc gga act ctg ctg tct ctc ctc tcc ctg ggc agt gcc agc      816
Leu Gly Pro Gly Thr Leu Leu Ser Leu Leu Ser Leu Gly Ser Ala Ser
            260                 265                 270 gcg gcg gcc gtg ccc gtg gcc atg ggg ctg ggt gat cac cgc tac aca      864
Ala Ala Ala Val Pro Val Ala Met Gly Leu Gly Asp His Arg Tyr Thr
        275                 280                 285 gcg ccc tgg agg gcg gcc gcc cgg agg tgg ctg cgg ggg ctg cgg ggg      912
Ala Pro Trp Arg Ala Ala Ala Arg Arg Trp Leu Arg Gly Leu Arg Gly
    290                 295                 300 aga ggc tcc cag gct agc cct ggc ccc agc act gcc tac cac acc agc      960
Arg Gly Ser Gln Ala Ser Pro Gly Pro Ser Thr Ala Tyr His Thr Ser
305                 310                 315                 320 agc caa agc agc gtg gac gtg gac ttg aac                              990
Ser Gln Ser Ser Val Asp Val Asp Leu Asn
                325                 330

<210> SEQ ID NO 10
<211> LENGTH: 330
<212> TYPE: PRT
<213> ORGANISM: Oryctolagus cuniculus

<400> SEQUENCE: 10

Met Thr Pro Asn Ser Thr Gly Glu Val Pro Gly Pro Ile Pro Arg Gly
1               5                   10                  15

Ala Leu Glu Leu Ser Leu Ala Leu Ala Ser Leu Ile Ile Ala Ala Asn
            20                  25                  30

Leu Leu Leu Ala Leu Gly Ile Ala Cys Asp Arg Arg Leu Arg Ser Pro
        35                  40                  45

Pro Ala Gly Cys Phe Phe Leu Ser Leu Leu Ala Gly Leu Leu Thr
    50                  55                  60

Gly Leu Ala Leu Pro Thr Leu Pro Gly Leu Trp Arg Gln Ser His Arg
65                  70                  75                  80

Gly Tyr Trp Ser Cys Leu Leu Val Tyr Leu Ala Pro Asn Phe Ser Phe
                85                  90                  95

Leu Ser Leu Leu Ala Asn Leu Leu Leu Val His Gly Glu Arg Tyr Val
            100                 105                 110

Ala Val Leu Arg Pro Leu Gln Pro Pro Gly Ser Ile Arg Leu Ala Leu
        115                 120                 125

Leu Leu Thr Trp Thr Gly Pro Leu Leu Phe Ala Ser Leu Pro Ala Leu
    130                 135                 140

Gly Trp Asn His Trp Gly Pro Glu Ala Asn Cys Ser Ser Gln Thr Ile
145                 150                 155                 160

Phe Pro Ala Pro Tyr Leu Tyr Leu Glu Val Tyr Gly Leu Leu Leu Pro
                165                 170                 175

Ala Val Gly Ala Ala Ala Leu Leu Ser Ala His Val Leu Leu Ala Ala
            180                 185                 190

His Arg Gln Leu Gln Asp Ile Arg Arg Leu Glu Arg Ala Val Cys Arg
        195                 200                 205

Asp Ala Pro Ser Ala Leu Ala Arg Ala Leu Thr Trp Arg Gln Ala Arg
    210                 215                 220
```

Ala Gln Ala Gly Ala Thr Leu Leu Phe Gly Leu Cys Trp Gly Pro Tyr
225                 230                 235                 240

Val Ala Thr Leu Phe Leu Ser Val Leu Ala Tyr Glu Gln Arg Pro Pro
                245                 250                 255

Leu Gly Pro Gly Thr Leu Leu Ser Leu Leu Ser Leu Gly Ser Ala Ser
            260                 265                 270

Ala Ala Ala Val Pro Val Ala Met Gly Leu Gly Asp His Arg Tyr Thr
        275                 280                 285

Ala Pro Trp Arg Ala Ala Arg Arg Trp Leu Arg Gly Leu Arg Gly
    290                 295                 300

Arg Gly Ser Gln Ala Ser Pro Gly Pro Ser Thr Ala Tyr His Thr Ser
305                 310                 315                 320

Ser Gln Ser Ser Val Asp Val Asp Leu Asn
                325                 330

<210> SEQ ID NO 11
<211> LENGTH: 1005
<212> TYPE: DNA
<213> ORGANISM: Guinea pig

<400> SEQUENCE: 11
atgccaaggc ccatgatgac acccaacagc accggggagg tgcctggccc cattttccca      60
ggggccttgg ggctctccct ggccctggcc agcctcatcg ttgcagccaa tctgctcctg     120
ggcctgggca tcgcctggga ccgccacctg cgcagcccac ctgccggctg cttcttcctg     180
agcctgttgc tggccgggct gctcactggg ttggcactgc ccatgctgcc agggctatgg     240
agccggaaac gccgggccta ctggccctgc tcctcctct acttgacccc caacttcacc      300
ttcctctctc tgctcgccaa cctgctactg gtgcacgggg agcgttacgt ggcagtgctg     360
cggccgctcc ggccccgagg gagcacccgg ctggccctgc tcctcacctg gatggccccc     420
atgctctttg ccagcctgcc tgccttgggt tggaaccgct ggagccctgg tgccaactgc     480
agctcccaga ctgtcttccc agccccctac ctctaccttg aagtctacgg actcctgctg     540
cctgccgtgg gggctgctgc cctcctctct atccgagtgc tagccacggc ccgccgccag     600
ctacaggaca tccgccggct cgagcaggca gtgtgccgca atgcaccctc caccttgacc     660
cggacccctca cctggcggca ggccaggccc caggctgggg ccacgctgct cttcgggctg    720
tgctggggggc cctatgtagc caccttgctc ctgtcagtcc aggcttatga aagcaccca      780
cccctggagc tggaactcct gctcttctta ttctcattgg gcagtgccag cgcagcggcc    840
gtgcctgtag ccatgggctt gggtgaccag cgctacacag cacctggag ggcggccacc      900
caaaggtggc tgcgggtgct gaggggaaga cgttcgaggg acagtcgcag ccccagcact    960
gcctaccaca ccagcaacca aagcagcgtt gatctggact tgaac                  1005

<210> SEQ ID NO 12
<211> LENGTH: 335
<212> TYPE: PRT
<213> ORGANISM: Guinea pig

<400> SEQUENCE: 12

Met Pro Arg Pro Met Met Thr Pro Asn Ser Thr Gly Glu Val Pro Gly
                5                   10                  15

Pro Ile Phe Pro Gly Ala Leu Gly Leu Ser Leu Ala Leu Ala Ser Leu
            20                  25                  30

Ile Val Ala Ala Asn Leu Leu Leu Gly Leu Gly Ile Ala Trp Asp Arg
        35                  40                  45

His Leu Arg Ser Pro Pro Ala Gly Cys Phe Phe Leu Ser Leu Leu Leu
        50                  55                  60

Ala Gly Leu Leu Thr Gly Leu Ala Leu Pro Met Leu Pro Gly Leu Trp
 65                  70                  75                  80

Ser Arg Lys Arg Arg Ala Tyr Trp Pro Cys Leu Leu Leu Tyr Leu Thr
                 85                  90                  95

Pro Asn Phe Thr Phe Leu Ser Leu Leu Ala Asn Leu Leu Leu Val His
            100                 105                 110

Gly Glu Arg Tyr Val Ala Val Leu Arg Pro Leu Arg Pro Arg Gly Ser
        115                 120                 125

Thr Arg Leu Ala Leu Leu Leu Thr Trp Met Ala Pro Met Leu Phe Ala
130                 135                 140

Ser Leu Pro Ala Leu Gly Trp Asn Arg Trp Ser Pro Gly Ala Asn Cys
145                 150                 155                 160

Ser Ser Gln Thr Val Phe Pro Ala Pro Tyr Leu Tyr Leu Glu Val Tyr
                165                 170                 175

Gly Leu Leu Leu Pro Ala Val Gly Ala Ala Ala Leu Leu Ser Ile Arg
            180                 185                 190

Val Leu Ala Thr Ala Arg Arg Gln Leu Gln Asp Ile Arg Arg Leu Glu
        195                 200                 205

Gln Ala Val Cys Arg Asn Ala Pro Ser Thr Leu Thr Arg Thr Leu Thr
210                 215                 220

Trp Arg Gln Ala Arg Ala Gln Ala Gly Ala Thr Leu Leu Phe Gly Leu
225                 230                 235                 240

Cys Trp Gly Pro Tyr Val Ala Thr Leu Leu Leu Ser Val Gln Ala Tyr
                245                 250                 255

Glu Lys His Pro Pro Leu Glu Pro Gly Thr Leu Leu Phe Leu Phe Ser
            260                 265                 270

Leu Gly Ser Ala Ser Ala Ala Ala Val Pro Val Ala Met Gly Leu Gly
        275                 280                 285

Asp Gln Arg Tyr Thr Ala Pro Trp Arg Ala Ala Thr Gln Arg Trp Leu
290                 295                 300

Arg Val Leu Arg Gly Arg Arg Ser Arg Asp Ser Arg Ser Pro Ser Thr
305                 310                 315                 320

Ala Tyr His Thr Ser Asn Gln Ser Ser Val Asp Leu Asp Leu Asn
                325                 330                 335

<210> SEQ ID NO 13
<211> LENGTH: 34
<212> TYPE: DNA
<213> ORGANISM: Artificial Sequence
<220> FEATURE:
<223> OTHER INFORMATION: Designed oligonucleotide primer to amplify
      DNA encoding TGR5

<400> SEQUENCE: 13
ggggtcgacc atgccaaggc ccatgatgac accc                              34

<210> SEQ ID NO 14
<211> LENGTH: 34
<212> TYPE: DNA
<213> ORGANISM: Artificial Sequence
<220> FEATURE:

```
<223> OTHER INFORMATION: Designed oligonucleotide primer to amplify
      DNA encoding TGR5

<400> SEQUENCE: 14
gggactagtc tagttcaagt ccagatcaac gctg                              34
```